US008636981B2

(12) United States Patent
Schenk et al.

(10) Patent No.: US 8,636,981 B2
(45) Date of Patent: *Jan. 28, 2014

(54) DETECTION OF AMYLOID DEPOSITS USING ANTI-AMYLOID ANTIBODIES

(75) Inventors: Dale B. Schenk, Burlingame, CA (US); Peter A. Seubert, San Francisco, CA (US); Jonathan Wall, Knoxville, TN (US)

(73) Assignee: Onclave Therapeutics, Dublin (IE)

( * ) Notice: Subject to any disclaimer, the term of this patent is extended or adjusted under 35 U.S.C. 154(b) by 36 days.

This patent is subject to a terminal disclaimer.

(21) Appl. No.: 13/314,160

(22) Filed: Dec. 7, 2011

(65) Prior Publication Data

US 2012/0189624 A1 Jul. 26, 2012

Related U.S. Application Data

(63) Continuation of application No. 13/032,412, filed on Feb. 22, 2011, now Pat. No. 8,404,815, which is a continuation of application No. 12/345,650, filed on Dec. 29, 2008, now Pat. No. 7,928,203.

(60) Provisional application No. 61/095,932, filed on Sep. 10, 2008, provisional application No. 61/007,544, filed on Dec. 28, 2007.

(51) Int. Cl.
*A61B 5/055* (2006.01)
*A61B 5/05* (2006.01)
*A61K 49/16* (2006.01)
*A61K 51/10* (2006.01)

(52) U.S. Cl.
USPC .................. 424/9.341; 424/9.1; 424/1.49

(58) Field of Classification Search
None
See application file for complete search history.

(56) References Cited

U.S. PATENT DOCUMENTS

| | | | |
|---|---|---|---|
| 5,562,903 A | 10/1996 | Co et al. | |
| 5,624,821 A | 4/1997 | Winter et al. | |
| 6,375,949 B1 | 4/2002 | Hirano et al. | |
| 6,743,427 B1 | 6/2004 | Schenk | |
| 6,875,434 B1 | 4/2005 | Schenk | |
| 6,890,535 B1 | 5/2005 | Schenk | |
| 6,913,745 B1 | 7/2005 | Schenk | |
| 6,923,964 B1 | 8/2005 | Schenk | |
| 6,936,246 B1 | 8/2005 | Schenk | |
| 7,928,203 B2 | 4/2011 | Schenk et al. | |
| 2004/0223912 A1 | 11/2004 | Montalto et al. | |
| 2005/0038117 A1 | 2/2005 | Kong et al. | |
| 2006/0280743 A1 | 12/2006 | Basi et al. | |
| 2007/0003552 A1 | 1/2007 | Gebbink et al. | |
| 2007/0178504 A1 | 8/2007 | Colpitts et al. | |

FOREIGN PATENT DOCUMENTS

| | | |
|---|---|---|
| CN | 101058608 | 10/2007 |
| EP | 0 872 558 | 10/1998 |
| WO | WO 95/30642 | 11/1995 |
| WO | WO 95/35503 | 12/1995 |
| WO | WO 97/04317 | 2/1997 |
| WO | WO 98/23635 | 6/1998 |
| WO | WO 01/77167 | 10/2001 |
| WO | WO 2004/032868 | 4/2004 |
| WO | WO 2005/025516 | 3/2005 |
| WO | WO 2006/020581 | 2/2006 |

OTHER PUBLICATIONS

Wall et al. (Dec. 2006) Radioimaging of light chain amyloid with a fibril-reactive monoclonal antibody. J. Nucl. Med. 47(12):2016-2024.*
Malle, Ernst et al, "Quantification and mapping of antigenic determinants of serum amyloid A (SAA) protein utilizing sequence-specific immunoglovulins and $Eu^{3+}$ as a specific probe for time-resolved fluorometric immunoassay," Journal of Immunological Methods (1995) 182: 131-144.
Miura, Katsutoshi et al "Generation and Use of Site-specific Antibodies to Serum Amyloid A for Probing Amyloid A Development," The Journal of Immunology (1990) vol. 144, 610-613 No. 2.
Anderson et al., "Cutting edge: biasing immune responses by directing antigen to macrophage Fc gamma receptors," J. Immunol. 168(8):3697-3701 (2002).
Axelrad et al., "Further characterization of amyloid-enhancing factor," Lab Invest., 47(2):139-146 (1982).
Bard et al., "Peripherally administered antibodies against amyloid beta-peptide enter the central nervous system and reduce pathology in a mouse model of Alzheimer disease," Nat. Med., 6(8):916-919 (2000).
Cevc et al., "Ultraflexible vesicles, Transfersomes, have an extremely low pore penetration resistance and transport therapeutic amounts of insulin across the intact mammalian skin," Biochem. Biophys. Acta., 1368(2): 201-215 (1998).
Chicz et al., "Specificity and promiscuity among naturally processed peptides bound to HLA-DR alleles," J. Exp. Med., 178:27-47 (1993).
Clayton et al., "The synucleins: a family of proteins involved in synaptic function, plasticity, neurodegeneration and disease," Trends Neurosci., 21(6):249-254 (1998).
Cunnane et al., "Amyloid precursors and amyloidosis in rheumatoid arthritis," Baillieres Best Pract. Res. Clin. Rheumatol., 13(4):615-28 (1999).
de Beer et al., "Identification of a novel serum amyloid A protein in BALB/c mice," Biochem J., 280(Pt 1):45-49 (1991).

(Continued)

Primary Examiner — Kimberly A Ballard
(74) Attorney, Agent, or Firm — Womble Carlyle Sandridge & Rice, LLP

(57) ABSTRACT

Methods useful for effecting prophylaxis or treatment of amyloidosis, including AA Amyloidosis and AL amyloidosis, by administering peptides comprising neoepitopes, such as AA fragments from a C-terminal region of AA, and antibodies specific for neoepitopes of aggregated amyloid proteins, for example, antibodies specific for the C-terminal region of AA fibrils. Antibodies for inhibition of formation and/or increasing clearance of amyloid deposits in a patient thus effecting prophylaxis or treating amyloid disease.

21 Claims, 40 Drawing Sheets

(56) References Cited

OTHER PUBLICATIONS de Beer et al., "Structure of the mouse Saa4 gene and its linkage to the serum amyloid A gene family," *Genomics*, May 15, 1996;34(1):139-42.
Falk et al., "Pool sequencing of natural HLA-DR, DQ, and DP ligands reveals detailed peptide motifs, constraints of processing, and general rules," *Immunogenetics*, 39(4):230-42 (1994).
Fykse et al., "The primary structure of the variable region of an immunoglobin IV light-chain amyloid-fibril protein (AL GIL)," *Biochem. J.*, Dec. 15, 1988;256(3):973-80.
Giannini et al., "The amino-acid sequence of two non-toxic mutants of diphtheria toxin: CRM45 and CRM197," *Nucleic Acids Res.*, May 25, 1984;12(10):4063-9.
Gillmore et al., "Amyloid load and clinical outcome in AA amyloidosis in relation to circulating concentration of serum amyloid A protein," *Lancet*, 358:24-29 (2001).
Glas et al., "Analysis of rearranged immunoglobulin heavy chain variable region genes obtained from a bone marrow transplant (BMT) recipient," *Clin. Exp. Immunol.*, Feb. 1997;107(2):372-80.
Glenn et al., "Skin immunization made possible by cholera toxin," *Nature*, 391(6670):851 (1998).
Hammer et al., "Promiscuous and allele-specific anchors in HLA-DR-binding peptides," *Cell*, 74(3):197-203 (1993).
Hanes, "New advances in microsphere-based single-dose vaccines," *Advanced Drug Delivery Reviews*, 28(1):97-119 (1997).
Hoffman et al., "Murine tissue amyloid protein AA. NH2-terminal sequence identity with only one of two serum amyloid protein (ApoSAA) gene products." *J. Exp. Med.* Feb. 1, 1984;159(2):641-6.
Hrncic Rudi et al, "Antibody-mediated resolution of light chain-associated amyloid deposits" *American Journal of Pathology*, vol. 157, No. 4, Oct. 2000, pp. 1239-1246.
Husby et al., "Interaction between circulating amyloid fibril protein precursors and extracellular tissue matrix components in the pathogenesis of systemic amyloidosis," *Clin. Immunol. Immunopathol.*, 70(1):2-9 (1994).
Husby et al., "Serum amyloid A (SAA): Biochemistry, genetics and the pathogenesis of AA amyloidosis," *Amyloid*, 1(2):119-137 (1994).
Kisilevsky et al., "Pathogenesis of amyloidosis," *Baillieres Clin. Rheumatol.*, 8(3):613-626 (1994).
Langer, New methods of drug delivery, *Science*, 249(4976):1527-1533 (1990).
Ludlage et al., "Systemic AA Amyloidosis in the Common Marmoset," *Vet. Pathol.* 42:117-124 (2005).
Lundmark et al., "Transmissibility of systemic amyloidosis by a prion-like mechanism," *Proc. Nat. Acad. Sci.*, May 14, 2002;99(10):6979-84.
Malle et al., "Mapping of antigenic determinants of purified, lipid-free human serum amyloid A proteins," *Scand. J. Immunol.*, 48:557-561 (1998).
Martin et al., "Structural families in loops of homologous proteins: automatic classification, modelling and application to antibodies," *J. Mol. Biol.*, 263(5):800-815 (1996).
Paul et al., "Transdermal immunization with large proteins by means of ultradeformable drug carriers," *Eur. J. Immunol.* 25(12):3521-3524 (1995).
Pepys et al., "Human serum amyloid P component is an invariant constituent of amyloid deposits and has a uniquely homogeneous glycostructure," *Proc. Natl. Acad. Sci. U.S.A.*, Jun. 7, 1994; 91(12):5602-6.
Pras et al., "The characterization of soluble amyloid prepared in water," *J. Clin. Invest.*, Apr. 1968;47(4):924-33.

Schenk et al., "Immunization with amyloid-beta attenuates Alzheimer-disease-like pathology in the PDAPP mouse," *Nature*, 400(6740):173-177 (1999).
Sellar et al., "The human serum amyloid A protein (SAA) superfamily gene cluster: mapping to chromosome 11p15.1 by physical and genetic linkage analysis," *Genomics* 19(2):221-227 (1994).
Senior, "Dosing in phase II trial of Alzheimer's vaccine suspended," *Lancet Neurol.* 1(1):3 (2002).
Shirai et al., "H3-rules: identification of CDR-H3 structures in antibodies," *FEBS Lett.*, 455(1-2):188-97 (1999).
Shiroo et al., "Specific deposition of serum amyloid A protein 2 in the mouse," *Scand J. Immunol.* 26(6):709-716 (1987).
Sinigaglia et al., "A malaria T-cell epitope recognized in association with most mouse and human MHC class II molecules," *Nature*, 336(6201):778-780 (1988).
Skinner et al., "Murine amyloid protein AA in casein-induced experimental amyloidosis," *Lab Invest.* 36(4):420-427 (1977).
Solomon et al., "Transgenic mouse model of AA amyloidosis," *Am. J. Pathol.* 154(4):1267-1272 (1999).
Southwood et al., "Several common HLA-DR types share largely overlapping peptide binding repertoires," *J. Immunology*, Apr. 1, 1998;160(7):3363-73.
Stearman et al., "The sequence and structure of a new serum amyloid A gene," *Nucleic Acids Research*, Jan. 24, 1986;14(2):797-809.
Tan et al., "Amyloidosis," *Histopathology*. 25(5):403-14 (1994).
Turnell et al. "Secondary structure prediction of human SAA1. Presumptive identification of calcium and lipid binding sites," *Mol. Biol. Med.* 3(5):387-407 (1986).
Wall et al., "Quantitative high-resolution microradiographic imaging of amyloid deposits in a novel murine model of AA amyloidosis." *Amyloid* 12(3):149-156 (2005).
Westermark, "The N-terminal segment of protein AA determines its fibrillogenic property," *Biochem. Biophys. Res. Commun.* 182(1):27-33 (1992).
Yamamoto et al., "Complete primary structures of two major murine serum amyloid A proteins deduced from cDNA sequences," *Proc. Natl. Acad. Sci. U.S.A.*, 82(9):2915-2919 (1985).
Kuçi, H. et a, "Anti-λ-light chain-peptide antibodies are suitable for the immunohistochemical classification of AL amyloid", *Histol Histopathol* (2007)22:379-387.
Novak et al, "AL-amyloidosis is underdiagnosed in renal biopsies", *Nephrol Dial Transplant*. (2004) 19: 3050-3. Epub Oct. 26, 2004.
O'Nuallain, Brian et al "Phage Display and Peptide Mapping of an Immunoglobulin Light Chain Fibril-Related Conformational Epitope", *Biochemistry 2007*, 46, 13049-13058.
Office Action dated Sep. 28, 2012 issued in Chinese counterpart application (No. 200880126599.6) with translation.
Office Action dated Jun. 27, 2012 issued in Eurasian counterpart application (No. 201070812) with translation.
Extended European search report dated Jan. 28, 2011 issued in European counterpart application (No. 08867535.0).
Official Action dated Dec. 7, 2011 issued in European counterpart application (No. 08867535.0).
Official Action dated Feb. 22, 2012 issued in New Zealand counterpart application (No. 586875).
Official Action dated May 30, 2012 issued in New Zealand counterpart application (No. 600224).
Official Action dated Jun. 18, 2012 issued in New Zealand counterpart application (No. 586875).
Official Action dated Nov. 9, 2012 issued in counterpart (U.S. Appl. No. 12/811,049).

* cited by examiner

```
HSAA1 (SEQ ID NO: 98)    1  MKLLTGLVFC SLVLGVSSRS FFSFLGEAFD GARDMWRAYS DMREANYIGS
HSAA2 (SEQ ID NO: 99)    1  MKLLTGLVFC SLVLSVSSRS FFSFLGEAFD GARDMWRAYS DMREANYIGS
HSAA3 (SEQ ID NO: 100)   1  MKLSTGIIFC SLVLGVSSQG WLTFLKAAGQ GAKDMWRAYS DMKEANYKKS
HSAA4 (SEQ ID NO: 101)   1  MRLFTGIVFC SLVMGVTSES WRSFFKEALQ GVGDMGRAYw DIMISNHQNS

HSAA1 (SEQ ID NO: 98)   51  DKYFHARGNY DAAKRGPGGV WAAEAISDAR ENIQRFFGHG A-------E
HSAA2 (SEQ ID NO: 99)   51  DKYFHARGNY DAAKRGPGGA WAAEVISNAR ENIQRLTGHG A-------E
HSAA3 (SEQ ID NO: 100)  51  DKYFHARGNY DAVQRGPGGV WATEVISDAR ENVQRLTGdh A-------E
HSAA4 (SEQ ID NO: 101)  51  NRYLYARGNY DAAQRGPGGV WAAKLISRSR vylqglidyy lfgnsstvlE HSAA1 (SEQ ID NO: 98)   93  DSLADQAANE WGRSGKDPNH FRPAGLPEKY
HSAA2 (SEQ ID NO: 99)   93  DSLADQAANK WGRSGRDPNH FRPAGLPEKY
HSAA3 (SEQ ID NO: 100)  93  DSLAGQATNK WGQSGKDPNH FRPAGLPEKY
HSAA4 (SEQ ID NO: 101) 101  DSKSNEKAEE WGRSGKDPDR FRPDGLPKKY
```

FIG. 1

```
HSAA1  (SEQ ID NO: 98)    1  mklltglvfc slvlgvssRS FFSFLGEAFD GARDMWRAYS DMREANYIGS
HAA1   (SEQ ID NO: 102)   1  ---------- --------RS FFSFLGEAFD GARDMWRAYS DMREANYIGS HSAA1  (SEQ ID NO: 98)   51  DKYFHARGNY DAAKRGPGGV WAAEAISDAR ENIQRFFGHG AEDsladqaa
HAA1   (SEQ ID NO: 102)  33  DKYFHARGNY DAAKRGPGGV WAAEAISDAR ENIQRFFGHG AEDS------

HSAA1  (SEQ ID NO: 98)  101  newgrsgkdp nhfrpaglpe ky
HAA1   (SEQ ID NO: 102)     ---------- ---------- --
```

FIG. 2

```
HSAA2(alpha) (SEQ ID NO: 99)    1   mklltglvfc slvlsvssRS FFSFLGEAFD GARDMWRAYS DMREANYIGS
HAA2(alpha)  (SEQ ID NO: 103)   1   ---------- --------RS FFSFLGEAFD GARDMWRAYS DMREANYIGS HSAA2(alpha) (SEQ ID NO: 99)   51   DKYFHARGNY DAAKRGPGGA WAAEVISNAR ENIQRLTGHG AEDSladqaa
HAA2(alpha)  (SEQ ID NO: 103)  33   DKYFHARGNY DAAKRGPGGA WAAEVISNAR ENIQRLTGHG AEDS------

HSAA2(alpha) (SEQ ID NO: 99)  101   nkwgrsgrdp nhfrpaglpe ky
HAA2(alpha)  (SEQ ID NO: 103)       ---------- ---------- --
```

FIG. 3

```
HSAA3  (SEQ ID NO: 100)    1  mklstgiifc slvlgvssQG WLTFLKAAGQ GAKDMWRAYS DMKEANYKKS
HAA3   (SEQ ID NO: 104)    1  ---------- --------QG WLTFLKAAGQ GAKDMWRAYS DMKEANYKKS HSAA3  (SEQ ID NO: 100)   51  DKYFHARGNY DAVQRGPGGV WATEVISDAR ENVQRLTGDH AEDSlaggat
HAA3   (SEQ ID NO: 104)   33  DKYFHARGNY DAVQRGPGGV WATEVISDAR ENVQRLTGDH AEDS------

HSAA3  (SEQ ID NO: 100)  101  nkwgqsgkdp nhfrpaglpe ky
HAA3   (SEQ ID NO: 104)       ---------- ---------- --
```

FIG. 4

```
HSAA4 (SEQ ID NO: 101)    1   mrlftgivfc slvmgvtsES WRSFFKEALQ GVGDMGRAYW DIMISNHQNS
HAA4  (SEQ ID NO: 105)    1   ---------- --------ES WRSFFKEALQ GVGDMGRAYW DIMISNHQNS HSAA4 (SEQ ID NO: 101)   51   NRYLYARGNY DAAQRGPGGV WAAKLISRSR VYLQGLIDYY LFGNSstvle
HAA4  (SEQ ID NO: 105)   33   NRYLYARGNY DAAQRGPGGV WAAKLISRSR VYLQGLIDYY LFGNS-----

HSAA4 (SEQ ID NO: 101)  101   dsksnekaee wgrsgkdpdr frpdglpkky
HAA4  (SEQ ID NO: 105)        ---------- ---------- ----------
```

FIG. 5

| | | | |
|---|---|---|---|
| HAA1 | (SEQ ID NO: 102) | 1 | RSFFSFLGEA FDGARDMWRA YSDMREANYI GSDKYFHARG NYDAAKRGPG |
| HAA2 | (SEQ ID NO: 103) | 1 | RSFFSFLGEA FDGARDMWRA YSDMREANYI GSDKYFHARG NYDAAKRGPG |
| HAA3 | (SEQ ID NO: 104) | 1 | QGWLTFLKAA GQGAKDMWRA YSDMKEANYK KSDKYFHARG NYDAVQRGPG |
| HAA4 | (SEQ ID NO: 105) | 1 | ESWRSFFKEA LQGVGDMGRA YWDIMISNHQ NSNRYLYARG NYDAAQRGPG |
| | | | |
| HAA1 | (SEQ ID NO: 102) | 51 | GVWAAEAISD ARENIQRF-- ---FGHGA-- -EDS |
| HAA2 | (SEQ ID NO: 103) | 51 | GAWAAEVISN ARENIQRL-- ---TGHGA-- -EDS |
| HAA3 | (SEQ ID NO: 104) | 51 | GVWATEVISD ARENVQRL-- ---TGdhA-- -EDS |
| HAA4 | (SEQ ID NO: 105) | 51 | GVWAAKLISR SRVYLQGLid yylFGNSStv lEDS |

FIG. 6

| | | | |
|---|---|---|---|
| HAA1 | (SEQ ID NO: 102) | 70 | GHGAEDS |
| HAA2 | (SEQ ID NO: 103) | 70 | GHGAEDS |
| HAA3 | (SEQ ID NO: 104) | 70 | GdhAEDS |
| HAA4 | (SEQ ID NO: 105) | 78 | stvlEDS |

FIG. 7

| | | | |
|---|---|---|---|
| Mouse SAA1 | (SEQ ID NO: 106) | 1 | MKLLTSLVFC SLLLGVCHGG FFSFVHEAFQ GAGDMWRAYT DMKEANWKNS |
| Mouse SAA2 | (SEQ ID NO: 107) | 1 | MKLLTSLVFC SLLLGVCHGG FFSFIGEAFQ GAGDMWRAYT DMKEAGWKDG |
| Mouse SAA3 | (SEQ ID NO: 108) | 1 | MKPSIAIILC ILILGVDSQR WVQFMKEAGQ GSRDMWRAYS DMKKANWKNS |
| Mouse SAA4 | (SEQ ID NO: 109) | 1 | MRLATVIVLC SLFLGVSGDG WYSFFREAVQ GTWDLWRAYR DnlEANYQNA |

| | | | |
|---|---|---|---|
| Mouse SAA1 | (SEQ ID NO: 106) | 51 | DKYFHARGNY DAAQRGPGGV WAAEKISDGR EAFQE----- FFG---RGHE |
| Mouse SAA2 | (SEQ ID NO: 107) | 51 | DKYFHARGNY DAAQRGPGGV WAAEKISDAR ESFQE----- FFG---RGHE |
| Mouse SAA3 | (SEQ ID NO: 108) | 51 | DKYFHARGNY DAARRGPGGA WAAKVISDAR EAVQK----- FTG---HGAE |
| Mouse SAA4 | (SEQ ID NO: 109) | 51 | DQYFYARGNY EAQQRGSGGI WAAKIISTSR KYFqgllnry YFGirnHGlE |

| | | | |
|---|---|---|---|
| Mouse SAA1 | (SEQ ID NO: 106) | 93 | DTIADQEANR HGRSGKDPNY YRPPGLPDKY |
| Mouse SAA2 | (SEQ ID NO: 107) | 93 | DTMADQEANR HGRSGKDPNY YRPPGLPAKY |
| Mouse SAA3 | (SEQ ID NO: 108) | 93 | DSRADQFANE WGRSGKDPNH FRPAGLPKRY |
| Mouse SAA4 | (SEQ ID NO: 109) | 101 | TLQATQKAEE WGRSGKNPNH FRPEGLPEKF |

FIG. 8

```
MSAA1  (SEQ ID NO: 106)    1  mklltslvfc slllgvchgG FFSFVHEAFQ GAGDMWRAYT DMKEANWKNS
MAA1   (SEQ ID NO: 110)    1  ---------- ---------G FFSFVHEAFQ GAGDMWRAYT DMKEANWKNS MSAA1  (SEQ ID NO: 106)   51  DKYFHARGNY DAAQRGPGGV WAAEKISDGR EAFQEFFGRG HEDTiadqea
MAA1   (SEQ ID NO: 110)   32  DKYFHARGNY DAAQRGPGGV WAAEKISDGR EAFQEFFGRG HEDT------

MSAA1  (SEQ ID NO: 106)  101  nrhgrsgkdp nyyrppglpd ky
MAA1   (SEQ ID NO: 110)       ---------- ---------- --
```

FIG. 9

```
MSAA2  (SEQ ID NO: 107)    1  mklltslvfc slllgvchgG FFSFIGEAFQ GAGDMWRAYT DMKEAGWKDG
MAA2   (SEQ ID NO: 111)    1  ---------- ---------G FFSFIGEAFQ GAGDMWRAYT DMKEAGWKDG MSAA2  (SEQ ID NO: 107)   51  DKYFHARGNY DAAQRGPGGV WAAEKISDAR ESFQEFFGRG HEDTmadqea
MAA2   (SEQ ID NO: 111)   32  DKYFHARGNY DAAQRGPGGV WAAEKISDAR ESFQEFFGRG HEDT------

MSAA2  (SEQ ID NO: 107)  101  nrhgrsgkdp nyyrppglpa ky
MAA2   (SEQ ID NO: 111)       ---------- ---------- --
```

FIG. 10

```
MSAA3 (SEQ ID NO: 108)    1  mkpsiaiilc ililgvdsqr wvqfmkEAGQ GSRDMWRAYS DMKKANWKNS
MAA3  (SEQ ID NO: 112)    1  ---------- ---------- ------EAGQ GSRDMWRAYS DMKKANWKNS MSAA3 (SEQ ID NO: 108)   51  DKYFHARGNY DAARRGPGGA WAAKVISDAR EAVQKFTGHG AEDSradqfa
MAA3  (SEQ ID NO: 112)   25  DKYFHARGNY DAARRGPGGA WAAKVISDAR EAVQKFTGHG AEDS------

MSAA3 (SEQ ID NO: 108)  101  newgrsgkdp nhfrpaglpk ry
MAA3  (SEQ ID NO: 112)       ---------- ---------- --
```

FIG. 11

```
MSAA4 (SEQ ID NO: 109)   1  mrlatvivlc slflgvsgdg WYSFFREAVQ GTWDLWRAYR DNLEANYQNA
MAA4  (SEQ ID NO: 113)   1  ---------- ---------- WYSFFREAVQ GTWDLWRAYR DNLEANYQNA MSAA4 (SEQ ID NO: 109)  51  DQYFYARGNY EAQQRGSGGI WAAKIISTSR KYFQGLLNRY YFGIRNHGLE
MAA4  (SEQ ID NO: 113)  31  DQYFYARGNY EAQQRGSGGI WAAKIISTSR KYFQGLLNRY YFGIRNHGLE MSAA4 (SEQ ID NO: 109) 101  TLqatqkaee wgrsgknpnh frpeglpekf
MAA4  (SEQ ID NO: 113)  81  TL-------- ---------- ----------
```

FIG. 12

```
MAA1 (SEQ ID NO: 110)  1  GFFSFVHEAF QGAGDMWRAY TDMKEANWKN SDKYFHARGN YDAAQRGPGG
MAA2 (SEQ ID NO: 111)  1  GFFSFIGEAF QGAGDMWRAY TDMKEAGWKD GDKYFHARGN YDAAQRGPGG
MAA3 (SEQ ID NO: 112)  1  ------EAG QGSRDMWRAY SDMKKANWKN SDKYFHARGN YDAARRGPGG
MAA4 (SEQ ID NO: 113)  1  -WYSFFREAV QGTWDLWRAY RDNLEANYQN ADQYFYARGN YEAQQRGSGG

MAA1 (SEQ ID NO: 110) 51  VWAAEKISDG REAFQE---- -FFG---RGH EDT
MAA2 (SEQ ID NO: 111) 51  VWAAEKISDA RESFQE---- -FFG---RGH EDT
MAA3 (SEQ ID NO: 112) 44  AWAAKVISDA REAVQK---- -FTG---HGA EDS
MAA4 (SEQ ID NO: 113) 50  IWAAKIISTS RKYFQgllnr yYFGirnHGL ETL
```

FIG. 13

| | | | |
|---|---|---|---|
| MAA1 | (SEQ ID NO: 110) | 69 | GRGHEDT |
| MAA2 | (SEQ ID NO: 111) | 69 | GRGHEDT |
| MAA3 | (SEQ ID NO: 112) | 62 | GHGAEDS |
| MAA4 | (SEQ ID NO: 113) | 76 | nHGLETL |

FIG. 14

HSAA1 (SEQ ID NO: 98)    1  MKLLTGLVFC SLVLGVSSRS FFSFLGEAFD GARDMWRAYS DMREANYIGS
MSAA1 (SEQ ID NO: 106)   1  MKLLTSLVFC SLLLGVCHGG FFSFVHEAFQ GAGDMWRAYT DMKEANWKNS

HSAA1 (SEQ ID NO: 98)   51  DKYFHARGNY DAAKRGPGGV WAAEAISDAR eniQRFFGHG AEDSLADQAA
MSAA1 (SEQ ID NO: 106)  51  DKYFHARGNY DAAQRGPGGV WAAEKISDGR eafQEFFGRG HEDTIADQEA HSAA1 (SEQ ID NO: 98)  101  NEWGRSGKDP NHFRPAGLPE KY
MSAA1 (SEQ ID NO: 106) 101  NRHGRSGKDP NYYRPPGLPD KY

FIG. 15

HAA1 (SEQ ID NO: 102)   1  rsFFSFLGEA FDGARDMWRA YSDMREANYi gSDKYFHARG NYDAAKRGPG
MAA1 (SEQ ID NO: 110)   1  g-FFSFVHEA FQGAGDMWRA YTDMKEANWk nSDKYFHARG NYDAAQRGPG

HAA1 (SEQ ID NO: 102)  51  GVWAAEAISD AREniQRFFG HGAEDS
MAA1 (SEQ ID NO: 110)  50  GVWAAEKISD GREafQEFFG RGHEDT

FIG. 16

HAA1 (SEQ ID NO: 102)  1  GHGAEDS
MAA1 (SEQ ID NO: 110)  1  GRGHEDT

FIG. 17

| | | | | | |
|---|---|---|---|---|---|
| HSAA1alpha (SEQ ID NO: 114) | 1 | mKLLTGLVFC | SLVLGVSSRS | FFSFLGEAFD | GARDMWRAYS | DMREANYIGS |
| HSAA1beta (SEQ ID NO: 115) | 1 | mKLLTGLVFC | SLVLGVSSRS | FFSFLGEAFD | GARDMWRAYS | DMREANYIGS |
| HSAA1gamma (SEQ ID NO: 116) | 1 | mKLLTGLVFC | SLVLGVSSRS | FFSFLGEAFD | GARDMWRAYS | DMREANYIGS |
| HSAA1alpha (SEQ ID NO: 114) | 51 | DKYFHARGNY | DAAKRGPGGV | WAAEAISDAR | ENIQRFFGHG | AEDSLADQAA |
| HSAA1beta (SEQ ID NO: 115) | 51 | DKYFHARGNY | DAAKRGPGGA | WAAEVISDAR | ENIQRFFGHD | AEDSLADQAA |
| HSAA1gamma (SEQ ID NO: 116) | 51 | DKYFHARGNY | DAAKRGPGGV | WAAEAISDAR | ENIQRFFGHD | AEDSLADQAA |
| HSAA1alpha (SEQ ID NO: 114) | 101 | NEWGRSGKDP | NHFRPAGLPE | KY | | |
| HSAA1beta (SEQ ID NO: 115) | 101 | NEWGRSGKDP | NHFRPAGLPE | KY | | |
| HSAA1gamma (SEQ ID NO: 116) | 101 | NEWGRSGKDP | NHFRPAGLPE | KY | | |

FIG. 18

```
HSAA2alpha  (SEQ ID NO: 114)    1   mKLLTGLVFC SLVLSVSSRS FFSFLGEAFD GARDMWRAYS DmREANYIGS
HSAA2beta   (SEQ ID NO: 115)    1   mKLLTGLVFC SLVLSVSSRS FFSFLGEAFD GARDMWRAYS DmREANYIGS HSAA2alpha  (SEQ ID NO: 114)   51   DKYFHARGNY DAAKRGPGGA WAAEVISNAR ENIQRLTGHG AEDSLADQAA
HSAA2beta   (SEQ ID NO: 115)   51   DKYFHARGNY DAAKRGPGGA WAAEVISNAR ENIQRLTGRG AEDSLADQAA HSAA2alpha  (SEQ ID NO: 114)  101   NKWGRSGRDP NHFRPAGLPE KY
HSAA2beta   (SEQ ID NO: 115)  101   NKWGRSGRDP NHFRPAGLPE KY
```

FIG. 19

```
                                  10                    20                30              40
Human    (SEQ ID NO: 119):RSFFSFLGEA          FDGARDMWRA        YSDMREANYI      GSDKYFHARG
Mouse    (SEQ ID NO: 120):G FFSFIGEA          FQGAGDMWRA        YTDMKEAGWK      DGDKYFHARG
Shar Pei (SEQ ID NO: 121):E WYSFVGEA          AQGAWDMLRA        YSDMREANYK      NSDKYFHARG 50                    60                70              80
Human    (SEQ ID NO: 119): NYDAAKRGPG         GVWAAEAISD        ARENIQRFFG      HGAEDSLADQ
Mouse    (SEQ ID NO: 120): NYDAAQRGPG         GVWAAEKISD        ARESFQEFFG      RGHEDTMADQ
Shar Pei (SEQ ID NO: 121): NYDAAQRGPG         GAWAAKVISD        ARENSQRDSG      HGAEDSKADQ ITDLLRFG
                                   90                  100       104
Human    (SEQ ID NO: 119): AANEWGRSGK         DPNHFRPAGL        PEKY
Mouse    (SEQ ID NO: 120): EANRHGRSGK         DPNYYRPPGL        PAKY
Shar Pei (SEQ ID NO: 121): AANEWG
```

FIG. 20

```
                    0          1          2          2        3      3          4       4    5
                    1          1          1        abc def    0      5          0       5    4
kp1a (SEQ ID NO:123) DIQMTQSPST LSASVGDRVT ITCRASQSI* *****SSWLA WYQQKPGKAP KLLIYKASSL
kp1b (SEQ ID NO:124) .........S .......... ....Q..D.. ......NY.N .......... ....D.N...
kp1c (SEQ ID NO:125) .........S .......... .......... ......Y.N. .......... ....A.....
kp1d (SEQ ID NO:126) .........S .......... .........G ......RND.G .......... ....R.A...
kp1e (SEQ ID NO:127) A..L......S .......... .........G ......NY... .......F.. .....S.A..
kp1f (SEQ ID NO:128) .........S .......... .........G ........A. .......... .......D..
kp1g (SEQ ID NO:129) .........S V......... .......... .......... .......... .......A..
kp2a (SEQ ID NO:130) ......V... .T.LS.PVTP.EPAS .S..S...LL DSDDGNTY.D ....L...QS. Q....TL.YR
kp2b (SEQ ID NO:131) ......V... .....LS.PVTP.EPAS .S..S...LL HS.NGYNY.D ....L...QS. Q....LG.NR
kp2c (SEQ ID NO:132) ......V... .T.LS.VTP.QPAS .S.KS...LL HS.DGKTY.Y ....L...QP. Q....EV.NR
kp3a (SEQ ID NO:133) E.V....... .A..V.P.E.A. LS........ .......N.. .......... Q....R..G.TR
kp3b (SEQ ID NO:134) E.VL....G. .....L.P.E.A. LS.....VS ......Y... .......... Q....R..G...R
kp3c (SEQ ID NO:135) E.VL....A. .....L.P.E.A. LS.....VS ......Y... .......... Q....R..D..NR
kp4  (SEQ ID NO:136) ......V...DS .AV.L.E.A. .N.KS...VL YSSNNKNY.. .......QP. Q......W..TR
kp5  (SEQ ID NO:137) ETTL....AF M..TP..K.N .S.K....D. .....DDDMN ........E.A IFI.QE.TT.

5          6          7          8        9
                       5         5  ab        3          3        3
kp1a (SEQ ID NO:123) ESGVPSRFSG SGSGTEFT LTISSLQPDD FATYCQQYN SYS***
kp1b (SEQ ID NO:124) .T........ .........D F.......E. I.......D NLP.....
kp1c (SEQ ID NO:125) Q......... .......... ........E. .....SY. .TP.....
kp1d (SEQ ID NO:126) Q......... .........D ........E. ........SY ..P.....
kp1e (SEQ ID NO:127) Q......... .......... ........E. ......L.H. ..P.....
kp1f (SEQ ID NO:128) Q......... .......... ........E. .........F. ..N.P...
kp1g (SEQ ID NO:129) Q......... .......... ........E. .........A. .FP.....
kp2a (SEQ ID NO:130) A......D.. .......... .K.RVEAE.. VGV..M.RI EFP.....
kp2b (SEQ ID NO:131) A......D.. .......... .K.RVEAE.. VGV..M.AL QTP.....
kp2c (SEQ ID NO:132) F......D.. .......... .K.RVEAE.. VGV..M.SI QLP.....
kp3a (SEQ ID NO:133) AT.I.A.... .......... .......SE. .V....... NWP.....
kp3b (SEQ ID NO:134) AT.I.D.... .......... .R.E.E.... .V....... G..SP...
kp3c (SEQ ID NO:135) AT.I.A.... .......... .E.E..... .V....... RS NWP....
kp4  (SEQ ID NO:136) .......D.. .......... ....AE.... V.V...Y .TP.....
kp5  (SEQ ID NO:137) VP.I.P.... .......Y.D NNIESE.... A.Y.F.L.HD NFP.....
```

FIG. 21

```
                 0         1           2                3            4       5
                 1         1  abc      1  abc def       0            5       4
          QSVLTQPPS* VSAAPGQKVT ISCSGSSSNI G****NNYVS WYQQLPGTAP KLLIYENNKR
lm1a (SEQ ID NO:138) QSVLTQPPS* VSAAPGQKVT ISCSGSSSNI G****NNYVS WYQQLPGTAP KLLIYENNKR
lm1b (SEQ ID NO:139) .........  A.GT...R..  ..........  ....S..Y.  ..........  .....R..Q.
lm1c (SEQ ID NO:140) ...V.....  ...G....R.  .......T..  ...A..GYD.H  ..........  ......G.SN
lm2a (SEQ ID NO:141) ..A....A.  ..GS....SI  ...T.T.DV  .S...Y.L..  ....H..K..  ...M...GS.
lm2b (SEQ ID NO:142) ..A.....R.  ..GS....VI  ...T.T.DV  .G....Y...  ....H..K..  ...M.DVS..
lm3a (SEQ ID NO:143) SY........  ..V...KTAR  .T.G.NNIG*  .....SKS.H  ....K..Q..  .V.VV.DDSD
lm3b (SEQ ID NO:144) SYE.......  ..VS...TAR  .T....DALP*  .....KQ.AY  ....K..Q..  .V.V..KDSE
lm3c (SEQ ID NO:145) SYE.......  ..VS...TAS  .T....DKLG*  .....DK.AC  ....K..QS.  .V.V..QDS.
lm4  (SEQ ID NO:146) S.E....D.A  ..V.L.T.R  .T.Q.D.LR*  .....SY.A.  ....K..Q..  .V.V..GK.N
lm6  (SEQ ID NO:147) NFM......H  ...ES...KT  ....TR..GS.  .....S...Q  ....R..SS.  .TTV...D.Q.
lm7  (SEQ ID NO:148) .T.V...E..  .LTVS..GT.  .LT.AS.TGAV  TS...GY.PN  .F..K..Q..  .RA...STSNK
lm8  (SEQ ID NO:149) ..L......S  .A..SL.AS.K  .LT.TL..G**  *..HSSYAIA  .H..Q.EKG.  .RY.MKL.SDG 5         6             7           8           9
                 5         5  ab         3           3           3
          PSGIPDRFSG SKSGTSAT LGITGLQTGD EADYYCGTWD SSLSA
lm1a (SEQ ID NO:138) PSGIPDRFSG SKSGTSAT LGITGLQTGD EADYYCGTWD SSLSA
lm1b (SEQ ID NO:139) ...V......  .........S  .A.S.RSE..  ..AA......  .D...G.
lm1c (SEQ ID NO:140) ...V......  .........S  ...A....AE  ......QSY.  .....G.
lm2a (SEQ ID NO:141) .VSN......  .......NT.S  .T.S...AE  ....CSYA.G.STL...
lm2b (SEQ ID NO:142) ...V......  .......NT.S  .T.S...AE  ....CSYA.G.YTF...
lm3a (SEQ ID NO:143) .......E..  ..N....NT..  .T-SRVEA..  ......QV..  ..SDH..
lm3b (SEQ ID NO:144) .......E..  ..S.....TV  .T.S.V.AE.  ......QSA.  ..G**..
lm3c (SEQ ID NO:145) .......E..  ..N....NT..  .T.S.T.AM.  ......QA..  ..TAH..
lm4  (SEQ ID NO:146) ..........  ..S....NT.S  .T...A.AE.  ......NSR.  ..GNH..
lm6  (SEQ ID NO:147) ...V......  .IDS.SN..S  .T.S.K.E..  ......QSY.  ..N**..
lm7  (SEQ ID NO:148) .H.WT.A...  .L.L.GK.A  .TLS.V.PE.  .E...LLYY.GGAQ*.
lm8  (SEQ ID NO:149) GD........  .S....AERY  .T..SS..SE.  .....Q..G.TGI**.
```

FIG. 22

```
1              10          21          31          35
NFLLTQPHS  VSESPGKTVT  ISCTRSSGSI  A****NNYVH  WYQQRPGSSP 45        55          65AB        73          82
TTVIFEDDHR  PSGVPDRFSG  SVDTSSNSAS  LTISGLKTED  EADYYCQSYD

93
HNN
```

Vλ6 Wil (SEQ ID NO: 150)

FIG. 23

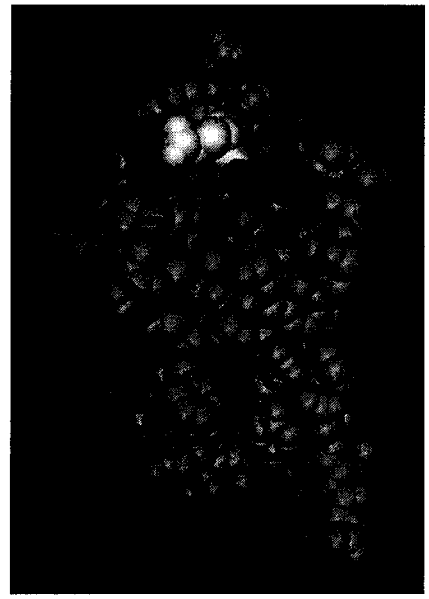
$V_\lambda 6$ Wil Glu81
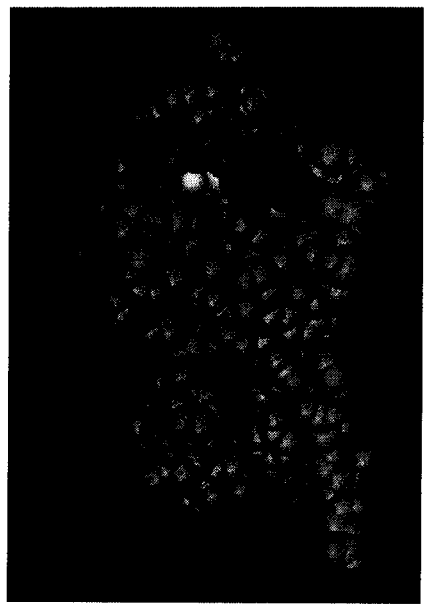
$V_\lambda 6$ Wil Asp82
FIG. 25

Murine VL(2A4 and 8G9)
MKLPVRLLVLMFWIPASSSDVVMTQTPLSLPVSLGDQASISCRSSQSLVHSTGNTYLHWYLQKPGQSPKLLIYKVSNRFSGVPDRFSGS
GSGTYFTLKISRVEAEDLGVYFCSQSTHVPFTFGGGTKLEIK (SEQ ID NO: 152)

Murine VL(7D8)
MKLPVRLLVLMFWIPASSSDVVMTQTPLSLPVSLGDQASISCRSSLSLVHSTGNTYLHWYLQKPGQSPKLLIYKVSNRFSGVPDRFSGS
GSGTYFTLKISRVEAEDLGVYFCSQSTHVPFTFGGGTKLEIK (SEQ ID NO: 153)

Murine VH (2A4, 7D8, 8G9)
MVLGLKWVFFVVFYQGVHCEVQLVESGGRLVQPKGSLKLSCAASGFTNTYAMYWIRQAPGKGLEWVARIRSKSNNYAIYYADSVK
DRFTIFRDDSQSMLYLQMNNLKTEDTAMYYCVRPYSDSFAYWGQGTLVTVSA (SEQ ID NO: 154)

FIG. 36A

Hum2A4 VL Version 1
DVVMTQSPLSLPVTPGEPASISCRSSQSLVHSTGNTYLHWYLQKPGQSPQLLIYKVSNRFSGVPDRFSGSGSGTyFTLKISRVEAEDVGV
YfCSQSTHVPFTFGGGTKVEIK (SEQ ID NO: 155)

Hum2A4 VL Version 2
DVVMTQSPLSLPVTPGEPASISCRSSQSLVHSTGNTYLHWYLQKPGQSPQLLIYKVSNRFSGVPDRFSGSGSGTDFTLKISRVEAEDVGV
YfCSQSTHVPFTFGGGTKVEIK (SEQ ID NO: 156)

Hum2A4 VL Version 3
DVVMTQSPLSLPVTPGEPASISCRSSQSLVHSTGNTYLHWYLQKPGQSPQLLIYKVSNRFSGVPDRFSGSGSGTDFTLKISRVEAEDVGV
YYCSQSTHVPFTFGGGTKVEIK (SEQ ID NO: 157)

FIG. 36B

Hum7D8 VL Version 1
DVVMTQSPLSLPVTPGEPASISCRSSLSLVHSTGNTYLHWYLQKPGQSPQLLIYKVSNRFSGVPDRFSGSGSGTyFTLKISRVEAEDVGV
YfCSQSTHVPFTFGQGTKLEIK (SEQ ID NO: 158)

Hum7D8 VL Version 2
DVVMTQSPLSLPVTPGEPASISCRSSLSLVHSTGNTYLHWYLQKPGQSPQLLIYKVSNRFSGVPDRFSGSGSGTDFTLKISRVEAEDVGV
YfCSQSTHVPFTFGQGTKLEIK (SEQ ID NO: 159)

Hum7D8 VL Version 3
DVVMTQSPLSLPVTPGEPASISCRSSLSLVHSTGNTYLHWYLQKPGQSPQLLIYKVSNRFSGVPDRFSGSGSGTDFTLKISRVEAEDVGV
YYCSQSTHVPFTFGQGTKLEIK (SEQ ID NO: 160)

Hum7D8 VL Version 4
DVVMTQSPLSLPVTPGEPASISCRSSLSLVHSTGNTYLHWYLQKPGQSPQLLIYKVSNRFSGVPDRFSGSGSGTyFTLKISRVEAEDVGV
YfCSQSTHVPFTFGGGTKLEIK (SEQ ID NO: 174)

Hum7D8 VL Version 5
DVVMTQSPLSLPVTPGEPASISCRSSLSLVHSTGNTYLHWYLQKPGQSPQLLIYKVSNRFSGVPDRFSGSGSGTDFTLKISRVEAEDVGV
YfCSQSTHVPFTFGGGTKLEIK (SEQ ID NO: 175)

Hum7D8 VL Version 6
DVVMTQSPLSLPVTPGEPASISCRSSLSLVHSTGNTYLHWYLQKPGQSPQLLIYKVSNRFSGVPDRFSGSGSGTDFTLKISRVEAEDVGV
YYCSQSTHVPFTFGGGTKLEIK (SEQ ID NO: 176)

FIG. 36C

Framework VL Gen Bank Accession No. BAC01562
DVVMTQSPLSLPVTPGEPASISCRSSQSLLHSNGYNYLDWYLQKPGQSPQLLIYLGSNRASGVPDRFSGSGSGTDFTLKISRVEAEDVGV
YYCMQALQTPLTFGGGTKVEIKR (SEQ ID NO: 166)

Framework VL Gen Bank Accession No. BAC01733
MKYLLPTAAAGLLLLAAQPAMADVVMTQSPLSLPVTPGEPASISCRSSQSLLHSNGYNYLDWYLQKPGQSPQLLIYLGSNRASGVPDR
FSGSGSGTDFTLKISRVEAEDVGVYYCMQALQTPYTFGQGTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTKSFNRGECSARQSTPFVCEYQGQSSDLPQPPVN
AGGGSGGGSG (SEQ ID NO: 167)

FIG. 36D

Hum2A4/7D8/8G9 VH Version 1
EVQLVESGGGLVQPGGSLRLSCAASGFTFNTYAMYWiRQAPGKGLEWVaRIRSKSNNYAIYYADSVKDRFTIfRDDSKNSLYLQMNSL
KTEDTAVYYCvRPYSDSFAYWGQGTLVTVSS (SEQ ID NO: 161)

Hum2A4/7D8/8G9 VH Version 2
EVQLVESGGGLVQPGGSLRLSCAASGFTFNTYAMYWiRQAPGKGLEWVaRIRSKSNNYAIYYADSVKDRFTISRDDSKNSLYLQMNSL
KTEDTAVYYCvRPYSDSFAYWGQGTLVTVSS (SEQ ID NO: 162)

Hum2A4/7D8/8G9 VH Version 3
EVQLVESGGGLVQPGGSLRLSCAASGFTFNTYAMYWiRQAPGKGLEWVaRIRSKSNNYAIYYADSVKDRFTISRDDSKNSLYLQMNSL
KTEDTAVYYCARPYSDSFAYWGQGTLVTVSS (SEQ ID NO: 163)

2A4_8G9_7D8 H_chain_pro (murine 2A4 VH)
EVQLVESGGRLVQPKGSLKLSCAASGFTFNTYAMYWIRQAPGKGLEWVARIRSKSNNYAIYYADSVKDRFTIFRDDSQSMLYLQMNN
LKTEDTAMYYCVRPYSDSFAYWGQGTLVTVSA (SEQ ID NO: 164)

Framework VH Gen Bank Accession No. AAC51024
EVQLVESGGGLVQPGGSLRLSCAASGFTFSDHYMDWVRQAPGKGLEWVGRTRNKANSYTTEYAASVKGRFTISRDDSKNSLYLQMN
SLKTEDTAVYYCARYVVGATLDYWGQGTLVTVSS (SEQ ID NO: 165)

FIG. 36E

DETECTION OF AMYLOID DEPOSITS USING ANTI-AMYLOID ANTIBODIES

CROSS-REFERENCES TO RELATED APPLICATIONS

This is a continuation of U.S. Application No. 13/032,412, filed Feb. 22, 2011, which is a continuation of U.S. application Ser. No. 12/345,650, filed Dec. 29, 2008, which issued as U.S. Pat. No. 7,928,203 on Apr. 19, 2011, and which claims priority to U.S. Provisional Application No. 61/095,932, filed Sep. 10, 2008, and to U.S. Provisional Application No. 61/007,544, filed Dec. 28, 2007, each of which is incorporated herein by reference in its entirety.

TECHNICAL FIELD

The invention resides in the technical fields of immunology and medicine.

BACKGROUND OF THE INVENTION

Amyloidosis is a general term that describes a number of diseases characterized by the existence of pathological forms of amyloid proteins, often involving extracellular deposition of protein fibrils, which form numerous "amyloid deposits" or "amyloid plaques," which may occur in local sites or systematically. These deposits or plaques are composed primarily of a naturally occurring soluble protein or peptide, assembled into extensive insoluble deposits 10-100 μm in diameter in a variety of tissue sites. The deposits are composed of generally lateral aggregates of fibrils that are approximately 10-15 nm in diameter. Amyloid fibrils produce a characteristic apple green birefringence in polarized light, when stained with Congo Red dye. Generally, the fibrillar composition of these deposits is an identifying characteristic for the various forms of amyloid disease.

The peptides or proteins forming the plaque deposits are often produced from a larger precursor protein. More specifically, the pathogenesis of amyloid aggregates such as fibril deposits generally involves proteolytic cleavage of an "abnormal" precursor protein into fragments that aggregate into anti-parallel β pleated sheets.

The fibrillar composition of these deposits is an identifying characteristic for the various forms of amyloid disease. For example, intracerebral and cerebrovascular deposits composed primarily of fibrils of beta amyloid peptide (β-AP) are characteristic of Alzheimer's disease (both familial and sporadic forms), islet amyloid protein peptide (IAPP; amylin) is characteristic of the fibrils in pancreatic islet cell amyloid deposits associated with type II diabetes, and β2-microglobulin is a major component of amyloid deposits which form as a consequence of long term hemodialysis treatment. More recently, prion-associated diseases, such as Creutzfeld-Jacob disease, have also been recognized as amyloid diseases.

In general, primary amyloidoses of the disease are characterized by the presence of "amyloid light chain-type" (AL-type) protein fibrils, so named for the homology of the N-terminal region of the AL fibrils to the variable fragment of immunoglobulin light chain (kappa or lambda).

The various forms of disease have been divided into classes, mostly on the basis of whether the amyloidosis is associated with an underlying systematic illness. Thus, certain disorders are considered to be primary amyloidoses, in which there is no evidence for preexisting or coexisting disease. In secondary or reactive (AA type) amyloidosis characterized by the presence deposition of amyloid protein A (AA) fibrils, there is an underlying or associated chronic inflammatory or infectious disease state.

Heredofamilial amyloidoses may have associated neuropathic, renal, or cardiovascular deposits of the ATTR transthyretin type. Other heredofamilial amyloidoses include other syndromes and may have different amyloid components (e.g., familial Mediterranean fever which is characterized by AA fibrils). Other forms of amyloidosis include local forms, characterized by focal, often tumor-like deposits that occur in isolated organs. Other amyloidoses are associated with aging, and are commonly characterized by plaque formation in the heart or brain. Also common are amyloid deposits associated with long term hemodialysis. These and other forms of amyloid disease are summarized in Table 1 (Tan, S. Y. and Pepys, Histopathology 25:403-414, 1994; Harrison's Handbook of Internal Medicine, 13th Ed., Isselbacher, K. J., et al, eds, McGraw-Hill, San Francisco, 1995) and are described in U.S. Pat. Nos. 6,875,434, 6,890,535, 6,913,745, 6,923,964, and 6,936,246, which are incorporated by reference herein in their entirety.

TABLE 1

Classification of Amyloid Diseases

| Amyloid Protein/Peptide | Protein Precursor | Protein Variants | Clinical |
| --- | --- | --- | --- |
| AA | Serum Amyloid A Protein (ApoSSA) | | Reactive (secondary) Amyloidosis: Familial Mediterranean fever Familial amyloid nephropathy with urticaria and deafness (Muckle-Wells syndrome) |
| AA | Serum amyloid A protein (ApoSSA) | | Reactive systemic amyloidosis associated with systemic inflammatory diseases |
| AL | Monoclonal immunoglobulin light chains (kappa, lambda) | Ak, A, (e.g., AkIII) | Idiopathic (primary) Amyloidosis: myeloma or macroglobulinemia-associated; systemic amyloidosis associated with immunocyte dyscrasia; monoclonal gammopathy; occult dyscrasia; local nodular |

TABLE 1-continued

Classification of Amyloid Diseases

| Amyloid Protein/ Peptide | Protein Precursor | Protein Variants | Clinical |
|---|---|---|---|
| | | | amyloidosis associated with chronic inflammatory diseases |
| AH | IgG (1(γ1)) | Aγ1 | Heavy chain amyloidosis associated with several immunocyte dyscrasias |
| ATTR | Transthyretin (TTR) | At least 30 known point mutations | Familial amyloid polyneuropathy (e.g., Met 30, Portuguese) |
| ATTR | Transthyretin (TTR) | e.g., Met 111 | Familial amyloid cardiomyopathy (Danish) |
| ATTR | Transthyretin (TTR) | Wild-type TTR or Ile 122 | Systemic senile amyloidosis |
| AapoAI | ApoAI | Arg 26 | Familial amyloid polyneuropathy |
| Agel | Gelsolin | Asn 187 | Familial amyloidosis (Finnish) |
| Acys | Cystatin C | Gln 68 | Hereditary cerebral hemorrhage with amyloidosis (Icelandic) |
| Aβ | Amyloid β protein precursor (e.g. β-APP$_{695}$) | Various: Gln 618, | Alzheimer's disease Down's syndrome Hereditary cerebral hemorrhage amyloidosis (Dutch) Sporadic cerebral amyloid angiopathy Inclusion body myositis |
| AB$_2$M | Beta$_2$ microglobulin | | Associated with chronic hemodialysis |
| Acal | (Pro)calcitonin | (Pro)calcitonin | Medullary carcinoma of thyroid |
| | | | Focal Senile Amyloidoses: |
| AANF | Atrial natriuretic factor | | Isolated atrial amyloid |
| Aβ | β-amyloid precursor protein | | Brain |
| SVEP[a] | — | | Seminal vesicles |
| AB$_2$M | Beta$_2$ microglobulin | | Prostate |
| | Keratin | | Primary localized cutaneous amyloid (macular, papular) |
| PrP | Prion precursor protein (33-35 kDa cellular form) | Scrapie protein 27-30 kDa | Sporadic Creutzfeldt-Jacob Disease Kuru (transmissible spongiform encephalopathies, prion diseases) |
| AIAPP | Islet amyloid Polypeptide (IAPP) | | Islets of Langerhans Diabetes type II, Insulinoma |
| Peptide hormones, fragments | e.g., precalcitonin | | Exocrine amyloidosis, associated with APUDomas |

[a]Seminal vesicle exocrine protein

Often, fibrils forming the bulk of an amyloid deposit are derived from one or more primary precursor proteins or peptides, and are usually associated with sulfated glycosaminoglycans. In addition, amyloid deposits may include minor proteins and peptides of various types, along with other components, such as proteoglycans, gangliosides and other sugars, as described in more detail in the sections that follow.

AA fibrils are composed of peptide fragments that range in size but are generally about 8000 daltons (AA peptide or protein) formed by proteolytic cleavage of serum amyloid A protein (SSA), a circulating apolipoprotein which is present in HDL particles and which is synthesized in hepatocytes in response to such cytokines as interleukin (IL)-1 and IL-6, as well as tumor necrosis factor α. See Husby, G. et al. *Amyloid* 1, 119-137 (1994). The proteolytic cleavage results in the pathologic deposition of an ~76-residue N-terminal two thirds of the SAA protein. In humans, the plasma concentration of SAA normally is ~0.1 mg/ml but can increase over 1,000-fold in response to an inflammatory stimulus. As part of this process, the SAA molecule undergoes proteolysis and the N-terminal cleavage product is deposited systemically as AA fibrils in vital organs, including the liver, spleen, kidneys, and adrenal glands. Deposition is also common in the heart and gastrointestinal tract.

Generally, AA amyloidosis is a manifestation of diseases that provoke a sustained acute phase response. Such diseases include chronic inflammatory disorders, chronic local or systemic microbial infections, and malignant neoplasms. AA amyloid diseases include, but are not limited to inflammatory diseases, such as rheumatoid arthritis, juvenile chronic arthritis, ankylosing spondylitis, psoriasis, psoriatic arthropathy, Reiter's syndrome, Adult Still's disease, Behcet's syndrome, and Crohn's disease. AA deposits are also produced as a result of chronic microbial infections, such as leprosy, tuberculosis, bronchiectasis, decubitus ulcers, chronic pyelonephritis, osteomyelitis, and Whipple's disease. Certain malignant neoplasms can also result in AA fibril amyloid deposits. These include such conditions such as Hodgkin's lymphoma, renal carcinoma, carcinomas of gut, lung and urogenital tract, basal cell carcinoma, and hairy cell leukemia. AA amyloid disease may also result from inherited inflammatory diseases such as Familial Mediterranean Fever. Additionally, AA amyloid disease may result from lymphoproliferative disorders such as Castleman's Disease.

AA Amyloidosis is insidious and progressive. Symptoms are generally presented in later stages of the disease. Frequently the patient is undiagnosed until significant organ damage has occurred. AA fibrils are deposited in vital organs leading to organ dysfunction and subsequently to death. The five year survival rate is 45-50%. Median survival after diagnosis is 4-8 years. End stage Renal Disease is the cause of death in 40-60% of cases. See Gillmore J. D. et al., *Lancet* 358:24-9 (2001).

Currently, there are no approved specific, amyloid-directed treatments for any of the amyloid diseases, including AA Amyloidosis. See Gillmore J. D. et al., *Lancet* 358:24-9 (2001). Where there is an underlying or associated disease state, therapy directed towards decreasing the production of amyloidogenic protein by treating the underlying disease. For example, current treatment strategy for AA Amyloidosis is to target underlying inflammation, reducing ApoSSA levels to below 10 mg/l. Currently employed therapies include chemotherapy (cholorambucil and MTX), immuno-suppressants (azathioprine), anti-inflammatory drugs (colchicine) and TNF inhibitors. The invention thus fulfills a longstanding need for therapeutic regimes for preventing or ameliorating the effects of AA Amyloidosis.

SUMMARY OF THE INVENTION

The present invention provides an isolated human, humanized, or chimeric antibody, or antigen-binding fragment thereof, that specifically binds to an epitope within residues 70-76 of human amyloid A peptide, for example, an epitope within residues 70-76 of SEQ ID NO: 2 or an epitope comprising residues set forth as SEQ ID NOs: 4, 5, 6, 7, 8, 9, 10, or 11. Antibodies or antigen-binding fragments of the invention include those that compete for binding to human amyloid A peptide with antibody 2A4 produced by ATCC Accession Number PTA-9662 or with antibody 7D8 produced by ATCC Accession Number PTA-9468. Additional antibodies of the invention compete for binding to human amyloid A peptide with an antibody having a light chain variable region set forth as residues 20-131 of SEQ ID NO: 152 or residues 20-131 of 153 and a heavy chain variable region set forth as residues 20-138 of SEQ ID NO: 154.

The disclosed antibodies include humanized and chimeric versions of antibody 2A4 produced by ATCC Accession Number PTA-9662 or a humanized or chimeric version of antibody 7D8 produced by ATCC Accession Number PTA-9468.

For example, representative antibodies and antigen-binding fragments comprise a light chain variable region comprising one or more complementarity regions of a 2A4 light chain variable region set forth as residues 20-131 of SEQ ID NO: 152 or one or more complementarity regions of a 7D8 light chain variable region set forth as residues 20-131 of SEQ ID NO: 153. As another example, representative antibodies and antigen-binding fragments comprise a light chain variable region comprising two complementarity regions of a 2A4 light chain variable region set forth as residues 20-131 of SEQ ID NO: 152 or two complementarity regions of a 7D8 light chain variable region set forth as residues 20-131 of SEQ ID NO: 153. Additional representative antibodies and antigen-binding fragments comprise a light chain variable region comprising three complementarity regions of a 2A4 light chain variable region set forth as residues 20-131 of SEQ ID NO: 152 or three complementarity regions of a 7D8 light chain variable region set forth as residues 20-131 of SEQ ID NO: 153. Representative humanized versions of a 2A4 or 7D8 antibody comprise at least one light chain framework residue selected from the group consisting of L87 and L90 (Kabat numbering convention), which is occupied by Y and F, respectively, and wherein the remainder of the light chain variable region is occupied by a corresponding residue in a human acceptor immunoglobulin light chain variable region. Representative antibodies and antigen-binding fragments comprise at least one light chain framework residue selected from the group consisting of +7, +14, +15, +17, +18, +50, +75, +88, +92, and +109 (linear numbering), which is occupied by T, S, L, D, Q, K, Y, L, F, and L, respectively, and wherein the remainder of the light chain variable region is occupied by a corresponding residue in a human acceptor immunoglobulin light chain variable region. For example, representative antibodies and antigen-binding fragments comprise at least one light chain framework residue selected from the group consisting of +75 and +92 (linear numbering), which is occupied by Y and F, respectively, and wherein the remainder of the light chain variable region is occupied by a corresponding residue in a human acceptor immunoglobulin light chain variable region. In other representative antibodies and antigen-binding fragments of the invention, the light chain variable region comprises a framework residue at +105 (linear numbering) occupied by Q.

For example, antibodies and antigen-binding fragments of the invention include those comprising a light chain variable region comprising a framework residue at +7 (linear numbering) occupied by T, wherein the remainder of the light chain variable region is occupied by a corresponding residue in a human acceptor immunoglobulin light chain variable region; antibodies and antigen-binding fragments a light chain variable region comprising a framework residue at +14 (linear numbering) occupied by S, wherein the remainder of the light chain variable region is occupied by a corresponding residue in a human acceptor immunoglobulin light chain variable region; antibodies and antigen-binding fragments a light chain variable region comprising a framework residue at +15 (linear numbering) occupied by L, wherein the remainder of the light chain variable region is occupied by a corresponding residue in a human acceptor immunoglobulin light chain variable region; antibodies and antigen-binding fragments a light chain variable region comprising a framework residue at +17 (linear numbering) occupied by D, wherein the remainder of the light chain variable region is occupied by a corresponding residue in a human acceptor immunoglobulin light chain variable region; antibodies and antigen-binding fragments a light chain variable region comprising a framework residue at +18 (linear numbering) occupied by Q, wherein the remainder of the light chain variable region is occupied by a corresponding residue in a human acceptor immunoglobulin light chain variable region; antibodies and antigen-binding fragments a light chain variable region comprising a framework residue at +50 (linear numbering) occupied by K, wherein the remainder of the light chain variable region is occupied by a corresponding residue in a human acceptor immunoglobulin light chain variable region; antibodies and antigen-binding fragments a light chain variable region comprising a framework residue at +75 (linear numbering) occupied by Y, wherein the remainder of the light chain variable region is occupied by a corresponding residue in a human acceptor immunoglobulin light chain variable region; antibodies and antigen-binding fragments a light chain variable region comprising a framework residue at +88 (linear numbering) occupied by L, wherein the remainder of the light chain variable region is occupied by a corresponding residue in a human acceptor immunoglobulin light chain variable region; antibodies and antigen-binding fragments a light chain variable region comprising a framework residue at +92 (linear numbering) occupied by F, wherein the remainder of the light chain variable region is occupied by a corresponding residue in a human acceptor immunoglobulin light chain variable region; antibodies and antigen-binding fragments a light chain variable region comprising a framework residue at +109 (linear numbering) occupied by L, wherein the remainder of the light chain variable region is occupied by a corresponding residue in a human acceptor immunoglobulin light chain variable region; and antibodies and antigen-binding fragments a light chain variable region comprising a framework residue at +105 (linear numbering) occupied by Q, wherein the remainder of the light chain variable region is occupied by a corresponding residue in a human acceptor immunoglobulin light chain variable region.

Human acceptor immunoglobulin light chain variable regions used in the invention include human kappa subgroup 2 light chain variable region (Kabat convention), for example, human subgroup 2 light chain variable region from human germline VKIIA19/A3, such as human Vk light chain variable region comprising a sequence set forth as SEQ ID NO: 166 or 167. In particular aspects of the invention, antibodies and antigen-binding fragments comprise a light chain variable region comprising an amino acid sequence set forth as residues 20-131 of SEQ ID NO: 152, residues 20-131 of SEQ ID NO: 153, or set forth as SEQ ID NO: 155, 156, 157, 158, 159, 160, 174, 175, or 176.

Representative antibodies and antigen-binding fragments of the invention also include those comprising a heavy chain variable region comprising one or more complementarity regions of a 2A4 heavy chain variable region set forth as residues 20-138 of SEQ ID NO: 154, for example, a heavy chain variable region comprising two complementarity regions of a 2A4 heavy chain variable region set forth as residues 20-138 of SEQ ID NO: 154, or a heavy chain variable region comprising three complementarity regions of a 2A4 heavy chain variable region set forth as residues 20-138 of SEQ ID NO: 154. Representative humanized 2A4 and 7D8 antibodies and antigen-binding fragments comprise at least one heavy chain framework residue selected from the group consisting of H37, H49, H70, and H93 (Kabat numbering convention), which is occupied by I, A, F, or V, respectively, and wherein the remainder of the heavy chain variable region is occupied by a corresponding residue in a human acceptor immunoglobulin heavy chain variable region. Representative humanized antibodies and antigen-binding fragments comprise at least one heavy chain framework residue selected from the group consisting of +10, +15, +19, +37, +49, +73, +78, +79, +80, +87, +95, +99, +119 (linear numbering), which is occupied by R, K, K, I, A, F, Q, S, M, N, M, V, or A, respectively, and wherein the remainder of the heavy chain variable region is occupied by a corresponding residue in a human acceptor immunoglobulin heavy chain variable region. For example, representative humanized antibodies and antigen-binding fragments comprise at least one heavy chain framework residue selected from the group consisting of +37, +49, +73, and +99 (linear numbering), which is occupied by I, A, F, or V, respectively, and wherein the remainder of the heavy chain variable region is occupied by a corresponding residue in a human acceptor immunoglobulin heavy chain variable region.

For example, antibodies and antigen-binding fragments of the invention include those comprising a heavy chain variable region comprising a framework residue at +10 (linear numbering) occupied by R, wherein the remainder of the heavy chain variable region is occupied by a corresponding residue in a human acceptor immunoglobulin heavy chain variable region; antibodies and antigen-binding fragments a heavy chain variable region comprising a framework residue at +15 (linear numbering) occupied by K, wherein the remainder of the heavy chain variable region is occupied by a corresponding residue in a human acceptor immunoglobulin heavy chain variable region; antibodies and antigen-binding fragments a heavy chain variable region comprising a framework residue at +19 (linear numbering) occupied by K, wherein the remainder of the heavy chain variable region is occupied by a corresponding residue in a human acceptor immunoglobulin heavy chain variable region; antibodies and antigen-binding fragments a heavy chain variable region comprising a framework residue at +37 (linear numbering) occupied by 1, wherein the remainder of the heavy chain variable region is occupied by a corresponding residue in a human acceptor immunoglobulin heavy chain variable region; antibodies and antigen-binding fragments a heavy chain variable region comprising a framework residue at +49 (linear numbering) occupied by A, wherein the remainder of the heavy chain variable region is occupied by a corresponding residue in a human acceptor immunoglobulin heavy chain variable region; antibodies and antigen-binding fragments a heavy chain variable region comprising a framework residue at +73 (linear numbering) occupied by F, wherein the remainder of the heavy chain variable region is occupied by a corresponding residue in a human acceptor immunoglobulin heavy chain variable region; antibodies and antigen-binding fragments a heavy chain variable region comprising a framework residue at +78 (linear numbering) occupied by Q, wherein the remainder of the heavy chain variable region is occupied by a corresponding residue in a human acceptor immunoglobulin heavy chain variable region; antibodies and antigen-binding fragments a heavy chain variable region comprising a framework residue at +79 (linear numbering) occupied by S, wherein the remainder of the heavy chain variable region is occupied by a corresponding residue in a human acceptor immunoglobulin heavy chain variable region; antibodies and antigen-binding fragments a heavy chain variable region comprising a framework residue at +80 (linear numbering) occupied by M, wherein the remainder of the heavy chain variable region is occupied by a corresponding residue in a human acceptor immunoglobulin heavy chain variable region; antibodies and antigen-binding fragments a heavy chain variable region comprising a framework residue at +87 (linear numbering) occupied by N, wherein the remainder of the heavy chain variable region is occupied by a corresponding residue in a human acceptor immunoglobulin heavy chain variable region; antibodies and antigen-binding fragments a heavy chain variable region comprising a framework residue at +95 (linear numbering) occupied by M, wherein the remainder of the heavy chain variable region is occupied by a corresponding residue in a human acceptor immunoglobulin heavy chain variable region; antibodies and antigen-binding fragments a heavy chain variable region comprising a framework residue at +99 (linear numbering) occupied by V, wherein the remainder of the heavy chain variable region is occupied by a corresponding residue in a human acceptor immunoglobulin heavy chain variable region; and antibodies and antigen-binding fragments a heavy chain variable region comprising a framework residue at +109 (linear numbering) occupied by A, wherein the remainder of the heavy chain variable region is occupied by a corresponding residue in a human acceptor immunoglobulin heavy chain variable region.

Human acceptor immunoglobulin heavy chain variable regions include a human gamma subgroup 3 heavy chain variable region (Kabat convention), for example, human gamma subgroup 3 heavy chain variable region comprising a sequence set forth as SEQ ID NO: 165, such as a heavy chain variable region comprising an amino acid sequence set forth as residues 20-138 of SEQ ID NO: 154 or set forth as SEQ ID NO: 161, 162, or 163.

Additional representative antibodies and antigen-binding fragments comprise a light chain variable region comprising three complementarity determining regions of a 2A4 light chain variable region set forth as residues 20-131 of SEQ ID NO: 152 or three complementarity regions of a 7D8 light chain variable region set forth as residues 20-131 of SEQ ID NO: 153, and a heavy chain variable region comprising three complementarity regions of a 2A4 heavy chain variable region set forth as residues 20-138 of SEQ ID NO: 154. For example, such antibodies and antigen-binding fragments include those having a light chain variable region comprising three complementarity determining regions set forth as SEQ ID NOs: 168, 169, and 170, and a heavy chain variable region comprising three complementarity regions set forth as SEQ ID NOs: 171, 172, and 173. As another example, such antibodies and antigen-binding fragments include those having a light chain variable region comprising three complementarity determining regions set forth as SEQ ID NOs: 177, 169, and 170, and a heavy chain variable region comprising three complementarity regions set forth as SEQ ID NOs: 171, 172, and 173. As another example, such antibodies and antigen-binding fragments include those comprising a light chain variable region comprising an amino acid sequence set forth as residues 20-131 of SEQ ID NO: 152 or as residues 20-131 of SEQ ID NO: 153, and a heavy chain variable region comprising an amino acid sequence set forth as residues 20-138 of SEQ ID NO: 154. As another example, such antibodies and antigen-binding fragments include those having a light chain variable region comprising an amino acid sequence set forth as SEQ ID NO: 155, 156, 157, 158, 159, 160, 174, 175, or 176, and a heavy chain variable region comprising an amino acid sequence set forth as SEQ ID NO: 161, 162, or 163.

In particular aspects of the invention, an antibody or antigen-binding fragment comprises a light chain variable region comprising an amino acid sequence set forth as SEQ ID NO: 155, and a heavy chain variable region comprising an amino acid sequence set forth as SEQ ID NO: 161; a light chain variable region comprising an amino acid sequence set forth as SEQ ID NO: 155, and a heavy chain variable region comprising an amino acid sequence set forth as SEQ ID NO: 162; a light chain variable region comprising an amino acid sequence set forth as SEQ ID NO: 155, and a heavy chain variable region comprising an amino acid sequence set forth as SEQ ID NO: 163; a light chain variable region comprising an amino acid sequence set forth as SEQ ID NO: 156, and a heavy chain variable region comprising an amino acid sequence set forth as SEQ ID NO: 161; a light chain variable region comprising an amino acid sequence set forth as SEQ ID NO: 156, and a heavy chain variable region comprising an amino acid sequence set forth as SEQ ID NO: 162; a light chain variable region comprising an amino acid sequence set forth as SEQ ID NO: 156, and a heavy chain variable region comprising an amino acid sequence set forth as SEQ ID NO: 163; a light chain variable region comprising an amino acid sequence set forth as SEQ ID NO: 157, and a heavy chain variable region comprising an amino acid sequence set forth as SEQ ID NO: 161; a light chain variable region comprising an amino acid sequence set forth as SEQ ID NO: 157, and a heavy chain variable region comprising an amino acid sequence set forth as SEQ ID NO: 162; a light chain variable region comprising an amino acid sequence set forth as SEQ ID NO: 157, and a heavy chain variable region comprising an amino acid sequence set forth as SEQ ID NO: 163; a light chain variable region comprising an amino acid sequence set forth as SEQ ID NO: 158, and a heavy chain variable region comprising an amino acid sequence set forth as SEQ ID NO: 161; a light chain variable region comprising an amino acid sequence set forth as SEQ ID NO: 158, and a heavy chain variable region comprising an amino acid sequence set forth as SEQ ID NO: 162; a light chain variable region comprising an amino acid sequence set forth as SEQ ID NO: 158, and a heavy chain variable region comprising an amino acid sequence set forth as SEQ ID NO: 163; a light chain variable region comprising an amino acid sequence set forth as SEQ ID NO: 159, and a heavy chain variable region comprising an amino acid sequence set forth as SEQ ID NO: 161; a light chain variable region comprising an amino acid sequence set forth as SEQ ID NO: 159, and a heavy chain variable region comprising an amino acid sequence set forth as SEQ ID NO: 162; a light chain variable region comprising an amino acid sequence set forth as SEQ ID NO: 159, and a heavy chain variable region comprising an amino acid sequence set forth as SEQ ID NO: 163; a light chain variable region comprising an amino acid sequence set forth as SEQ ID NO: 160, and a heavy chain variable region comprising an amino acid sequence set forth as SEQ ID NO: 161; a light chain variable region comprising an amino acid sequence set forth as SEQ ID NO: 160, and a heavy chain variable region comprising an amino acid sequence set forth as SEQ ID NO: 162; a light chain variable region comprising an amino acid sequence set forth as SEQ ID NO: 160, and a heavy chain variable region comprising an amino acid sequence set forth as SEQ ID NO: 163; SEQ ID NO: 174, and a heavy chain variable region comprising an amino acid sequence set forth as SEQ ID NO: 161; a light chain variable region comprising an amino acid sequence set forth as SEQ ID NO: 174, and a heavy chain variable region comprising an amino acid sequence set forth as SEQ ID NO: 162; a light chain variable region comprising an amino acid sequence set forth as SEQ ID NO: 174, and a heavy chain variable region comprising an amino acid sequence set forth as SEQ ID NO: 163; a light chain variable region comprising an amino acid sequence set forth as SEQ ID NO: 175, and a heavy chain variable region comprising an amino acid sequence set forth as SEQ ID NO: 161; a light chain variable region comprising an amino acid sequence set forth as SEQ ID NO: 175, and a heavy chain variable region comprising an amino acid sequence set forth as SEQ ID NO: 162; a light chain variable region comprising an amino acid sequence set forth as SEQ ID NO: 175, and a heavy chain variable region comprising an amino acid sequence set forth as SEQ ID NO: 163; a light chain variable region comprising an amino acid sequence set forth as SEQ ID NO: 176, and a heavy chain variable region comprising an amino acid sequence set forth as SEQ ID NO: 161; a light chain variable region comprising an amino acid sequence set forth as SEQ ID NO: 176, and a heavy chain variable region comprising an amino acid sequence set forth as SEQ ID NO: 162; or a light chain variable region comprising an amino acid sequence set forth as SEQ ID NO: 176, and a heavy chain variable region comprising an amino acid sequence set forth as SEQ ID NO: 163.

Also provided are isolated nucleic acids encoding a human, humanized, or chimeric antibody, or antigen-binding fragment thereof, that specifically binds to an epitope within residues 70-76 of human amyloid A peptide, including all such antibodies and antigen-binding fragments as described herein above and as set forth in the claims. Further provided are cells expressing such nucleic acids.

In other aspects, the present invention provides an isolated antibody, or antigen-binding fragment thereof, which specifically binds to an epitope comprising $X_1EDX_2$ in an aggregated amyloid protein, wherein $X_1$ and $X_2$ are any amino acid. Such antibodies and antigen-binding fragments include human, humanized, or chimeric antibodies, and antigen-binding fragments thereof, for example, those that specifically bind to an epitope within residues 70-76 of human amyloid A peptide.

Additional representative antibodies and antigen-binding fragments include those wherein $X_1$ is H, T, F, S, P, A, L, C, Q, R, E, K, D, G, V, Y, I, or W, and wherein $X_2$ is T, S, E, R, I, V, F, D, A, G, M, L, N, P, C, K, Y, or Q; or $X_1$ is H, T, F, S, P, or A and wherein $X_2$ is T, S, E, R, I, V, F, D, or A; or $X_1$ is H, T, F, or A; or $X_2$ is T, S, E, D, or A; or $X_1$ is H, T, F, or A and $X_2$ is T, S, E, D, or A; or $X_1$ is H, T, or A and $X_2$ is T, S, E, or A; or $X_1$ is H or A and $X_2$ is T, S, or A; or $X_1$ is H and $X_2$ is T or A; or $X_1$ is A and $X_2$ is S, T, E or V; or $X_1$ is A and $X_2$ is S, T or E; or $X_1$ is T and $X_2$ is E; or $X_1$ is F and $X_2$ is D; or $X_1$ is S and $X_2$ is E, F or A; or $X_1$ is P and $X_2$ is E, I or F. For example, such antibodies and antigen-binding fragments bind an epitope consisting of an amino acid sequence selected from the group consisting of GHEDT (SEQ ID NO: 3), HEDT (SEQ ID NO: 12), AEDS (SEQ ID NO: 13), AEDT (SEQ ID NO: 14), HEDA (SEQ ID NO: 15), TEDE (SEQ ID NO: 16), FEDD (SEQ ID NO: 17), SEDE (SEQ ID NO: 18), AEDE (SEQ ID NO: 19), PEDE (SEQ ID NO: 20), PEDI (SEQ ID NO: 21), PEDF (SEQ ID NO: 22), AEDV (SEQ ID NO: 23), SEDF (SEQ ID NO: 24), and SEDA (SEQ ID NO: 25); or an epitope consisting of an amino acid sequence selected from the group consisting of GHEDT (SEQ ID NO: 3), HEDT (SEQ ID NO: 12), AEDS (SEQ ID NO: 13), AEDT (SEQ ID NO: 14), HEDA (SEQ ID NO: 15), TEDE (SEQ ID NO: 16), FEDD (SEQ ID NO: 17), SEDE (SEQ ID NO: 18), AEDE (SEQ ID NO: 19), PEDE (SEQ ID NO: 20), PEDI (SEQ ID NO: 21), PEDF (SEQ ID NO: 22), SEDF (SEQ ID NO: 24), and SEDA (SEQ ID NO: 25); or an epitope consisting of an amino acid sequence selected from the group consisting of GHEDT (SEQ ID NO: 3), HEDT (SEQ ID NO: 12), AEDS (SEQ ID NO: 13), AEDT (SEQ ID NO: 14), HEDA (SEQ ID NO: 15), and TEDE (SEQ ID NO: 16). The disclosed epitopes may be found in an aggregated amyloid protein, for example, an epitope comprising an amino acid sequence selected from the group consisting of GHGAEDS (SEQ ID NO: 4), GHDAEDS (SEQ ID NO: 5), GDHAEDS (SEQ ID NO: 7), STVIEDS (SEQ ID NO: 8), and GRGHEDT (SEQ ID NO: 9); or an epitope comprising an amino acid sequence GHGAEDS (SEQ ID NO:4); or an epitope comprising amino acids HEDT (SEQ ID NO: 12); or an epitope comprising amino acids HEDA (SEQ ID NO: 15); or an epitope comprising amino acids AEDS (SEQ ID NO: 13) or an epitope comprising amino acids AEDT (SEQ ID NO: 14); or an epitope comprising amino acids TEDE (SEQ ID NO: 16); or an epitope comprising the amino acid sequence AEDV (SEQ ID NO: 23); or an epitope comprising the amino acid sequence SEDF (SEQ ID NO: 24) or PEDF (SEQ ID NO: 22); or an epitope of comprising an amino sequence selected from the group consisting of PEDS (SEQ ID NO: 26), PEDL (SEQ ID NO: 27), TEDV (SEQ ID NO: 28), AEDE (SEQ ID NO: 19), SEDI (SEQ ID NO: 29) and TEDT (SEQ ID NO: 30); or an epitope comprising an amino sequence selected from the group consisting of LEDG (SEQ ID NO: 31), AEDM (SEQ ID NO: 32), HEDS (SEQ ID NO: 33), CEDD (SEQ ID NO: 34), QEDS (SEQ ID NO: 35), REDS (SEQ ID NO: 36), TEDG (SEQ ID NO: 16), QEDR (SEQ ID NO: 38), TEDL (SEQ ID NO: 39), PEDN (SEQ ID NO: 40), EEDP (SEQ ID NO: 41), LEDL (SEQ ID NO: 42), KEDA (SEQ ID NO: 43), SEDC (SEQ ID NO: 44), EEDD (SEQ ID NO: 45), SEDK (SEQ ID NO: 46), DEDD (SEQ ID NO: 47), DEDG (SEQ ID NO: 13), LEDE (SEQ ID NO: 49), GEDA (SEQ ID NO: 13), VEDF (SEQ ID NO: 51), YEDE (SEQ ID NO: 52), IEDL (SEQ ID NO: 53), WEDY (SEQ ID NO: 54), DEDW (SEQ ID NO: 55), SEDL (SEQ ID NO: 56), YEDQ (SEQ ID NO: 57), LEDW (SEQ ID NO: 58), YEDR (SEQ ID NO: 59) and PEDK (SEQ ID NO: 60).

The antibodies and antigen-binding fragments described herein include those that bind to the amyloid protein in monomeric form with an affinity of less than about $10^7$ M$^{-1}$. Representative amyloid proteins include serum amyloid A protein (SAA), immunoglobulin light chain protein (such as Vλ6 Wil and Vκ), human islet amyloid precursor polypeptide (IAPP), beta amyloid peptide, transthyretin (TTR), and ApoA1.

Also provided are isolated nucleic acids encoding an antibody, or antigen-binding fragment thereof, which specifically binds to an epitope comprising $X_1EDX_2$ in an aggregated amyloid protein, wherein $X_1$ and $X_2$ are any amino acid., including all such antibodies and antigen-binding fragments as described herein above and as set forth in the claims. Further provided are cells expressing such nucleic acids.

The present invention further provides methods of therapeutically treating or prophylactically treating a subject having AA amyloidosis using a human, humanized, or chimeric antibody, or antigen-binding fragment thereof, that specifically binds to an epitope within residues 70-76 of human amyloid A peptide, for example, an epitope within residues 70-76 of SEQ ID NO: 2. Subjects that may benefit from the disclosed therapeutic methods of treating AA amyloidosis include those subjects suffering from an amyloid disease selected from the group consisting of rheumatoid arthritis, juvenile chronic arthritis, ankylosing spondylitis, psoriasis, psoriatic arthropathy, Reiter's syndrome, Adult Still's disease, Behcet's syndrome, Crohn's disease, leprosy, tuberculosis, bronchiectasis, decubitus ulcers, chronic pyelonephritis, osteomyelitis, Whipple's disease, Hodgkin's lymphoma, renal carcinoma, carcinomas of gut, lung and urogenital tract, basal cell carcinoma, hairy cell leukemia, Familial Mediterranean Fever, and Castleman's Disease. Subjects that may benefit from the disclosed prophylactic methods include those subjects susceptible to or at risk of developing any of the foregoing disorders.

Also provided are methods of therapeutically treating or prophylactically treating a subject having amyloidosis associated with an aggregated amyloid protein comprising the amino acid sequence ED using an antibody or antigen-binding fragment that specifically binds to an epitope comprising $X_1EDX_2$ in an aggregated amyloid protein, wherein $X_1$ and $X_2$ are any amino acid. Subjects that may benefit from the disclosed therapeutic methods of treating amyloidosis associated with an aggregated amyloid protein include those subjects suffering from AA amyloidosis, AL amyloidosis, Alzheimer's disease, Mild Cognitive Impairment, amyloid polyneuropathy, Mediterranean fever, Muckle-Wells syndrome, reactive systemic amyloidosis associated with systemic inflammatory diseases, myeloma or macroglobulinemia associated amyloidosis, amyloidosis associated with immunocyte dyscrasia, monoclonal gammopathy, occult dyscrasia, and local nodular amyloidosis associated with chronic inflammatory diseases. Subjects that may benefit from the disclosed prophylactic methods include those subjects susceptible to or at risk of developing any of the foregoing disorders. In one aspect of the invention, the amyloid protein comprises the sequence AEDV (SEQ ID NO: 23), and the amyloidogenic disease treated therapeutically or prophylactically using the disclosed methods is AA amyloidosis, AL amyloidosis, amyloid polyneuropathy, Mediterranean fever, Muckle-Wells syndrome, reactive systemic amyloidosis associated with systemic inflammatory diseases, myeloma or macroglobulinemia associated amyloidosis, amyloidosis associated with immunocyte dyscrasia, monoclonal gammopathy, occult dyscrasia, and local nodular amyloidosis associated with chronic inflammatory diseases.

The disclosed therapeutic and prophylactic methods are useful for treating human subjects.

Representative indices of efficacious therapeutic treatment include slowing the progression of amyloidosis, inhibiting deposition of amyloid fibril aggregates, and/or clearing of amyloid fibril aggregates. Representative indices of efficacious prophylactic treatment include delaying onset of amyloidosis and/or reducing a risk of amyloidosis.

Still further provided are methods of detecting an amyloid deposit associated with AA amyloidosis in a subject human, humanized, or chimeric antibody, or antigen-binding fragment thereof, that specifically binds to an epitope within residues 70-76 of human amyloid A peptide, which antibody or antigen-binding fragment is bound to a detectable label, and then detecting the detectable label in the subject. Additional methods comprise detecting an aggregated amyloid protein comprising the amino acid sequence ED using an antibody or antigen-binding fragment that specifically binds to an epitope comprising $X_1EDX_2$ in an aggregated amyloid protein, wherein $X_1$ and $X_2$ are any amino acid. The foregoing detection methods may be used, for example, for monitoring onset or progression of disease or therapy in any of the above-noted diseases and disorders. As for the treatment methods disclosed herein, such monitoring may be performed in humans as well as non-human subjects. Useful detectable labels include radiolabels, such as $^{125}I$. In performing such detection methods, the step of detecting the detectable label may be accomplished by non-invasive techniques, such as SPECT/CT imaging and NMR spectroscopy.

Still further provided are methods of active immunotherapy of a subject having AA amyloidosis using an agent that induces an immune response to residues 70-76 of amyloid A peptide effective to induce an immune response comprising antibodies against residues 70-76 of an amyloid A peptide. Representative agents for inducing the immune response include residues 70-76 of amyloid A peptide or a subfragment of at least 3 contiguous residues thereof having fewer than 20 contiguous amino acids from an AA peptide. These methods are useful both therapeutically and/or prophylactically for treatment of the subjects described herein above with respect to passive immunotherapy, i.e., by administering an antibody or antigen-binding fragment that specifically binds to residues 70-76 of amyloid A peptide. Indices of therapeutic and prophylactic efficacy are also as noted herein above with respect to passive immunotherapy.

The foregoing summarizes particular aspects of the invention, and additional aspects of the invention are described herein.

BRIEF DESCRIPTION OF THE DRAWINGS

FIG. 1: Sequence alignment of human SAA1, human SAA2, human SAA3 and human SAA4.

FIG. 2: Sequence alignment of human SAA1 and human AA1.

FIG. 3: Sequence alignment of human SAA2 and human AA2.

FIG. 4: Sequence alignment t of human SAA3 and human AA3.

FIG. 5: Sequence alignment of human SAA4 and hHuman AA4.

FIG. 6: Sequence alignment of human AA1, human AA2, human AA3 and human AA4.

FIG. 7: Sequence alignment of the last seven residues of human AA1, hHuman AA2, human AA3 and human AA4.

FIG. 8: Sequence alignment of mouse SAA1, mouse SAA2, mouse SAA3 and mouse SAA4.

FIG. 9: Sequence alignment of mouse SAA1 and mouse AA1.

FIG. 10: Sequence alignment of mouse SAA2 and mouse AA2.

FIG. 11: Sequence alignment of mouse SAA3 and mouse AA3.

FIG. 12: Sequence alignment of mouse SAA4 and mMouse AA4.

FIG. 13: Sequence alignment of mouse AA1, mouse AA2, mouse AA3 mouse AA4.

FIG. 14: Sequence alignment of the last seven residues of mouse AA1, mouse AA2, mouse AA3 mouse AA4.

FIG. 15: Sequence alignment of human SAA1 and mouse SAA1.

FIG. 16: Sequence alignment of human AA1 and mouse AA1.

FIG. 17: Sequence alignment of human SAA1 and mouse SAA1 Fragment.

FIG. 18: Sequence alignment of human SAA1 alpha, human SAA1 beta, and human SAA1 gamma.

FIG. 19: Sequence alignment of human SAA2 alpha and human SAA2 beta.

FIG. 20: Sequence comparison of SAA proteins. The peptide region used to generate 2A4, 8G9 and 7D8 is shown in dashed lines. The 8 amino acid insert between positions 67 and 68 in the Shar Pei sequence is indicated by the underline and arrow. Alignment performed with CLUSTALW.

FIG. 21: Germline sequences of Vκ light chains.

FIG. 22: Germline sequences of Vλ light chains.

FIG. 23: Amino acid sequence of Vλ6 Wil.

FIG. 25: X-ray crystal of Vλ6 Wil showing position of Glu81-Asp82

FIGS. 36A-36E: Sequences of murine 2A4, 7D8, and 8G9 light chain and heavy chain variable regions (FIG. 36A); sequences of humanized 2A4/8G9 and 7D8 light chain variable regions (FIGS. 36B-36C); sequences of human light chain variable regions used as acceptor frameworks (FIG. 36D); sequences of humanized 2A4/7D8/8G9 heavy chain variable regions and human heavy chain variable region used as acceptor framework (FIG. 36E). Underlining, CDRs; double underlining, leader sequences; lower case, back mutations.

DETAILED DESCRIPTION OF THE INVENTION

Figure 24:
FIG. 24: X-ray crystal of Vλ6 Wil showing position of Glu50-Asp51.

The invention provides an isolated antibody or antigen-binding fragment thereof, which specifically binds to an epitope including $X_1EDX_2$ in an aggregated amyloid protein, wherein $X_1$ and $X_2$ are any amino acid.

Representative antibodies of the invention also include antibodies or fragments thereof that (a) compete for binding to an epitope including $X_1EDX_2$ with a 2A4, 7D8, or 8G9 antibody; (b) bind to the same epitope including $X_1EDX_2$ as a 2A4, 7D8, or 8G9 antibody; (c) include an antigen binding domain of a 2A4, 7D8, or 8G9 antibody; or (d) include the six complementarity determining regions (CDRs) of a 2A4, 7D8, or 8G9 antibody.

The invention also provides an isolated antibody variable region including (a) a light chain variable region of an antibody derived from a 2A4, 7D8, or 8G9 antibody; or (b) a heavy chain variable region of an antibody derived from a 2A4, 7D8, or 8G9 antibody.

The invention also provides an isolated nucleic acid encoding an antibody light chain variable region or heavy chain variable region including (a) a nucleotide sequence that encodes a light chain or heavy chain variable region of a 7D8, 2A4, or 8G9 antibody; (b) a nucleotide sequence that is identical to a nucleotide sequence of a 7D8, a 2A4, or an 8G9 antibody that encodes a light chain or heavy chain variable region; (c) a nucleotide sequence that is substantially identical to a nucleotide sequence of (a) or (b); or (d) a nucleic acid that specifically hybridizes to a nucleic acid having a nucleotide sequence that is the complement of a nucleotide sequence of (a) or (b) under stringent hybridization conditions.

Cells expressing the antibodies and antigen-binding fragments of the present invention are also provided. The invention further provides cells expressing nucleic acids of the invention.

The invention also includes methods of treating amyloid diseases and methods of prophylaxis of amyloid diseases using the antibodies and antigen-binding fragments of the invention. Currently, there are no approved specific amyloid-directed treatments for any of the amyloid diseases, including AA Amyloidosis and AL amyloidosis. See Gillmore J. D. et al., *Lancet* 358:24-9 (2001). Where there is an underlying or associated disease state, therapy directed towards decreasing the production of amyloidogenic protein by treating the underlying disease. For example, current treatment strategy for AA Amyloidosis is to target underlying inflammation, reducing ApoSSA levels to below 10 mg/l. Currently employed therapies include chemotherapy (cholorambucil and MTX), immuno-suppressants (azathioprine), anti-inflammatory drugs (colchicine) and TNF inhibitors. The invention provides pharmaceutical compositions and methods for treating a number of amyloid diseases, including amyloidosis, such as, for example, AA amyloidosis and AL amyloidosis. According to one aspect, the invention includes pharmaceutical compositions that include, as an active ingredient, an agent that is effective to induce an immune response in a patient against an amyloid component. The agent can be a peptide comprising a fragment consisting of the amino acid sequence $X_1EDX_2$ derived from an amyloid protein. The agent can be an antibody that specifically binds to an epitope comprising $X_1EDX_2$. In other embodiments, the agent can be an antigen-binding fragment of an antibody. Such compositions will generally also include excipients and in preferred embodiments may include adjuvants. In further preferred embodiments, the adjuvants include, for example, aluminum hydroxide, aluminum phosphate, MPL™, QS-21 (STIMULON™) or incomplete Freund's adjuvant. According to a related embodiment, such pharmaceutical compositions may include a plurality of agents effective to induce an immune response against more than one amyloid component in the patient.

In a related embodiment, the agent is effective to produce an immune response directed against an aggregated amyloid protein, such as a fibril peptide or protein amyloid component. Preferably, such a fibril peptide or protein is derived from a fibril precursor protein known to be associated with certain forms of amyloid diseases, as described herein. Such precursor proteins include, but are not limited to, Serum Amyloid A protein (ApoSSA), immunoglobulin light chain, immunoglobulin heavy chain, ApoAI, transthyretin, lysozyme, fibrogen a chain, gelsolin, cystatin C, Amyloid β protein precursor (β-APP), Beta$_2$ microglobulin, prion precursor protein (PrP), atrial natriuretic factor, keratin, islet amyloid polypeptide, a peptide hormone, and synuclein. Such precursors also include mutant proteins, protein fragments and proteolytic peptides of such precursors. In a preferred embodiment, the agent is effective to induce an immune response directed against a neoepitope formed by a fibril protein or peptide, with respect to a fibril precursor protein. That is, as described in more detail herein, many fibril-forming peptides or proteins are fragments of such precursor proteins, such as those listed above. When such fragments are formed, such as by proteolytic cleavage, epitopes may be revealed that are not present on the precursor and are therefore not immunologically available to the immune system when the fragment is a part of the precursor protein. Agents directed to such epitopes may be preferred therapeutic agents, since they may be less likely to induce an autoimmune response in the patient. Preferably, such agents preferentially produce an immune response directed against a pathological form of the amyloid protein, for example, an aggregated amyloid protein, relative to nonpathological forms of the amyloid protein.

According to a related embodiment, pharmaceutical compositions of the invention include agents directed to amyloid aggregates, such as those selected from the group including, but not limited to the following aggregated (e.g., fibril) peptides or proteins: AA, AL, ATTR, AApoA1, Alys, Agel, Acys, Aβ, AB$_2$M, AScr, Acal, AIAPP and synuclein-NAC fragment. The full names and compositions of these peptides are described herein. Such peptides can be made according to methods well known in the art, as described herein.

The methods comprise administering to the patient an effective dosage of an antibody that specifically binds to an epitope comprising $X_1EDX_2$ in an amyloid protein, wherein $X_1$ is H, T, F, S, P, A or any other amino acid residue immediately preceding ED in such amyloid protein; and wherein $X_2$ is T, S, E, R, I, V, F, A or any other amino acid residue immediately following ED in such amyloid protein. In some methods, the patient is suffering from an amyloidosis associated with an aggregated amyloid protein comprising the amino acid sequence ED. Some antibodies specifically bind to an epitope consisting of such $X_1EDX_2$. In some antibodies, $X_1$ is H, T, F, S, P, or A and $X_2$ is T, S, E, D, R, 1, V, F or A. In some such antibodies, when $X_1$ is H, $X_2$ is T or A; when $X_1$ is A, $X_2$ is S, T, E or V; when $X_1$ is T, $X_2$ is E; when $X_1$ is F, $X_2$ is D; when $X_1$ is S, $X_2$ is E, F or A; and when $X_1$ is P, $X_2$ is E, I or F. In some antibodies, $X_1$ is H, T, F, S, P, or A and $X_2$ is T, S, E, D, R, I, V, F or A, with the proviso that if $X_1$ is A, $X_2$ is not V. In some antibodies, when $X_1$ is A, $X_2$ is S, T or E.

Some antibodies specifically bind an epitope comprising the amino acid sequence GHEDT, (SEQ ID NO: 3), HEDT, (SEQ ID NO: 12), AEDS, (SEQ ID NO 13), AEDT (SEQ ID NO: 14), HEDA (SEQ ID NO: 15), TEDE, (SEQ ID NO: 16), FEDD, (SEQ ID NO: 17), SEDE, (SEQ ID NO: 18), AEDE, (SEQ ID NO: 19), PEDE, (SEQ ID NO: 20), PEDI, (SEQ ID NO: 21), PEDF, (SEQ ID NO: 22), AEDV, (SEQ ID NO: 23), SEDF (SEQ ID NO: 24), or SEDA, (SEQ ID NO: 25).

Some antibodies specifically bind to a peptide comprising an amino acid sequence selected from the group consisting of GHEDT, (SEQ ID NO: 3), HEDT, (SEQ ID NO: 12), AEDS, (SEQ ID NO: 13), AEDT, (SEQ ID NO: 14), HEDA, (SEQ ID NO: 15), TEDE, (SEQ ID NO: 16), FEDD, (SEQ ID NO: 17), SEDE, (SEQ ID NO: 18), AEDE, (SEQ ID NO: 19), PEDE, (SEQ ID NO: 20), PEDI, (SEQ ID NO: 21), PEDF, (SEQ ID NO: 22), SEDF, (SEQ ID NO: 24), and SEDA, (SEQ ID NO: 25). Some antibodies specifically bind to a peptide comprising an amino acid sequence selected from the group consisting of GHEDT, (SEQ ID NO: 3, HEDT, (SEQ ID NO: 12), AEDS, (SEQ ID NO: 13), AEDT, (SEQ ID NO: 14), HEDA, (SEQ ID NO: 15), and TEDE, (SEQ ID NO: 16).

Some antibodies specifically bind to an epitope within residues 70 to 76 of AA. Some antibodies specifically bind to an epitope within residues 71 to 75 of AA. Some antibodies are raised to a peptide comprising GHEDT, (SEQ ID NO: 3).

Some antibodies specifically bind to a peptide comprising the amino acid sequence PEDS, (SEQ ID NO: 26), PEDL, (SEQ ID NO: 27), TEDV, (SEQ ID NO: 28), AEDE, (SEQ ID NO: 19), SEDI, (SEQ ID NO: 29), and TEDT, (SEQ ID NO: 30). Some antibodies specifically bind to a peptide comprising the amino acid sequence LEDG, (SEQ ID NO: 31), AEDM, (SEQ ID NO: 32), HEDS, (SEQ ID NO: 33), CEDD, (SEQ ID NO: 34), QEDS, (SEQ ID NO: 35), REDS, (SEQ ID NO: 36), TEDG, (SEQ ID NO: 37), QEDR, (SEQ ID NO: 38), TEDL, (SEQ ID NO: 39), PEDN, (SEQ ID NO: 40), EEDP, (SEQ ID NO: 41), LEDL, (SEQ ID NO: 42), KEDA, (SEQ ID NO: 43), SEDC, (SEQ ID NO: 44), EEDD, (SEQ ID NO: 45), SEDK, (SEQ ID NO: 46), DEDD, (SEQ ID NO: 47), DEDG, (SEQ ID NO: 48), LEDE, (SEQ ID NO: 49), GEDA, (SEQ ID NO: 50), VEDF, (SEQ ID NO: 51), YEDE, (SEQ ID NO: 52), IEDL, (SEQ ID NO: 53), WEDY, (SEQ ID NO: 54), DEDW, (SEQ ID NO: 55), SEDL, (SEQ ID NO: 56), YEDQ, (SEQ ID NO: 57), LEDW, (SEQ ID NO: 58), YEDR, (SEQ ID NO: 59), and PEDK, (SEQ ID NO: 60).

Some antibodies specifically bind to a peptide comprising the amino acid sequence AEDV, (SEQ ID NO: 23). Some antibodies specifically bind to a peptide comprising the amino acid sequence SEDF, (SEQ ID NO: 24) or PEDF, (SEQ ID NO: 22). Some antibodies specifically bind to a peptide comprising the amino acid sequence AEDS, (SEQ ID NO: 13). Some antibodies specifically bind to a peptide comprising the amino acid sequence PEDI (SEQ ID NO: 21), AEDV, (SEQ ID NO 23), SEDF, (SEQ ID NO: 24), SEDA, (SEQ ID NO: 25), SEDE, (SEQ ID NO: 18), AEDE, (SEQ ID NO: 19), and PEDE, (SEQ ID NO: 20). Some antibodies bind to a peptide comprising the amino acid sequence TEDE, (SEQ ID NO: 16).

Some antibodies specifically bind to a peptide comprising the amino acid sequence AEDV, (SEQ ID NO: 23). Some antibodies specifically bind to a peptide comprising the amino acid sequence SEDF, (SEQ ID NO: 24) or PEDF, (SEQ ID NO: 22). Some antibodies specifically bind to a peptide comprising the amino acid sequence AEDS, (SEQ ID NO: 13). Some antibodies specifically bind to a peptide comprising the amino acid sequence PEDI (SEQ ID NO: 21), AEDV, (SEQ ID NO 23), SEDF, (SEQ ID NO: 24), SEDA, (SEQ ID NO: 25), SEDE, (SEQ ID NO: 18), AEDE, (SEQ ID NO: 19), and PEDE, (SEQ ID NO: 20). Some antibodies bind to a peptide comprising the amino acid sequence TEDE, (SEQ ID NO: 16).

Any of the antibodies described above can be administered in the methods described above to treat or effect prophylaxis of a disease characterized by the deposition of an amyloid protein, such as, for example, an amyloid protein comprising the amino acid sequence ED. In some methods, if the amyloid protein comprises the amino acid sequence AEDV, (SEQ ID NO: 23), then the antibody is not administered to treat or effect prophylaxis of Alzheimer's disease or Mild Cognitive Impairment. The amyloid protein can be any of serum amyloid A protein, immunoglobulin light chain protein, such as, for example, Vλ6 Wil or Vκ, human islet amyloid precursor polypeptide (IAPP), beta amyloid peptide, transthyretin (TTR) or ApoA1.

Optionally, the patient is human. Optionally, the antibody specifically binds to a peptide whose residues consist of SEQ ID NOS. 4, 5, 6, 7, 8, 9, 10, or 11. Optionally, the antibody specifically binds to an epitope within residues 70-76 of (SEQ ID NO: 2). Optionally, the antibody is a human antibody, humanized antibody or chimeric antibody. Optionally, the human antibody is of human isotype IgG1, IgG4, IgG2 or IgG3. Optionally, the humanized antibody is of human isotype IgG1, IgG4, IgG2 or IgG3. Optionally, the chimeric antibody is of human isotype IgG1, IgG4, IgG2 or IgG3. Optionally, the antibody is a mouse antibody. Optionally, the antibody is a polyclonal antibody. Optionally, the antibody is a monoclonal antibody.

In some treatment methods, the antibody comprises two copies of the same pair of light and heavy chains. In other methods, the antibody is a bispecific antibody comprising a first light and heavy chain pair that specifically binds to the epitope of Aβ and a second light and heavy chain pair that specifically binds to an Fc receptor on microglial cells. In other methods, a chain of the antibody is fused to a heterologous polypeptide.

Some treatment methods, the dosage of antibody is at least 1 mg/kg body weight of the patient. In other methods, the dosage of antibody is at least 10 mg/kg body weight of the patient.

In some treatment methods, the antibody is administered with a carrier as a pharmaceutical composition. In other methods, wherein the antibody is a human antibody to AA prepared from B cells from a human immunized with an AA peptide. Optionally, the human immunized with AA peptide is the patient. In some methods, the antibody is administered intraperitoneally, orally, intranasally, subcutaneously, intramuscularly, topically or intravenously.

In some treatment methods, the antibody is administered by administering a polynucleotide encoding at least one antibody chain to the patient and the polynucleotide is expressed to produce the antibody chain in the patient. Optionally, the polynucleotide encodes heavy and light chains of the antibody and the polynucleotide is expressed to produce the heavy and light chains in the patient.

Some of the above treatment methods further comprise administering an effective dosage of at least one other antibody that binds to a different epitope of AA. Some of the above treatment methods further comprise monitoring the patient for level of administered antibody in the blood of the patient. In other methods, the antibody is administered in multiple dosages over a period of at least six months. In other methods, the antibody is administered as a sustained release composition.

The invention further provides methods of effecting prophylaxis of AA amyloidosis in a patient susceptible to AA amyloidosis. The methods comprise administering to the patient an effective dosage of an antibody that specifically binds to an epitope within residues 70 to 76 of AA. Optionally, the patient is human. Optionally, the antibody specifically binds to a peptide whose residues consist of SEQ ID NOS. 4, 5, 6, 7, 8, 9, 10, or 11. Optionally, the antibody specifically binds to an epitope within residues 70-76 of (SEQ ID NO: 2). In some methods, the patient suffers from an underlying amyloid disease selected from the group consisting of rheumatoid arthritis, juvenile chronic arthritis, ankylosing spondylitis, psoriasis, psoriatic arthropathy, Reiter's syndrome, Adult Still's disease, Behcet's syndrome, Crohn's disease, leprosy, tuberculosis, bronchiectasis, decubitus ulcers, chronic pyelonephritis, osteomyelitis, Whipple's disease, Hodgkin's lymphoma, renal carcinoma, carcinomas of gut, lung and urogenital tract, basal cell carcinoma, hairy cell leukemia, Familial Mediterranean Fever, and Castleman's Disease.

The invention further provides a human, humanized, or chimeric antibody that specifically binds to an epitope within residues 70 to 76 of AA. Optionally, the humanized antibody specifically binds to an epitope within residues 70 to 76 of AA. Optionally, the humanized antibody is a humanized version 7D8 antibody (ATCC Accession Number PTA-9468). Optionally, the humanized antibody is a humanized version 7D29 antibody. Optionally, the humanized antibody is a humanized version 7D19 antibody. Optionally, the humanized antibody is a humanized version 7D47 antibody. Optionally, the humanized antibody is a humanized version 7D39 antibody. Optionally, the humanized antibody is a humanized version 7D66 antibody. Optionally, the humanized antibody is a humanized version 8G9 antibody. Optionally, the humanized antibody is a humanized version 8G3 antibody. Optionally, the humanized antibody is a humanized version 8G4 antibody. Optionally, the humanized antibody is a humanized version 8G51 antibody. Optionally, the humanized antibody is a humanized version 8G22 antibody. Optionally, the humanized antibody is a humanized version 8G30 antibody. Optionally, the humanized antibody is a humanized version 8G46 antibody. Optionally, the humanized antibody is a humanized version 2A4 antibody (ATCC Accession Number PTA-9662). Optionally, the humanized antibody is a humanized version 2A20 antibody. Optionally, the humanized antibody is a humanized version 2A44 antibody. Optionally, the humanized antibody is a humanized version 2A77 antibody. Optionally, the humanized antibody is a humanized version 2A13 antibody. Optionally, the humanized antibody is a humanized version 2A14 antibody.

The invention further provides pharmaceutical compositions. The pharmaceutical compositions comprise an antibody that specifically binds to an epitope within residues 70 to 76 of AA, and a pharmaceutically acceptable carrier. Some pharmaceutical compositions comprise a human, humanized, or chimeric antibody that specifically binds to an epitope within residues 70 to 76 of AA, and a pharmaceutically acceptable carrier. Other pharmaceutical compositions comprise an antibody that specifically binds to an epitope within residues 70 to 76 of AA and a pharmaceutically acceptable carrier, where the isotype of the antibody is human IgG1, and a pharmaceutically acceptable carrier. In some pharmaceutical compositions the isotype of the antibody is human IgG2, IgG3, or IgG4. In some pharmaceutical compositions the antibody is human. In some pharmaceutical compositions the antibody is humanized. In some pharmaceutical compositions the antibody is chimeric. In some pharmaceutical compositions the antibody is a polyclonal antibody. In some pharmaceutical compositions the antibody is a monoclonal antibody.

In some pharmaceutical compositions the antibody comprises two copies of the same pair of light and heavy chains. In some pharmaceutical compositions the antibody is a bispecific antibody comprising a first light and heavy chain pair that specifically binds to the epitope of AA and a second light and heavy chain pair that specifically binds to an Fc receptor on microglial cells. In some pharmaceutical compositions a chain of the antibody is fused to a heterologous polypeptide. In some pharmaceutical compositions the carrier is a physiologically acceptable diluent for parenteral administration. Some pharmaceutical compositions are adapted to be administered intraperitoneally, orally, intranasally, subcutaneously, intramuscularly, topically or intravenously. Some pharmaceutical compositions are adapted to be administered in multiple dosages over a period of at least six months. Some pharmaceutical compositions are adapted to be administered as a sustained release composition. Some pharmaceutical compositions further comprise at least one other antibody that binds to a different epitope of AA.

The invention provides methods of treating AA amyloidosis in a patient. The methods comprise administering an agent that induces an immune response to AA70-76 in a regime effective to induce an immune response comprising antibodies against AA70-76 in a regime effective to induce an immune response comprising antibodies against AA70-76. In some methods the patient is human. Optionally, the agent comprises AA70-76 or a subfragment of at least 3 contiguous residues thereof and has fewer than 20 contiguous amino acids from an AA peptide. Optionally, the agent is a peptide having a sequence selected from the group consisting of SEQ ID NOS 4, 5, 6, 7, 8, 9, 10 and 11. and subfragments of at least 3 contiguous residues thereof and has fewer than 20 amino acids from an AA peptide. Optionally, the agent is linked at its N and C termini to first and second heterologous polypeptides. Optionally, the agent is linked at its N terminus to a heterologous polypeptide, and at its C-terminus to at least one additional copy of the N-terminal segment. In some methods the heterologous polypeptide induces a T-cell response against the heterologous polypeptide and thereby a B-cell response against AA. In some methods the polypeptide further comprises at least one additional copy of AA. Optionally, the polypeptide comprises from N-terminus to C-terminus, AA, a plurality of additional copies of AA, and the heterologous amino acid segment.

In some treatment methods the polypeptide is administered with an adjuvant that enhances an immune response to the N-terminal segment. Optionally, the adjuvant and the polypeptide are administered together as a composition. Optionally, the adjuvant is administered before the polypeptide. Optionally, the adjuvant is administered after the polypeptide. In some methods the adjuvant is alum. In some methods the adjuvant is MPL. In some methods the adjuvant is QS-21. In some methods the adjuvant is incomplete Freund's adjuvant. In some methods the immune response comprises T-cells that bind to the AA peptide as a component of an MHC I or MHC II complex.

The invention provides methods of effecting prophylaxis of AA amyloidosis in a patient. The methods comprise administering an agent that induces an immune response to AA70-76 in a regime effective to induce an immune response comprising antibodies against AA70-76 in a regime effective to induce an immune response comprising antibodies against AA70-76. In some methods the patient is human. In some methods the patient is asymptomatic. In some methods the patient suffers from an underlying amyloid disease selected from the group consisting of rheumatoid arthritis, juvenile chronic arthritis, ankylosing spondylitis, psoriasis, psoriatic arthropathy, Reiter's syndrome, Adult Still's disease, Behcet's syndrome, Crohn's disease, leprosy, tuberculosis, bronchiectasis, decubitus ulcers, chronic pyelonephritis, osteomyelitis, Whipple's disease, Hodgkin's lymphoma, renal carcinoma, carcinomas of gut, lung and urogenital tract, basal cell carcinoma, hairy cell leukemia, Familial Mediterranean Fever, and Castleman's Disease.

In some methods of effecting prohylaxis, the agent comprises AA70-76 or a subfragment of at least 3 contiguous residues thereof and has fewer than 20 contiguous amino acids from an AA peptide. Optionally, the agent is a peptide having a sequence selected from the group consisting of SEQ ID NOS 4, 5, 6, 7, 8, 9, 10 and 11. and subfragments of at least 3 contiguous residues thereof and has fewer than 20 amino acids from an AA peptide. Optionally, the agent is linked at its N and C termini to first and second heterologous polypeptides. Optionally, the agent is linked at its N terminus to a heterologous polypeptide, and at its C-terminus to at least one additional copy of the N-terminal segment. In some methods the heterologous polypeptide induces a T-cell response against the heterologous polypeptide and thereby a B-cell response against AA. In some methods the polypeptide further comprises at least one additional copy of AA. Optionally, the polypeptide comprises from N-terminus to C-terminus, AA, a plurality of additional copies of AA, and the heterologous amino acid segment.

The invention further provides pharmaceutical compositions. The pharmaceutical compositions comprise an AA fragment consisting of residues beginning at residue 70 of AA and ending at residue 76 of AA. Optionally, the AA fragment is linked at its C-terminus to a heterologous polypeptide. Optionally, the AA fragment is linked at its N-terminus to a heterologous polypeptide. Optionally, the AA fragment is linked at its N and C termini to first and second heterologous polypeptides. Optionally, the AA fragment is linked at its N terminus to a heterologous polypeptide, and at its C-terminus to at least one additional copy of the N-terminal segment. Optionally, the polypeptide further comprises at least one additional copy of the N-terminal segment. Optionally, the polypeptide comprises from N-terminus to C-terminus, AA, a plurality of additional copies of the N-terminal segment, and the heterologous amino acid segment. In some pharmaceutical compositions the heterologous polypeptide induces a T-cell response against the heterologous polypeptide and thereby a B-cell response against the N-terminal segment.

Some pharmaceutical compositions further comprise an adjuvant that enhances an immune response to AA. Optionally, the adjuvant is alum. Optionally, the adjuvant is MPL. Optionally, the adjuvant is QS-21. Optionally, the adjuvant is incomplete Freund's adjuvant. Optionally, the adjuvant further comprises GM-CSF. Optionally, the adjuvant is M-CSF. Optionally, the composition comprises greater than 10 micrograms of the polypeptide.

The invention provides methods of treating AA amyloidosis in a patient. The methods comprise administering an agent effective to induce an immune response against a peptide component of an amyloid deposit in the patient and a different agent that treats an underlying disease, and thereby treating AA amyloidosis in the patient. In some methods the underlying disease is selected from the group consisting of rheumatoid arthritis, juvenile chronic arthritis, ankylosing spondylitis, psoriasis, psoriatic arthropathy, Reiter's syndrome, Adult Still's disease, Behcet's syndrome, Crohn's disease, leprosy, tuberculosis, bronchiectasis, decubitus ulcers, chronic pyelonephritis, osteomyelitis, Whipple's disease, Hodgkin's lymphoma, renal carcinoma, carcinomas of gut, lung and urogenital tract, basal cell carcinoma, hairy cell leukemia, Familial Mediterranean Fever, and Castleman's Disease.

The invention provides methods of effecting prophylaxis of AA amyloidosis in a patient. The methods comprise administering an agent effective to induce an immune response against a peptide component of an amyloid deposit in the patient and a different agent that treats an underlying disease, and thereby treating AA amyloidosis in the patient. In some methods the underlying disease is selected from the group consisting of rheumatoid arthritis, juvenile chronic arthritis, ankylosing spondylitis, psoriasis, psoriatic arthropathy, Reiter's syndrome, Adult Still's disease, Behcet's syndrome, Crohn's disease, leprosy, tuberculosis, bronchiectasis, decubitus ulcers, chronic pyelonephritis, osteomyelitis, Whipple's disease, Hodgkin's lymphoma, renal carcinoma, carcinomas of gut, lung and urogenital tract, basal cell carcinoma, hairy cell leukemia, Familial Mediterranean Fever, and Castleman's Disease.

The invention provides methods of screening an antibody for activity in treating a patient having AA amyloidosis. The methods comprise contacting the antibody with AA peptide and determining whether the antibody specifically binds to AA, specific binding providing an indication that the antibody has activity in treating AA amyloidosis.

The invention provides methods of screening an antibody for activity in clearing a biological entity physically associated with an antigen. The methods comprise combining the antigen-associated biological entity, the antibody and phagocytic cells bearing Fc receptors in a medium; and monitoring the amount of the antigen-associated biological entity remaining in the medium, a reduction in amount of the antigen-associated biological entity indicating the antibody has clearing activity against the antigen. In some methods the monitoring step monitors the amount of the antigen remaining in the medium. In some methods the combining comprises adding antigen-associated biological entity to the medium, and contacting the medium with the phagocytic cells bearing Fc receptors. In some methods the antigen-associated biological entity is provided as a tissue sample. In some methods the antigen is the biological entity. In some methods the tissue sample comprises an amyloid deposit. Optionally, the tissue sample is from the patient or a mammal having AA Amyloidosis pathology. In some methods, the antigen is AA. In some methods the phagocytic cells are microglial cells. In some methods the tissue sample is selected from the group consisting of a cancerous tissue sample, a virally infected tissue sample, a tissue sample comprising inflammatory cells, a nonmalignant abnormal cell growth, and a tissue sample comprising an abnormal extracellular matrix.

The invention provides methods of detecting an amyloid deposit in a patient. The methods comprise administering to the patient an antibody that specifically binds to an epitope within amino acids 70-76 of AA and detecting presence of the antibody in the patient. Optionally, the antibody is labeled. Optionally, the antibody is labeled with a paramagnetic label. Optionally, the labeled antibody is detected by nuclear magnetic resonance. Optionally, the labeled antibody is detected with SPECT/CT imaging. In some methods, the antibody lacks capacity to induce a clearance response on binding to an amyloid deposit in the patient.

The invention provides diagnostic kits. The kits comprise an antibody that specifically binds to an epitope with residues 70-76 of AA. Some kits further comprise labeling describing use of the antibody for in vivo diagnosis or monitoring of a disease associated with amyloid deposits of AA in a patient. In some embodiments, the kits include instructions for use of the antibody or antigen-binding fragment thereof in detecting AA.

The invention further provides a method of diagnosing amyloidosis in a subject comprising: (a) administering to the subject an antibody or antigen-binding fragment thereof that is bound to a detectable label, wherein the antibody or fragment thereof specifically binds to an epitope comprising $X_1EDX_2$ in an aggregated amyloid protein, wherein $X_1$ and $X_2$ are any amino acid; and (b) detecting the presence or absence of the bound antibody or fragment thereof, wherein the presence of the bound antibody or fragment indicates a diagnosis of AA amyloidosis.

Further provided herein is a method of treatment or prophylaxis of amyloidosis using an antibody or antigen-binding fragment thereof, which specifically binds to an epitope comprising $X_1EDX_2$ in an aggregated amyloid protein, wherein $X_1$ and $X_2$ are any amino acid.

The present invention provides an antibody or antigen-binding fragment thereof that binds specifically to an epitope comprising $X_1EDX_2$, in an aggregated amyloid protein, wherein $X_1$ and $X_2$ are any amino acid. For example, $X_1$ includes H, T, F, S, P, A, L, C, Q, R, E, K, D, G, V, Y, I or W, such as H, T, F, S, P, or A, or such as H, T, F, or A. $X_2$ includes T, S, E, R, I, V, F, D, A, G, M, L, N, P, C, K, Y, or Q, such as T, S, E, R, I, V, F, D, or A, or such as T, S, E, D, or A. In other examples, $X_1$ is H, T, or A and $X_2$ is T, S, E, or A, such as $X_1$ is H or A and $X_2$ is T, S, or A. In yet additional examples, $X_1$ is H and H$_2$ is T or A; or $X_1$ is A and $X_2$ is S, T, E, or V, such as $X_1$ is A and $X_2$ is S, T, or E, or $X_1$ is T and $X_2$ is E, or $X_1$ is F and $X_2$ is D, or $X_1$ is S and $X_2$ is E, F, or A; or $X_1$ is P and $X_2$ is E, I, or F.

In particular, the epitopes include amino acid sequences such as those set forth in SEQ ID NO: 3 through to SEQ ID NO: 25, such as SEQ ID NOS: 3, 12, 13, 14, 15, and 16. Additional examples include SEQ ID NOS: 4, 5, 7, 8, and 9, such as SEQ ID NO: 4. Antibodies of the invention that bind to the epitopes, such as to SEQ ID NO: 3, include the 2A4, 7D8, and 8G9 antibodies.

The aggregated amyloid proteins to which antibodies of the invention bind are non-monomeric proteins. Such aggregated amyloid proteins include serum amyloid A protein (SAA), immunoglobulin light chain protein, human islet amyloid precursor polypeptide (LAPP), beta amyloid peptide, transthyretin (TTR), and ApoA1, such as SAA.

The invention further provides antibodies or antigen-binding fragments thereof that (a) compete for binding to an epitope that includes $X_1EDX_2$ with a 2A4, 7D8, or 8G9 antibody; (b) bind to the same epitope that includes $X_1EDX_2$ as a 2A4, 7D8, or 8G9 antibody; (c) have an antigen-binding domain of a 2A4, 7D8, or 8G9 antibody; or (d) include the six complementarity determining regions (CDRs) of a 2A4, 7D8, or 8G9 antibody. The invention also provides chimeric or humanized versions of a 2A4, 7D8, or 8G9 antibody.

Representative antibodies, which specifically bind to an epitope that includes $X_1EDX_2$, also include antibodies having at least one, two, or three of the complementarity determining regions (CDRs) of a light chain of a 2A4, 7D8 or 8G9 antibody. Antibodies of the invention, which specifically bind to an epitope that includes $X_1EDX_2$, also include antibodies having at least one, two, or three of the CDRs of a heavy chain of a 2A4, 7D8, or 8G9 antibody.

CDRs can be identified according to methods known in the art. For example, numbering systems for identifying CDRs are in common use. The Kabat definition is based on sequence variability, and the Chothia definition is based on the location of the structural loop regions. The AbM definition is a compromise between the Kabat and Chothia approaches. The CDRs of the light chain variable region are bounded by the residues at positions 24 and 34 (CDR1-L), 50 and 56 (CDR2-L), and 89 and 97 (CDR3-L) according to the Kabat, Chothia, or AbM algorithm. According to the Kabat definition, the CDRs of the heavy chain variable region are bounded by the residues at positions 31 and 35B (CDR1-H), 50 and 65 (CDR2-H), and 95 and 102 (CDR3-H) (numbering according to Kabat). According to the Chothia definition, the CDRs of the heavy chain variable region are bounded by the residues at positions 26 and 32 (CDR1-H), 52 and 56 (CDR2-H), and 95 and 102 (CDR3-H) (numbering according to Chothia). According to the AbM definition, the CDRs of the heavy chain variable region are bounded by the residues at positions 26 and 35B (CDR1-H), 50 and 58 (CDR2-H), and 95 and 102 (CDR3-H) (numbering according to Kabat). See Martin et al. (1989) *Proc. Natl. Acad. Sci. USA* 86: 9268-9272; Martin et al. (1991) *Methods Enzymol.* 203: 121-153; Pedersen et al. (1992) *Immunomethods* 1: 126; and Rees et al: (1996) In Sternberg M. J. E. (ed.), *Protein Structure Prediction*, Oxford University Press, Oxford, pp. 141-172.

The antibodies of the invention further include an antibody that binds specifically to an epitope comprising $X_1EDX_2$, in an aggregated amyloid protein, wherein $X_1$ and $X_2$ are any amino acid, having variable regions derived from variable regions of a 2A4, 7D8, or 8G9 antibody. Antibodies having variable regions of 2A4, 7D8, or 8G9 antibodies are also included.

The antibodies of the invention further include chimeric antibodies, human antibodies, humanized antibodies, single chain antibodies, tetrameric antibodies, tetravalent antibodies, multispecific antibodies domain-specific antibodies, domain-deleted antibodies or fusion proteins.

Fragments of the antibodies of the invention are also provided. The fragments of the invention may be Fab fragments, Fab' fragment, F(ab')$_2$ fragments, Fv fragments or ScFv fragments. Such antibodies or fragments thereof can be coupled with a cytotoxic agent, a radiotherapeutic agent, or a detectable label.

The invention also provides an isolated antibody variable region comprising (a) a light chain variable region derived from a 7D8, 2A4, or 8G9 antibody light chain variable region, or (b) a heavy chain variable region derived from a 7D8, 2A4, or 8G9 antibody light chain variable region. Isolated variable regions are also provided having a light chain or heavy chain variable region of a 7D8, 2A4, or 8G9 antibody. The isolated antibody variable regions are useful in antibody production.

The invention also provides isolated nucleic acids encoding an antibody light chain variable region or a heavy chain variable region having (a) a nucleotide sequence that encodes a light chain or heavy chain variable region of a 7D8, 2A4, or 8G9 antibody; (b) a nucleotide sequence that is identical to a nucleotide sequence of a 7D8, a 2A4, or an 8G9 antibody that encodes a light or heavy chain variable region; or (c) a nucleotide sequence that is substantially identical, i.e., at least 50%, 55%, 60%, 65%, 70%, 75%, 80%, 85%, 87%, 88%, 89%, 90%, 91%, 92%, 93%, 94%, 95%, 96%, 97%, 98%, 99%, 99.5%, or 99% to a nucleotide sequence of (a) or (b); or (d) a nucleic acid that specifically hybridizes to a nucleic acid having a nucleotide sequence that is the complement of a nucleotide sequence of (a) or (b) under stringent hybridization conditions, for example, final wash conditions of 0.1× SSC at 65° C.

The present invention further provides cells and cell lines expressing the antibodies or nucleic acids of the invention. Representative host cells include mammalian and human cells, such as CHO cells, HEK-293 cells, HeLa cells, CV-1 cells, and COS cells. Methods for generating a stable cell line following transformation of a heterologous construct into a host cell are known in the art. Representative non-mammalian host cells include insect cells (Potter et al. (1993) *Int. Rev. Immunol.* 10(2-3):103-112). Antibodies may also be produced in transgenic animals (Houdebine (2002) *Curr. Opin. Biotechnol.* 13(6):625-629) and transgenic plants (Schillberg et al. (2003) *Cell Mol. Life. Sci.* 60(3):433-45).

The invention also provides methods of treating or effecting prophylaxis of amyloidosis associated using immunogenic fragments of an amyloid protein comprising $X_1EDX_2$, wherein $X_1$ is H, T, F, S, P, A or any other amino acid residue immediately preceding ED in such amyloid protein; and wherein $X_2$ is T, S, E, R, I, V, F, A or any other amino acid residue immediately following ED in such amyloid protein. Without wishing to be bound by a particular theory, it is believed that an epitope comprising $X_1EDX_2$ can become exposed when an amyloid protein aggregates, or undergoes fibrillogenesis or otherwise enters a fibrillar structure, whether by cleavage from a larger precursor protein or by conformational change. For example, representative methods of treatment or prophylaxis of AA amyloidosis include administration of AA 70-76 fragments or immunogenic fragments thereof. The invention also provides methods of treating or effecting prophylaxis of amyloidosis associated with deposition of amyloid protein using antibodies reactive with $X_1EDX_2$ in an aggregated amyloid protein, wherein $X_1$ is H, T, F, S, P, A or any other amino acid residue immediately preceding ED in such aggregated amyloid protein; and wherein $X_2$ is T, S, E, R, I, V, F, A or any other amino acid residue immediately following ED in such aggregated amyloid protein. Preferably, such antibodies are preferentially reactive with aggregated amyloid protein relative to non-pathological amyloid protein. For example, methods of treatment or prophylaxis of AA amyloidosis associated with AA fibrils may include administration of antibodies specific for C-terminal region of AA fibrils (residues 70-76 of AA). The antibodies can inhibit formation of AA aggregates (e.g., fibrils) or result in their disaggregation and clearance, thus treating or effecting prophylaxis of AA amyloidosis.

I. Definitions

The term "substantial identity" means that two peptide sequences, when optimally aligned, such as by the programs GAP or BESTFIT using default gap weights, share at least 65 percent sequence identity, preferably at least 80 or 90 percent sequence identity, more preferably at least 95 percent sequence identity or more (e.g., 99 percent sequence identity or higher). Preferably, residue positions, which are not identical differ by conservative amino acid substitutions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra). One example of algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (http://www.ncbi.nlm.nih.gov/). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89, 10915 (1989))

For purposes of classifying amino acids substitutions as conservative or nonconservative, amino acids are grouped as follows: Group I (hydrophobic sidechains): norleucine, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

The term "all-D" refers to peptides having 75%, 80%, 85%, 90%, 95%, and 100% D-configuration amino acids.

The term "agent" is used to describe a compound that has or may have a pharmacological activity. Agents include compounds that are known drugs, compounds for which pharmacological activity has been identified but which are undergoing further therapeutic evaluation, and compounds that are members of collections and libraries that are to be screened for a pharmacological activity.

"Amyloid disease" or "amyloidosis" refers to any number of disorders which have as a symptom or as part of its pathology the accumulation or formation of amyloid plaques. An "amyloid plaque" is an extracellular deposit composed mainly of proteinaceous fibrils. Generally, the fibrils are composed of a dominant protein or peptide; however, the plaque may also include additional components that are peptide or non-peptide molecules, as described herein.

An "amyloid protein" or "amyloid peptide" is a protein or peptide capable of undergoing cleavage, conformational change, aggregation or fibrillogenesis, resulting in the formation of pathological oligomers, amyloid fibrils, amyloid plaques and/or amyloid components.

An "amyloid component" is any molecular entity that is present in an amyloid plaque including antigenic portions of such molecules. Amyloid components include but are not limited to proteins, peptides, proteoglycans, and carbohydrates.

An "anti-amyloid agent" is an agent which is capable of producing an immune response against an amyloid plaque component in a vertebrate subject, when administered by active or passive immunization techniques.

An "AA protein" or "AA peptide" refers to the form of amyloid protein A protein or peptide formed by proteolytic cleavage of serum amyloid A protein (SAA), whether monomeric or aggregated, soluble or insoluble.

An "aggregated amyloid protein" or "aggregated amyloid peptide" or "amyloid aggregate" refers to a pathological, non-monomeric, aggregated form of an amyloid protein or amyloid peptide. Aggregated amyloid proteins and amyloid peptides can be soluble or insoluble. Some aggregated amyloid proteins and aggregated amyloid peptides can form oligomers, fibrils and/or amyloid plaques. Examples of such aggregated amyloid proteins and amyloid peptides, including fibril peptides and proteins are provided herein.

An "AA aggregate" refers to an aggregated form of AA.

Therapeutic agents of the invention are typically substantially pure from undesired contaminant. This means that an agent is typically at least about 50% w/w (weight/weight) purity, as well as being substantially free from interfering proteins and contaminants. Sometimes the agents are at least about 80% w/w and, more preferably at least 90 or about 95% w/w purity. However, using conventional protein purification techniques, homogeneous peptides of at least 99% w/w can be obtained. Therapeutic agents of the invention may prevent, effect prophylaxis of, or treat a disease associated with amyloid deposits.

Specific binding between two entities means the entities have a mutual affinity for each other that is at least 10-, 100- or 100-fold greater than the affinity of either entity for a control, such as unrelated antigen or antibody to a different antigen. The mutual affinity of the two entities for each other is usually at least $10^7$ $M^{-1}$, $10^8$ $M^{-1}$, $10^9$ $M^{-1}$, or $10^{10}$ $M^{-1}$. Affinities greater than $10^8$ $M^{-1}$ are preferred.

The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. "Constant" domains on the light chain are referred to interchangeably as "light chain constant regions", "light chain constant domains", "CL" regions or "CL" domains. "Constant" domains on the heavy chain are referred to interchangeably as "heavy chain constant regions", "heavy chain constant domains", "CH" regions or "CH" domains. "Variable" domains on the light chain are referred to interchangeably as "light chain variable regions", "light chain variable domains", "VL" regions or "VL" domains. "Variable" domains on the heavy chain are referred to interchangeably as "heavy chain constant regions", "heavy chain constant domains", "CH" regions or "CH" domains.

The term "region" refers to a part or portion of an antibody chain and includes constant or variable domains as defined herein, as well as more discrete parts or portions of said domains. For example, light chain variable domains or regions include "complementarity determining regions" or "CDRs" interspersed among "framework regions" or "FRs", as defined herein.

Immunoglobulins or antibodies can exist in monomeric or polymeric form. The term "antigen-binding fragment" refers to a polypeptide fragment of an immunoglobulin or antibody binds antigen or competes with intact antibody (i.e., with the intact antibody from which they were derived) for antigen binding (i.e., specific binding). The term "conformation" refers to the tertiary structure of a protein or polypeptide (e.g., an antibody, antibody chain, domain or region thereof). For example, the phrase "light (or heavy) chain conformation" refers to the tertiary structure of a light (or heavy) chain variable region, and the phrase "antibody conformation" or "antibody fragment conformation" refers to the tertiary structure of an antibody or fragment thereof.

"Specific binding" of an antibody mean that the antibody exhibits appreciable affinity for antigen or a preferred epitope and, preferably, does not exhibit significant crossreactivity. "Appreciable" or preferred binding include binding with an affinity of at least $10^6$, $10^7$, $10^8$, $10^9$ $M^{-1}$, or $10^{10}$ $M^{-1}$. Affinities greater than $10^7$ $M^{-1}$, preferably greater than $10^8$ $M^{-1}$ are more preferred. Values intermediate of those set forth herein are also intended to be within the scope of the present invention and a preferred binding affinity can be indicated as a range of affinities, for example, $10^6$ to $10^{10}$ $M^{-1}$, preferably $10^7$ to $10^{10}$ $M^{-1}$, more preferably $10^8$ to $10^{10}$ $M^{-1}$. An antibody that "does not exhibit significant crossreactivity" is one that will not appreciably bind to an undesirable entity (e.g., an undesirable proteinaceous entity). For example, an antibody that specifically binds to AA will appreciably bind AA but will not significantly react with non-AA proteins or peptides (e.g., non-AA proteins or peptides included in plaques). An antibody specific for a preferred epitope will, for example, not significantly crossreact with remote epitopes on the same protein or peptide. Specific binding can be determined according to any art-recognized means for determining such binding. Preferably, specific binding is determined according to Scatchard analysis and/or competitive binding assays.

Antigen-binding antibody fragments are produced by recombinant DNA techniques, or by enzymatic or chemical cleavage of intact immunoglobulins. Binding fragments include Fab, Fab', F(ab')$_2$, Fabc, Fv, single chains, and single-chain antibodies. Additional antibody fragments and effector function variants are disussed herein in the section entitled "Antibodies". Other than "bispecific" or "bifunctional"

immunoglobulins or antibodies, an immunoglobulin or antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

The phrase "substantially from a human immunoglobulin or antibody" or "substantially human" means that, when aligned to a human immunoglobulin or antibody amino sequence for comparison purposes, the region shares at least 80-90%, preferably 90-95%, more preferably 95-99% identity (i.e., local sequence identity) with the human framework or constant region sequence, allowing, for example, for conservative substitutions, consensus sequence substitutions, germline substitutions, backmutations, and the like. The introduction of conservative substitutions, consensus sequence substitutions, germline substitutions, backmutations, and the like, is often referred to as "optimization" of a humanized antibody or chain. The phrase "substantially from a non-human immunoglobulin or antibody" or "substantially non-human" means having an immunoglobulin or antibody sequence at least 80-95%, preferably 90-95%, more preferably, 96%, 97%, 98%, or 99% identical to that of a non-human organism, e.g., a non-human mammal.

Accordingly, all regions or residues of a humanized immunoglobulin or antibody, or of a humanized immunoglobulin or antibody chain, except possibly the CDRs, are substantially identical to the corresponding regions or residues of one or more native human immunoglobulin sequences. The term "corresponding region" or "corresponding residue" refers to a region or residue on a second amino acid or nucleotide sequence which occupies the same (i.e., equivalent) position as a region or residue on a first amino acid or nucleotide sequence, when the first and second sequences are optimally aligned for comparison purposes.

The terms "humanized immunoglobulin" or "humanized antibody" are not intended to encompass chimeric immunoglobulins or antibodies, as defined infra. Although humanized immunoglobulins or antibodies are chimeric in their construction (i.e., comprise regions from more than one species of protein), they include additional features (i.e., variable regions comprising donor CDR residues and acceptor framework residues) not found in chimeric immunoglobulins or antibodies, as defined herein.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species.

An "antigen" is an entity (e.g., a protenaceous entity or peptide) to which an antibody specifically binds.

The term "epitope" or "antigenic determinant" refers to a site on an antigen to which an immunoglobulin or antibody (or antigen binding fragment thereof) specifically binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation: Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, G. E. Morris, Ed. (1996).

Representative antibodies of the invention include an antibody or fragment thereof that specifically binds to an epitope that includes $X_1EDX_2$ in an aggregated amyloid protein, which binds to the epitope including $X_1EDX_2$ that is also bound by e.g. a 2A4, 7D8, or 8G9 antibody. Antibodies that recognize the same epitope can be identified in a simple immunoassay showing the ability of one antibody to block the binding of another antibody to a target antigen, i.e., a competitive binding assay. Competitive binding is determined in an assay in which the immunoglobulin under test inhibits specific binding of a reference antibody to a common antigen, such as Aβ. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

An epitope is also recognized by immunologic cells, for example, B cells and/or T cells. Cellular recognition of an epitope can be determined by in vitro assays that measure antigen-dependent proliferation, as determined by $^3$H-thymidine incorporation, by cytokine secretion, by antibody secretion, or by antigen-dependent killing (cytotoxic T lymphocyte assay).

The term "neoepitope" refers to a new and/or unique site on an antigen to which B and/or T cells respond.

The term "neoepitope antibodies" refer to antibodies that specifically recognize a new N- or C-terminal amino acid sequence exposed by proteolytic cleavage of a molecule, but does not bind to such an epitope on the native (uncleaved) molecule. The term "neoepitope antibodies" may refer to antibodies that specifically recognize a new N- or C-terminal amino acid sequence exposed by proteolytic cleavage of SAA, but do not bind to such an epitope on the native (uncleaved) SAA molecule. Some neoepitope antibodies bind to either soluble or insoluble AA and result in dissociation of AA aggregates, including AA fibrils. A "neoepitope antibody" may also be an antibody that specifically recognizes a new epitope that is only available to bind to an antibody after a protein undergoes a conformation change, for example, as in the case of AL amyloidosis and light chain, when only the light chain is expressed and forms amyloid.

The term "immunological" or "immune" response is the development of a beneficial humoral (antibody mediated) and/or a cellular (mediated by antigen-specific T cells or their secretion products) response directed against an amyloid peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific CD4$^+$ T helper cells and/or CD8$^+$ cytotoxic T cells. The response may also involve activation of monocytes, macrophages, NK cells, basophils, dendritic cells, astrocytes, microglia cells, eosinophils or other components of innate immunity. The presence of a cell-mediated immunological response can be determined by proliferation assays (CD4$^+$ T cells) or CTL (cytotoxic T lymphocyte) assays (see Burke, supra; Tigges, supra). The relative contributions of humoral and cellular responses to the protective or therapeutic effect of an immunogen can be distinguished by separately isolating antibodies and T-cells from an immunized syngeneic animal and measuring protective or therapeutic effect in a second subject.

An "immunogenic agent" or "immunogen" is capable of inducing an immunological response against itself on administration to a mammal, optionally in conjunction with an adjuvant.

The term "naked polynucleotide" refers to a polynucleotide not complexed with colloidal materials. Naked polynucleotides are sometimes cloned in a plasmid vector.

The term "adjuvant" refers to a compound that when administered in conjunction with an antigen augments the immune response to the antigen, but when administered alone does not generate an immune response to the antigen. Adjuvants can augment an immune response by several mechanisms including lymphocyte recruitment, stimulation of B and/or T cells, and stimulation of macrophages.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the infection and the general state of the patient's own immune system.

The term "patient" includes human and other mammalian subjects that receive either prophylactic or therapeutic treatment.

The invention provides antibodies or antigen-binding fragments thereof that specifically bind to an epitope that includes $X_1EDX_2$ in an aggregated amyloid protein, and which competes for binding to the epitope comprising $X_1EDX_2$ with e.g., a 2A4, 7D8, or 8G9 antibody. Competition between antibodies is determined by an assay in which the immunoglobulin under test inhibits specific binding of a reference antibody to a common antigen, such as AA. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology*, 9:242-253 (1983)); solid phase direct biotin-avidin EIA (see Kirkland et al., *J. Immunol.* 137:3614-3619 (1986)); solid phase direct labeled assay, solid phase direct labeled sandwich assay (see Harlow and Lane, "*Antibodies, A Laboratory Manual*," Cold Spring Harbor Press (1988)); solid phase direct label RIA using 1-125 label (see Morel et al., *Molec. Immunol.* 25(1):7-15 (1988)); solid phase direct biotin-avidin EIA (Cheung et al., *Virology,* 176:546-552 (1990)); and direct labeled RIA (Moldenhauer et al., *Scand. J. Immunol.*, 32:77-82 (1990)). Typically, such an assay involves the use of purified antigen bound to a solid surface or cells expressing the antigen, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50% to 75%.

An antibody that specifically binds to an amyloid protein means an antibody that binds to the amyloid protein with an affinity of at least $10^7$ M$^{-1}$. Some antibodies bind to the amyloid protein with affinities between $10^8$ M$^{-1}$ and $10^{11}$ M$^{-1}$.

An antibody that specifically binds to aggregated amyloid protein such as aggregated AA without specifically binding to monomeric amyloid protein means an antibody that binds to aggregated amyloid protein, such as, for example fibrils (e.g., AA in aggregated β-pleated sheet form such as from a cadaver of a former AA Amyloidosis patient or a transgenic animal model) as described above and has at least a ten fold and usually at least 100-fold lower specific binding affinity for monomeric forms of the amyloid protein. For example, such an antibody might bind to soluble AA with an affinity of $10^9$ M$^{-1}$ and to plaques with an affinity less than $10^7$ M$^{-1}$. The affinity of such antibodies for plaques is usually less than $10^7$ or $10^6$ M$^{-1}$. Such antibodies are additionally or alternatively defined by fluorescence intensity relative to an irrelevant control antibody (e.g., an antibody or mixture of polyclonal antibodies to a reversemer AA peptide) when the antibodies are contacted with fibrils and binding assessed by fluorescently labeling. The fluorescence intensity of antibodies that bind to soluble AA peptide without binding to plaques is within a factor of five, sometimes within a factor of two and sometimes indistinguishable within experimental error from that of the control antibody.

Compositions or methods "comprising" one or more recited elements may include other elements not specifically recited. For example, a composition that comprises AA peptide encompasses both an isolated AA peptide and AA peptide as a component of a larger polypeptide sequence.

II. Amyloid Diseases

1. Overview and Pathogenesis

Amyloid diseases or amyloidoses include a number of disease states having a wide variety of outward symptoms. These disorders have in common the presence of abnormal extracellular deposits of protein fibrils, known as "amyloid deposits" or "amyloid plaques" that are usually about 10-100 μm in diameter and are localized to specific organs or tissue regions. Such plaques are composed primarily of a naturally occurring soluble protein or peptide. These insoluble deposits are composed of generally lateral aggregates of fibrils that are approximately 10-15 nm in diameter. Amyloid fibrils produce a characteristic apple green birefringence in polarized light, when stained with Congo Red dye. The disorders are classified on the basis of the major fibril components forming the plaque deposits, as discussed below.

The peptides or proteins forming the plaque deposits are often produced from a larger precursor protein. More specifically, the pathogenesis of amyloid fibril deposits generally involves proteolytic cleavage of an "abnormal" precursor protein into fragments. These fragments generally aggregate into anti-parallel β pleated sheets; however, certain undegraded forms of precursor protein have been reported to aggregate and form fibrils in familial amyloid polyneuropathy (variant transthyretin fibrils) and dialysis-related amyloidosis ($\beta_2$ microglobulin fibrils) (Tan, et al., 1994, supra).

2. Clinical Syndromes

This section provides descriptions of major types of amyloidoses, including their characteristic plaque fibril compositions. It is a general discovery of the present invention that amyloid diseases can be treated by administering agents that serve to stimulate an immune response against a component or components of the various disease-specific amyloid deposits. As discussed in more detail in Section C below, such components are preferably constituents of the fibrils that form the plaques. The sections below serve to exemplify major forms of amyloidosis and are not intended to limit the invention.

a. AL Amyloidoses

AL amyloid deposition is generally associated with almost any dyscrasia of the B lymphocyte lineage, ranging from malignancy of plasma cells (multiple myeloma) to benign monoclonal gammopathy. At times, the presence of amyloid deposits may be a primary indicator of the underlying dyscrasia.

Fibrils of AL amyloid deposits are composed of monoclonal immunoglobulin light chains or fragments thereof. More specifically, the fragments are derived from the N-terminal region of the light chain (kappa or lambda) and contain all or part of the variable ($V_L$) domain thereof. Deposits generally occur in the mesenchymal tissues, causing peripheral and autonomic neuropathy, carpal tunnel syndrome, macroglossia, restrictive cardiomyopathy, arthropathy of large joints, immune dyscrasias, myelomas, as well as occult dyscrasias. However, it should be noted that almost any tissue, particularly visceral organs such as the heart, may be involved.

b. Hereditary Systemic Amyloidoses

There are many forms of hereditary systemic amyloidoses. Although they are relatively rare conditions, adult onset of symptoms and their inheritance patterns (usually autosomal dominant) lead to persistence of such disorders in the general population. Generally, the syndromes are attributable to point mutations in the precursor protein leading to production of variant amyloidogenic peptides or proteins. Table 2 summarizes the fibril composition of exemplary forms of these disorders.

TABLE 2

Hereditary Amyloidoses[a]

| Fibril Peptide/Protein | Genetic variant | Clinical Syndrome |
|---|---|---|
| Transthyretin and fragments (ATTR) | Met30, many others | Familial amyloid polyneuropathy (FAP), (mainly peripheral nerves) |
| Transthyretin and fragments (ATTR) | Thr45, Ala60, Ser84, Met111, Ile122 | Cardiac involvement predominant without neuropathy |
| N-terminal fragment of Apolipoprotein A1 (apoAI) | Arg 26 | Familial amyloid polyneuropathy (FAP), (mainly peripheral nerves) |
| N-terminal fragment of Apolipoprotein A1 (AapoAI) | Arg26, Arg50, Arg 60, others | Ostertag-type, non-neuropathic (predominantly visceral involvement) |
| Lysozyme (Alys) | Thr56, His67 | Ostertag-type, non-neuropathic (predominantly visceral involvement) |
| Fibrogen α chain fragment | Leu554, Val 526 | Ostertag-type, non-neuropathic (predominantly visceral involvement) |
| Gelsolin fragment (Agel) | Asn187, Tyr187 | Cranial neuropathy with lattice corneal dystrophy |
| Cystatin C fragment | Glu68 | Hereditary cerebral hemorrhage (cerebral amyloid angiopathy) - Icelandic type |
| β-amyloid protein (Aβ) derived from Amyloid Precursor Protein (APP) | Gln693 | Hereditary cerebral hemorrhage (cerebral amyloid angiopathy) - Dutch type |
| β-amyloid protein (Aβ) derived from Amyloid Precursor Protein (APP) | Ile717, Phe717, Gly717 | Familial Alzheimer's Disease |

TABLE 2-continued

Hereditary Amyloidoses[a]

| Fibril Peptide/Protein | Genetic variant | Clinical Syndrome |
|---|---|---|
| β-amyloid protein (Aβ) derived from Amyloid Precursor Protein (APP) | Asn670, Leu671 | Familial Dementia - probable Alzheimer's Disease |
| Prion Protein (PrP) derived from PrP precursor protein 51-91 insert | Leu102, Val167, Asn178, Lys200 | Familal Creutzfeldt-Jakob disease; Gerstmann-Sträussler-Scheinker syndrome (hereditary spongiform encephalopathies, prion diseases) |
| AA derived from Serum amyloid A protein (ApoSSA) | | Familal Mediterranean fever, predominant renal involvement (autosomal recessive) |
| AA derived from Serum amyloid A protein (ApoSSA) | | Muckle-Well's syndrome, nephropathy, deafness, urticaria, limb pain |
| Unknown | | Cardiomyopathy with persistent atrial standstill |
| Unknown | | Cutaneous deposits (bullous, papular, pustulodermal) |

[a]Data derived from Tan & Pepys, 1994, supra.

The data provided in Table 2 are exemplary and are not intended to limit the scope of the invention. For example, more than 40 separate point mutations in the transthyretin gene have been described, all of which give rise to clinically similar forms of familial amyloid polyneuropathy.

Transthyretin (TTR) is a 14 kilodalton protein that is also sometimes referred to as prealbumin. It is produced by the liver and choroid plexus, and it functions in transporting thyroid hormones and vitamin A. At least 50 variant forms of the protein, each characterized by a single amino acid change, are responsible for various forms of familial amyloid polyneuropathy. For example, substitution of proline for leucine at position 55 results in a particularly progressive form of neuropathy; substitution of methionine for leucine at position 111 resulted in a severe cardiopathy in Danish patients. Amyloid deposits isolated from heart tissue of patients with systemic amyloidosis have revealed that the deposits are composed of a heterogeneous mixture of TTR and fragments thereof, collectively referred to as ATTR, the full length sequences of which have been characterized. ATTR fibril components can be extracted from such plaques and their structure and sequence determined according to the methods known the art (e.g., Gustaysson, A., et al., Laboratory Invest. 73: 703-708, 1995; Kametani, F., et al., Biochem. Biophys. Res. Commun. 125: 622-628, 1984; Pras, M., et al., PNAS 80: 539-42, 1983).

Persons having point mutations in the molecule apolipoprotein AI (e.g., Gly→Arg26; Trp→Arg50; Leu→Arg60) exhibit a form of amyloidosis ("Östertag type") characterized by deposits of the protein apolipoprotein AI or fragments thereof (AApoAI). These patients have low levels of high density lipoprotein (HDL) and present with a peripheral neuropathy or renal failure.

A mutation in the alpha chain of the enzyme lysozyme (e.g., Ile→Thr56 or Asp→His57) is the basis of another form of Östertag-type non-neuropathic hereditary amyloid reported in English families. Here, fibrils of the mutant lysozyme protein (Alys) are deposited, and patients generally exhibit impaired renal function. This protein, unlike most of the fibril-forming proteins described herein, is usually present in whole (unfragmented) form (Benson, M. D., et al. CIBA Fdn. Symp. 199: 104-131, 1996).

β-amyloid peptide (Aβ) is a 39-43 amino acid peptide derived by proteolysis from a large protein known as beta amyloid precursor protein (βAPP). Mutations in βAPP result in familial forms of Alzheimer's disease, Down's syndrome and/or senile dementia, characterized by cerebral deposition of plaques composed of Aβ fibrils and other components, which are described in further detail below. Known mutations in APP associated with Alzheimer's disease occur proximate to the cleavage sites of β or γ secretase, or within Aβ. For example, position 717 is proximate to the site of γ-secretase cleavage of APP in its processing to Aβ, and positions 670/671 are proximate to the site of β-secretase cleavage. Mutations at any of these residues may result in Alzheimer's disease, presumably by causing an increase the amount of the 42/43 amino acid form of Aβ generated from APP. The structure and sequence of Aβ peptides of various lengths are well known in the art. Such peptides can be made according to methods known in the art (e.g., Glenner and Wong, Biochem Biophys. Res. Comm. 129: 885-890, 1984; Glenner and Wong, Biochem Biophys. Res. Comm. 122: 1131-1135, 1984). In addition, various forms of the peptides are commercially available.

Synuclein is a synapse-associated protein that resembles an alipoprotein and is abundant in neuronal cytosol and presynaptic terminals. A peptide fragment derived from α-synuclein, termed NAC, is also a component of amyloid plaques of Alzheimer's disease. (Clayton, et al., 1998). This component also serves as a target for immunologically-based treatments of the present invention, as detailed below.

Gelsolin is a calcium binding protein that binds to and fragments actin filaments. Mutations at position 187 (e.g., Asp→Asn; Asp→Tyr) of the protein result in a form of hereditary systemic amyloidosis, usually found in patients from Finland, as well as persons of Dutch or Japanese origin. In afflicted individuals, fibrils formed from gelsolin fragments (Agel), usually consist of amino acids 173-243 (68 kDa carboxyterminal fragment) and are deposited in blood vessels and basement membranes, resulting in corneal dystrophy and cranial neuropathy which progresses to peripheral neuropathy, dystrophic skin changes and deposition in other organs. (Kangas, H., et al. Human Mol. Genet. 5(9): 1237-1243, 1996).

Other mutated proteins, such as mutant alpha chain of fibrinogen (AfibA) and mutant cystatin C (Acys) also form fibrils and produce characteristic hereditary disorders. AfibA fibrils form deposits characteristic of a nonneuropathic hereditary amyloid with renal disease; Acys deposits are characteristic of a hereditary cerebral amyloid angiopathy reported in Iceland. (Isselbacher, et al., Harrison's Principles of Internal Medicine, McGraw-Hill, San Francisco, 1995; Benson, et al., supra.). In at least some cases, patients with cerebral amyloid angiopathy (CAA) have been shown to have amyloid fibrils containing a non-mutant form of cystatin C in conjunction with beta protein. (Nagai, A., et al. Molec. Chem. Neuropathol. 33: 63-78, 1998).

Certain forms of prion disease are now considered to be heritable, accounting for up to 15% of cases, which were previously thought to be predominantly infectious in nature. (Baldwin, et al., in *Research Advances in Alzheimer's Disease and Related Disorders*, John Wiley and Sons, New York, 1995). In such prion disorders, patients develop plaques composed of abnormal isoforms of the normal prion protein ($PrP^c$). A predominant mutant isoform, $PrP^{sc}$, also referred to as AScr, differs from the normal cellular protein in its resistance to protease degradation, insolubility after detergent extraction, deposition in secondary lysosomes, post-translational synthesis, and high β-pleated sheet content. Genetic linkage has been established for at least five mutations resulting in Creutzfeldt-Jacob disease (CJD), Gerstmann-Sträussler-Scheinker syndrome (GSS), and fatal familial insomnia (FFI). (Baldwin) Methods for extracting fibril peptides from scrapie fibrils, determining sequences and making such peptides are known in the art. (e.g., Beekes, M., et al. J. Gen. Virol. 76: 2567-76, 1995).

For example, one form of GSS has been linked to a PrP mutation at codon 102, while telencephalic GSS segregates with a mutation at codon 117. Mutations at codons 198 and 217 result in a form of GSS in which neuritic plaques characteristic of Alzheimer's disease contain PrP instead of Aβ peptide. Certain forms of familial CJD have been associated with mutations at codons 200 and 210; mutations at codons 129 and 178 have been found in both familial CJD and FFI. (Baldwin, supra).

c. Senile Systemic Amyloidosis

Amyloid deposition, either systemic or focal, increases with age. For example, fibrils of wild type transthyretin (TTR) are commonly found in the heart tissue of elderly individuals. These may be asymptomatic, clinically silent, or may result in heart failure. Asymptomatic fibrillar focal deposits may also occur in the brain (Aβ), corpora amylacea of the prostate ($A\beta_2$ microglobulin), joints and seminal vesicles.

d. Cerebral Amyloidosis

Local deposition of amyloid is common in the brain, particularly in elderly individuals. The most frequent type of amyloid in the brain is composed primarily of Aβ peptide fibrils, resulting in dementia or sporadic (non-hereditary) Alzheimer's disease. In fact, the incidence of sporadic Alzheimer's disease greatly exceeds forms shown to be hereditary. Fibril peptides forming these plaques are very similar to those described above, with reference to hereditary forms of Alzheimer's disease (AD).

e. Dialysis-Related Amyloidosis

Plaques composed of $\beta_2$ microglobulin ($A\beta_2M$) fibrils commonly develop in patients receiving long term hemodialysis or peritoneal dialysis. $\beta_2$ microglobulin is a 11.8 kilodalton polypeptide and is the light chain of Class I MHC antigens, which are present on all nucleated cells. Under normal circumstances, it is continuously shed from cell membranes and is normally filtered by the kidney. Failure of clearance, such as in the case of impaired renal function, leads to deposition in the kidney and other sites (primarily in collagen-rich tissues of the joints). Unlike other fibril proteins, $A\beta_2M$ molecules are generally present in unfragmented form in the fibrils. (Benson, supra).

f. Hormone-Derived Amyloidoses

Endocrine organs may harbor amyloid deposits, particularly in aged individuals. Hormone-secreting tumors may also contain hormone-derived amyloid plaques, the fibrils of which are made up of polypeptide hormones such as calcitonin (medullary carcinoma of the thyroid), islet amyloid polypeptide (amylin; occurring in most patients with Type II diabetes), and atrial natriuretic peptide (isolated atrial amyloidosis). sequences and structures of these proteins are well known in the art.

g. Miscellaneous Amyloidoses

There are a variety of other forms of amyloid disease that are normally manifest as localized deposits of amyloid. In general, these diseases are probably the result of the localized production and/or lack of catabolism of specific fibril precursors or a predisposition of a particular tissue (such as the joint) for fibril deposition. Examples of such idiopathic deposition include nodular AL amyloid, cutaneous amyloid, endocrine amyloid, and tumor-related amyloid.

III. AA Amyloid Diseases

AA amyloidosis, formerly called secondary or reactive amyloidosis because it develops secondary to a preexisting or coexisting disease. Such diseases include, but are not limited to inflammatory diseases, such as rheumatoid arthritis, juvenile chronic arthritis, ankylosing spondylitis, psoriasis, psoriatic arthropathy, Reiter's syndrome, Adult Still's disease, Behcet's syndrome, and Crohn's disease. AA deposits are also produced as a result of chronic microbial infections, such as leprosy, tuberculosis, bronchiectasis, decubitus ulcers, chronic pyelonephritis, osteomyelitis, and Whipple's disease. Certain malignant neoplasms can also result in AA fibril amyloid deposits. These include such conditions as Hodgkin's lymphoma, renal carcinoma, carcinomas of gut, lung and urogenital tract, basal cell carcinoma, and hairy cell leukemia. AA amyloid disease may also result from inherited inflammatory diseases such as Familial Mediterranean Fever. Additionally, AA amyloid disease may result from lymphoproliferative disorders such as Castleman's Disease.

1. Inflammatory Diseases Associated with AA Amyloidosis

Rheumatoid arthritis is a chronic systemic disease primarily of the joints. The symptoms of rheumatoid arthritis are marked by inflammatory changes in the synovial membranes and articular structures (joints) and by atrophy and rarefaction (bone density decreases) of the bones. In late stages of rheumatoid arthritis, deformity and ankylosis (immobility of the joint) develop. A model of rheumatoid arthritis can be induced in mice or rats by administering type II collagen in complete Freund's adjuvant.

Juvenile chronic arthritis comes in many forms; the most common being juvenile rheumatoid arthritis. It can occur in children at any age, but first appears more commonly between the ages of 2 and 6 years. There are 3 main types of juvenile rheumatoid arthritis, namely, pauci-articular arthritis, polyarticular arthritis, and systemic arthritis (also known as Still's disease). Pauci-articular arthritis typically affects 4 or fewer joints, usually the larger ones such as the knees. It can be accompanied by stiffness, causing the child to limp. Polyarticular arthritis is characterized by 5 or more joints being affected, most commonly the smaller joints in the hands and feet. Children with polyarticular arthritis often have a more severe form of the disease. Systemic arthritis is characterized by joint swelling in combination with fever and a pink rash. The joints may not start to swell until some months or years after the fevers begin. It may also affect internal organs such as the liver, heart, spleen and lymph nodes, and anemia is common. While systemic arthritis tends to abate of its own accord, a small percentage of these children can have severe arthritis that continues into adulthood.

Ankylosing spondylitis is a rheumatic disease that causes arthritis of the spine and sacroiliac joints and can cause inflammation of the eyes, lungs, and heart valves. It varies from intermittent episodes of back pain that occur throughout life to a severe chronic disease that attacks the spine, peripheral joints and other body organs, resulting in severe joint and back stiffness, loss of motion and deformity as life progresses.

Psoriasis is a common chronic, squamous dermatosis, marked by exacerbation and remissions and having a polygenic inheritance pattern. The symptoms of psoriasis are marked by the presence of rounded, dry scaling patches of various sizes, covered by a grayish white or silvery white scales that have a predilection for the extensor surfaces, nails, scalp, genitalia and the lumbosacral region.

Psoriatic arthropathy is a disorder in which psoriasis is linked to the development of arthritis. The disorder can be exhibited in a variety of ways. The arthritis is generally mild and involves only a few joints. In a few patients, the disease is severe and usually affects the fingers and the spine. When the spine is affected, the symptoms are very much like those of ankylosing spondylitis.

Reiter's syndrome is a group of symptoms consisting of arthritis, urethritis (inflammation of the urogenital tract), conjunctivitis (inflammation of the lining of the eye), and lesions of the skin and mucous membranes. Reiter's syndrome is also referred to as reactive arthritis, which means that the arthritis occurs as a "reaction" to an infection that started elsewhere in the body. *Chlamydia trachomatis* is the bacteria most often associated with Reiter's syndrome acquired through sexual contact. Several different bacteria are associated with Reiter's syndrome acquired through the digestive tract, including *Salmonella, Shigella, Yersinia,* and *Campylobacter.*

Adult Still's disease, also called Adult Onset Still's Disease is a rare inflammatory condition that attacks internal organs, joints and other parts of the body. It can appear and disappear suddenly. In very severe cases, adult Still's disease becomes chronic and extremely debilitating, causing terrible pain and stiffness. After many years, the disease cripples vital organs such as the heart and lungs.

Behcet's syndrome is a multisystem disorder presenting with recurrent oral and/or genital ulcerations, chronic relapsing uveitis that may cause blindness and neurologic impairments. It is characterized by 4 major symptoms: oral aphthous ulcers, skin lesions, ocular symptoms, and genital ulcerations, and occasionally by inflammation in tissues and organs throughout the body, including the gastrointestinal tract, central nervous system, vascular system, lungs, and kidneys. The arthritis of Behcet's syndrome is usually intermittent, self-limited, not deforming and localized to the knees and ankles.

Crohn's disease is a chronic granulomatous (small grain-like body or growth) inflammatory disease involving any part of the gastrointestinal tract from the mouth to anus; but commonly involving the ileum (lower three-fifths of the small intestines) with scarring and thickening of the bowel wall. The symptoms of Crohn's disease include the presence of chronic diarrhea, increased bowel sounds, cramping, possibly evidenced by weight loss and aversion to eating.

2. Chronic Microbial Infection Diseases Associated with AA Amyloidosis

Leprosy is an infectious disease characterized by disfiguring skin sores, peripheral nerve damage, and progressive debilitation. Leprosy is caused by the organism *Mycobacterium leprae*, which is not very contagious and has a long incubation period. Leprosy has two common forms, tuberculoid and lepromatous. Both forms produce sores on the skin, but the lepromatous form is most severe, producing large, disfiguring nodules (lumps and bumps). Leptosy eventually causes peripheral neurological damage. Patients with long-term leprosy may lose the use of their hands or feet due to repeated injury resulting from lack of sensation.

Tuberculosis is a contagious bacterial infection caused by *Mycobacterium tuberculosis*. The disease is characterized by the development of granulomas (granular tumors) in the infected tissues. The lungs are primarily involved, but the infection can spread to other organs. Bronchiectasis is an abnormal destruction and dilation of the large airways.

Bronchiectasis is often caused by recurrent inflammation or infection of the airways. A classic bacterium that is seen in patients with bronchiectasis is *Pseudomonas aeruginosa*, which is notoriously hard to eradicate. Repeated infections of the airways by this bacterium can lead to colonization of the bronchi by this organism which predisposes such people to *Pseudomonal pneumonias*, which requires special antibiotics to treat.

Decubitus ulcer also known as pressure ulcer or bedsore is an ulceration of the skin and underlying tissues caused by prolonged pressure over the affected area. They start as reddened skin but gets progressively worse, forming a blister, then an open sore, and finally a crater. These ulcerations usually occur over bony prominences such as heels, coccyx area of the buttock and the back of the head.

Chronic pyelonephritis is an infection of the kidney and the ureters (ducts that carry urine away from the kidney). Pyelonephritis most often occurs as a result of urinary tract infection, particularly in the presence of occasional or persistent backflow of urine from the bladder into the ureters or kidney pelvis.

Osteomyelitis is an acute or chronic bone infection, usually caused by bacteria. Often the infection initiates in another part of the body and spreads to the bone via the blood. When the bone is infected, pus is produced within the bone, which may result in an abscess. The abscess then deprives the bone of its blood supply. Chronic osteomyelitis results when bone tissue dies as a result of the lost blood supply. Chronic infection can persist intermittently for years.

Whipple's disease is a rare condition that causes inadequate absorption of nutrients from the intestinal tract due to infection of the intestine. It is caused by the bacteria, *Tropheryma whippelii*. Symptoms include diarrhea, intestinal bleeding, abdominal pain, loss of appetite, weight loss, fatigue, and weakness. Arthritis and fever often occur several years before intestinal symptoms develop. Patients may experience neurological symptoms as well. Diagnosis is based on symptoms and the results of a biopsy of tissue from the small intestine or other organs that are affected. When recognized and treated, Whipple's disease can usually be cured. Without treatment, the condition is usually fatal.

3. Malignant Neoplasms Associated with AA Amyloidosis

Hodgkin's lymphoma is a cancer of lymphatic tissue found in the lymph nodes, spleen, liver, and bone marrow. The first sign of this cancer is often an enlarged lymph node. The disease can spread to nearby lymph nodes and later may spread to the lungs, liver, or bone marrow.

Renal carcinoma is cancer of the kidney. The cancerous cells are found in the lining of tubules in the kidney. The first symptom is usually blood in the urine. Sometimes both kidneys are involved. The cancer spreads easily, most often to the lungs and other organs. Renal cell carcinoma is the most common type of kidney cancer followed by papillary renal cell carcinoma, chromophobe renal carcinoma and collecting duct renal carcinoma. About 5% of renal carcinoma are unclassified because their appearance doesn't fit into any of the other categories.

Carcinomas of the gut include gastrointestinal cancers such as colorectal, pancreatic, stomach and esophageal. Colorectal cancer is cancer that starts in the large intestine or the rectum. Almost all colorectal cancers begin as benign polyps which, over a period of many years, develop into cancers. Most cases of colorectal cancer have no symptoms. Pancreatic cancer is a malignancy of the pancreas. Symptoms include abdominal pain, loss of appetite, significant weight loss and painless jaundice. Stomach cancer, also called gastric cancer, can develop in any part of the stomach and may spread throughout the stomach and to other organs; particularly the esophagus and the small intestine. It may also spread, through the stomach wall, to nearby lymph nodes and organs such as the liver, pancreas, and the lungs, or to distant organs such as the lymph nodes above the collar bone, the colon, and the ovaries. Stomach cancer is often asymptomatic. Esophageal cancer is malignancy of the esophagus. Symptoms include dysphagia (difficulty swallowing), pain and substantial weight loss.

Carcinomas of the lung are a cancer of the lungs characterized by the presence of malignant tumours. There are two main types of lung cancer: non-small cell lung cancer and small cell lung cancer. Symptoms depend on the specific type of cancer, but may include chronic cough, coughing up blood, shortness of breath, wheezing, chest pain, loss of appetite, weight loss and fatigue.

Carcinomas of the urogenital tract include but are not limited to prostate cancer, bladder cancer, endometrial cancer, cervical cancer and ovarian cancer. Prostate cancer involves a malignant tumor growth within the prostate gland. Symptoms may include frequent urination, difficulty starting and maintaining a steady stream of urine, blood in the urine, painful urination, difficulty achieving erection or painful ejaculation. Bladder cancer refers to any of several types of malignant growths of the urinary bladder. Symptoms include blood in the urine, frequent urination, painful urination, and urinary urgency. Endometrial cancer involves cancerous growth of the endometrium (lining of the uterus). It mainly occurs after menopause, and presents with vaginal bleeding. Cervical cancer is a malignancy of the cervix. The early stages of cervical cancer may be completely asymptomatic. Vaginal bleeding may indicate the presence of malignancy. In advanced stages, metastases may be present in the abdomen, lungs or elsewhere. Ovarian cancer is a malignant neoplansm of the ovaries. Ovarian cancer symptoms are often vague and non-specific, which include vague lower abdominal discomfort, sense of pelvic heaviness, abnormal menstrual cycle, vaginal bleeding, weight gain or loss, nonspecific gastrointestinal symptoms. Ovarian cancers shed cancer cells that often implant on the uterus, bladder, bowel, and lining of the bowel wall. These cancer cells can begin forming new tumor growths before cancer is even suspected.

Basal cell carcinoma is a slow-growing skin tumor involving cancerous changes in basal skin cells. Symptoms include skin lesions located on the face, ear, neck, chest, back, or scalp; visible blood vessels in the lesion or adjacent skin; and persistent, non-healing sores. This cancer usually remains local and almost never spreads to distant parts of the body, but it may continue to grow and invade nearby tissues and structures, including the nerves, bones, and brain.

Hairy cell leukemia is a cancer of lymphocytes (B cells) that leads to low blood counts. The disease is caused by the abnormally shaped B cells with hair-like projections. Symptoms are often vague. The low blood counts caused by hairy cell leukemia can lead to infections, fatigue, and excessive bleeding.

4. Inherited Inflammatory Disease Associated with AA

Familial. Mediterranean Fever is an inherited disorder characterized by recurrent fever and inflammation, often involving the abdomen or the lung. Symptoms include inflammation in the lining of the abdominal cavity, chest cavity, skin, or joints occurs, along with high fevers that usually peak in 12 to 24 hours. Attacks may vary in severity of symptoms, and people are usually symptom free between attacks. This disease is very rare. Risk factors include a family history of familial Mediterranean Fever or having Mediterranean ancestry.

5. Lymphoproliferative Disorders Associated with AA Amyloidosis

Castleman's Disease is a form of lympoproliferative disorder characterized pathologicaly by the presence of giant lymp node hyperplasia with plasma cell infiltration. Patients with Castleman's Disease commonly have fever, anemia, hypergammaglobulinaemia, and an increase in the serum concentrations of acute phase reactant proteins, all of which are ascribed to the large amount of IL-6 produced in the lymph nodes.

IV. Serum Amyloid A

1. Human Serum Amyloid A

Serum amyloid A (SAA) is the circulating precursor of amyloid A protein, the fibrillar component of amyloid deposits. The structural studies showed that the human SAA is heterogeneous and represents a family of polymorphic SAA genes and protein products. The SAA gene superfamily comprises a cluster of closely linked genes localized to 11p15.1. See Sellar, G C et al. *Genomics* 19: 221-227 (1994). Four SAA genes have been described in humans. Representative amino acid sequences of proteins encoded by the four SAA genes are illustrated by FIG. 1. Two genes (SAA1 and SAA2) encode acute-phase serum amyloid A (A-SAA) and are coordinately induced in response to inflammation. SAA1 and SAA2 share 95% sequence identity in both coding and non-coding regions. There are alpha, beta and gamma isoforms of human SAA1 and alpha and beta isoforms of human SAA2 as illustrated by FIGS. 18 and 19. SAA3 is a pseudogene. SAA4 encodes constitutive SAA and is minimally inducible. See Cunnane G. *Bailliere's Clin. Rheumatol.* 13(4): 615-628. All human SAA/AA molecules contains a theoretical calcium-binding tetrapeptide sequence, Gly-Pro-Gly-Gly, of possible importance for self aggregation and with extrafibrillar moieties of amyloid in fibrillogenesis. See Fykse, E. M. et al. *Biochem. J.* 256:973-980 (1988) and Turnell et al. *Mol. Biol. Med.* 3:387-407 (1986). The N terminal portion of SAA/AA is strongly hydrophobic, probably of importance for self aggregation and other components in amyloid deposits. See Husby et al. *Clin. Immunol. Immunopathol.* 70(1):2-9 (1994). The sequence of each isoform of AA and its relationship to its corresponding SAA isoform is illustrated by FIGS. 2-5. For example, human SAA1 alpha isoform has the sequence:

```
                                                        (SEQ ID NO: 1)
H2N-Met-Lys-Leu-Leu-Thr-Gly-Leu-Val-Phe-Cys-Ser-

Leu-Val-Leu-Gly-Val-Ser-Ser-Arg-Ser-Phe-Phe-Ser-

Phe-Leu-Gly-Glu-Ala-Phe-Asp-Gly-Ala-Arg-Asp-Met-

Try-Arg-Ala-Tyr-Ser-Asp-Met-Arg-Glu-Ala-Asn-Tyr-

Ile-Gly-Ser-Asp-Lys-Tyr-Phe-His-Ala-Arg-Gly-Asn-

Tyr-Asp-Ala-Ala-Lys-Arg-Gly-Pro-Gly-Gly-Ala-Try-

Ala-Ala-Glu-Val-Ile-Ser-Asp-Ala-Arg-Glu-Asn-Ile-

Gln-Arg-Phe-Phe-Gly-His-Gly-Ala-Glu-Asp-Ser-Leu-

Ala-Asp-Gln-Ala-Ala-Asn-Glu-Try-Gly-Arg-Ser-Gly-

Lys-Asp-Pro-Asn-His-Phe-Arg-Pro-Ala-Gly-Leu-Pro-

Glu-Lys-Tyr-OH.
```

AA, which is a proteolytic fragment of SAA, is also heterogeneous. The predominant human AA peptide consists of 76 amino acids. An example of AA has the sequence:

```
                                                        (SEQ ID NO: 2)
H2N-Arg-Ser-Phe-Phe-Ser-Phe-Leu-Gly-Glu-Ala-Phe-

Asp-Gly-Ala-Arg-Asp-Met-Try-Arg-Ala-Tyr-Ser-Asp-

Met-Arg-Glu-Ala-Asn-Tyr-Ile-Gly-Ser-Asp-Lys-Tyr-

Phe-His-Ala-Arg-Gly-Asn-Tyr-Asp-Ala-Ala-Lys-Arg-

Gly-Pro-Gly-Gly-Ala-Try-Ala-Ala-Glu-Val-Ile-Ser-

Asp-Ala-Arg-Glu-Asn-Ile-Gln-Arg-Phe-Phe-Gly-His-

Gly-Ala-Glu-Asp-Ser-OH.
```

AA70-76 refers to an AA fragment beginning at residue 70 and ending at residue 76 of (SEQ ID NO:2) consisting of the sequence GHGAEDS, (SEQ ID NO: 4), or corresponding segment from another naturally occurring AA protein from a human or other species when the sequence of that protein is maximally aligned with SEQ ID NO:2.

2. Murine Serum Amyloid A

In the mouse, four SAA genes have been described. Representative amino acid sequences of proteins encoded by the four murine SAA genes are illustrated by FIG. 8. Mouse SAA gene family comprises four members that are closely linked in the chromosome 7. Two of these genes encoding major mouse SAA isotypes (SAA1 and SAA2) share high sequence identity not only in exons but also in introns and flanking regions and are induced in approximately equal quantities in response to amyloid induction models. These two isotypes differ in only 9 of 103 amino acid residues; however, only SAA2 is selectively deposited into amyloid fibrils. See de Beer M. C. *Biochem J.* 1991 280(Pt 1): 45-49 (1991); Hoffman J. S. et al. *J. Exp Med.* 159:641-646 (1984); Shiroo M et al. *Scand J. Immunol.* 26:709-716 (1987). SAA3 is a minor HDL apolipoprotein and peripherally produced acute phase. SAA4 is a constitutive subfamily that is a minor normal HDL apolipoprotein comprising more than 90% of the SAA during homeostasis. See Stearman R. S. et al. *Nucleic Acids Research*, 14(2)797-809 (1986) and de Beer M. C. *Genomics*, 34(1):139-42 (1996).

Murine AA which is a proteolytic fragment of SAA is also heterogeneous. The sequence of each murine isoform of AA and its relationship to its corresponding SAA isoform is illustrated by FIGS. 9-12. A sequence alignment of murine AA1, AA2, AA3 and AA4 is illustrated by FIG. 13.

Murine AA1 is the murine equivalent of human AA1. See FIG. 16. In particular, residues 69-75 of murine AA1 (GRGHEDT, SEQ ID NO: 9) are maximally aligned with residues 70-76 of human AA1 (GHGAEDS, SEQ ID NO: 4). See also FIG. 17.

3. Shar Pei Serum Amyloid A

The Shar Pei sequence is indicated in FIG. 20. Interestingly, the homologous region in the human SAA protein –AEDS, (SEQ ID NO: 13) contains a conserved Thr to Ser substitution at position 76, as well as significantly different side chain of the residue at position 73 (His to Ala; FIG. 1). The –AEDS, (SEQ ID NO: 13), sequence is also observed in the Shar Pei species of dog, a breed that is particularly susceptible to AA-amyloidosis and could provide a naturally occurring model of systemic AA in which to evaluate novel diagnostic and therapeutic applications of AA amyloid-specific antibodies and other compounds.

4. The N-Terminal Segment of AA Protein Determines its Fibrillogenic Property

The amyloid fibril protein AA consists of a varying long N-terminal part of the precursor protein serum AA. Evidence shows that the amyloidogenic part of the molecule is the N-terminal 10-15 amino acid long segment. Amino acid substitutions in this part of the molecule may explain why only one of the two mouse SAA isoforms is amyloidogenic. See Westermark G. T. *Biochem Biophys Res Commun.* 182(1):27-33 (1992).

V. Other Human Amyloidogenic Proteins

The Genbank Accession Numbers and $X_1EDX_2$ sequences are provided below in Table 3 for several human amyloidogenic proteins, including some of those listed above in Table 2.

TABLE 3

Human Amyloidogenic Proteins

| Human amyloidogenic protein | Consensus sequence | GenBank Accession Number |
|---|---|---|
| SAA1 | AEDS, (SEQ ID NO: 13) | |
| SAA2 | AEDS, (SEQ ID NO: 13) | |
| SAA3 | AEDS, (SEQ ID NO: 13) | |
| SAA4 | AEDS, (SEQ ID NO: 13) | |
| anti-Sm immunoglobulin kappa light chain V region; monoclonal antibody 4B4 kappa chain | AEDV, (SEQ ID NO: 23) | AAB26897 |

TABLE 3-continued

Human Amyloidogenic Proteins

| Human amyloidogenic protein | Consensus sequence | GenBank Accession Number |
|---|---|---|
| immunoglobulin variable region used by the ITC52 kappa light chain (subgroup V kappa III | PEDS, (SEQ ID NO: 26) | AAC61608 |
| immunoglobulin variable region used by the 1TC48 kappa light chain (subgroup V kappa IV) | AEDV, (SEQ ID NO: 23) | AAC61606 |
| anti-RhD monoclonal T125 kappa light chain precursor | SEDF, (SEQ ID NO: 24) | AAW82027 |
| immunoglobulin kappa light chain precursor | AEDV, (SEQ ID NO: 23) | CAA45496 |
| immunoglobulin kappa light chain variable region | PEDF, (SEQ ID NO: 22) | AAT44350 |
| immunoglobulin kappa light chain variable region | PEDF, (SEQ ID NO: 22) | AAT44349 |
| immunoglobulin kappa light chain variable region | PEDF, (SEQ ID NO: 22) | AAT44348 |
| immunoglobulin kappa light chain | PEDF, (SEQ ID NO: 22) | CAA09185 |
| immunoglobulin kappa light chain | SEDF, (SEQ ID NO: 24) | CAA09181 |
| immunoglobulin kappa light chain variable region | SEDF, (SEQ ID NO: 24) | AAU14891 |
| anti-rabies SOJA immunoglobulin kappa light chain | PEDF, (SEQ ID NO: 22) | AAO17825 |
| anti-*streptococcal*/anti-myosin immunoglobulin kappa light chain variable region | SEDF, (SEQ ID NO: 24) | AAB68786 |
| anti-*streptococcal*/anti-myosin immunoglobulin kappa light chain variable region | PEDF, (SEQ ID NO: 22) | AAB68785 |
| anti-HLA-A2/anti-HLA-A28 immunoglobulin kappa light chain variable region | PEDF, (SEQ ID NO: 22) | AAC99644 |
| immunoglobulin kappa light chain V region; anti-DNA antibody 18/2 | PEDF, (SEQ ID NO: 22) | AAB62946 |
| immunoglobulin kappa light chain | PEDF, (SEQ ID NO: 22) | BAF75949 |
| anti-HIV-1 gp120 immunoglobulin 48d kappa light chain | PEDF, (SEQ ID NO: 22) | AAR88370 |
| immunoglobulin kappa light chain | PEDL, (SEQ ID NO: 27) | BAA97671 |
| anti-*Entamoeba histolytica* immunoglobulin kappa light chain | PEDF, (SEQ ID NO: 22) | BAA82105 |
| anti-*Entamoeba histolytica* immunoglobulin kappa light chain | TEDV, (SEQ ID NO: 28) | BAA82102 |
| immunoglobulin kappa light chain | PEDF, (SEQ ID NO: 22) | AAC41705 |
| anti-GM2 glanglioside IgM monoclonal kappa light chain variable region | AEDV, (SEQ ID NO: 23) | AAC26480 |
| anti-SARS-CoV immunoglobulin kappa light chain variable region | PEDV, (SEQ ID NO: 151) | AAT51719 |
| anti-SARS-CoV immunoglobulin kappa light chain variable region | PEDF, (SEQ ID NO: 22) | AAT51718 |
| immunoglobulin kappa light chain VLJ region | PEDF, (SEQ ID NO: 22) | BAD27502 |
| immunoglobulin kappa light chain VLJ region | SEDF, (SEQ ID NO: 24) | BAD27497 |

TABLE 3-continued

Human Amyloidogenic Proteins

| Human amyloidogenic protein | Consensus sequence | GenBank Accession Number |
|---|---|---|
| anti-HIV-1 gp120 immunoglobulin 47e kappa light chain | PEDF, (SEQ ID NO: 22) | AAR88378 |
| anti-HIV-1 gp120 immunoglobulin 16c kappa light chain | PEDF, (SEQ ID NO: 22) | AAR88374 |
| anti-HIV-1 gp120 immunoglobulin 41lg kappa light chain | SEDF, (SEQ ID NO: 24) | AAR88372 |
| immunoglobulin kappa light chain variable region | PEDF, (SEQ ID NO: 22) | AAF14212 |
| immunoglobulin kappa light chain variable region | PEDF, (SEQ ID NO: 22) | AAF14211 |
| immunoglobulin kappa light chain variable region | PEDF, (SEQ ID NO: 22) | AAF14210 |
| immunoglobulin kappa light chain variable region | PEDF, (SEQ ID NO: 22) | AAF14209 |
| immunoglobulin V-region kappa light chain | PEDI, (SEQ ID NO: 21) | AAR02415 |
| immunoglobulin kappa light chain | PEDF, (SEQ ID NO: 22) | AAM46647 |
| immunoglobulin kappa light chain | AEDV, (SEQ ID NO: 23) | AAM46643 |
| anti-*Entamoeba histolytica* immunoglobulin kappa light chain | PEDF, (SEQ ID NO: 22) | BAA82103 |
| immunoglobulin light chain kappa variable region | AEDV, (SEQ ID NO: 23) | AAL65723 |
| immunoglobulin light chain kappa variable region | PEDF, (SEQ ID NO: 22) | AAL65718 |
| immunoglobulin light chain kappa variable region | SEDF, (SEQ ID NO: 24) | AAL65717 |
| immunoglobulin light chain kappa variable region | SEDF, (SEQ ID NO: 24) | AAL65716 |
| immunoglobulin light chain kappa variable region | PEDF, (SEQ ID NO: 22) | AAL65714 |
| immunoglobulin light chain kappa variable region | PEDF, (SEQ ID NO: 22) | AAL65713 |
| immunoglobulin light chain kappa variable region | PEDF, (SEQ ID NO: 22) | AAL65712 |
| immunoglobulin light chain kappa variable region | PEDF, (SEQ ID NO: 22) | AAL65711 |
| immunoglobulin light chain kappa variable region | PEDF, (SEQ ID NO: 22) | AAL65710 |
| immunoglobulin light chain kappa variable region | LEDG, (SEQ ID NO: 31) PEDF, (SEQ ID NO: 22) | AAL65709 |
| immunoglobulin light chain kappa variable region | LEDG, (SEQ ID NO: 31) PEDF, (SEQ ID NO: 22) | AAL65708 |
| immunoglobulin light chain kappa variable region | PEDF, (SEQ ID NO: 22) | AAL65707 |
| immunoglobulin light chain kappa variable region | PEDF, (SEQ ID NO: 22) | AAL65706 |
| immunoglobulin light chain kappa variable region | PEDF, (SEQ ID NO: 22) | AAL65705 |
| immunoglobulin light chain kappa variable region | PEDF, (SEQ ID NO: 22) | AAL65704 |

TABLE 3-continued

Human Amyloidogenic Proteins

| Human amyloidogenic protein | Consensus sequence | GenBank Accession Number |
|---|---|---|
| immunoglobulin light chain kappa variable region | PEDF, (SEQ ID NO: 22) | AAL65703 |
| immunoglobulin kappa light chain variable region | SEDF, (SEQ ID NO: 24) | AAC64146 |
| immunoglobulin kappa light chain variable region | SEDF, (SEQ ID NO: 24) | AAC64144 |
| immunoglobulin kappa light chain variable region | PEDF, (SEQ ID NO: 22) | ABI64139 |
| anti-pneumococcal capsular polysaccharide immunoglobulin kappa light chain | AEDV, (SEQ ID NO: 23) | AAL04535 |
| immunoglobulin light chain kappa variable region | AEDV, (SEQ ID NO: 23) | AAL65722 |
| immunoglobulin light chain kappa variable region | AEDV, (SEQ ID NO: 23) | AAL65720 |
| immunoglobulin light chain V-J region | PEDF, (SEQ ID NO: 22) | BAA19563 |
| immunoglobulin light chain V-J region | AEDE, (SEQ ID NO: 19) | BAA19562 |
| immunoglobulin light chain V-J region | AEDE, (SEQ ID NO: 19) | BAA19561 |
| immunoglobulin light chain V-J region | PEDF, (SEQ ID NO: 22) | BAA19560 |
| immunoglobulin light chain V-J region | PEDF, (SEQ ID NO: 22) | BAA19559 |
| immunoglobulin light chain V-J region | AEDV, (SEQ ID NO: 23) | BAA19558 |
| immunoglobulin light chain V-J region | PEDI, (SEQ ID NO: 21) | BAA19556 |
| immunoglobulin kappa light chain variable region | PEDF, (SEQ ID NO: 22) | AAA71907 |
| immunoglobulin kappa light chain variable region | AEDV, (SEQ ID NO: 23) | AAA71905 |
| immunoglobulin G1 Fab light chain variable region | AEDV, (SEQ ID NO: 23) | BAF49281 |
| immunoglobulin G1 Fab light chain variable region | PEDF, (SEQ ID NO: 22) | BAF48998 |
| immunoglobulin G1 Fab light chain variable region | PEDF, (SEQ ID NO: 22) | BAF48996 |
| kappa light chain V-region | AEDM, (SEQ ID NO: 32) | CAA37675 |
| immunogloburin G1 Fab light chain variable region | SEDF, (SEQ ID NO: 24) | BAF48994 |
| immunogloburin G1 Fab light chain variable region | PEDF, (SEQ ID NO: 22) | BAF48992 |
| Ig kappa chain precursor V-J-C region | AEDV, (SEQ ID NO: 23) | A53261 |
| Ig kappa chain precursor V region | AEDV, (SEQ ID NO: 23) | A49137 |
| Ig kappa chain precursor V-I region | SEDI, (SEQ ID NO: 29) | PN0445 |
| Ig kappa chain precursor V-III region (EVI-15) | PEDF, (SEQ ID NO: 22) | A32274 |
| Ig kappa chain V-IV region (Dep) | AEDV, (SEQ ID NO: 23) | A34153 |
| Ig kappa chain V-IV region (Fue) | AEDV, (SEQ ID NO: 23) | B34153 |
| Ig kappa chain V-II region (Pec) | AEDV, (SEQ ID NO: 23) | C34153 |
| Chain L, Igg Fab Fragment (Cd25-Binding). | AEDA, (SEQ ID NO: 62) | 1MIM_L |

TABLE 3-continued

Human Amyloidogenic Proteins

| Human amyloidogenic protein | Consensus sequence | GenBank Accession Number |
|---|---|---|
| Chain H, Igg Fab Fragment (Cd25-Binding). | HEDS, (SEQ ID NO: 33) | 1MIM_H |
| Ig mu chain C region, secreted splice form | CEDD, (SEQ ID NO: 34) | MHHU |
| immunoglobulin kappa-chain VJ region | AEDV, (SEQ ED NO: 23) | AAA58923 |
| recombinant monoclonal antibody IgM 12 kappa light chain variable region | PEDF, (SEQ ID NO: 22) | ABA41551 |
| immunoglobulin light chain | AEDE, (SEQ ID NO: 19) | CAA65054 |
| immunoglobulin light chain lambda variable region | AEDE, (SEQ ID NO: 19) | AAL65769 |
| immunoglobulin light chain lambda variable region | AEDE, (SEQ ID NO: 19) | AAL65767 |
| immunoglobulin light chain lambda variable region | AEDE, (SEQ ID NO: 19) | AAL65765 |
| immunoglobulin light chain lambda variable region | TEDE, (SEQ ID NO: 16) | AAL65764 |
| immunoglobulin light chain lambda variable region | AEDE, (SEQ ID NO: 19) | AAL65763 |
| immunoglobulin light chain lambda variable region | SEDE, (SEQ ID NO: 18) | AAL65762 |
| immunoglobulin light chain lambda variable region | SEDE, (SEQ ID NO: 18) | AAL65761 |
| immunoglobulin light chain lambda variable region | SEDE, (SEQ ID NO: 18) | AAL65760 |
| immunoglobulin light chain lambda variable region | AEDE, (SEQ ID NO: 19) | AAL65759 |
| immunoglobulin light chain lambda variable region | AEDE, (SEQ ID NO: 19) | AAL65758 |
| immunoglobulin light chain V-J region | PEDF, (SEQ ID NO: 22) | BAA19563 |
| immunoglobulin light chain V-J region | AEDE, (SEQ ID NO: 19) | BAA19562 |
| immunoglobulin light chain V-J region | AEDE, (SEQ ID NO: 19) | BAA19561 |
| immunoglobulin light chain V-J region | PEDF, (SEQ ID NO: 22) | BAA19560 |
| immunoglobulin light chain V-J region | PEDF, (SEQ ID NO: 22) | BAA19559 |
| immunoglobulin light chain V-J region | AEDV, (SEQ ID NO: 23) | BAA19558 |
| immunoglobulin light chain V-J region | PEDI, (SEQ ID NO: 21) | BAA19556 |
| 30-lambda immunoglobulin light chain variable region | AEDE, (SEQ ID NO: 19) | AAK95335 |
| PREDICTED: similar to Low affinity immunoglobulin gamma Fc region receptor II-a precursor (Fc-gamma RII-a)(FcRII-a) (IgG Fc receptor II-a)(Fc-gamma-RIIa) (CD32 antigen)(CDw32) | QEDS, (SEQ ID NO: 35) | XP_001129584 |
| Fc fragment of IgG, high affinity Ia, receptor (CD64) | REDS, (SEQ ID NO: 36)<br>TEDG, (SEQ ID NO: 37)<br>QEDR, (SEQ ID NO: 38) | NP_000557 |
| Fc fragment of IgG, low affinity IIb, receptor for (CD32) isoform 2 | QEDS, (SEQ ID NO: 35) | NP_001002273<br>XP_943944 |
| Fc fragment of IgG, low affinity IIb, receptor for (CD32) isoform 1 | QEDS, (SEQ ID NO: 35) | NP_003992 |

TABLE 3-continued

Human Amyloidogenic Proteins

| Human amyloidogenic protein | Consensus sequence | GenBank Accession Number |
|---|---|---|
| Fc fragment of IgG, low affinity IIb, receptor for (CD32) isoform 4 | QEDS, (SEQ ID NO: 35) | NP_001002275 |
| Fc fragment of IgG, low affinity IIb, receptor for (CD32) isoform 3 | QEDS, (SEQ ID NO: 35) | NP_001002274 XP_001129592 |
| Fc fragment of IgG, high affinity Ib, receptor (CD64) isoform a | QEDR, (SEQ ID NO: 38) | NP_001017986 |
| Fc fragment of IgG, high affinity Ib, receptor (CD64) isoform b | QEDR, (SEQ ID NO: 38) | NP_001004340 XP_496386 |
| Fc fragment of IgG, low affinity IIa, receptor (CD32) | QEDS, (SEQ ID NO: 35) | NP_067674 XP_943942 |
| low affinity immunoglobulin gamma Fc region receptor III-B precursor | TEDL, (SEQ ID NO: 39) PEDN, (SEQ ID NO: 40) EEDP, (SEQ ID NO: 41) | NP_000561 |
| Fc fragment of IgG, low affinity IIIa, receptor for (CD16) | TEDL, (SEQ ID NO: 39) PEDN, (SEQ ID NO: 40) EEDP, (SEQ ID NO: 41) | NP_000560 XP_001133750 |
| Low affinity immunoglobulin gamma Fc region receptor II-a precursor (Fv-gamma RII-a)(FcRII-a)(IgG Fc receptor II-a)(Fc-gamma-RIIa)(CD32 antigen)(CDw32) | QEDS, (SEQ ID NO: 35) | P12318 |
| Low affinity immunoglobulin gamma Fc region receptor III-B precursor (IgG Fc receptor III-1)(Fc-gamma RIII-beta)(Fc-gamma RIIIb)(FcRIIIb)(Fc-gamma RIII)(FcRIII)(FcR-10)(CD16b antigen) | TEDL, (SEQ ID NO: 39) PEDN, (SEQ ID NO: 40) EEDP, (SEQ ID NO: 41) | O75015 |
| Low affinity immunoglobulin gamma Fc region receptor III-A precursor (IgG Fc receptor III-2)(Fc-gamma RIII-alpha)(Fc-gamma RIIIa)(FcRIIIa)(Fc-gamma RIII)(FcRIII)(FcR-10)(CD16a antigen) | TEDL, (SEQ ID NO: 39) PEDN, (SEQ ID NO: 40) EEDP, (SEQ ID NO: 41) | P08637 |
| High affinity immunoglobulin gamma Fc receptor I precursor (Fc-gamma RI)(FcRI)(IgG Fc receptor I)(CD64 antigen). | REDS, (SEQ ID NO: 36) TEDG, (SEQ ID NO: 37) QEDR, (SEQ ID NO: 38) | P12314 |
| IGHG1 immunoglobulin heavy constant gamma 1 (G1m marker) | AEDT, (SEQ ID NO: 14) | Q6PJA4 |
| apoA1 [Homo sapiens] | LEDL, (SEQ ID NO: 42) | CAA01253 |
| apolipoprotein C-III precursor [Homo sapiens] | AEDA, (SEQ ID NO: 62) | NP_000031 |
| apolipoprotein A-IV precursor [Homo sapiens]. | AEDV, (SEQ ID NO: 23) | NP_000473 |
| gelsolin (amyloidosis, Finnish type) [Homo sapiens] | TEDT, (SEQ ID NO: 30) KEDA, (SEQ ID NO: 43) SEDC, (SEQ ID NO: 44) QEDL, (SEQ ID NO: 63) | CAM20459 |
| gelsolin (amyloidosis, Finnish type) [Homo sapiens] | TEDT, (SEQ ID NO: 30) KEDA, (SEQ ID NO: 43) SEDC, (SEQ ID NO: 44) QEDL, (SEQ ID NO: 63) | CAI14413 |
| gelsolin (amyloidosis, Finnish type), isoform CRA_c [Homo sapiens]. | TEDT, (SEQ ID NO: 30) KEDA, (SEQ ID NO: 43) SEDC, (SEQ ID NO: 44) QEDL, (SEQ ID NO: 63) | EAW87491 |
| gelsolin (amyloidosis, Finnish type), isoform CRA_b [Homo sapiens] | TEDT, (SEQ ID NO: 30) KEDA, (SEQ ID NO: 43) SEDC, (SEQ ID NO: 44) QEDL, (SEQ 1D NO: 63) | EAW87490 |

TABLE 3-continued

Human Amyloidogenic Proteins

| Human amyloidogenic protein | Consensus sequence | GenBank Accession Number |
|---|---|---|
| gelsolin (amyloidosis, Finnish type), isoform CRA_a [Homo sapiens] | TEDT, (SEQ ID NO: 30)<br>KEDA, (SEQ ID NO: 43)<br>SEDC, (SEQ ID NO: 44)<br>QEDL, (SEQ ID NO: 63) | EAW87489 |
| amyloid precursor protein; APP [Homo sapiens]. | AEDV, (SEQ ID NO: 23) | AAB23646 |
| amyloid precursor protein; APP [Homo sapiens]. | AEDV, (SEQ ID NO: 23) | AAB19991 |
| amyloid peptide | AEDV, (SEQ ID NO: 23) | AAA51768 |
| Amyloid beta A4 protein precursor (APP) (ABPP)(Alzheimer disease amyloid protein) (Cerebral vascular amyloid peptide)(CVAP) (Protease nexin-II)(PN-II)(APPI)(PreA4) [Contains: Soluble APP-alpha (S-APP-alpha); Soluble APP-beta (S-APP-beta); C99; Beta-amyloid protein 42 (Beta-APP42); Beta-amyloid protein 40 (Beta-APP40); C83; P3(42); P3(40); Gamma-CTF(59)(Gamma-secretase C-terminal fragment 59)(Amyloid intracellular domain 59)(AID(59))(AICD-59); Gamma-CTF(57)(Gamma-secretase C-terminal fragment 57)(Amyloid intracellular domain 57)(AID(57))(AICD-57); Gamma-CTF(50)(Gamma-secretase C-terminal fragment 50)(Amyloid intracellular domain 50)(AID(50))(AICD-50); C31]. | EEDD, (SEQ ID NO: 45)<br>SEDK, (SEQ ID NO: 46)<br>DEDD, (SEQ ID NO: 47)<br>DEDG, (SEQ ID NO: 48)<br>AEDV, (SEQ ID NO: 23) | P05067 |
| APP protein [Homo sapiens]. | EEDD, (SEQ ID NO: 45)<br>SEDK, (SEQ ID NO: 46)<br>DEDD, (SEQ ID NO: 47)<br>DEDG, (SEQ ID NO: 48) | AAH65523 |
| APP protein [Homo sapiens]. | EEDD, (SEQ ID NO: 45)<br>SEDK, (SEQ ID NO: 46)<br>DEDD, (SEQ ID NO: 47)<br>DEDG, (SEQ ID NO: 48) | AAH04369 |
| amyloid beta (A4) precursor protein (protease nexin-II, Alzheimer disease) [Homo sapiens]. | EEDD, (SEQ ID NO: 45)<br>SEDK, (SEQ ID NO: 46)<br>DEDD, (SEQ ID NO: 47)<br>DEDG, (SEQ ID NO: 48)<br>AEDV, (SEQ ID NO: 23) | AAW82435 |
| Calcitonin | SEDE, (SEQ ID NO: 18) | AAA58403 |
| calcitonin precursor | SEDE, (SEQ ID NO: 18) | AAA35501 |
| preprocalcitonin [Homo sapiens] | SEDE, (SEQ ID NO: 18) | CAA25103 |
| Preprocalcitonin | SEDE, (SEQ ID NO: 18) | AAA51913 |
| Calcitonin precursor [Contains: Calcitonin; Katacalcin (Calcitonin carboxyl-terminal peptide)(CCP)(PDN-21)] | SEDE, (SEQ ID NO: 18) | P01258 |
| calcitonin isoform CALCA preproprotein [Homo sapiens]. | SEDE, (SEQ ID NO: 18) | NP_001029124 |
| calcitonin isoform CALCA preproprotein [Homo sapiens]. | SEDE, (SEQ ID NO: 18) | NP_001732 |
| calcitonin isoform CGRP preproprotein [Homo sapiens]. | SEDE, (SEQ ID NO: 18) | NP_001029125 |
| Calcitonin gene-related peptide 1 precursor (Calcitonin gene-related peptide I)(CGRP-I) (Alpha-type CGRP). | SEDE, (SEQ ID NO: 18) | P06881 |
| atrial natriuretic factor | LEDE, (SEQ ID NO: 49) | AAA35528 |

TABLE 3-continued

Human Amyloidogenic Proteins

| Human amyloidogenic protein | Consensus sequence | GenBank Accession Number |
|---|---|---|
| atrial natriuretic factor propeptide [Homo sapiens]. | LEDE, (SEQ ID NO: 49) | CAA25700 |
| atrial natriuretic factor | LEDE, (SEQ ID NO: 49) | I101403A |
| Atrial natriuretic factor precursor (ANF) (Atrial natriuretic peptide) (ANP) (Prepronatriodilatin) (CDD-ANF) [Contains: Cardiodilatin-related peptide(CDP)]. | LEDE, (SEQ ID NO: 49) | P01160 |
| atrial natriuretic peptide | LEDE, (SEQ ID NO: 49) | AAA35529 |
| keratin [Homo sapiens] | GEDA, (SEQ ID NO: 50) | AAB30058 |
| keratin [Homo sapiens]. | VEDF, (SEQ ID NO: 51)<br>YEDE, (SEQ ID NO: 52) | CAA31695 |
| Keratin | IEDL, (SEQ ID NO: 53)<br>GEDA, (SEQ ID NO: 50) | AAB59562 |
| Keratin, type II cytoskeletal 6C (Cytokeratin-6C) (CK 6C) (K6c keratin) (Cytokeratin-6E) (CK 6E) (Keratin K6h). | VEDL, (SEQ ID NO: 64)<br>YEDE, (SEQ ID NO: 52)<br>LEDA, (SEQ ID NO: 65) | P48668 |
| fibrinogen [Homo sapiens] | WEDY, (SEQ ID NO: 54) | CAA50740 |
| fibrinogen alpha subunit precursor [Homo sapiens]. | DEDW, (SEQ ID NO: 55)<br>SEDL, (SEQ ID NO: 56)<br>YEDQ, (SEQ ID NO: 57)<br>SEDG, (SEQ ID NO: 66)<br>LEDW, (SEQ ID NO: 58) | AAC97142 |
| Fibrinogen alpha chain [Homo sapiens] | DEDW, (SEQ ID NO: 55)<br>SEDL, (SEQ ID NO: 56)<br>YEDQ, (SEQ ID NO: 57)<br>SEDG, (SEQ ID NO: 66) | AAI01936 |
| Fibrinogen alpha chain [Homo sapiens] | DEDW, (SEQ ID NO: 55)<br>SEDL, (SEQ ID NO: 56)<br>YEDQ, (SEQ ID NO: 57)<br>SEDG, (SEQ ID NO: 66) | AAH98280 |
| fibrinogen alpha chain, isoform CRA_b [Homo sapiens]. | DEDW, (SEQ ID NO: 55)<br>SEDL, (SEQ ID NO: 56)<br>YEDQ, (SEQ ID NO: 57)<br>SEDG, (SEQ ID NO: 66)<br>LEDW, (SEQ ID NO: 58) | EAX04926 |
| fibrinogen alpha chain, isoform CRA_c [Homo sapiens]. | DEDW, (SEQ ID NO: 55)<br>SEDL, (SEQ ID NO: 56)<br>YEDQ, (SEQ ID NO: 57)<br>SEDG, (SEQ ID NO: 66) | EAX04928 |
| fibrinogen alpha chain, isoform CRA_a [Homo sapiens] | DEDW, (SEQ ID NO: 55)<br>SEDL, (SEQ ID NO: 56) | EAX04924 |
| prion protein precursor; PRNP [Homo sapiens] | YEDR, (SEQ ID NO: 59) | AAC62750 |
| Major prion protein precursor (PrP) (PrP27-30) (PrP33-35C) (ASCR) (CD230 antigen) | YEDR, (SEQ ID NO: 59) | P04156 |
| prion protein preproprotein [Homo sapiens]. | YEDR, (SEQ ID NO: 59) | NP_000302 |
| prolactin [Homo sapiens] | PEDK, (SEQ ID NO: 60) | CAA38264 |
| Prolactin [Homo sapiens]. | PEDK, (SEQ ID NO: 60) | AAH88370 |

VI. Amyloid Peptides for Active Immunization

Therapeutic agents for use in the methods of the invention are immunogenic peptides, such as AA peptides and AL peptides, that on administration to a patient generate antibodies that specifically bind to one or more epitopes comprising $X_1EDX_2$, such as, for example, epitopes between residues 70-76 of AA ("AA agents"). Additional examples of agents include immunogenic peptides that comprise a fragment consisting of $X_1EDX_2$ derived from other amyloid proteins ("X₁EDX₂ fragments"), such as AL Vκ fragments consisting of the amino acid sequence PEDI, (SEQ ID NO: 21), PEDF, (SEQ ID NO: 22), AEDV, (SEQ ID NO: 23), SEDF, (SEQ ID NO: 24), or SEDA, (SEQ ID NO: 25), and AL Vλ fragments consisting of the amino acid sequence SEDE, (SEQ ID NO: 18), AEDE, (SEQ ID NO: 19), TEDE, (SEQ ID NO: 16) or PEDE, (SEQ ID NO: 20). An AL Vλ fragment consisting of the amino acid sequence FEDD, (SEQ ID NO: 17) may also be used. Some suitable amyloid proteins include Serum amyloid A protein, immunoglobulin light chain protein, human islet amyloid precursor polypeptide (IAPP), beta amyloid peptide, transthyretin (TTR), ApoA1 and other amyloid proteins listed in Table 1 and which comprise the sequence X₁EDX₂. In some agents X₁ is H, T, F, S, P, A or any other amino acid residue immediately preceding ED in an amyloid protein; and X₂ is T, S, E, R, 1, V, F, D, A or any other amino acid residue immediately following ED in such amyloid protein. In some agents, X₁ is H, T, F, S, P, or A and X₂ is T, S, E, D, R, I, V, F or A. In some such agents, when X₁ is H, X₂ is T or A; when X₁ is A, X₂ is S, T, E or V; when X₁ is T, X₂ is E; when X₁ is F, X₂ is D; when X₁ is S, X₂ is E, F or A; and when X₁ is P, X₂ is E, I or F. In some agents, X₁ is H, T, F, S, P, or A and X₂ is T, S, E, D, R, 1, V, F or A, with the proviso that if X₁ is A, X₂ is not V. In some agents, when X₁ is A, X₂ is S, T or E.

Some agents comprise the amino acid sequence GHEDT, (SEQ ID NO: 3), HEDT, (SEQ ID NO: 12), AEDS, (SEQ ID NO: 13), AEDT, (SEQ ID NO: 14), HEDA, (SEQ ID NO: 15), TEDE, (SEQ ID NO: 16), FEDD, (SEQ ID NO: 17), SEDE, (SEQ ID NO: 18), AEDE, (SEQ ID NO: 19), PEDE, (SEQ ID NO: 20), PEDI, (SEQ ID NO: 21), PEDF, (SEQ ID NO: 22), AEDV, (SEQ ID NO: 23), SEDF, (SEQ ID NO: 24) or SEDA, (SEQ ID NO: 25). Some agents consist of an amino acid sequence selected from the group consisting of GHEDT, (SEQ ID NO: 3, HEDT, (SEQ ID NO: 12), AEDS, (SEQ ID NO: 13), AEDT, (SEQ ID NO: 14), HEDA, (SEQ ID NO: 15), TEDE, (SEQ ID NO: 16), FEDD, (SEQ ID NO: 17), SEDE, (SEQ ID NO: 18), AEDE, (SEQ ID NO: 19), PEDE, (SEQ ID NO: 20), PEDI, (SEQ ID NO: 21), PEDF, (SEQ ID NO: 22), AEDV, (SEQ ID NO: 23), SEDF, (SEQ ID NO: 24), or SEDA, (SEQ ID NO: 25), linked to a carrier to form a conjugate. Some agents comprise the amino acid sequence GHEDT, (SEQ ID NO: 3, HEDT, (SEQ ID NO: 12), AEDS, (SEQ ID NO: 13), AEDT, (SEQ ID NO: 14), HEDA, (SEQ ID NO: 15), TEDE, (SEQ ID NO: 16), FEDD, (SEQ ID NO: 17), SEDE, (SEQ ID NO: 18), AEDE, (SEQ ID NO: 19), PEDE, (SEQ ID NO: 20), PEDI, (SEQ ID NO: 21), PEDF, (SEQ ID NO: 22), AEDV, (SEQ ID NO: 23), SEDF, (SEQ ID NO: 24) and SEDA, (SEQ ID NO: 25), linked to a carrier to form a conjugate. Some agents comprise an amino acid sequence selected from the group consisting of GHEDT, (SEQ ID NO: 3), HEDT, (SEQ ID NO: 12), AEDS, (SEQ ID NO: 13), AEDT, (SEQ ID NO: 14), HEDA, (SEQ ID NO: 15) and TEDE, (SEQ ID NO: 16).

Preferred AA fragments are human AA1 (HAA1) alpha isoform residues 70-76 (GHGAEDS, SEQ ID NO:4), HAA1 beta isoform residues 70-76 (GHDAEDS, SEQ ID NO:5), HAA1 gamma isoform residues 70-76 (GHDAEDS, SEQ ID NO: 5), HAA2 alpha and beta isoforms residues 70-76 (GHGAEDS, SEQ ID NO: 4), HAA3 residues 70-76 (GDHAEDS, SEQ ID NO:7), HAA4 residues 78-84 (STVIEDS, SEQ ID NO:8), mouse AA1 (MAA1) residues 69-75 (GRGHEDT, SEQ ID NO:9), MAA2 residues 69-75 (GRGHEDT, SEQ ID NO: 9), MAA3 residues 62-68 (GHGAEDS, SEQ ID NO:10), and MAA4 residues 76-82 (NHGLETL, SEQ ID NO:11) or subfragments of at least three contiguous amino acids of any of these. Some AA fragments contain no residues of an AA amyloidosis peptide other than the segment designated above. Other AA fragments contain additional flanking residues from an AA amyloidosis peptide but contain no more than 20 or preferably no more than 10 contiguous residues in total from an AA amyloidosis peptide. Additional preferred X₁EDX₂ and AL fragments include GHEDT, (SEQ ID NO: 3), HEDT, (SEQ ID NO: 12), AEDS, (SEQ ID NO: 13), AEDT, (SEQ ID NO: 14), HEDA, (SEQ ID NO: 15), and TEDE, (SEQ ID NO: 16).

Therapeutic agents for use in the methods of the invention also include immunogenic AA peptides that on administration to a patient generate antibodies that specifically bind to N-terminal epitopes of AA. Preferred agents induce an immunogenic response directed to an epitope within residues 1-15 of human AA.

Preferably, the fragment of AA or AL or other agents such as X₁EDX₂ fragments administered lack an epitope that would generate a T-cell response to the fragment. Generally, T-cell epitopes are greater than 10 contiguous amino acids. Therefore, preferred fragments of amyloid proteins such as AA or X₁EDX₂ fragments are of size 4-10 or preferably 7-10 contiguous amino acids; i.e., sufficient length to generate an antibody response without generating a T-cell response. Absence of T-cell epitopes is preferred because these epitopes are not needed for immunogenic activity of fragments, and may cause an undesired inflammatory response in a subset of patients (Anderson et al., (2002) *J. Immunol.* 168, 3697-3701; Senior (2002) Lancet *Neurol.* 1, 3).

Preferred AA fragments are human AA1 (HAA1) alpha isoform residues 70-76 (GHGAEDS) (SEQ ID NO: 4), HAA1 beta isoform residues 70-76 (GHDAEDS) (SEQ ID NO:5), HAA1 gamma isoform residues 70-76 (GHDAEDS, SEQ ID NO: 5), HAA2 alpha and beta isoforms residues 70-76 (GHGAEDS, SEQ ID NO: 4), HAA3 residues 70-76 (GDHAEDS) (SEQ ID NO:7), HAA4 residues 78-84 (STVIEDS) (SEQ ID NO:8), mouse AA1 (MAA1) residues 69-75 (GRGHEDT) (SEQ ID NO:9), MAA2 residues 69-75 (GRGHEDT, SEQ ID NO: 9), MAA3 residues 62-68 (GHGAEDS) (SEQ ID NO:10), and MAA4 residues 76-82 (NHGLETL) (SEQ ID NO:11) or subfragments of at least three contiguous amino acids of any of these. Some AA fragments contain no residues of an AA amyloidosis peptide other than the segment designated above. Other AA fragments contain additional flanking residues from an AA amyloidosis peptide but contain no more than 20 or preferably no more than 10 contiguous residues in total from an AA amyloidosis peptide. Additional preferred X₁EDX₂ and AL fragments include GHEDT, (SEQ ID NO: 3), HEDT, (SEQ ID NO: 12), AEDS, (SEQ ID NO: 13), AEDT, (SEQ ID NO: 14), HEDA, (SEQ ID NO: 15), and TEDE, (SEQ ID NO: 16).

Analogs of the natural AA amyloidosis, AL amyloidosis, and other amyloidosis peptides can also be used to induce an immune response in the methods and compositions of the invention. Analogs including allelic, species and induced variants. Analogs of AA induce antibodies that specifically bind with a natural AA 70-76 peptide. Some such analogs fail to induce antibodies that specifically binds to epitopes outside AA70-76. Analogs of AA typically differ from naturally occurring peptides at up to 30% of amino acid positions by up to 1, 2, 3, 4, 5, 6, 7, 8, 9 or 10 position changes. Each deletion or substitution of a natural amino acid residue is considered a position change as is the insertion of a residue without substitution. Amino acids substitutions are often conservative substitutions.

Some analogs of AA or AA fragments or AL or AL fragments or other amyloid protein fragments such as $X_1EDX_2$ fragments also include unnatural amino acids or modifications of N or C terminal amino acids at one, two, five, ten or even all positions. For example, the natural aspartic acid residue can be replaced with iso-aspartic acid. Examples of unnatural amino acids are D, alpha, alpha-disubstituted amino acids, N-alkyl amino acids, lactic acid, 4-hydroxyproline, gamma-carboxyglutamate, epsilon-N,N,N-trimethyllysine, epsilon-N-acetyllysine, O-phosphoserine, N-acetylserine, N-formylmethionine, 3-methylhistidine, 5-hydroxylysine, omega-N-methylarginine, β-alanine, ornithine, norleucine, norvaline, hydroxproline, thyroxine, gamma-amino butyric acid, homoserine, citrulline, and isoaspartic acid. Some therapeutic agents of the invention are all-D peptides, e.g., all-D AA or all-D AA fragments, and all-D peptide analogs. Some therapeutic agents of the invention are 90% all-D peptides, e.g., 90% all-D AA or 90% all-D AA fragments, and 90% all-D peptide analogs. Some therapeutic agents of the invention are 80% all-D peptides, e.g., 80% all-D AA or 80% all-D AA fragments, and 80% all-D peptide analogs. Fragments and analogs can be screened for prophylactic or therapeutic efficacy in transgenic animal models in comparison with untreated or placebo controls as described below.

AA, AL, their fragments, and analogs and $X_1EDX_2$ fragments and their analogs can be synthesized by solid phase peptide synthesis or recombinant expression, or can be obtained from natural sources. Automatic peptide synthesizers are commercially available from numerous suppliers, such as Applied Biosystems, Foster City, Calif. Recombinant expression can be in bacteria, such as *E. coli*, yeast, insect cells or mammalian cells. Procedures for recombinant expression are described by Sambrook et al., *Molecular Cloning: A Laboratory Manual* (C.S.H.P. Press, NY 2d ed., 1989.)

Therapeutic agents also include longer polypeptides that include, for example, an immunogenic fragment of AA peptide, AL peptide or an $X_1EDX_2$ fragment, together with one or more other amino acids flanking the AA peptide, AL peptide or $X_1EDX_2$ fragment on one or one or both sides. For example, preferred agents include fusion proteins comprising a segment of AA, AL or $X_1EDX_2$ fragment fused to a heterologous amino acid sequence that induces a helper T-cell response against the heterologous amino acid sequence and thereby a B-cell response against the AA segment, AL segment or $X_1EDX_2$ fragment. One or more flanking heterologous amino acids can also be used to cap an AA or AL peptide or $X_1EDX_2$ fragment to protect it from degradation in manufacture, storage or use. Such polypeptides can be screened for prophylactic or therapeutic efficacy in animal models in comparison with untreated or placebo controls as described below. Therapeutic agents of the invention include an immunogenic fragment of AA or AL or $X_1EDX_2$ fragment flanked by polylysine sequences. The polylysine sequences can be fused to the N-terminus, the C terminus, or both the N- and C-terminus of AA or AL or an immunogenic fragment of AA or AL or $X_1EDX_2$ fragment. The AA or AL peptide, $X_1EDX_2$ fragment, analog, active fragment of AA or other polypeptide can be administered in associated or multimeric form or in dissociated form. Therapeutic agents also include multimers of monomeric immunogenic agents.

In a further variation, an immunogenic fragment of AA or AL or $X_1 EDX_2$ fragment can be presented by a virus or a bacterium as part of an immunogenic composition. A nucleic acid encoding the immunogenic peptide is incorporated into a genome or episome of the virus or bacteria. Optionally, the nucleic acid is incorporated in such a manner that the immunogenic peptide is expressed as a secreted protein or as a fusion protein with an outer surface protein of a virus or a transmembrane protein of a bacterium so that the peptide is displayed. Viruses or bacteria used in such methods should be nonpathogenic or attenuated. Suitable viruses include adenovirus, HSV, Venezuelan equine encephalitis virus and other alpha viruses, vesicular stomatitis virus, and other rhabdo viruses, vaccinia and fowl pox. Suitable bacteria include *Salmonella* and *Shigella*. Fusion of an immunogenic peptide to HBsAg of HBV is particularly suitable.

Therapeutic agents also include peptides and other compounds that do not necessarily have a significant amino acid sequence similarity with AA or AL or $X_1EDX_2$ fragment but nevertheless serve as mimetics of AA or AL or $X_1EDX_2$ fragment and induce a similar immune response. For example, any peptides and proteins forming β-pleated sheets can be screened for suitability. Anti-idiotypic antibodies against monoclonal antibodies to AA or AL or other amyloidogenic peptides such as or $X_1EDX_2$ fragments can also be used. Such anti-Id antibodies mimic the antigen and generate an immune response to it (see Essential Immunology (Roit ed., Blackwell Scientific Publications, Palo Alto, 6th ed.), p. 181). Agents other than AA peptides should induce an immunogenic response against one or more of the preferred segments of AA listed above (e.g., AA70-76 or GHEDT, (SEQ ID NO: 3) or an AL or $X_1EDX_2$ fragment listed above, such as, for example, HEDT, (SEQ ID NO: 12), AEDS, (SEQ ID NO: 13), AEDT, (SEQ ID NO: 14), HEDA, (SEQ ID NO: 15) and TEDE, (SEQ ID NO: 16).

Preferably, such agents induce an immunogenic response that is specifically directed to one of these segments without being directed to other segments of AA or AL or amyloid protein from which the $X_1EDX_2$ fragment was derived.

Random libraries of peptides or other compounds can also be screened for suitability. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). Peptide libraries can also be generated by phage display methods. See, e.g., Devlin, WO 91/18980.

Combinatorial libraries and other compounds are initially screened for suitability by determining their capacity to specifically bind to antibodies or lymphocytes (B or T) known to be specific for AA or other amyloidogenic peptides. For example, initial screens can be performed with any polyclonal sera or monoclonal antibody to AA or AL or a fragment thereof or to an $X_1EDX_2$ fragment. Compounds can then be screened for specifically binding to a specific epitope within AA (e.g., AA70-76 or GHEDT, (SEQ ID NO: 3) or AL or to an $X_1EDX_2$ fragment listed above, such as, for example, HEDT, (SEQ ID NO: 12), AEDS, (SEQ ID NO: 13), AEDT, (SEQ ID NO: 14), HEDA, (SEQ ID NO: 15) and TEDE, (SEQ ID NO: 16).

Compounds can be tested by the same procedures described for mapping antibody epitope specificities. Compounds identified by such screens are then further analyzed for capacity to induce antibodies or reactive lymphocytes to AA or AL or fragments thereof or to an $X_1EDX_2$ fragment. For example, multiple dilutions of sera can be tested on microtiter plates that have been precoated with AA or AL or a fragment thereof or an $X_1EDX_2$ fragment and a standard ELISA can be performed to test for reactive antibodies to AA or AL or the fragment or to the $X_1EDX_2$ fragment. Compounds can then be tested for prophylactic and therapeutic efficacy in transgenic animals predisposed to amyloidosis, such as, for example, AA Amyloidosis or AL amyloidosis. The same screening approach can be used on other potential agents, analogs of AA, analogs of AL and longer peptides, including fragments of AA, AL and $X_1EDX_2$ fragments, described above.

VII. Conjugates

Some agents for inducing an immune response contain the appropriate epitope for inducing an immune response against AA but are too small to be immunogenic. In this situation, a peptide immunogen can be linked to a suitable carrier molecule to form a conjugate which helps elicit an immune response. A single agent can be linked to a single carrier, multiple copies of an agent can be linked to multiple copies of a carrier, which are in turn linked to each other, multiple copies of an agent can be linked to a single copy of a carrier, or a single copy of an agent can be linked to multiple copies of a carrier, or different carriers. Suitable carriers include serum albumins, keyhole limpet hemocyanin, immunoglobulin molecules, thyroglobulin, ovalbumin, tetanus toxoid, or a toxoid from other pathogenic bacteria, such as diphtheria, E. coli, cholera, or H. pylori, or an attenuated toxin derivative. T cell epitopes are also suitable carrier molecules. Some conjugates can be formed by linking agents of the invention to an immunostimulatory polymer molecule (e.g., tripalmitoyl-5-glycerine cysteine ($Pam_3Cys$), mannan (a manose polymer), or glucan (a beta 1→2 polymer)), cytokines (e.g., IL-1, IL-1 alpha and beta peptides, IL-2, gamma-INF, IL-10, GM-CSF), and chemokines (e.g., MIP1alpha and beta, and RANTES). Immunogenic agents can also be linked to peptides that enhance transport across tissues, as described in O'Mahony, WO 97/17613 and WO 97/17614. Immunogens may be linked to the carries with or without spacers amino acids (e.g., gly-gly).

Some conjugates can be formed by linking agents of the invention to at least one T cell epitope. Some T cell epitopes are promiscuous while other T cell epitopes are universal. Promiscuous T cell epitopes are capable of enhancing the induction of T cell immunity in a wide variety of subjects displaying various HLA types. In contrast to promiscuous T cell epitopes, universal T cell epitopes are capable of enhancing the induction of T cell immunity in a large percentage, e.g., at least 75%, of subjects displaying various HLA molecules encoded by different HLA-DR alleles.

A large number of naturally occurring T-cell epitopes exist, such as, tetanus toxoid (e.g., the P2 and P30 epitopes), Hepatitis B surface antigen, pertussis, toxoid, measles virus F protein, Chlamydia trachomitis major outer membrane protein, diphtheria toxoid (e.g., CRM197), Plasmodium falciparum circumsporozite T, Plasmodium falciparum CS antigen, Schistosoma mansoni triose phosphate isomersae, Escherichia coli TraT, and Influenza virus hemagluttinin (HA). The immunogenic peptides of the invention can also be conjugated to the T-cell epitopes described in Sinigaglia F. et al., Nature, 336:778-780 (1988); Chicz R. M. et al., J. Exp. Med., 178:27-47 (1993); Hammer J. et al., Cell 74:197-203 (1993); Falk K. et al., Immunogenetics, 39:230-242 (1994); WO 98/23635; Southwood S. et al. J. Immunology; 160: 3363-3373 (1998); and, Giannini, G. et al. Nucleic Acids Res. 12: 4063-4069 (1984), (each of which is incorporated herein by reference for all purposes). Further examples include:

```
Influenza Hemagluttinin: HA307-319.

Malaria CS:
                                   (SEQ ID NO: 67)
T3 epitope EKKIAKMEKASSVFNV,.

Hepatitis B surface antigen:
                                   (SEQ ID NO: 68)
HBsAg19-28 FFLLTRILTI,.

Heat Shock Protein 65:
                                   (SEQ ID NO: 69)
hsp65153-171 DQSIGDLIAEAMDKVGNEG,.

bacille Calmette-Guerin
                                   (SEQ ID NO: 70)
QVHFQPLPPAVVKL,.

Tetanus toxoid:
                                   (SEQ ID NO: 71)
TT830-844 QYIKANSKFIGITEL,.

Tetanus toxoid:
                                   (SEQ ID NO: 72)
TT947-967 FNNFTVSFWLRVPKVSASHLE,.

HIV gp120 T1:
                                   (SEQ ID NO: 73)
KQIINMWQEVGKAMYA,.

Tetanus toxoid:
TT947-967 FNNFTVSFWLRVPKVSASHLE

HIV gp 20 T1:
KQIINMWQEVGKAMYA.
```

Alternatively, the conjugates can be formed by linking agents of the invention to at least one artificial T-cell epitope capable of binding a large proportion of MHC Class II molecules., such as the pan DR epitope ("PADRE"). PADRE is described in U.S. Pat. No. 5,736,141, WO 95/07707, and Alexander J et al., Immunity, 1:751-761 (1994) (each of which is incorporated herein by reference for all purposes). A preferred PADRE peptide is AKXVAAWTLKAAA, (SEQ ID NO: 74), (common residues bolded) wherein X is preferably cyclohexylalanine tyrosine or phenylalanine, with cyclohexylalanine being most preferred.

Immunogenic agents can be linked to carriers by chemical crosslinking. Techniques for linking an immunogen to a carrier include the formation of disulfide linkages using N-succinimidyl-3-(2-pyridyl-thio)propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the epsilon-amino on a lysine, or other free amino group in other amino acids. A variety of such disulfide/amide-forming agents are described by Immun. Rev. 62, 185 (1982). Other bifunctional coupling agents form a thioether rather than a disulfide linkage. Many of these thio-ether-forming agents are commercially available and include reactive esters of 6-maleimidocaproic acid, 2-bromoacetic acid, and 2-iodoacetic acid, 4-(N-maleimido-methyl)cyclohexane-1-carboxylic acid. The carboxyl groups can be activated by combining them with succinimide or 1-hydroxyl-2-nitro-4-sulfonic acid, sodium salt.

Immunogenicity can be improved through the addition of spacer residues (e.g., Gly-Gly) between the $T_h$ epitope and the peptide immunogen of the invention. In addition to physically separating the $T_h$ epitope from the B cell epitope (i.e., the peptide immunogen), the glycine residues can disrupt any artificial secondary structures created by the joining of the $T_h$ epitope with the peptide immunogen, and thereby eliminate interference between the T and/or B cell responses. The conformational separation between the helper epitope and the antibody eliciting domain thus permits more efficient interactions between the presented immunogen and the appropriate $T_h$ and B cells.

To enhance the induction of T cell immunity in a large percentage of subjects displaying various HLA types to an agent of the present invention, a mixture of conjugates with different $T_h$ cell epitopes can be prepared. The mixture may contain a mixture of at least two conjugates with different $T_h$ cell epitopes, a mixture of at least three conjugates with different $T_h$ cell epitopes, or a mixture of at least four conjugates with different $T_h$ cell epitopes. The mixture may be administered with an adjuvant.

Immunogenic peptides can also be expressed as fusion proteins with carriers (i.e., heterologous peptides). The immunogenic peptide can be linked at its amino terminus, its carboxyl terminus, or both to a carrier. Optionally, multiple repeats of the immunogenic peptide can be present in the fusion protein. Optionally, an immunogenic peptide can be linked to multiple copies of a heterologous peptide, for example, at both the N and C termini of the peptide. Optionally, multiple copies of an immunogenic peptide can be linked to multiple copies of a heterologous peptide, which are linked to each other. Some carrier peptides serve to induce a helper T-cell response against the carrier peptide. The induced helper T-cells in turn induce a B-cell response against the immunogenic peptide linked to the carrier.

Some examples of fusion proteins suitable for use in the invention are shown below. Some of these fusion proteins comprise segments of AA linked to tetanus toxoid epitopes such as described in U.S. Pat. No. 5,196,512, EP 378,881 and EP 427,347. Some fusion proteins comprise segments of AA linked to at least one PADRE peptide described in U.S. Pat. No. 5,736,142. Some heterologous peptides are promiscuous T-cell epitopes, while other heterologous peptides are universal T-cell epitopes. In some methods, the agent for administration is simply a single fusion protein with an AA segment linked to a heterologous segment in linear configuration. The therapeutic agents of the invention can be represented using a formula. For example, in some methods, the agent is multimer of fusion proteins represented by the formula $2^x$, in which x is an integer from 1-5. Preferably x is 1, 2 or 3, with 2 being most preferred. When x is two, such a multimer has four fusion proteins linked in a preferred configuration referred to as MAP4 (see U.S. Pat. No. 5,229,490).

The MAP4 configuration is shown below, where branched structures are produced by initiating peptide synthesis at both the N terminal and side chain amines of lysine. Depending upon the number of times lysine is incorporated into the sequence and allowed to branch, the resulting structure will present multiple N termini. In this example, four identical N termini have been produced on the branched lysine-containing core. Such multiplicity greatly enhances the responsiveness of cognate B cells. In the examples below, Z refers to an immunogenic fragment of AA, AL or an $X_1EDX_2$ fragment, and Z1-4 refer to immunogenic fragment(s) of AA, AL or an $X_1EDX_2$ fragment. The fragments can be the same as each other or different.

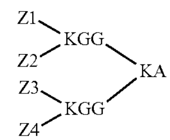

Other examples of fusion proteins include:

Z-Tetanus toxoid 830-844 in a MAP4 configuration:

(SEQ ID NO: 71)
Z-QYIKANSKFIGITEL,

Z-Tetanus toxoid 947-967 in a MAP4 configuration:

(SEQ ID NO: 72)
Z-FNNFTVSFWLRVPKVSASHLE,

Z-Tetanus toxoid 830-844 in a MAP4 configuration:

(SEQ ID NO: 71)
Z-QYIKANSKFIGITEL,

Z-Tetanus toxoid 830-844+947-967 in a linear configuration:

(SEQ ID NO: 75)
Z-QYIKANSKFIGITELFNNFTVSFWLRVPKVSASHLE,.

PADRE peptide (all in linear configurations), wherein X is preferably cyclohexylalanine, tyrosine or phenylalanine, with cyclohexylalanine being most preferred-Z:

(SEQ ID NO: 74)
AKXVAAWTLKAAA-Z,.

Z x 3-PADRE peptide:

(SEQ ID NO: 74)
Z-Z-Z-AKXVAAWTLKAAA,.

Z-ovalbumin 323-339 in a linear configuration:

(SEQ ID NO: 76)
Z-ISQAVHAAHAEINEAGR,.

Further examples of fusion proteins include:

(SEQ ID NO: 74)
AKXVAAWTLKAAA-Z-Z-Z-Z,.

(Z-(SEQ ID NO: 74)
Z-AKXVAAWTLKAAA,.

(SEQ ID NO: 77)
PKYVKQNTLKLAT-Z-Z-Z,.

(SEQ ID NO: 77)
Z-PKYVKQNTLKLAT-Z,.

-continued

```
                                           (SEQ ID NO: 77)
Z-Z-Z-PKYVKQNTLKLAT,.

(Z-Z-(SEQ ID NO: 77)
Z-Z-PKYVKQNTLKLAT, (SEQ ID NO: 78)
Z-PKYVKQNTLKLAT-EKKIAKMEKASSVFNV-QYIKANSKFIGITEL-

FNNFTVSFWLRVPKVSASHLE- (SEQ ID NO: 79)
Z-Z-Z-QYIKANSKFIGITEL-FNNFTVSFWLRVPKVSASHLE,.

(SEQ ID NO: 79)
Z-QYIKANSKFIGITELCFNNFTVSFWLRVPKVSASHLE-Z,.

(SEQ ID NO: 79)
QYIKANSKFIGITELCFNNFTVSFWLRVPKVSASHLE-Z,
```

Z-QYIKANSKFIGITEL, (SEQ ID NO: 71) on a 2 branched resin: fragments can be the same as each other or different.

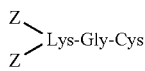

The same or similar carrier proteins and methods of linkage can be used for generating immunogens to be used in generation of antibodies against AA or an immunogenic fragment of AA, AL or an $X_1EDX_2$ fragment. For example, AA or an immunogenic fragment of AA, AL or an $X_1EDX_2$ fragment linked to a carrier can be administered to a laboratory animal in the production of monoclonal antibodies to AA or an immunogenic fragment of AA, AL or an $X_1EDX_2$ fragment.

VIII. Nucleic Acid Encoding Therapeutic Agents

Therapeutic agents of the invention also include nucleic acids. Immune responses against amyloid deposits can also be induced by administration of nucleic acids encoding segments of AA peptide, and fragments thereof, other peptide immunogens such as $X_1EDX_2$ fragments, or antibodies and their component chains, such as antibodies 2A4, 8G9 and 7D8, used for passive immunization. Such agents for use in the methods of the invention include nucleic acids encoding AA peptides that on administration to a patient generate antibodies that specifically bind to one or more epitopes between residues 70-76 of AA, AL or nucleic acids encoding peptides comprising $X_1EDX_2$ fragments. Such agents for use in the methods of the invention also include nucleic acids encoding antibodies that specially bind to a C-terminal neoepitope of AA or to $X_1EDX_2$. In particular, such nucleic acids encode antibodies that specifically bind to HAA1 alpha isoform within residues 70-76 (GHGAEDS, (SEQ ID NO: 4), HAA1 beta isoform within residues 70-76 (GHDAEDS, (SEQ ID NO: 5), HAA1 gamma isoform within residues 70-76 (GHDAEDS, (SEQ ID NO: 5), HAA2 alpha and beta isoforms within residues 70-76 (GHGAEDS, (SEQ ID NO: 4), HAA3 within residues 70-76 (GDHAEDS, (SEQ ID NO: 7), HAA4 within residues 78-84 (STVIEDS, (SEQ ID NO: 8), mouse AA1 (MAA1) within residues 69-75 (GRGHEDT, (SEQ ID NO: 9), MAA2 within residues 69-75 (GRGHEDT, (SEQ ID NO: 9), MAA3 within residues 62-68 (GHGAEDS, (SEQ ID NO: 4), and MAA4 within residues 76-82 (NHGLETL, (SEQ ID NO: 11). Such nucleic acids can be DNA or RNA. Additional preferred nucleic acids encode antibodies that specifically bind to HEDT, (SEQ ID NO: 12), AEDS, (SEQ ID NO: 13), AEDT, (SEQ ID NO: 14), HEDA, (SEQ ID NO: 15) or TEDE, (SEQ ID NO: 16) or other $X_1EDX_2$ peptides listed above. A nucleic acid segment encoding an immunogen is typically linked to regulatory elements, such as a promoter and enhancer, that allow expression of the DNA segment in the intended target cells of a patient. For expression in blood cells, as is desirable for induction of an immune response, promoter and enhancer elements from light or heavy chain immunoglobulin genes or the CMV major intermediate early promoter and enhancer are suitable to direct expression. The linked regulatory elements and coding sequences are often cloned into a vector. For administration of double-chain antibodies, the two chains can be cloned in the same or separate vectors. The nucleic acids encoding therapeutic agents of the invention can also encode at least one T cell epitope. The disclosures herein which relate to the use of adjuvants and the use of carriers apply mutatis mutandis to their use with the nucleic acids encoding the therapeutic agents of the present invention.

A number of viral vector systems are available including retroviral systems (see, e.g., Lawrie and Tumin, *Cur. Opin. Genet. Develop.* 3, 102-109 (1993)); adenoviral vectors (see, e.g., Bett et al., *J. Virol.* 67, 5911 (1993)); adeno-associated virus vectors (see, e.g., Zhou et al., *J. Exp. Med.* 179, 1867 (1994)), viral vectors from the pox family including vaccinia virus and the avian pox viruses, viral vectors from the alpha virus genus such as those derived from Sindbis and Semliki Forest Viruses (see, e.g., Dubensky et al., *J. Virol.* 70, 508-519 (1996)), Venezuelan equine encephalitis virus (see U.S. Pat. No. 5,643,576) and rhabdoviruses, such as vesicular stomatitis virus (see WO 96/34625) and papillomaviruses (Ohe et al., *Human Gene Therapy* 6, 325-333 (1995); Woo et al., WO 94/12629 and Xiao & Brandsma, *Nucleic Acids. Res.* 24, 2630-2622 (1996)).

DNA encoding an immunogen, or a vector containing the same, can be packaged into liposomes. Suitable lipids and related analogs are described by U.S. Pat. Nos. 5,208,036, 5,264,618, 5,279,833 and 5,283,185. Vectors and DNA encoding an immunogen can also be adsorbed to or associated with particulate carriers, examples of which include polymethyl methacrylate polymers and polylactides and poly (lactide-co-glycolides), see, e.g., McGee et al., *J. Micro Encap.* (1996).

Gene therapy vectors or naked DNA can be delivered in vivo by administration to an individual patient, typically by systemic administration (e.g., intravenous, intraperitoneal, nasal, gastric, intradermal, intramuscular, subdermal, or intracranial infusion) or topical application (see e.g., U.S. Pat. No. 5,399,346). Such vectors can further include facilitating agents such as bupivacine (U.S. Pat. No. 5,593,970). DNA can also be administered using a gene gun. (See Xiao & Brandsma, supra.) The DNA encoding an immunogen is precipitated onto the surface of microscopic metal beads. The microprojectiles are accelerated with a shock wave or expanding helium gas, and penetrate tissues to a depth of several cell layers. For example, The Accel™ Gene Delivery Device manufactured by Agacetus, Inc. Middleton Wis. is suitable. Alternatively, naked DNA can pass through skin into the blood stream simply by spotting the DNA onto skin with chemical or mechanical irritation (see WO 95/05853).

In a further variation, vectors encoding immunogens can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

IX. Adjuvants

Immunogenic agents of the invention, such as peptides, are sometimes administered in combination with an adjuvant. The adjuvant increases the titer of induced antibodies and/or the binding affinity of induced antibodies relative to the situation if the peptide were used alone. A variety of adjuvants can be used in combination with an immunogenic fragment of AA, to elicit an immune response. Preferred adjuvants augment the intrinsic response to an immunogen without causing conformational changes in the immunogen that affect the qualitative form of the response. Preferred adjuvants include aluminum hydroxide and aluminum phosphate, 3 De-O-acylated monophosphoryl lipid A (MPL™) (see GB 2220211 (RIB1 ImmunoChem Research Inc., Hamilton, Mont., now part of Corixa), RC-529 (Corixa, Hamilton, Mont.). STIMULON™ QS-21 is a triterpene glycoside or saponin isolated from the bark of the Quillaja Saponaria Molina tree found in South America (see Kensil et al., in Vaccine Design: The Subunit and Adjuvant Approach (eds. Powell & Newman, Plenum Press, NY, 1995); U.S. Pat. No. 5,057,540), (Aquila BioPharmaceuticals, Framingham, Mass.). Other adjuvants are oil in water emulsions (such as squalene or peanut oil), optionally in combination with immune stimulants, such as monophosphoryl lipid A (see Stoute et al., N. Engl. J. Med. 336, 86-91 (1997)), pluronic polymers, and killed mycobacteria. Another adjuvant is CpG (WO 98/40100). Adjuvants can be administered as a component of a therapeutic composition with an active agent or can be administered separately, before, concurrently with, or after administration of the therapeutic agent.

A preferred class of adjuvants is aluminum salts (alum), such as alum hydroxide, alum phosphate, alum sulfate. Such adjuvants can be used with or without other specific immunostimulating agents such as MPL or 3-DMP, QS-21, polymeric or monomeric amino acids such as polyglutamic acid or polylysine. Another class of adjuvants is oil-in-water emulsion formulations. Such adjuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) THERAMIDE™), or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (c) RIBI™ adjuvant system (RAS), (Ribi ImmunoChem, Hamilton, Mont.) containing 2% squalene, 0.2% Tween 80, and one or more bacterial cell wall components from the group consisting of monophosphoryllipid A (MPL), trehalose dimycolate (TDM), and cell wall skeleton (CWS), preferably MPL+CWS (DETOX™).

Another class of preferred adjuvants is saponin adjuvants, such as STIMULON™ (QS-21, Aquila, Framingham, Mass.) or particles generated therefrom such as ISCOMs (immunostimulating complexes) and ISCOMATRIX. Other adjuvants include RC-529, GM-CSF and Complete Freund's Adjuvant (CFA) and Incomplete Freund's Adjuvant (IFA). Other adjuvants include cytokines, such as interleukins (e.g., IL-1α and β peptides, IL-2, IL-4, IL-6, IL-12, IL13, and IL-15), macrophage colony stimulating factor (M-CSF), granulocyte-macrophage colony stimulating factor (GM-CSF), tumor necrosis factor (TNF), chemokines, such as MIP1α and β and RANTES. Another class of adjuvants is glycolipid analogues including N-glycosylamides, N-glycosylureas and N-glycosylcarbamates, each of which is substituted in the sugar residue by an amino acid, as immuno-modulators or adjuvants (see U.S. Pat. No. 4,855,283). Heat shock proteins, e.g., HSP70 and HSP90, may also be used as adjuvants.

An adjuvant can be administered with an immunogen as a single composition, or can be administered before, concurrent with, or after administration of the immunogen. Immunogen and adjuvant can be packaged and supplied in the same vial or can be packaged in separate vials and mixed before use. Immunogen and adjuvant are typically packaged with a label indicating the intended therapeutic application. If immunogen and adjuvant are packaged separately, the packaging typically includes instructions for mixing before use. The choice of an adjuvant and/or carrier depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Alum, MPL and QS-21 are preferred. Optionally, two or more different adjuvants can be used simultaneously. Preferred combinations include alum with MPL, alum with QS-21, MPL with QS-21, MPL or RC-529 with GM-CSF, and alum, QS-21 and MPL together. Also, Incomplete Freund's adjuvant can be used (Chang et al., Advanced Drug Delivery Reviews 32, 173-186 (1998)), optionally in combination with any of alum, QS-21, and MPL and all combinations thereof.

X. Passive Administration of Antibodies

Therapeutic agents of the present invention include antibodies that specifically bind to to an epitope comprising $X_1EDX_2$ in an aggregated amyloid protein, wherein $X_1$ is H, T, F, S, P, A or any other amino acid residue immediately preceding ED in such aggregated amyloid protein; and wherein $X_2$ is T, S, E, R, I, V, F, A or any other amine acid residue immediately following ED in such aggregated amyloid protein, including epitopes within amyloid peptides such as AA. The antibodies used for passive administration can be antibodies that bind to C-terminal or N-terminal epitopes of AA. Other amyloid proteins in addition to Serum amyloid A protein include serum amyloid A protein, immunoglobulin light chain protein, such as, for example, Vλ6 Wil or Vκ, human islet amyloid precursor polypeptide (IAPP), beta amyloid peptide, transthyretin (TTR) and ApoA1, as well as others listed in Table 1 above.

AA is formed by proteolytic cleavage of SAA. Preferred antibodies specifically bind to neoepitopes of AA which form upon proteolytic cleavage of SAA. Preferred antibodies specially bind to a C-terminal neoepitope of AA, especially, such antibodies specifically bind to HAA1 alpha isoform within residues 70-76 (GHGAEDS, SEQ ID NO:4), HAA1 beta isoform within residues 70-76 (GHDAEDS, SEQ ID NO:5), HAA1 gamma isoform within residues 70-76 (GHDAEDS, SEQ ID NO: 5), HAA2 alpha and beta isoforms within residues 70-76 (GHGAEDS, SEQ ID NO: 10), HAA3 within residues 70-76 (GDHAEDS, SEQ ID NO:7), HAA4 within residues 78-84 (STVIEDS, SEQ ID NO:8), mouse AA1

(MAA1) within residues 69-75 (GRGHEDT, SEQ ID NO:9), MAA2 within residues 69-75 (GRGHEDT, SEQ ID NO: 9), MAA3 within residues 62-68 (GHGAEDS, SEQ ID NO:10), and MAA4 within residues 76-82 (NHGLETL, SEQ ID NO:11). Some antibodies only bind to an epitope within one of these peptides. Other antibodies bind to epitopes within more than one of these peptides. For example, some antibodies specifically bind to a GHGAEDS, (SEQ ID NO: 4) peptide and a GHDAEDS, SEQ ID NO: 5) peptide. Some antibodies bind to a GHGAEDS, SEQ ID NO: 4) peptide without specifically binding to a GHDAEDS, SEQ ID NO: 5) peptide. Binding to at least one of the human AA peptides is preferable. Binding to at least one of the human AA peptides and a corresponding mouse peptide is useful in that the same antibody can be tested in a mouse model and subsequently used in humans. Some preferred antibodies specifically bind to epitopes within HAA1 alpha isoform residues 71-76, 72-76, 73-76, 74-76, 70-75, 70-74, 70-73, 70-72, 71-75, 72-75, 73-75, 71-74, 71-73, 72-74, or MAA1 residues 70-75, 71-75, 72-75, 73-75, 69-74, 69-73, 69-72, 69-71, 70-74, 71-74, 72-74, 70-73, 70-72. Such antibodies typically specifically bind to amyloid deposits but may or may not bind to soluble AA. When an antibody is said to specifically bind to an epitope within specified residues, such as HAA1 alpha isoform residues 70-76 of for example, what is meant is that the antibody specifically binds to a polypeptide containing the specified residues (i.e., residues 70-76 of HAA1 alpha isoform in this an example). Such an antibody does not necessarily contact every residue within residues 70-76 of HAA1 alpha isoform. Nor does every single amino acid substitution or deletion with in residues 70-76 of HAA1 alpha isoform necessarily significantly affect binding affinity. Such neoepitope antibodies bind to AA but not to SAA. Epitope specificity of an antibody can be determined, for example, as described by WO 00/72880.

The antibodies used for passive administration can be antibodies to N-terminal epitopes of AA. Preferred antibodies specifically bind to a N-terminal neoepitope of AA, especially, such antibodies specifically bind to HAA1 residues 1-15 (RSFFSFLGEAFDGAR, SEQ ID NO. 80), HAA2 residues 1-15 (RSFFSFLGEAFDGAR, SEQ ID NO. 80), HAA3 residues 1-15 (QGWLTFLKAAGQGAK, SEQ ID NO: 81), HAA4 residues 1-15 (ESWRSFFKEA, (SEQ ID NO: 82), MAA1 residues 1-15 (GFFSFVHEAFQGAGD, SEQ ID NO: 83), MAA2 residues 1-15 (GFFSFVHEAFQGAGD, SEQ ID NO: 83), MAA3 residues 1-9 (EAGQGSRD, (SEQ ID NO: 84), and residues 1-14 MAA4 (WYSFFREAVQGTWD, SEQ ID NO: 85). Some antibodies only bind to an epitope within one of these peptides. Other antibodies bind to epitopes within more than one of these peptides. For example, some antibodies specifically bind to a RSFFSFLGEAFDGAR, SEQ ID NO: 80) peptide and a QGWLTFLKAAGQGAK, SEQ ID NO: 81) peptide. Some antibodies bind to a RSFFSFLGEAFDGAR, SEQ ID NO: 80) peptide without specifically binding to a QGWLTFLKAAGQGAK, SEQ ID NO: 81) peptide. Binding to at least one of the human AA peptides is preferable. Binding to at least one of the human AA peptides and a corresponding mouse peptide is useful in that the same antibody can be tested in a mouse model and subsequently used in humans.

Some antibodies specifically bind to an epitope consisting of such $X_1EDX_2$ Preferably such antibodies specifically bind to such epitope in an aggregated amyloid protein. Some of such antibodies preferentially specifically bind to an aggregated amyloid protein relative to the monomeric form of such amyloid protein. In some antibodies, $X_1$ is H, T, F, S, P, or A and $X_2$ is T, S, E, D, R, I, V, F or A. In some such antibodies, when $X_1$ is H, $X_2$ is T or A; when $X_1$ is A, $X_2$ is S, T, E or V; when $X_1$ is T, $X_2$ is E; when $X_1$ is F, $X_2$ is D; when $X_1$ is S, $X_2$ is E, F or A; and when $X_1$ is P, $X_2$ is E, I or F. In some antibodies, $X_1$ is H, T, F, S, P, or A and $X_2$ is T, S, E, D, R, I, V, F or A, with the proviso that if $X_1$ is A, $X_2$ is not V. In some antibodies, when $X_1$ is A, $X_2$ is S, T or E.

Some antibodies specifically bind an epitope comprising the amino acid sequence GHEDT, (SEQ ID NO 3), HEDT, (SEQ ID NO: 12), AEDS, (SEQ ID NO: 13), AEDT, (SEQ ID NO: 14), HEDA, (SEQ ID NO: 15), TEDE, (SEQ ID NO: 16), FEDD, (SEQ ID NO: 17), SEDE, (SEQ ID NO: 18), AEDE, (SEQ ID NO: 19), PEDE, (SEQ ID NO: 20), PEDI, (SEQ ID NO: 21), PEDF, (SEQ ID NO: 22), AEDV, (SEQ ID NO: 23), SEDF, (SEQ ID NO: 24) or SEDA, (SEQ ID NO: 25).

Some antibodies specifically bind to a peptide comprising an amino acid sequence selected from the group consisting of GHEDT, (SEQ ID NO: 3), HEDT, (SEQ ID NO: 12), AEDS, (SEQ ID NO: 13), AEDT, (SEQ ID NO: 14), HEDA, (SEQ ID NO: 15), TEDE, (SEQ ID NO: 16), FEDD, (SEQ ID NO: 17), SEDE, (SEQ ID NO: 18), AEDE, (SEQ ID NO: 19), PEDE, (SEQ ID NO: 20), PEDI, (SEQ ID NO: 21), PEDF, (SEQ ID NO: 22), SEDF, (SEQ ID NO: 24) and SEDA, (SEQ ID NO: 25). Some antibodies specifically bind to a peptide comprising an amino acid sequence selected from the group consisting of GHEDT, (SEQ ID NO: 3), HEDT, (SEQ ID NO: 12), AEDS, (SEQ ID NO: 13), AEDT, (SEQ ID NO: 14), HEDA, (SEQ ID NO: 15) and TEDE, (SEQ ID NO: 16).

Some antibodies are raised to a peptide comprising GHEDT, (SEQ ID NO: 3), such as, for example, 2A4, 7D8 and 8G9, or are humanized or chimeric versions thereof.

Antibodies can be polyclonal or monoclonal. Polyclonal sera typically contain mixed populations of antibodies specifically binding to several epitopes along the length of AA. However, polyclonal sera can be specific to a particular segment of AA, such as residues 70-76 of HAA1 alpha isoform. Preferred antibodies are chimeric, or humanized (see Queen et al., Proc. Natl. Acad. Sci. USA 86:10029-10033 (1989) and WO 90/07861, U.S. Pat. No. 5,693,762, U.S. Pat. No. 5,693, 761, U.S. Pat. No. 5,585,089, U.S. Pat. No. 5,530,101 and Winter, U.S. Pat. No. 5,225,539), or human (Lonberg et al., WO93/12227 (1993); U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625,126, U.S. Pat. No. 5,569, 825, U.S. Pat. No. 5,545,806, Nature 148, 1547-1553 (1994), Nature Biotechnology 14, 826 (1996), Kucherlapati, WO 91/10741 (1991)). An alternative approach for humanizing an antibody, also known as veneering, is described in U.S. Pat. No. 6,797,492. Several mouse antibodies of different binding specificities are available as starting materials for making humanized antibodies.

Representative humanized antibodies are humanized version 7D8 antibody (ATCC Accession Number PTA-9468), humanized version 7D29 antibody, humanized version 7D19 antibody, humanized version 7D47 antibody, humanized version 7D39 antibody, humanized version 7D66 antibody, humanized version 8G9 antibody, humanized version 8G3 antibody, humanized version 8G4 antibody, humanized version 8G51 antibody, humanized version 8G22 antibody, humanized version 8G30 antibody, humanized version 8G46 antibody, humanized version 2A4 antibody (ATCC Accession Number PTA-9662), humanized version 2A20 antibody, humanized version 2A44 antibody, humanized version 2A77 antibody, humanized version 2A13 antibody, and humanized version 2A14 antibody. Hybridomas that produce the 7D8 antibody (JH80 7D8.29.19.47) and the 2A4 antibody (JH80 2A4.20.44077) were deposited on Sep. 4, 2008, and on Dec.

17, 2008, respectively, with the American Type Culture Collection (ATCC), currently located at 10801 University Boulevard, Manassas, Va. 20110-2209, under the provisions of the Budapest Treaty for the International Recognition of the Deposit of Microorganisms for the Purpose of Patent Procedure ("Budapest Treaty"). The ATCC has assigned the hybridoma producing 7D8 ATCC Accession No. PTA-9468, and the hybridoma producing 2A4 ATCC Accession No. PTA-9662.

Human isotype IgG1 is preferred for antibodies to the C terminal region of AA because of it having highest affinity of human isotypes for the FcRI receptor on phagocytic cells. Some antibodies specifically bind to AA with a binding affinity greater than or equal to about $10^7$, $10^8$, $10^9$, or $10^{10}$ $M^{-1}$.

Active immunization with fragments of AA can be combined with passive administration of antibodies. Examples of specific combinations include AA fragments comprising HAA1 alpha isoform residues 70-76 with antibodies that specifically bind to epitope within HAA1 alpha isoform residues 70-76; AA fragments comprising HAA1 alpha isoform residues 70-76 with antibodies that specifically bind to epitope within HAA1 alpha isoform residues 71-76; AA fragments comprising HAA1 alpha isoform residues 70-76 with antibodies that specifically bind to epitope within HAA1 alpha isoform residues 72-76; AA fragments comprising HAA1 alpha isoform residues 70-76 with antibodies that specifically bind to epitope within HAA1 alpha isoform residues 73-76; AA fragments comprising HAA1 alpha isoform residues 70-76 with antibodies that specifically bind to epitope within HAA1 alpha isoform residues 74-76; AA fragments comprising HAA1 alpha isoform residues 70-76 with antibodies that specifically bind to epitope within HAA1 alpha isoform residues 70-75; AA fragments comprising HAA1 alpha isoform residues 70-76 with antibodies that specifically bind to epitope within HAA1 alpha isoform residues 70-74; AA fragments comprising HAA1 alpha isoform residues 70-76 with antibodies that specifically bind to epitope within HAA1 alpha isoform residues 70-73; AA fragments comprising HAA1 alpha isoform residues 70-76 with antibodies that specifically bind to epitope within HAA1 alpha isoform residues 70-72; AA fragments comprising HAA1 alpha isoform residues 70-76 with antibodies that specifically bind to epitope within HAA1 alpha isoform residues 71-75; AA fragments comprising HAA1 alpha isoform residues 70-76 with antibodies that specifically bind to epitope within HAA1 alpha isoform residues 72-75; AA fragments comprising HAA1 alpha isoform residues 70-76 with antibodies that specifically bind to epitope within HAA1 alpha isoform residues 73-75; AA fragments comprising HAA1 alpha isoform residues 70-76 with antibodies that specifically bind to epitope within HAA1 alpha isoform residues 73-75; AA fragments comprising HAA1 alpha isoform residues 70-76 with antibodies that specifically bind to epitope within HAA1 alpha isoform residues 71-74; AA fragments comprising HAA1 alpha isoform residues 70-76 with antibodies that specifically bind to epitope within HAA1 alpha isoform residues 71-73; AA fragments comprising HAA1 alpha isoform residues 70-76 with antibodies that specifically bind to epitope within HAA1 alpha isoform residues 72-74. Additionally, AA fragments comprising HAA1 alpha isoform residues 71-76, 72-76, 73-76, 74-76, 70-75, 70-74, 70-73, 70-72, 71-75, 72-75, 73-75, 71-74, 71-73, 72-74 may be combined with antibodies that specifically bind to an epitope within HAA1 alpha isoform residues 71-76, 72-76, 73-76, 74-76, 70-75, 70-74, 70-73, 70-72, 71-75, 72-75, 73-75, 71-74, 71-73, 72-74. AA fragments comprising HAA1 alpha isoform residues 70-76, HAA1 beta isoform residues 70-76, HAA1 gamma isoform residue 70-76, HAA2 alpha and beta isoforms residues 70-76, MAA1 residues 69-75, MAA2 residues 69-75, or MAA3 residues 62-68 may be combined with antibodies that specifically bind to an epitope within HAA1 alpha isoform residues 70-76, HAA1 beta isoform residues 70-76, HAA1 gamma isoform residue 70-76, HAA2 alpha and beta isoforms residues 70-76, MAA1 residues 69-75, MAA2 residues 69-75, or MAA3 residues 62-68.

Some of the antibodies described above do not specifically bind the monomeric or precursor form of the amyloid protein. Some of such antibodies specifically bind to a neoepitope generated upon cleavage of a precursor protein resulting in an amyloid protein. For example, some antibodies specifically bind to the C-terminal residues of mouse AA fibrils –HEDT, (SEQ ID NO: 12), but do not specifically bind to a peptide that extends into the non-amyloid portion of SAA (GHEDT-MADQE, SEQ ID NO: 61). Some antibodies specifically bind to a conformational epitope. Some of such conformational epitopes are linear. Some of such conformational epitopes are exposed when an amyloid protein enters an aggregated (e.g., fibrillar) structure or becomes partially denatured. Examples of such antibodies include murine monoclonal antibodies 2A4 (ATCC Accession Number PTA-9662) and 7D8 (ATCC Accession Number PTA-9468), human, humanized and chimeric forms thereof, other antibodies that specifically bind to the same epitope as 2A4, 8G9 or 7D8, and antigen-binding fragments of any such antibodies. Some antibodies specifically bind to an amyloid protein comprising the amino acid sequence ED. Some antibodies specifically bind to an amyloid protein selected from the group consisting of immunoglobulin light chain protein, human islet amyloid precursor polypeptide (IAPP), beta amyloid peptide, transthyretin (TTR) and ApoA1.

The basic antibody structural unit is known to comprise a tetramer of subunits. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

1. Antibodies

The invention includes intact antibodies and antigen-binding antibody fragments, as well as pegylated antibodies and antibody fragments, as well as antibodies with altered (e.g., reduced or eliminated) effector function, for example, antibodies comprising mutations or substituted residues in the Fc region. Examples of immunologically active portions of immunoglobulin molecules include F(ab) and F(ab')2 tri-Fab', Fab', Fv, scFv, di-Fab' fragments which can be generated by treating the antibody with an enzyme such as pepsin or produced by art-recognized recombinant engineering techniques. Additional antigen-binding fragments of antibodies of the invention include therapeutic antibody fragments, including pegylated antibody fragments, such as PEGylated Fab' and PEGylated di-Fab'. Examples of effector function mutants are described in U.S. Pat. No. 5,624,821, which is incorporated by reference herein in its entirety. Some antibodies have reduced binding affinity for Fc gamma RI receptor. Effector function mutant antibodies include antibodies comprising mutations in the hinge region. Some mutant IgG antibodies comprise a mutation in the heavy chain constant region at one or more of positions 234, 235, 236, 237, 297, 318, 320 and 322. In some antibodies one or more of residues 234, 236 and 237 are substituted with alanine. In some antibodies, residue 235 is substituted with glutamine. In some antibodies, residue 297 is substituted with alanine. In some antibodies, residues 318, 320 and 322 are substituted with alanine. In some antibodies, residue 318 is substituted with valine. In some antibodies, residue 322 is substituted with glutamine. Antibodies with enhanced effector function include antibodies single S239D and I332E and the double and triple mutants S239D/I332E and S239D/I332E/A330L (Kabat numbering).

2. Polyclonal Antibodies

Polyclonal antibodies can be prepared as described above by immunizing a suitable subject with an immunogen. The antibody titer in the immunized subject can be monitored over time by standard techniques, such as with an enzyme linked immunosorbent assay (ELISA) using immobilized target antigen. If desired, the antibody molecules directed against the target antigen can be isolated from the mammal (e.g., from the blood) and further purified by well known techniques, such as protein A Sepharose chromatography to obtain the antibody, e.g., IgG, fraction. At an appropriate time after immunization, e.g., when the anti-antigen antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75). For the preparation of chimeric polyclonal antibodies, see Buechler et al. U.S. Pat. No. 6,420,113.

3. Monoclonal Antibodies

Any of the many well known protocols used for fusing lymphocytes and immortalized cell lines can be applied for the purpose of generating a monoclonal antibody (see, e.g., G. Galfre et al. (1977) *Nature* 266:55052; Gefter et al. Somatic Cell Genet., cited supra; Lerner, Yale *J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a target antigen, e.g., Aβ, using a standard ELISA assay.

4. Recombinant Antibodies

Alternative to preparing monoclonal antibody-secreting hybridomas, a monoclonal antibody can be identified and isolated by screening a recombinant combinatorial immunoglobulin library (e.g., an antibody phage display library) with a target antigen to thereby isolate immunoglobulin library members that bind the target antigen. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al. U.S. Pat. No. 5,223, 409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246: 1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrad et al. (1991) *Bio/Technology* 9:1373-1377; Hoogenboom et al. (1991) *Nuc. Acid Res.* 19:4133-4137; Barbas et al. (1991) *Proc. Natl. Acad. Sci. USA* 88:7978-7982; and McCafferty et al. *Nature* (1990) 348:552-554.

5. Chimeric and Humanized Antibodies

Additionally, recombinant antibodies, such as chimeric and humanized monoclonal antibodies, comprising both human and non-human portions, which can be made using standard recombinant DNA techniques, are within the scope of the invention.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

The phrase "substantially from a human immunoglobulin or antibody" or "substantially human" means that, when aligned to a human immunoglobulin or antibody amino sequence for comparison purposes, the region shares at least 80-90%, 90-95%, or 95-99% identity (i.e., local sequence identity) with the human framework or constant region sequence, allowing, for example, for conservative substitutions, consensus sequence substitutions, germline substitutions, backmutations, and the like. The introduction of conservative substitutions, consensus sequence substitutions, germline substitutions, backmutations, and the like, is often referred to as "optimization" of a humanized antibody or chain. The phrase "substantially from a non-human immunoglobulin or antibody" or "substantially non-human" means having an immunoglobulin or antibody sequence at least 80-95%, preferably, at least 90-95%, more preferably, 96%, 97%, 98%, or 99% identical to that of a non-human organism, e.g., a non-human mammal.

Accordingly, all regions or residues of a humanized immunoglobulin or antibody, or of a humanized immunoglobulin or antibody chain, except the CDRs, are substantially identical to the corresponding regions or residues of one or more native human immunoglobulin sequences. The term "corresponding region" or "corresponding residue" refers to a region or residue on a second amino acid or nucleotide sequence which occupies the same (i.e., equivalent) position as a region or residue on a first amino acid or nucleotide sequence, when the first and second sequences are optimally aligned for comparison purposes.

The term "significant identity" means that two polypeptide sequences, when optimally aligned, such as by the programs GAP or BESTFIT using default gap weights, share at least 50-60% sequence identity, preferably at least 60-70% sequence identity, more preferably at least 70-80% sequence identity, more preferably at least 80-90% sequence identity, even more preferably at least 90-95% sequence identity, and even more preferably at least 95% sequence identity or more (e.g., 99% sequence identity or more). The term "substantial identity" means that two polypeptide sequences, when optimally aligned, such as by the programs GAP or BESTFIT using default gap weights, share at least 80-90% sequence identity, preferably at least 90-95% sequence identity, and more preferably at least 95% sequence identity or more (e.g., 99% sequence identity or more): For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., Current Protocols in Molecular Biology). One example of algorithm that is suitable for determining percent sequence identity and sequence similarity is the BLAST algorithm, which is described in Altschul et al., *J. Mol. Biol.* 215:403 (1990). Software for performing BLAST analyses is publicly available through the National Center for Biotechnology Information (publicly accessible through the National Institutes of Health NCBI internet server). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

Preferably, residue positions which are not identical differ by conservative amino acid substitutions. For purposes of classifying amino acids substitutions as conservative or non-conservative, amino acids are grouped as follows: Group I (hydrophobic sidechains): leu, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Preferably, humanized immunoglobulins or antibodies bind antigen with an affinity that is within a factor of three, four, or five of that of the corresponding non-humanized antibody. For example, if the nonhumanized antibody has a binding affinity of $10^{-9}$ M, humanized antibodies will have a binding affinity of at least $3 \times 10^{-8}$ M, $4 \times 10^{-8}$ M, $5 \times 10^{-8}$ M, or $10^{-9}$ M. When describing the binding properties of an immunoglobulin or antibody chain, the chain can be described based on its ability to "direct antigen (e.g., Aβ) binding". A chain is said to "direct antigen binding" when it confers upon an intact immunoglobulin or antibody (or antigen binding fragment thereof) a specific binding property or binding affinity. A mutation (e.g., a backmutation) is said to substantially affect the ability of a heavy or light chain to direct antigen binding if it affects (e.g., decreases) the binding affinity of an intact immunoglobulin or antibody (or antigen binding fragment thereof) comprising said chain by at least an order of magnitude compared to that of the antibody (or antigen binding fragment thereof) comprising an equivalent chain lacking said mutation. A mutation "does not substantially affect (e.g., decrease) the ability of a chain to direct antigen binding" if it affects (e.g., decreases) the binding affinity of an intact immunoglobulin or antibody (or antigen binding fragment thereof) comprising said chain by only a factor of two, three, or four of that of the antibody (or antigen binding fragment thereof) comprising an equivalent chain lacking said mutation.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species. The terms "humanized immunoglobulin" or "humanized antibody" are not intended to encompass chimeric immunoglobulins or antibodies, as defined infra. Although humanized immunoglobulins or antibodies are chimeric in their construction (i.e., comprise regions from more than one species of protein), they include additional features (i.e., variable regions comprising donor CDR residues and acceptor framework residues) not found in chimeric immunoglobulins or antibodies, as defined herein.

Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987)

Canc. Res. 47:999-1005; Wood et al. (1985) Nature 314:446-449; and Shaw et al. (1988) J. Natl. Cancer Inst. 80:1553-1559); Morrison, S. L. (1985) Science 229:1202-1207; Oi et al. (1986) BioTechniques 4:214; Winter U.S. Pat. No. 5,225,539; Jones et al. (1986) Nature 321:552-525; Verhoeyan et al. (1988) Science 239:1534; and Beidler et al. (1988) J. Immunol. 141:4053-4060. Therapeutic agents also include antibody mimetics such as complementarity determining region (CDR) mimetics.

6. Human Antibodies from Transgenic Animals and Phage Display

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice results in the production of human antibodies upon antigen challenge. See, e.g., U.S. Pat. Nos. 6,150,584; 6,114,598; and 5,770,429.

Fully human antibodies can also be derived from phage-display libraries (Hoogenboom et al., J. Mol. Biol., 227:381 (1991); Marks et al., J. Mol. Biol., 222:581-597 (1991)). Chimeric polyclonal antibodies can also be obtained from phage display libraries (Buechler et al. U.S. Pat. No. 6,420,113).

7. Bispecific Antibodies, Antibody Fusion Polypeptides, and Single-Chain Antibodies Bispecific antibodies (BsAbs) are antibodies that have binding specificities for at least two different epitopes. Such antibodies can be derived from full length antibodies or antibody fragments (e.g. F(ab)'2 bispecific antibodies). Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of different antibody molecules (see, WO 93/08829 and in Traunecker et al., EMBO J., 10:3655-3659 (1991)).

Bispecific antibodies also include cross-linked or "heteroconjugate" antibodies. For example, one of the antibodies in the heteroconjugate can be coupled to avidin, the other to biotin or other payload. Heteroconjugate antibodies may be made using any convenient cross-linking methods. Suitable cross-linking agents are well known in the art, and are disclosed in U.S. Pat. No. 4,676,980, along with a number of cross-linking techniques.

In yet another aspect, the antibody can be fused, chemically or genetically, to a payload such as a reactive, detectable, or functional moiety, for example, an immunotoxin to produce an antibody fusion polypeptide. Such payloads include, for example, immunotoxins, chemotherapeutics, and radioisotopes, all of which are well-known in the art.

Single chain antibodies are also suitable for stabilization according to the invention. The fragments comprise a heavy-chain variable domain (VH) connected to a light-chain variable domain (VL) with a linker, which allows each variable region to interface with each other and recreate the antigen binding pocket of the parent antibody from which the VL and VH regions are derived. See Gruber et al., J. Immunol., 152:5368 (1994).

It is understood that any of the foregoing polypeptide molecules, alone or in combination, are suitable for preparation as stabilized formulations according to the invention.

XI. Subjects Amenable to Treatment

Subjects or patients amenable to treatment include individuals at risk of disease but not showing symptoms, as well as patients presently showing symptoms. Therefore, the present methods can be administered prophylactically to the general population without the need for any assessment of the risk of the subject patient. The present methods are especially useful for individuals who do have a known genetic risk autoimmune disorders. Such individuals include those having relatives who have experienced this disease and those whose risk is determined by analysis of genetic or biochemical markers.

Patients suffering from AA amyloidosis can be asymptomatic for a prolonged period of time. Therefore, clinical diagnosis of AA amyloidosis is often delayed or missed until the amyloid deposits are extensive. For those patients who are symptomatic, it is estimated that only 53% of the cases are diagnosed. See L.E.K. Consulting, Independent Market Research (2003).

The invention provides methods useful to treat or effect prophylaxis of a disease characterized by the deposition of an amyloid protein, such as, for example, the diseases described above, including those listed in Table 1. Some methods are useful to treat or effect prophylaxis of a disease characterized by the deposition of an amyloid protein comprising the amino acid sequence ED. In some methods, if the amyloid protein comprises the amino acid sequence AEDV, then the antibody is not administered to treat or effect prophylaxis of Alzheimer's disease or Mild Cognitive Impairment. The amyloid protein can be any of the amyloid proteins described above, including those listed in Table 1, such as, for example, serum amyloid A protein, immunoglobulin light chain protein, such as, for example, Vλ6 Wil or Vκ, human islet amyloid precursor polypeptide (IAPP), beta amyloid peptide, transthyretin (TTR) or ApoA1.

The present methods are especially useful for individuals who do have a known risk of, are suspected to have, or have been diagnosed with AA amyloidosis or AL amyloidosis. Such individuals include but are not limited to those having chronic inflammatory diseases, inherited inflammatory diseases, and chronic microbial infections, such as rheumatoid arthritis, juvenile chronic arthritis, ankylosing spondylitis, psoriasis, psoriatic arthropathy, Reiter's syndrome, Adult Still's disease, Behcet's syndrome, Crohn's disease, Familial Mediterranean Fever, leprosy, tuberculosis, bronchiectasis, decubitus ulcers, chronic pyelonephritis, osteomyelitis, Whipple's disease, myeloma, macroglobulinemia, immunocyte dyscrasia, monoclonal gammopathy, occult dyscrasia. Chronic inflammatory and infectious conditions are prerequisite to the development of AA amyloidosis and AL amyloidosis manifested by local nodular amyloidosis can be associated with chronic inflammatory diseases. Individuals who do have known risk of AA amyloidosis also include but are not limited to those having malignant neoplasms as Hodgkin's lymphoma, renal carcinoma, carcinomas of gut, lung and urogenital tract, basal cell carcinoma, and hairy cell leukemia. Additionally, individuals who do have known risk of AA amyloidosis also include but are not limited to those having lymphoproliferative disorders such as Castleman's Disease.

In both asymptomatic and symptomatic patients, treatment can begin at any time before or after the diagnosis of the underlying AA or AL amyloid diseases. Treatment typically entails multiple dosages over a period of time. Treatment can be monitored by assaying antibody, activated T-cell (a side effect) or B-cell responses to the therapeutic agent (e.g.; AA peptide), or employing radiolabeled SAP Scintigraphy over time. If the response falls, a booster dosage is indicated.

XII. Treatment Regimes

In general, treatment regimes involve administering an agent effective to induce an immunogenic response to an amyloid protein, and preferably to an aggregated form of such amyloid protein, such as, for example, AA or AL. Preferably an immunogenic fragment of AA or AL or an $X_1EDX_2$ fragment is administered to a patient. In prophylactic applications, pharmaceutical compositions or medicaments are administered to a patient susceptible to, or otherwise at risk of, amyloidosis such as AA Amyloidosis or AL amyloidosis, in an amount sufficient to eliminate or reduce the risk, lessen the severity, or delay the Onset of the disease, including physiological, biochemical, histologic and/or behavioral symptoms of the disease, its complications and intermediate pathological phenotypes presenting during development of the disease. In therapeutic applications, an agent is administered to a patient suspected of, or already suffering from such a disease in a regime comprising an amount and frequency of administration of the agent sufficient to cure, or at least partially arrest, or inhibit deterioration of the symptoms of the disease (physiological, biochemical, histologic and/or behavioral), including its complications and intermediate pathological phenotypes in development of the disease. In some methods, administration of agent reduces or eliminates early symptomology in patients that have not yet developed characteristic AA or AL Amyloidosis pathology. An amount adequate to accomplish therapeutic or prophylactic treatment is defined as a therapeutically- or prophylactically-effective dose. A combination of amount and dosage frequency adequate to accomplish the therapeutic or prophylactic treatment is defined as a therapeutically- or prophylactically-effective regime. In both prophylactic and therapeutic regimes, agents are usually administered in several dosages until a sufficient immune response has been achieved. A dosage and frequency of administrations adequate to accomplish therapeutic or prophylactic treatment is defined as a therapeutically- or prophylactically-effective regime. Typically, the patient's immune response is monitored and repeated dosages are given if the immune response starts to wane. The immune response can be monitored by detecting antibodies, for example, to AA or AL in the blood in the patient or detecting levels of, for example, AA or AL.

Effective doses of the agents and compositions of the present invention, for the treatment of the above described conditions Vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy. The amount of immunogen depends on whether adjuvant is also administered, with higher dosages being required in the absence of adjuvant. The amount of an immunogen for administration sometimes varies from 1-500 μg per patient and more usually from 5-500 μg per injection for human administration. Occasionally, a higher dose of 1-2 mg per injection is used. Typically at least 10, 20, 50 or 100 μg is used for each human injection. The mass of immunogen also depends on the mass ratio of immunogenic epitope within the immunogen to the mass of immunogen as a whole. Typically, $10^{-3}$ to $10^{-5}$ micromoles of immunogenic epitope are used for microgram of immunogen. The timing of injections can vary significantly from once a day, to once a year, to once a decade. On any given day that a dosage of immunogen is given, the dosage is greater than 1 μg/patient and usually greater than 10 μg/patient if adjuvant is also administered, and greater than 10 μg/patient and usually greater than 100 μg/patient in the absence of adjuvant. A typical regimen consists of an immunization followed by booster injections at time intervals, such as 6 week intervals. Another regimen consists of an immunization followed by booster injections 1, 2 and 12 months later. Another regimen entails an injection every two months for life. Alternatively, booster injections can be on an irregular basis as indicated by monitoring of immune response.

Doses for nucleic acids encoding immunogens range from about 10 ng to 1 g, 100 ng to 100 mg, 1 μg to 10 mg, or 30-300 μg DNA per patient. Doses for infectious viral vectors vary from 10-100, or more, virions per dose.

For passive immunization with an antibody (in combination therapies), the dosage ranges from about 0.0001 to 100 mg/kg, 0.5 to less than 5 mg/kg, and more usually 0.01 to 5 mg/kg, 0.5 to 3 mg/kg, of the host body weight. For example dosages can be 1 mg/kg body weight or 10 mg/kg body weight or within the range of 1-10 mg/kg or in other words, 70 mg or 700 mg or within the range of 70-700 mg, respectively, for a 70 kg patient. As an additional example, dosages can be less than 5 mg/kg body weight or 1.5 mg/kg body weight or within the range of 0.5 to 1.5 mg/kg, preferably at least 1.5 mg/kg. An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody to AA in the patient. In some methods, dosage is adjusted to achieve a plasma antibody concentration of 1-1000 μg/ml and in some methods 25-300 μg/ml. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Agents for inducing an immune response can be administered by parenteral, topical, intravenous, oral, subcutaneous, intraarterial, intracranial, intraperitoneal, intranasal or intramuscular means for prophylactic and/or therapeutic treatment. The most typical route of administration of an immunogenic agent is subcutaneous although other routes can be equally effective. The next most common route is intramuscular injection. This type of injection is most typically performed in the arm or leg muscles. In some methods, agents are injected directly into a particular tissue where deposits have accumulated, e.g., intracranial injection. Intramuscular injection or intravenous infusion is preferred for administration of antibody (in combination therapies). In some methods, particular therapeutic antibodies are injected directly into the cranium. In some methods, antibodies are administered as a sustained release composition or device, such as a MEDIPAD™ device.

Agents of the invention are often administered as pharmaceutical compositions comprising an active therapeutic agent, i.e., and a variety of other pharmaceutically acceptable components. See *Remington's Pharmaceutical Science* (15th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized SEPHAROSE™, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, agents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl. Compositions for parenteral administration are typically substantially sterile, isotonic and manufactured under GMP conditions of the FDA or similar body.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, *Science* 249, 1527 (1990) and Hanes, *Advanced Drug Delivery Reviews* 28, 97-119 (1997). The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins (See Glenn et al., *Nature* 391, 851 (1998)). Co-administration can be achieved by using the components as a mixture or as linked molecules obtained by chemical crosslinking or expression as a fusion protein.

Alternatively, transdermal delivery can be achieved using a skin path or using transferosomes (Paul et al., *Eur. J. Immunol.* 25, 3521-24 (1995); Cevc et al., *Biochem. Biophys. Acta* 1368, 201-15 (1998)).

XIII. Combinational Drug Therapy Treatment Regimes

Combination therapy according to the invention may be performed alone or in conjunction with another therapy to treat or effect prophylaxis of AA amyloidosis. Combination therapy according to the invention may also be performed in conjunction with another therapy which treats or effects prophylaxis of an underlying amyloid disease such as inflammatory diseases, chronic microbial infections, malignant neoplasms, inherited inflammatory diseases, and lymphoproliferative disorders. There are large numbers of treatments available in commercial use, in clinical evaluation and in pre-clinical development, which could be selected for use with the presently disclosed invention for effecting prophylaxis and treatment of AA amyloidosis by combination drug therapy. Such treatments can be one or more compounds selected from, but not limited to several major categories, namely, (i) non-steroidal anti-inflammatory drugs (NSAIDs; e.g., detoprofen, diclofenac, diflunisal, etodolac, fenoprofen, flurbiprofen, ibuprofen, indomethacin, ketoprofen, meclofenameate, mefenamic acid, meloxicam, nabumeone, naproxen sodium, oxaprozin, piroxicam, sulindac, tolmetin, celecoxib, rofecoxib, aspirin, choline salicylate, salsalte, and sodium and magnesium salicylate); (ii) steroids (e.g., cortisone, dexamethasone, hydrocortisone, methylprednisolone, prednisolone, prednisone, triamcinolone); (iii) DMARDs, i.e., disease modifying antirheumatic drugs (e.g., cyclosporine, azathioprine, methotrexate, leflunomide, cyclophosphamide, hydroxychloroquine, sulfasalazine, D-penicillamine, minocycline, and gold); or (iv) recombinant proteins (e.g., ENBREL® (etanercept, a soluble TNF receptor) and REMICADE® (infliximab) a chimeric monoclonal anti-TNF antibody).

The duration of the combination therapy depends on the type of underlying disease being treated, the age and condition of the patient, the stage and type of the patient's disease, and how the patient responds to the treatment. The doctor can observe the therapy's effects closely and make any adjustments that are needed. Additionally, a person having a greater risk of developing AA Amyloidosis (e.g., a person who is genetically predisposed or previously had an inflammatory disorder or other underlying diseases) or AL amyloidosis may receive prophylactic treatment to inhibit or delay the development of AA AL aggregates such as fibrils.

The dosage, frequency and mode of administration of each component of the combination can be controlled independently. For example, one compound may be administered orally three times per day, while the second compound may be administered intramuscularly once per day. Combination therapy may be given in on-and-off cycles that include rest periods. The compounds may also be formulated together such that one administration delivers both compounds. The combination of the invention can also be provided as components of a pharmaceutical pack. The drugs can be formulated together or separately and in individual dosage amounts. Each compound is admixed with a suitable carrier substance, and is generally present in an amount of 1-95% by weight of the total weight of the composition.

The composition may be provided in a dosage form that is suitable for oral, parenteral (e.g., intravenous, intramuscular, subcutaneous), rectal, transdermal, nasal, vaginal, inhalant, or ocular administration. Thus, the composition may be in form of, e.g., tablets, capsules, pills, powders, granulates, suspensions, emulsions, solutions, gels including hydrogels, pastes, ointments, creams, plasters, drenches, delivery devices, suppositories, enemas, injectables, implants, sprays, or aerosols. The pharmaceutical compositions may be formulated according to conventional pharmaceutical practice (see, e.g., Remington: The Science and Practice of Pharmacy, (19th ed.) ed. A. R. Gennaro, 1995, Mack Publishing Company, Easton, Pa. and Encyclopedia of Pharmaceutical Technology, eds. J. Swarbrick and J. C. Boylan, 1988-1999, Marcel Dekker, N.Y.

XIV. Methods of Monitoring or Diagnosing AA or AL Amyloidosis

Methods of monitoring or diagnosing AA or AL amyloidosis include measuring the plasma concentrations of SAA and C-reactive protein, performing tissue biopsy (renal, rectal, gastric, gingival, fat, salivary, labial glands) and histology with congo red staining and/or immunostaining with specific antibodies directed against AA or AL aggregates such as fibrils. The invention provides methods of detecting an antibody response against AA peptide in a patient suffering from or susceptible to AA Amyloidosis. The methods are particularly useful for monitoring a course of treatment being administered to a patient. The methods can be used to monitor both therapeutic treatment on symptomatic patients and prophylactic treatment on asymptomatic patients. Some methods entail determining a baseline value of an antibody response in a patient before administering a dosage of an immunogenic agent, and comparing this with a value for the immune response after treatment. A significant increase (i.e., greater than the typical margin of experimental error in repeat measurements of the same sample, expressed as one standard deviation from the mean of such measurements) in value of the antibody response signals a positive treatment outcome (i.e., that administration of the agent has achieved or augmented an immune response). If the value for the antibody response does not change significantly, or decreases, a negative treatment outcome is indicated. In general, patients undergoing an initial course of treatment with an immunogenic agent are expected to show an increase in antibody response with successive dosages, which eventually reaches a plateau. Administration of agent is generally continued while the antibody response is increasing. Attainment of the plateau is an indicator that the administered of treatment can be discontinued or reduced in dosage or frequency.

In other methods, a control value (i.e., a mean and standard deviation) of an antibody response is determined for a control population. Typically the individuals in the control population have not received prior treatment. Measured values of the antibody response in a patient after administering a therapeutic agent are then compared with the control value. A significant increase relative to the control value (e.g., greater than one standard deviation from the mean) signals a positive treatment outcome. A lack of significant increase or a decrease signals a negative treatment outcome. Administration of agent is generally continued while the antibody response is increasing relative to the control value. As before, attainment of a plateau relative to control values in an indicator that the administration of treatment can be discontinued or reduced in dosage or frequency.

In other methods, a control value of antibody response (e.g., a mean and standard deviation) is determined from a control population of individuals who have undergone treatment with a therapeutic agent and whose antibody responses have reached a plateau in response to treatment. Measured values of antibody response in a patient are compared with the control value. If the measured level in a patient is not significantly different (e.g., more than one standard deviation) from the control value, treatment can be discontinued. If the level in a patient is significantly below the control value, continued administration of agent is warranted. If the level in the patient persists below the control value, then a change in treatment regime, for example, use of a different adjuvant, fragment or switch to passive administration may be indicated.

In other methods, a patient who is not presently receiving treatment but has undergone a previous course of treatment is monitored for antibody response to determine whether a resumption of treatment is required. The measured value of antibody response in the patient can be compared with a value of antibody response previously achieved in the patient after a previous course of treatment. A significant decrease relative to the previous measurement (i.e., greater than a typical margin of error in repeat measurements of the same sample) is an indication that treatment can be resumed. Alternatively, the value measured in a patient can be compared with a control value (mean plus standard deviation) determined in a population of patients after undergoing a course of treatment. Alternatively, the measured value in a patient can be compared with a control value in populations of prophylactically treated patients who remain free of symptoms of disease, or populations of therapeutically treated patients who show amelioration of disease Characteristics. In all of these cases, a significant decrease relative to the control level (i.e., more than a standard deviation) is an indicator that treatment should be resumed in a patient.

Some methods employ iodine-123-labeled or iodine-125-labeled serum amyloid P component ($^{123}$I-SAP or $^{125}$I-SAP) Scintigraphy. $^{123}$I-SAP or $^{125}$I-SAP is intravaneously injected into patients and viewed with gamma camera. Radiolabeled SAP Scintigraphy is a useful method to monitor the progression of amyloidosis in patients and evaluate treatments. It is specific for amyloid and can be used to quantitatively monitor the location and amount of amyloid deposits in patients. $^{123}$I-SAP and $^{125}$I-SAP do not accumulate in healthy subjects or in non-amyloid patients. Radiolabeled SAP scintigraphy can be used to monitor dynamic turnover of amyloid, and can assess the efficacy of treatments aimed at regressing amyloid deposits. Further, radiolabeled SAP Scintigraphy is non-invasive and provides whole body scan. Methods of the invention entail determining a baseline value of an antibody response in a patient before administering a dosage of an agent, and comparing this with a value for the immune response after treatment in a patient. A significant increase (i.e., greater than the typical margin of experimental error in repeat measurements of the same sample, expressed as one standard deviation from the mean of such measurements) in value of the antibody response signals a positive treatment outcome (i.e., that administration of the agent has achieved or augmented an immune response). If the value for the antibody response does not change significantly, or decreases, a negative treatment outcome is indicated. In general, patients undergoing an initial course of treatment with an immunogenic agent are expected to show an increase in antibody response with successive dosages, which eventually reaches a plateau. Administration of agent is generally continued while the antibody response is increasing. Attainment of the plateau is an indicator that the administered of treatment can be discontinued or reduced in dosage or frequency.

The tissue sample for analysis is typically blood, plasma, serum, mucous or cerebrospinal fluid from the patient. The sample is analyzed for indication of an immune response to any form of AA or AL peptide. The immune response can be determined from the presence of antibodies that specifically bind to AA or AL peptide. Antibodies can be detected in a binding assay to a ligand that specifically binds to the antibodies. Typically the ligand is immobilized. Binding can be detected using a labeled anti-idiotypic antibody.

In combination regimes employing both active and passive administration, analogous approaches can be used to monitor levels of antibody resulting from passive administration.

Methods of diagnosing amyloidosis can also be employed by, e.g., administering to a subject an antibody or antigen-binding fragment thereof, that is bound to a detectable label, wherein the antibody or fragment thereof specifically binds to an epitope including $X_1EDX_2$ in an aggregated amyloid protein, wherein $X_1$ and $X_2$ are any amino acids, and detecting the presence or absence of the bound antibody or fragment thereof. Detection of the bound antibody or fragment supports a diagnosis of amyloidosis. Antibodies and fragments useful in the diagnosis of amyloidosis include the disclosed antibodies of the invention.

The diagnostic antibodies or fragments of the invention can be administered, by e.g., intravenous injection into the body of a patient, or directly into the brain by intracranial injection. The antibody dosage is readily determined by one skilled in the art. Typically, the antibody is labeled, although in some methods, the antibody is unlabeled and a secondary labeling agent is used to bind to the antibody. The choice of label depends on the means of detection. For example, a fluorescent label is suitable for optical detection. Use of paramagnetic labels is suitable for tomographic detection without surgical intervention. Radiolabels may be used including $^{211}$At, $^{212}$Bi, $^{67}$Cu, $^{125}$I, $^{131}$I, $^{111}$In, $^{32}$P, $^{212}$Pb, $^{186}$Re, $^{188}$Re, $^{153}$Sm, $^{99m}$Tc, or $^{90}$Y. Such labels may be detected using PET or SPECT or other suitable technique.

Diagnosis may also be performed by comparing the number, size, and/or intensity of labeled loci, to corresponding baseline values. The base line values can represent the mean levels in a population of undiseased individuals. Baseline values can also represent previous levels determined in the same patient. For example, baseline values can be determined in a patient, and measured values thereafter compared with the baseline values. An increase in values relative to baseline signals supports a diagnosis of AA amyloidosis.

The diagnostic methods of the invention may be used to diagnose amyloidosis diseases including AA amyloidosis, AL amyloidosis, Alzheimer's disease, Mild Cognitive Impairment, amyloid polyneuropathy, Mediterranean fever, Muckle-Wells syndrome, reactive systemic amyloidosis associated with systemic inflammatory diseases, myeloma or macroglobulinemia associated amyloidosis, amyloidosis associated with immunocyte dyscrasia, monoclonal gammopathy, occult dyscrasia, or local nodular amyloidosis associated with chronic inflammatory diseases.

XV. Animal Models of AA Amyloidosis

AA amyloidosis can be induced experimentally in mice in which SAA concentrations are markedly increased by injection of silver nitrate, casein, or lipopolysaccharide. These agents stimulate the production of cytokines. See Skinner et al. *Lab Invest.* 36:420-427 (1997) and Kisilevsky et al. *Bailliere's Clin. Immunol. Immunopathol.* 8(3) 613-626 (1994). Within 2 or 3 weeks after the inflammatory stimulus, animals develop systemic AA deposits, as found in patients with AA Amyloidosis. This lag phase is dramatically shortened when mice are given, concomitantly, an intravenous injection of protein extracted from AA amyloid-laden mouse spleen or liver. See Axelrad et al. *Lab Invest.* 47(2):139-46 (1982). The amyloidogenic accelerating activity of such preparations was termed "amyloid enhancing factor" (AEF). Lundmark et al. reports that the active principle of AEF is unequivocally the AA fiber itself. Further, they demonstrated that this material is extremely potent, being active in doses less than 1 ng, and that it retained its biologic activity over a considerable length of time. Notably, the AEF was also effective when administered orally. They concluded that AA and perhaps other forms of amyloidosis are transmissible diseases, akin to the prion-associated disorders. See Lundmark et al. *Proc. Nat. Acad. Sci.* 99: 6979-6984 (2002).

AA amyloid can also be induced in transgenic strains of mice carrying the human interleukin 6 gene under the control of the metallothionein-I promoter resulting in markedly increased concentrations of SAA and developing amyloid in the spleen, liver and kidneys by 3 months of age. At the time of death at about 8-9 months, organs from these transgenic mice have extensive amyloid deposits. See Solomon et al., *Am. J. Pathol.* 154(4):1267-1272 (1999).

The Transgenic Rapidly Induced Amyloid Disease (TRIAD) transgenic mouse model is an improvement to the above described transgenic mouse model. TRIAD mice carry the human interleukin 6 gene under the control of the $H-2L^D$ histocompatibility promoter. Administration of AEF to 8-week old TRIAD mice results in prominent spenic and hepatic AA amyloid deposits within 3 to 4 weeks. Subsequently, this process progresses to other organs, leading to death 4-6 weeks later. The development of the systemic amyloidosis is accelerated compared to the above-described transgenic mouse model. See University of Tennessee Research Corporation, WO 01/77167, Pharmacopeia, WO 95/35503 and Scripps, WO 95/30642 Wall et al. *Amyloid* 12(3): 149-156 (2005) (each of which is incorporated by reference for all purposes).

The common marmoset (*Callithrix jacchus*) is a small New World primate native to Brazil that has been used extensively in biomedical research. Ludlage et al. reports that common marmoset were found to have amyloid deposits in one or more organs, including the liver, adrenal glands, kidneys, and intestine. The authors posit that hereditary factors might be responsible for the development of AA amyloidosis in this primate. In this regard, the common marmoset could serve as a unique experimental model for study of the pathogenesis and therapy of AA and other systemic amyloid disorders. See Ludlage et al. *Vet Pathol* 42:117-124 (2005).

The Shar Pei species of dog, a breed having an AA sequence with the –AEDS motif and that is particularly susceptible to AA-amyloidosis, provides a naturally occurring model of systemic AA in which to evaluate novel diagnostic and therapeutic applications of AA amyloid-specific antibodies and other compounds.

EXAMPLES

Example I

AA Fragments

Peptides corresponding to amino acids 71-75—GHEDT, as described by Yamamoto and Migita *Proc. Natl. Acad. Sci. USA* 82:2915-2919 were synthesized by AnaSpec, San Jose, Calif., USA. Polyclonal antibodies (Pab) AA were raised and the immunoglobulin fraction isolated, as previously described by Bard, F. et al., (2000) *Nat. Med.* 6, 916-919.

Example II

Immunogen for Preparation of Murine Antibodies

The epitope used was GHEDT, (SEQ ID NO: 3) with a CG linker at its N terminus. The peptide EPRB-39 which contains the epitope is coupled to sheep anti mouse antibody. EPRB-39 is obtained from Anasec, San Jose, Calif. The antibodies produced appear to be neoepitope specific because they don't specifically bind to a peptide that spans the region GHEDTIADQE, (SEQ ID NO: 89).

Example III

Immunization Procedures

Six-week-old A/J mice were intraperitoneal injected with 50 ug EPRB-39/sheep anti-mouse IgG with Complete Freund's Adjuvant (CFA) followed by Incomplete Freund's adjuvant (IFA) once every other week for a total of three injections. Three days before fusion, the tail vein was injected with 50 ug EPRB-39 SAM IgG in 90 ul PBS. The titer was estimated at 1/10000 from ELISA with high background JH80 is the fusion number for EPRB-39. The following is a list of the clones and limiting dilution clones that are active:

| 7D8.29.19.47*, 39, 66 | IgG2b k |
| 8G9.3.4.51.22*, 30, 46 | IgG2b k |
| 2A4.20.44.77*, 13, 14 | IgG2b k |

7D47, 8G9 and 2A77 indicate preferred subclones. The antibodies produced appear to be neoepitope specific because they don't react with a peptide that spans the C-terminus cleavage site of SAA.

Example IV

Antibody Binding to Aggregated and Soluble AA

Serum titers (determined by serial dilution) and monoclonal antibody binding to aggregated AA were performed by ELISA as previously described by Schenk D. et al., (1999) *Nature* 400, 173-177. Soluble AA refers to the AA fibrils sonicated in dimethyl sulfoxide. Serial dilutions of antibody were incubated with 50,000 cpm of $^{125}$I-AA overnight at room temperature. 50 μl of a slurry containing 75 mg/ml protein A sepharose (Amersham Biosciences, Uppsala, Sweden)/200 μg rabbit anti-mouse IgG (H+L) (Jackson ImmunoResearch, West Grove, Pa., USA) was incubated with the diluted antibodies for 1 hr at room temperature, washed twice, and counted on a Wallac gamma counter (PerkinElmer Life Science, Grove, Ill., USA). All steps were performed in radioimmunoassay buffer consisting of 10 mM Tris, 0.5 M NaCl, 1 mg/ml gelatin, and 0.5% Nonidet P-40, pH 8.0.

Example V

Analysis of Vλ6 Wil Structure

The sequences of the expressed human Vκ and Vλ immunoglobulin light chain germline genes are as illustrated in FIGS. 21 and 22. With exception of the κ1a, λ1a, λ3a, and λ3c subgroups there is a Glu-Asp residue pairing at positions 81 and 82 in all, Vκ and Vλ germline gene sequences (FIGS. 21 and 22). In addition, a second germline encoded Glu-Asp pairing at positions 50 and 51 is unique to Vλ6 germline gene. Thus, Vλ6 Wil contains both the 50-51 and 81-82 Glu-Asp pairs. The side chains of residues 50 and 51 are both accessible on the surface of Vλ6 Wil, as shown by x-ray crystallography (FIG. 24). In contrast, only the Glu81 side chain is surface exposed and the Asp82 side chain is partially buried and appears to interact (either by electrostatic interactions or H-bonding) with the side chains of Lys79 and Arg61 (FIG. 25).

Based on these analyses of the x-ray crystal structure and the relative availability of the Glu-Asp side chains Applicants conclude that the buried Glu81 becomes accessible as the domain enters an aggregated (e.g., fibrillar) structure (or becomes partially denatured), thus exposing what is otherwise a hidden, cryptic epitope.

Example VI

Analysis of Anti-AA Monoclonal Antibody Binding to Vλ6

A. Surface Plasmon Resonance

Figure 26:
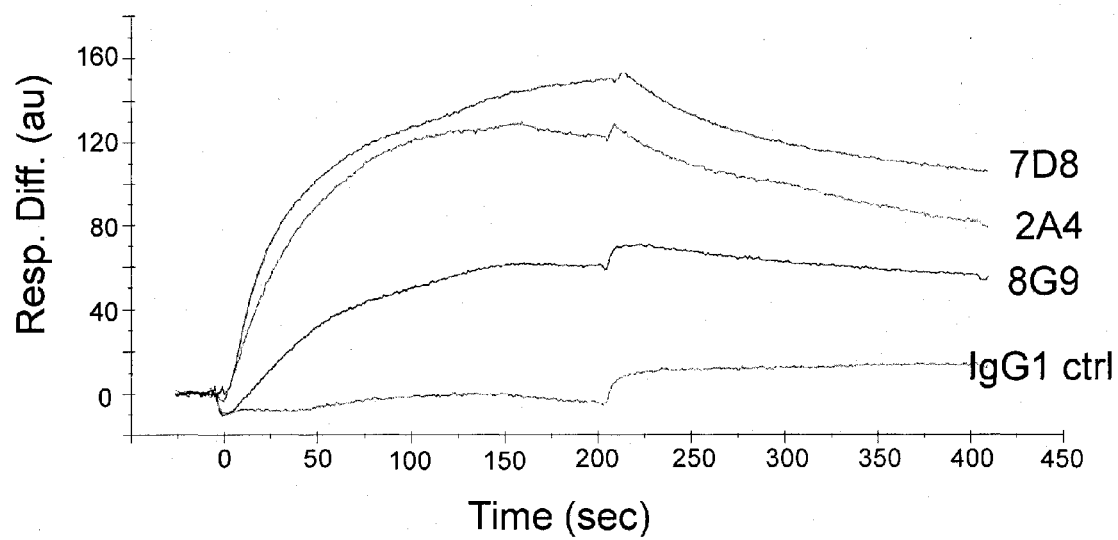
FIG. 26: Binding kinetics of Elan mAbs to synthetic Vλ6 Wil fibrils. BIAcore measurements of the interaction of mAbs 2A4, 7D8 and 8G9 at 6.6 nM to immobilized Vλ6 Wil fibrils. The calculated KD for each interaction was ~1 nM.

Surface plasmon resonance was used to establish the binding kinetics of several monoclonal antibodies with Vλ6 Wil fibrils and monomer. At a concentration of 6.6 nM all 3 antibodies bound to the immobilized synthetic Vλ6 Wil fibrils with a KD of 1 nM—a value comparable to that found for their reactivity with murine AA fibrils (FIG. 26). The deflection (expressed in RU) during the binding phase was similar for mAbs 7D8 and 2A4 but was 50% lower for 8G9. This suggests that the density of this antibody on the fibrils was lower than the other 2 reagents, as the calculated affinities were similar for all 3 antibodies. An IgG1 mAb served as a control and exhibited no binding to Vλ6 Wil fibrils.

Figure 27:
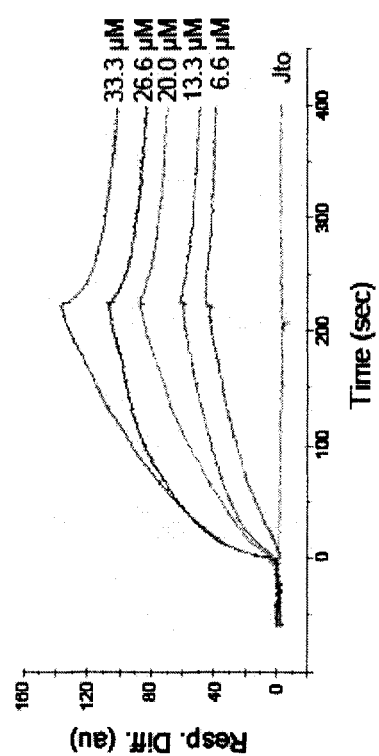
FIG. 27: Concentration-dependent binding kinetics of mAb 7D8 to synthetic Vλ6 Wil fibrils. The antibody interaction at a concentration of 6.6-33.3 nM to immobilized Vλ6 Wil fibrils was measured by BIAcore.

Titration of the mAb 7D8 over the range of 6.6 nM to 33.3 nM produced the expected decrease in the maximal deflection associated with kon (FIG. 27). In general, the binding kinetics were similar at each concentration, although in these pilot experiments the KD value for 7D8 at 26.6 nM did differ from that obtained at the other concentrations.

Figure 28:
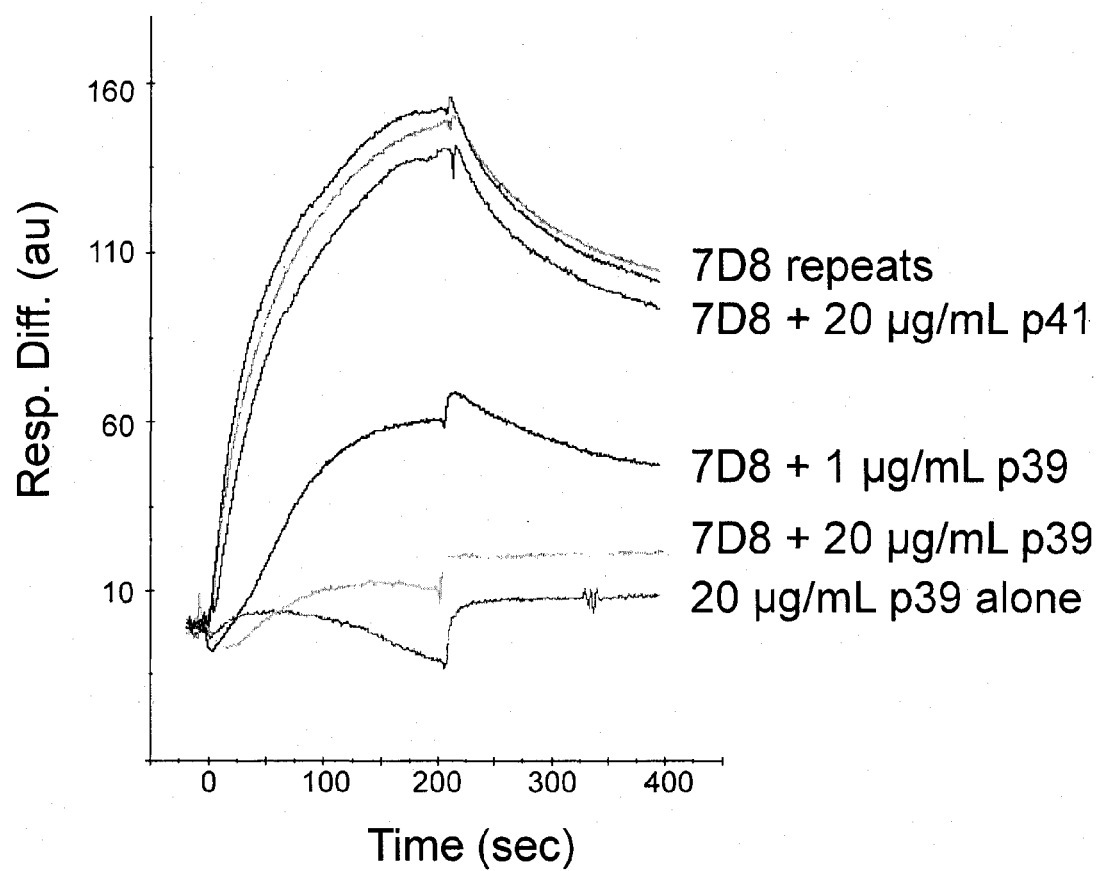
FIG. 28: Binding kinetics of mAb 7D8 to synthetic Vλ6 Wil fibrils in the presence of the p39 and p41 peptides. The interaction of the mAb 7D8 at 6.6 nM with immobilized Vλ6 Will fibrils was measured by BIAcore in the presence of peptides p39 and p41 at 1 or 20 µg/mL.

To assess the specificity of the reaction and ensure that the binding of the mAbs with the fibrils occurred via the classic F(ab)-antigen interaction (as opposed to Fc-mediated binding or non-specific adsorption), binding data were acquired in the presence of the immunogen peptide (p39) at 20 and 1 µg/mL (FIG. 8). Peptide p41 which does not bind the mAb 7D8 at low concentrations, served as a control. In the presence of 20 µg/mL p41 peptide, the binding kinetics for mAb 7D8 with Vλ6 Wil fibrils were identical to 7D8 alone. In contrast, the immunogen peptide p39 at 1 µg/mL caused a >2-fold decrease in the extent of binding as judged by the deflection of the measured signal (FIG. 28). Inhibition of fibril binding by 7D8 was almost completely inhibited when 20 µg/mL of p39 peptide was used. These data indicated that mAb 7D8 bound fibrils via the F(ab) region of the molecule inasmuch as this interaction could be completely inhibited by the immunogen peptide.

The reactivity of the mAb 7D8 with Vλ6 monomer immobilized on a chip was examined using the BIAcore. The antibody did not react with the monomeric protein. These data indicate that the binding site recognized by the mAb 7D8 is present on fibrils, but not on the soluble precursor protein, implying that the antigen is conformational or cryptic in nature.

B. Immunohistochemistry

Figure 29:
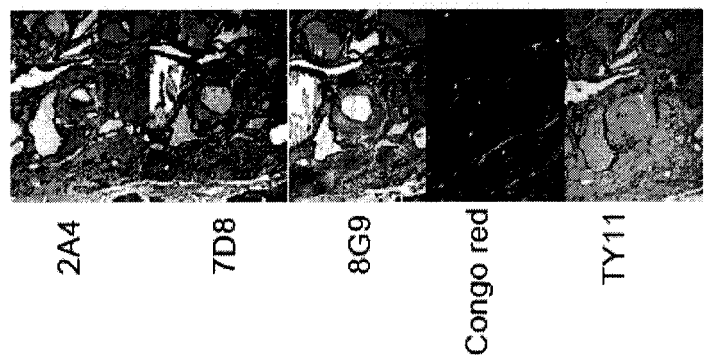
FIG. 29: Reactivity of monoclonal antibodies with ALλ tissue amyloid deposits.
Figure 30:
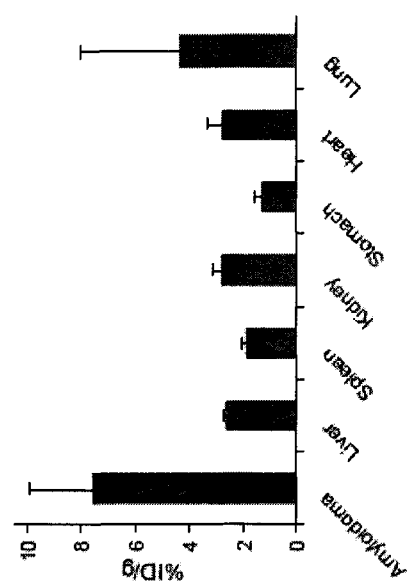
FIG. 30: Biodistribution of $^{125}$I-labeled mAb 7D8 in mice bearing a human ALλ amyloidoma.

Immunohistochemistry was performed as follows: 6 µm-thick sections, cut from formalin-fixed, paraffin embedded blocks, were subjected to and antigen retrieval by incubation with CitraPlus (BioGenex, San Ramon, Calif.) for 30 min at 90° C. Tissues were immunostained with a 3 µg/mL solution of mAbs 2A4, 7D8, or 8G9. The IgG2a mAb TY11 served as a control. A HRPO-conjugated horse anti-mouse Ig antibody (ImmPRESS Universal Reagent, Vector Labs, Burlingame, Calif.) was used as the secondary reagent. Slides were developed using 3,3'-diaminobezidene (Vector Labs) and examined using a Leica DM500 microscope. The interaction of the monoclonal antibodies with ALκ and ALλ amyloid tissues deposits was also studied using immunohistochemistry. As illustrated in FIG. 29, amyloid deposits in a patient's thyroid gland which were composed of λ2 fragments were immunostained by 7D8, 2A4 and 8G9. The areas of reactivity correlated with the amyloid deposits, indicated by the green-gold birefringence seen in the Congo red-stained tissue section. The most impressive reactivity was achieved with mAbs 7D8 and 2A4 mAbs while 8G9, although positive, was considerably weaker. These qualitative data correspond well with the BIAcore analyses in which 8G9 bound less to the Vλ6 Wil fibrils than the other 2 reagents (FIG. 26). The isotype matched mAb TY11 that served as a control exhibited no amyloid immunoreactivity.

The amino acid sequence of this λ2 protein (SEQ ID NO: 86) (shown below) contains the germline encoded Glu and Asp residues at position 81 and 82, respectively.

```
1          11         21         27d     35
GSVVIQPPS  VSGAPRQTVA ISCSGSSSNI GNNAVN  WYQQLPGKAP 45         55         65         73
KVLIYYDDLL PAGVSDRFSG SKSGTSAS   LAIRGLQSED 83         93
EGDYYCAAWD DSLSAL
```

Examination of an ALκ amyloid tissue deposit revealed 2A4, and to a lesser degree the 7D8 and 8G9, to have positive reactivity. Again there was concordance between the immunostaining and birefringent, congophilic amyloid regions. The TY11 mAb was unreactive.

C. Radioimaging of AL Amyloidoma Using $^{125}$I-Labeled 7D8

The experimental in vivo model of AL amyloidoma was used to study if radiolabeled mAb 7D8 would image human AL amyloid. The radiolabelling efficiency of 7D8, as determined by SDS-PAGE, revealed that both the IgH and IgL chains incorporated the 1-125 label, and no evidence of bands associated with fragmentation or aggregation were observed. SPECT/CT imaging of a mouse bearing an induced AL amyloidoma revealed that the $^{125}$I-labeled antibody localized to the induced, dorsally-located amyloid mass, as evidenced by accumulation of the radiolabeled antibodies in the amyloid, relative to amyloid-free tissues (e.g., liver, heart, spleen, and kidneys). Radioloabeled irrelevant IgG mAb did not accumulate in the mass; however free radioiodide was observed accumulating in the thyroid, indicative of the catabolism and dehalogention of the IgG antibody. The distribution of the $^{125}$I-7D8 mAb in the amyloidoma-bearing mice was quantified by measuring the activity associated with the amyloid mass as compared to that of the liver, spleen, kidney, stomach, heart, and lung. These data confirmed the SPETC/CT imaging study. At 72-h post injection (at which time the images were acquired and the tissues harvested), the amyloidoma contained ~8% ID which is ~4-fold higher than that seen in the liver—the site of mAb catabolism- and the heart where residual blood-pool activity would expected to be high. The activity shown in the lung was due to the mode of euthanasia (data not shown).

To confirm the biodistribution data, the amyloidoma as well as the liver, spleen, heart, and kidneys were harvested and tissue sections prepared for autoradiographic analysis. Radiolabelling was performed as follows: The 7D8 antibody was labeled with 2 mCi of reductant-free $^{125}$I (Perkin Elmer) using limiting amounts of Chloramine T and suspended in PBS containing 5 mg/ml of bovine serum albumin (BSA/PBS). Unbound isotope and protein aggregates were removed by size-exclusion liquid chromatography through an Ultrogel AcA34 column (Amersham Pharmacia). Fractions containing IgG monomer were pooled for imaging experiments. The radiochemical yield was ~50%, providing a specific activity of 25 µCi/µg. $^{125}$I-labeled mAb was subjected to SDS/PAGE (10% gels) in the presence or absence of a reducing agent and analyzed with a Cyclone phosphor-imager. In accordance with the SPECT imaging and biodistribution measurements, the autoradiographs confirmed significant accumulation of $^{125}$I-7D8 in the amyloidoma, relative to the liver. There was no evidence of uptake of radiolabeled antibody $^{125}$I-7D8 in any other organs (other than the expected hepatic activity associate with catabolism of the antibody). Although mAb 7D8 was relatively uniformly distributed throughout the bulk of the amyloid mass, a moderately higher density was observed in the peripheral areas at the abdomen-amyloid boundary. There was no uptake of the radiolabeled control IgG in any organs.

D. Summary and Conclusions

Surface plasmon resonance, immunohistochemistry and in vivo radioimaging establish that AA-reactive antibodies 2A4, 7D8, and 8G9 bind AL amyloid and fibrils (Kd ~1 nM) derived from immunoglobulin light chains. This interaction likely occurs at the highly-conserved Glu and Asp amino acids at position 81 and 82, respectively, which form a cryptic linear epitope that becomes exposed only when the amyloidogenic light chain is incorporated into fibrils.

Example VII

ELISA Analysis Demonstrates Antibody Binding to $X_1EDX_2$ Peptides

BIAcore analysis was performed to evaluate binding of antibodies 2A4, 7D8 and 8G4 on peptides of various sequences. As shown below in Table 4, the antibodies were found to react with peptides having the sequence $X_1EDX_2$. Interestingly, the antibodies did not react with peptides having additional C-terminal residues. This suggests that the antibodies specifically bind to a neoepitope generated cleavage of SAA to generate a free C-terminal end However, as demonstrated in Example V, the free end is not essential for binding of these antibodies to Vλ2 Wil, but rather the $X_1EDX_2$ domain adopts a conformation favorable to binding to the antibodies as it enters an aggregated (e.g., fibrillar) structure (or becomes partially denatured), exposing an otherwise hidden, cryptic epitope.

TABLE 4

| Antibody | Peptide | pos/neg |
|---|---|---|
| 2A4(39) | CGGHEDT, (SEQ ID NO 87) | POS |
| 40 | CGGAEDS, (SEQ ID NO: 88) | pos |
| 41 | GHEDTIADQE, (SEQ ID NO: 89) | NEG |
| 64 | CGGAEDT, (SEQ ID NO: 90) | POS |
| 65 | CGGHADT, (SEQ ID NO: 91) | WEAK |
| 66 | CGGHEAT, (SEQ ID NO: 92) | NEG |
| 67 | CGGHEDA, (SEQ ID NO: 93) | POS |
| 68 | CGGHEDTM, (SEQ ID NO: 94) | NEG |
| 69 | CGGHEDTMA, (SEQ ID NO: 95) | NEG |
| 70 | CGGHEDTMAD, (SEQ ID NO: 96) | NEG |
| 71 | CGGHED, (SEQ ID NO: 97) | FALSE POS? |
| 7d8 (39) | CGGHEDT, (SEQ ID NO: 87) | POS |
| 40 | CGGAEDS, (SEQ ID NO: 88) | POS |
| 41 | GHEDTIADQE, (SEQ ID NO: 89) | NEG |
| 64 | CGGAEDT, (SEQ ID NO: 90) | POS |
| 65 | CGGHADT, (SEQ ID NO: 91) | NEG |
| 66 | CGGHEAT, (SEQ ID NO: 92) | NEG |
| 67 | CGGHEDA, (SEQ ID NO: 93) | POS |
| 68 | CGGHEDTM, (SEQ ID NO: 94) | NEG |
| 69 | CGGHEDTMA, (SEQ ID NO: 95) | NEG |
| 70 | CGGHEDTMAD, (SEQ ID NO: 96) | NEG |
| 71 | CGGHED, (SEQ ID NO: 97) | NEG |
| 8g4 (39) | CGGHEDT, (SEQ ID NO: 87) | POS |
| 40 | CGGAEDS, (SEQ ID NO: 88) | POS |
| 41 | GHEDTIADQE, (SEQ ID NO: 89) | NEG |
| 64 | CGGAEDT, (SEQ ID NO: 90) | POS |
| 65 | CGGHADT, (SEQ ID NO: 91) | NEG |
| 66 | CGGHEAT, (SEQ ID NO: 92) | NEG |
| 67 | CGGHEDA, (SEQ ID NO: 93) | WEAK |
| 68 | CGGHEDTM, (SEQ ID NO: 94) | FALSE + ? |
| 69 | CGGHEDTMA, (SEQ ID NO: 95) | FALSE + ? |
| 70 | CGGHEDTMAD, (SEQ ID NO: 96) | NEG |
| 71 | CGGHED, (SEQ ID NO: 97) | NEG |

Example VIII

Immunohistochemical Analysis of Mouse AA

The reactivity of supernatants from hybridomas expressing antibodies 2A4, 8G9 and 7D8 to murine AA splenic and hepatic amyloid deposits (the principal sites of amyloid deposition) was documented immunohistochemically. For these studies, sections of tissue harvested from a TRIAD mouse with extensive AA amyloid in the liver and spleen (as evidenced by green birefringent Congophilic deposits) were stained with the mAb-containing supernatants. All 3 bound to the hepatic and splenic amyloid. In contrast, there was no reactivity with culture supernatants derived from irrelevant hybridomas. The capability of the amyloid using 2A4, 8G9 and 7D8 to immunostain amyloid in fresh (unfixed), OCT-embedded murine liver and spleen was tested. There was evidence that the mAbs retained their ability to bind AA amyloid in the hepatic sinusoid. In addition, the antibody reactivity with splenic tissue was easier to interpret, and the perifollicular amyloid was intensely immunostained. To demonstrate that the mAbs was specifically bound AA amyloid, the mAb supernatants at a 1:25 dilution were preincubated with 50 μg/mL of either peptide #39 (p#39) or #41 (p#41) for 1 h at room temperature. With formalin-fixed tissue as a substrate, the p#39 peptide (50 μg/mL) significantly inhibited the amyloid reactivity of both 2A4 and 7D8 mAbs (the results with 8G9 are pending). In contrast, the p#41 peptide was ineffective. Comparable results were obtained with fresh tissues.

Example IX

Immunohistochemical Analysis of Human AA

Comparison of the amino acid sequence of mouse and human SAA from position 73-76 reveals 2 identical residues, a conserved Ser to Thr substitution, and a non-conserved Ala to His exchange. To test if the 2A4, 8G9 and 7D8 mAbs would cross-react with human AA amyloid deposits, we tested their reactivity to human AA-containing kidney, adrenal, ovary and liver. In all cases, the mAb supernatants immunostained the amyloid deposits. In ovarian tissue, the p#39 peptide effectively blocked the binding of the mAbs to the perivascular AA amyloid, whereas the p#41 peptide did not inhibit this reaction.

Example X

Interaction of Anti-AA of Culture Supernatants with Murine-Derived AA Fibrils

Figure 31:
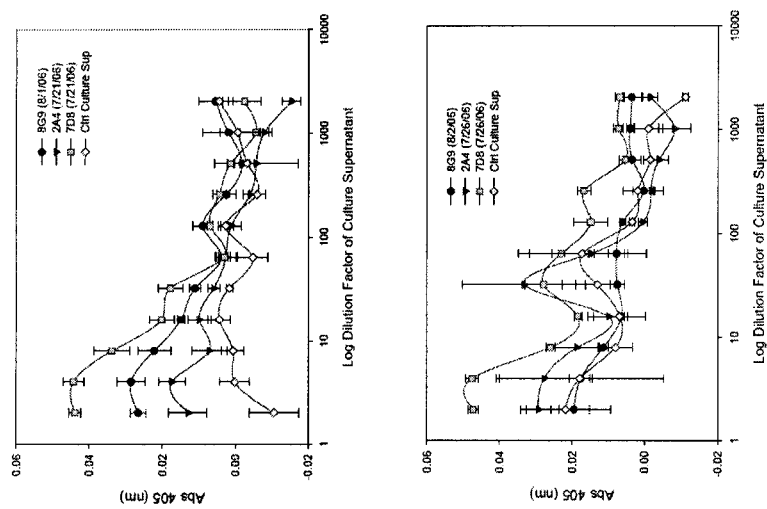
FIG. 31: Interaction of anti-AA of culture supernatants with murine-derived AA fibrils. Results of mAb culture supernatants binding murine AA AEF. Upper and lower panels are data on first and second culture fluid harvest, respectively.
Figure 32:
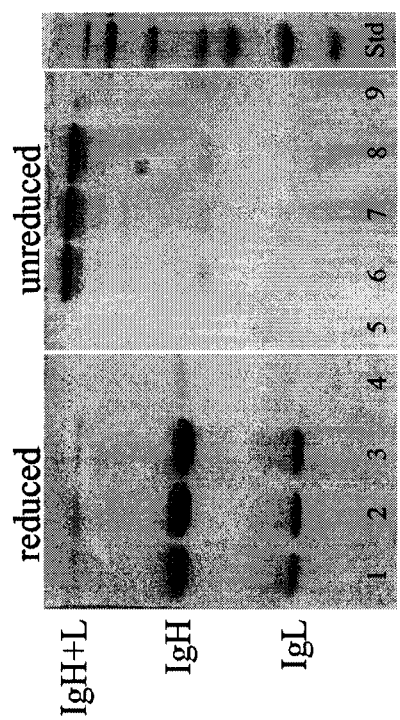
FIG. 32: SDS-PAGE analysis of protein A-purified 2A4, 8G9 and 7D8 mAbs.

The interaction of 2A4, 8G9 and 7D8 mAbs with AA amyloid was initially tested by ELISA and the data, given in FIG. 31, analyzed using SigmaPlot (SPSS Inc.). Each point represents the mean±SE (n=3). A culture supernatant from an irrelevant hybridoma was used as a control (Ctrl Culture Sup). There was an extremely low signal-noise ratio and the results showed that the first harvest contained more mAb relative to the second, as evidenced by the greater absorbance signal relative to the control supernatant. (In addition, the immunohistochemical reactivity of the day 1 material was greater than the day 2 samples). Although the SE values were large, it appeared from these data that the binding affinity of 2A4, 8G9 and 7D8 was approximately equivalent with reactivity absent after ~1:64 dilution. The binding data also suggest that the capacity, i.e., the amount of mAb bound, varied with 7D8>8G9>2A4; however, these data were not corrected for mAb concentration and in subsequent studies this trend was not observed. Because of the low signal and high variability found with the culture supernatants and to determine more accurately the relative binding affinity of the mAbs for murine and human AA amyloid fibrils (as well as to provide material for in vivo biodistribution studies) it was necessary to isolate the mAbs by protein A affinity chromatography. The purity of the isolated mAbs was established SDS-PAGE using 10% acrylamide gels under reducing and non-reducing conditions (FIG. 32). Samples in lanes 1-4 treated with mercaptoethanol, lanes 5-9 without. Gel was stained with Coomassie blue: mAb 8G9, lanes 1 and 6; mAb 2A4, lanes 2 and 7; mAb 7D8, lanes 3 and 8; SP2/0 control supernatant, lanes 4 and 9; blank, lane 5. Protein Mr markers (Std) are, form top to bottom: 176, 119, 75, 49, 39, 25 and 19 kDa. The interaction of the purified mAbs with immunizing peptide p#39, control peptide (p#41), murine and human AA extracts were determined by ELISA as described above. These data were analyzed by fitting a sigmoidal curve using the SigmaPlot software and the mAb concentration at 50% saturation (EC50), determined (Table 5).

TABLE 5

EC$_{50}$ values for purified mAb binding

| mAb | Substrate | | | |
|---|---|---|---|---|
| | Human AA | Mouse AA (AEF) | Peptide 39 | Peptide 41 |
| 8G9 | 31.7 nM | 5.64 nM | 4.0 nM | >>100 nM |
| 2A4 | 26.4 nM | 4.09 nM | 3.4 nM | >>100 nM |
| 7D8 | 13.3 nM | 1.84 nM | 2.3 nM | >>100 nM |

Figure 33:
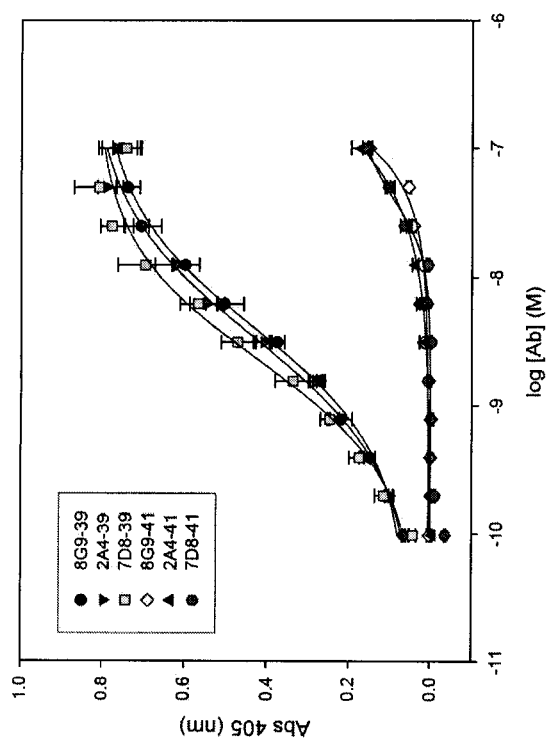
FIG. 33: Binding of purified mAbs to immunizing (p#39) and control peptide (p#41).
Figure 34:
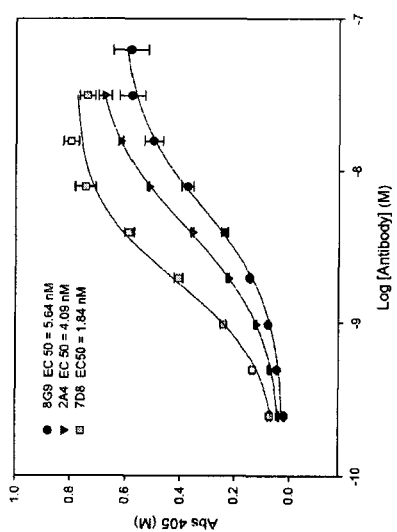
FIG. 34: Binding to murine AA amyloid extract (AEF).
Figure 35:
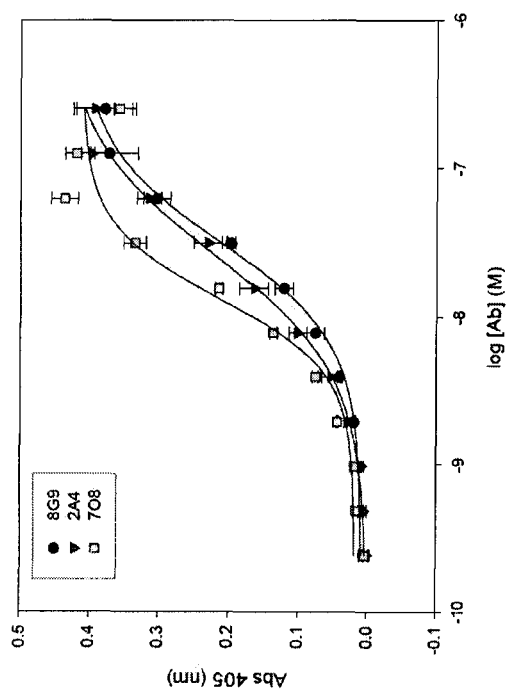
FIG. 35: Binding of purified mAbs to human renal AA amyloid extract.

The interaction of the 3 mAbs with peptide p#39 exhibited saturable binding with EC50 values in the low nanomolar range (see above Table 5). In contrast, even at the highest concentration of mAb used (100 nM) there was little detectable binding to the p#41 peptide (FIG. 33—Each point represents the mean±SE, (n=3 at each concentration)). These data confirmed the immunohistochemical results described above, i.e., that peptide p#39 was capable of completely blocking the binding of the mAbs to AA amyloid laden tissues. The calculated EC50s for the binding of each mAb with p#39 peptide were essentially identical as was the case when a murine AA amyloid extract was used as the substrate (FIG. 34—Each point represents the mean±SE (n=3 at each concentration)). The calculated EC50 values for the mAbs binding to mouse AA extract were essentially identical to those obtained when the p#39 peptide was used as the substrate (FIG. 34; Table 5). In contrast, when human AA amyloid extract was dried onto the wells of the microplate, the EC50 values were between 5 and 7× lower than that observed for mouse AA and peptide p#39 (FIG. 35—Each point represents the mean±SE (n=3 at each concentration); Table 5). Because the EC50 value for 7D8 mAb binding was the lowest of the 3 antibodies tested, Applicants selected this reagent for in vivo co-localization and imaging studies. The 2 amino acid substitutions in the human SAA sequence with respect to the murine protein affected the EC50 values. While not wishing to be bound by a particular theory, Applicants attribute the higher EC50 for the human AA to a poorer "fit" of the amino acid side chains in the antigen binding site, however, this effect corresponds to only a 5-fold decrease in the relative affinity when the amyloid extracts are surface adsorbed, as in the ELISA. Furthermore, these data support the observation that all 3 mAbs bound to both murine and human tissue AA amyloid deposits.

Example XI

Competitive Binding of Mabs to Mouse and Human AA Amyloid

To determine the effect, if any, of potential denaturation when adsorbed to the surface of the microtiter well, the reactivity of the 2A4, 8G9 and 7D4 was evaluated using a competition ELISA in which murine or human AA amyloid extract was used as a soluble competitor for the interaction of the mAbs with surface-bound AA extract.

In all cases, soluble (non-adsorbed) AA amyloid fibrils of both human and mouse origin were capable of competing for the 3 mAbs, indicating that the epitope recognized by the reagents is not dependent upon the partial denaturation that results from surface adsorption. In general, the murine AA (AEF) extract was a better competitor than the human AA (Table 6).

TABLE 6

| IC$_{50}$ values (µg/mL) for mAb binding to AA amyloid | | |
|---|---|---|
| mAb | Human AA† | Mouse AA (AEF)‡ |
| 8G9 | >119.5 | 17.3 |
| 2A4 | >211.7 | 14.7 |
| 7D8 | >881.1 | 26.8 |

†Human AA amyloid in solution competing for adsorbed mouse AA (AEF);
‡Mouse AA (AEF) in solution competing for adsorbed human AA amyloid extract on plate.

The IC50 values (concentration of AA (by weight) that reduced the mAb binding by 50%) for murine AEF in solution were ~20 µg/mL, whereas for human AA the values were 6- to 44-fold greater (in contrast, the EC50s for human AA were only 7-fold lower than those for mouse AA). This may reflect the fact that, when in solution, the epitope on the amyloid fibrils is less accessible in human AA preparations as compared to murine AA.

As expected, the 7D8 mAb that exhibited the highest relative affinity for the human and murine AA fibrils when they were surface-adsorbed required the highest concentration of AA amyloid to achieve competition.

Example XII

Radiolabeled MAb 7D8

The radiolabeling efficiency of 7D8 was determined by SDS-PAGE. Reduced and native mAb were analyzed and the proteins visualized using a phosphor imager. Both the IgH and IgL chains incorporated the I-125 label, and no evidence of bands associated with fragmentation or aggregation were observed.

Example XIII

Imaging of AA Amyloid Using $^{125}$I-Labeled 7D8

To study the in vivo localization of radiolabeled mAb 7D8 three groups of mice were used: transgenic IL-6; AgNO3/

AEF induced, and amyloid-lacking controls (WT). The SPECT/CT imaging revealed that the $^{125}$I-7D8 mAb localized to murine AA amyloid deposits in the spleen and liver, as evidenced by the accumulation of the radiolabeled mAb in these tissues relative to the control mouse, which showed only low blood pool activity in the liver and free iodide the thyroid gland.

In contrast to these mice, the AgNO3-injected mouse showed thyroid uptake of free iodide, some hepatic activity, but the major site of $^{125}$I-7D8 binding was seen at the site of s.c. AgNO3 injection (the lower right dorsal area). The activity in this area is clearly circumscribed by the x-ray-attenuating silver solution as seen by CT. The 7D8 mAb has been shown to bind to AA amyloid deposits in both the liver and spleen in the presence of circulating sAA in the TRIAD mouse, as evidenced in the SPECT images.

A. Biodistribution of $^{125}$I-7D8 in Mice 48 h post-injection of $^{125}$I-7D8 there was radioactivity in the blood pool, which accounted for the relatively high uptake In the lung (which fill with blood when the mice are sacrificed). Of note, the hepatosplenic accumulation of mAb in the IL-6 mouse is indicative of the presence of amyloid. The SPECT/CT images confirmed the distribution of the mAb in these organs. 72 h post-injection the blood pool values have changed little as evidenced by the unchanged activity in the heart and lung relative to the mice sacrificed at 48 h, due to the relatively long $T_{1/2bio}$ for this mAb (~60 h). There was significant accumulation of the radiolabeled mAb in the IL-6 mouse, which correlated with the SPECT images that were acquired showing impressive splenic and, to a lesser degree, hepatic uptake. Of the other organs, most important was the liver (which is the site of catabolism of IgG and the source of sAA during the acute phase response). In the WT mice, with no inflammatory challenge or amyloid, the liver contained <6% ID/g, which is comparable to the kidney and heart where the blood pool contributes almost exclusively to the signal.

B. Autoradiographic and Histochemical Analyses

In order to determine if the increased hepatic accumulation of $^{125}$I-7D8 in the IL-6 and AgNO$_3$ mice resulted from amyloid uptake, catabolic clearance or binding to newly synthesized sAA, liver as well as other tissues were subjected to autoradiographic analysis.

Based on the SPECT imaging and biodistribution measurements, it was presumed that the greatest amount of amyloid in the transgenic IL-6 mice was in the liver and spleen. This supposition was confirmed in the Congo red-stained sections in which significant amyloid was observed throughout the red pulp as well as in the perivascular regions and sinusoids of the liver. Additional, more discreet birefringent deposits were present in the kidneys and heart. The distribution of the $^{125}$I-7D8 within these tissues correlated well with the Congo red and AA-reactive material. There was no accumulation in hepatocytes that were devoid of amyloid.

Based on the biodistribution data, the AgNO$_3$-treated mouse had more uptake of $^{125}$I-7D8 in the liver than the spleen, which was unexpected since this is not the normal pattern of accumulation of AA in such animals. Congo red-staining revealed small amounts of amyloid in a single perifollicular region in the spleen (upper right corner) and extensive hepatic perivascular deposits both of which were evident in the autoradiographs. Additionally, the s.c. site of the AgNO$_3$ injection was seen in the SPECT images to have a significant concentration of $^{125}$I-7D8 (we also have observed this when radioiodinated SAP was used as the imaging agent). This site does not contain amyloid (i.e., Congo red-birefringent material); however, it was immunostained by anti-AA mAb. Without wishing to be bound to a particular theory, it is possible that the mAb 7D8 localizes to sites of inflammation or "pre-amyloid" (as well as mature amyloid deposits). In contrast to the impressive accumulation of 7D8 in the organs of the IL-6 mouse, the tissues of the control mice were found to have little or no tracer in any organ other than the blood pool. No amyloid was found in Congo red-stained sections of any organ of these controls.

C. Pharmacokinetics of $^{125}$I-7D8.

After injection of the radiolabeled 7D8 antibody, the rate of disappearance of the molecule was determined and the half-life determinations summarized in Table 7. These results indicated that the $T_{1/2bio}$ of 7D8 was ~60 h, consistent with that of an IgG2b murine mAb (note, 7D8 is of the IgG2b subclass). The slightly more rapid clearance of the $^{125}$I-7D8 in the IL-6 (TRIAD) mice was not considered significant. Based on these data, retention of the mAb by tissue amyloid, as evidenced in the SPECT data, over 72 h does not influence the excretion rate.

TABLE 7 half-life analyses for $^{125}$I-7D8 in mice

| Mouse | A (S.E.) | K (S.E. × 10$^{-4}$) | R$^2$ | t$_{1/2\ bio}$ | t$_{1/2\ eff}$ |
|---|---|---|---|---|---|
| IL-6, 48 h | 191.7 (2.96) | 0.0117 (7.0) | 0.98 | 59.2 h | 56.2 |
| IL-6, 72 h | 175.2 (3.99) | 0.012 (8.9) | 0.97 | 57.7 h | |
| AgNO$_3$, 48 h | 181.0 (1.99) | 0.0106 (4.9) | 0.99 | 65.3 h | 61.1 |
| AgNO$_3$, 72 h | 174.1 (2.97) | 0.0112 (5.8) | 0.98 | 62.2 h | |
| Ctrl, 48 h | 185.1 (3.19) | 0.0108 (7.6) | 0.98 | 64.3 h | 61.3 |
| Ctrl, 72 h | 185.1 (3.09) | 0.0109 (5.6) | 0.98 | 63.7 h | |

1. Method of Identifying Agents that Prevent or Treat Amyloidosis Using Transgenic or TRIAD Mouse. Procedures for preparation of agents are described in Schenk et al. Nature 400:173-177. Agents are emulsified 1:1 (v/v) with complete Freund's adjuvant for the first immunization of transgenic mice, followed by a boost in complete Freund's adjuvant at 2 weeks and monthly thereafter. PBS injections followed the same schedule and mice were injected with 1:1 mix of PBS/adjuvant for control. The life span of the transgenic mice is compared to determine whether the agents are effective in preventing AA Amyloidosis by increasing the life of the animal.

2. Histopathology. For light and polarizing microscopy, 4- to 6-µm-thick tissue sections were cut and stained with hematoxylin and eosin (HE) and a freshly prepared alkaline Congo red solution, respectively. For electron microscopy, sections were embedded in Epon (Ted Pella, Redding, Calif.), sectioned, and examined with a JEOL 100S transmission electron microscope. See Ludlage et al. Vet Pathol 42:117-124 (2005).

3. Immunohistochemistry. Paraffin-embedded tissue sections (6-µm-thick) were cut on a microtome, mounted on poly-L-lysine-coated slides, dried overnight at room temperature, and deparaffinized. Immunostaining was performed using the avidinbiotin complex (ABC-elite) technique as described previously. The primary antibodies were mouse anti-human amyloid A (Accurate Chemical and Scientific Corporation, Westbury, N.Y.) and anti-mouse SAA polyclonal antisera. Affinity-purified horse anti-mouse immunoglobulin-G (IgG) horseradish peroxidase conjugate (Vector Laboratories, Burlingame, Calif.) or goat anti-rabbit, -mouse, or -rat IgG horse-radish peroxidase conjugates (BioRad Laboratories, Richmond, Calif.) were used as the secondary antibodies.

4. SAA Quantitation by ELISA. SAA concentrations were measured by an enzyme-linked immunosorbent assay (ELISA) using the Multispecies SAA ELISA kit according to directions supplied by the manufacturer (Biosource, Camarillo, Calif.). Standard curves were prepared using known amounts of human SAA protein and absorbance was measured at 405 nm with a model 4450 BioRad plate reader (Fullerton, Calif.).

5. Radiolabeled SAP Scintigraphy Turnover Studies in Mice. SAP was oxidatively iodinated with $^{125}$I (2-5 MBq/mg) by using N-bromosuccinimide. 6-12 weeks old mice received 2-10 μg of $^{125}$I-SAP in 200 μL intravenously. Precisely measured tail bleeds (0.01-0.04 g) were taken at specific time intervals and trichloroacetic acid-precipitable radioactivity was counted in the same run at the end of each experiment together with standard aliquots of the injected tracer. Pepys et al. *Proc Natl. Acad. Sci. USA* 91:5602-5606 (1994).

6. Radiolabeled SAP Scintigraphy Turnover and Imaging Studies in Man. SAP for use in man was isolated from the plasma of a single normal accredited donor and was oxidatively iodinated with $^{125}$I (2-5 MBq/mg) or $^{123}$I (110 MBq/50 μg of protein) by using N-bromosuccinimide. After injection of $^{123}$I SAP, data were acquired and processed on an IGE Starcam gamma camera (IGE Medical Systems, Slough, U.K. Clearance of $^{125}$I-labeled SAP was studied in healthy individuals and patients suffering from AA amyloidosis. Pepys et al. *Proc Natl. Acad. Sci. USA* 91:5602-5606 (1994)

7. Amyloid Extraction and Purification. The methods used to extract amyloid from tissue were as described by Pras et al. See Pras et al. *J. Clin. Invest.* 47:924-933 (1968) In brief, a portion of liver or tissues from other organs obtained at necropsy and maintained at −80 C was homogenized with cold saline in an ice bath using an Omni-Mixer (Omni International, Waterbury, Conn.). The extract was centrifuged at 10,000 rpm for 30 minutes at 4 C and the pellet reextracted twice more with cold saline, once with 0.1 M sodium citrate Tris-buffered saline, pH 8.0, and then again with saline until the A280 of the supernatant was <0.10. The resultant pellet was homogenized with cold distilled water, and the mixture centrifuged at 35,000 rpm for 3 hours at 4 C. The pellet obtained from the water extract was then lyophilized.

8. Surface Plasmon Resonance. Binding kinetics were measured on a BIAcore X instrument. Fibrils prepared from the Vλ6 Wil were sonicated briefly with a probe sonicator and then coupled to a CM-5 chip using amine chemistry, as per the BIAcore protocol. This process utilizes EDC and NHS to activate the carboxyl groups on the chip for coupling with free amino groups on the fibrils. Coupling was conducted in a NaOAc buffer, pH 4.0 at a concentration of 100 μg/mL. The control channel was "mockcoupled" and both channels were reacted with ethanolamine to saturate unreacted sites. Approximately 16,000 RU of Vλ6 Wil fibrils were coupled.

Sensograms were run in HBS-EP buffer from BIAcore at 20 μL/min in the Fc1 (Vλ6 Wil fibrils) minus Fc-2 (control) mode. Samples containing mAb or mAb plus peptide inhibitors were injected (70 μL) and the sensograms collected using the delayed-wash function for 200 sec. Data were analyzed in the BIAevalutation software, using the 1:1 Langmuir model with mass-action correction.

9. MicroSPECT/CT. Two cohorts of 3 mice each were injected s.c. with 50 mg of human AL amyloid extract between the scapulae. After 7 days, one group of mice received an iv tail vein injection of ~300 μCi of $^{125}$I-labeled mAb 7D8. The second group was administered an equal quantity of murine mAb MOPC 31C as a control. After 72 hr, the mice were sacrificed by isoflurane overdose and SPECT/CT images acquired. To provide vascular contrast-enhancement in the CT images, mice were given a 200-μL iv dose of Fenestra VC™ (Advanced Research Technologies, Montreal, Canada) 5 min prior to scanning.

SPECT data were collected with a microCAT II+SPECT dual modality imaging platform (Siemens Preclinical Solutions, Knoxville, Tenn.), capable of submillimeter spatial resolution when equipped with a 0.5 mm-pore diameter pinhole collimator. When imaging, the 2 detectors (composed of a 50 mm-diameter Hamamatsu R2486-02 multi-anode photomultiplier tube coupled to a 1×1×8 mm CsI (Tl) crystal array arranged on a 1.2 mm$^2$ grid) were positioned ~45 mm from the center of rotation. Each SPECT dataset comprised 45 projections collected over 360° during the course of ~50 min. Images were reconstructed using an implementation of the expectation maximization-maximum likelihood (EM-ML) algorithm.

After collection of SPECT data, high-resolution CT images were obtained. The microCAT II scanner has a circular orbit cone beam geometry, equipped with a 20-80 kVp microfocus x-ray source, and captures a 90 mm×60 mm field of view using a 2048×3072 CCD array detector, optically coupled to a minR phosphor screen via a fiber-optic bundle. Each CT dataset, composed of 360 projections at 1° azimuths, was acquired in 8 min. Images were reconstructed in real-time on isotropic 77-μm voxels using an implementation of the Feldkamp backprojection algorithm.

To facilitate co-registration of the reconstructed SPECT and CT images, Co-57 sealed sources were placed on the imaging bed. The microSPECT and CT datasets were visualized and co-registered manually with a 3-D image analysis software package (Amira, Version 3.1: Mercury Computer Systems).

10. Biodistribution. Samples of liver, spleen, kidney, heart, lung, and implanted amyloid tumors (i.e., amyloidoma) were harvested from the mice and placed into tared vials, weighed, and the radioactivity measured. The primary index values were expressed as % injected dose/g tissue (% ID/g).

11. Autoradiography. 6 μm-thick sections cut from formalin-fixed, paraffin-embedded blocks of tissue obtained from mice sacrificed 72 h post-injection of $^{125}$I-7D8 were placed on Probond microscope slides (Fisher Scientific), dipped in NTB-2 emulsion (Eastman Kodak), stored in the dark, and developed after a 24-h exposure. The sections were counterstained with hematoxylin and eosin (H&E), cover-slipped using Permount (Fisher Scientific), and examined by light microscopy. In addition, consecutive slides were stained with alkaline Congo red and viewed under cross-polarized illumination. Finally, a third slide was immunostained using as primary reagent our AA-reactive mAb. Digital camera microscopic images were taken and evaluated using an image analysis software package (Image Pro Plus, Media, Cybernetics).

Example XIV

Preparation of Humanized 2A4 and 7D8 Antibodies

Humanized 2A4, 7D8, and 8G9 antibodies were prepared by grafting of murine 2A4, 7D8, and 8G9 CDRs onto human acceptor frameworks according to techniques known in the art. Back mutations were made to reduce antigenicity while preserving binding affinity. The light chain and heavy chain variable regions of murine 2A4 are set forth as residues 20-131 of SEQ ID NO: 152 and as residues 20-138 of SEQ ID NO: 154, respectively. The light chain and heavy chain variable regions of 7D8 are set forth as residues 20-131 of SEQ ID NO: 153 and as residues 20-138 of SEQ ID NO: 154, respectively. The light chain variable regions of murine 2A4 and 8G9 are identical to each other and differ from the light chain variable region of 7D8 in a single residue in CDR1. The heavy chain variable regions of each of 2A4, 7D8, and 8G9 are identical.

The variable kappa (Vk) of 2A4 and 7D8 belong to mouse subgroup 2, which corresponds to human subgroup 2 and the variable heavy (Vh) to mouse subgroup 3c which corresponds to human subgroup 3 (Kabat et al. (1991) Sequences of Proteins of Immunological Interest, Fifth Edition. NIH Publication No. 91-3242). CDR-L1 includes 16 residues and belongs to canonical class 4 in Vk. CDR-L2 includes 7 residues and belongs to class 1 in Vk. CDR-L3 includes 9 residues and belongs to class 1 in Vk. See Martin A C, Thornton J M. (1996) J Mol Biol. 263, 800-15. The leucine at position 27 in the 7D8 is rather unusual, and the glutamine in 2A4 is more usual. A model shows the sidechain is on the surface of the binding site, and therefore should be important for antigen binding. CDR-H1 includes 5 residues and belongs to class 1, and CDR-H2 includes 19 residues and belongs to class 4 (Martin & Thornton, 1996). CDR-H3 has no canonical classes, but the 8 residue loop probably has a kinked base according to the rules of Shirai et al. (1999) FEBS Lett. 455, 188-97. This is conserved in a model although the conformation of the apex of CDR-H3 may be different. The residues at the interface between the Vk and Vh domains are the ones commonly found for 2A4 Vk, 7D8 Vk and 2A4 Vh.

A search was made of the PDB database (Deshpande et al. (2005) Nucleic Acids Res. 33: D233-7) to find structures which would guide the choice of back mutations. A search of the non-redundant protein sequence database from NCBI allowed selection of suitable human frameworks into which to graft the murine CDRs. For Vk, a human kappa light chain with NCBI accession code BAC01562 (gi:21669075) (SEQ ID NO: 166) was chosen. This has the same length CDR-L3 and belongs to human germline VKIIA19/A3 and human kappa subgroup 2. A similar framework which only differed in the J-region was also found with NCBI accession code BAC01733 (gi:21669417) (SEQ ID NO: 167). BAC01562 was used as a framework for 2A4 Vk, and BAC01733 was used as a framework for 7D8 Vk. For Vh, human Ig heavy chain AAC51024 (gi:1791061) (SEQ ID NO: 165) was used. See Glas et al. (1997) *Clin. Exp. Immunol.* 107: 372-380. This belongs to human germline VH3-72 and human heavy subgroup 3.

Representative humanized 2A4 light chain variable regions are set forth as SEQ ID NOs: 155, 156, and 157. Representative humanized 7D8 light chain variable regions are set forth as SEQ ID NOs: 158, 159, 160, 174, 175, and 176. Representative humanized 2A4/7D8 heavy chain variable regions are set forth as SEQ ID NOs: 161, 162, and 163. See FIGS. 36A-36E.

Representative humanized antibodies of the invention include antibodies having a light chain variable region selected from one of residues 20-131 of SEQ ID NO: 152, residues 20-131 of SEQ ID NO: 153, and SEQ ID NOs: 155, 156, 157, 157, 159, 160, 174, 175, and 176; and a heavy chain variable region selected from one of residues 20-138 of SEQ ID NO: 154 and SEQ ID NOs: 161, 162, and 163.

Example XV

Therapeutic Effects of Mab 2A4 in Mice with Severe Systemic AA Amyloidosis

The therapeutic efficacy of mAb 2A4 was evaluated in H2/huIL-6 mice with severe systemic amyloidosis. The transgenic H2/huIL-6 mice, which constitutively express a human IL-6 transgene, are prove to rapid and irreversible systemic AA amyloidosis. In a first and second study, mice treated with isotype-matched mAb TY-11, which has no reported activity in mice, was used as a control. Before administering the amyloid enhancing factor to induce AA, H2/huIL-6 mice were sampled and bled via the retro-orbital sinus, serum prepared, and the sAA concentration determined using a commercially available ELISA kit. Representative values were as follows: 2196.7 µg/mL, 823.91 µg/mL, 1415.00 µg/mL, 1673.01 µg/mL, 814.53 µg/mL, 1088.18 µg/mL, 736.34 µg/mL, 1546.35 µg/mL, 953.70 µg/mL, 886.46 µg/mL, mean=1213.4±478 µg/mL.

At the start of the second study (week 0), H2/huIL-6 mice were injected iv with 100 µg of amyloid enhancing factor (AEF). After induction of AA pathology by injecting AEF, the mice were administered 5 injections of 100 µg subcutaneously in alternate limbs of mAb 2A4 (13 animals) or TY11 (11 animals). The therapy was initiated at approximately 1 week post AEF injection. The survival of animals in each treatment group was plotted and analyzed. The results are shown in Table 8. Only 45% of the mAb TY11-treated mice survived to the end of the study. In contrast, none of the 2A4-treated mice were lost over the course of the study. Analysis of the survival data using standard methods showed a significant difference in the survival curves (P<0.0025) in both groups. The median survival of the TY11-treated mice was calculated to be 41 days, comparable to that observed in a prior study (38.5 days).

TABLE 8

Percentage of animals surviving

| Days post injection | TY11-treated | 2A4-treated |
|---|---|---|
| 0 | 100.00 | 100.00 |
| 22 | 81.82 | 100.00 |
| 33 | 72.73 | 100.00 |
| 37 | 63.64 | 100.00 |
| 41 | 45.45 | 100.00 |
| 42 | 45.45 | 100.00 |

At week 6, post-AEF, mice were bled and sacrificed, and their organs harvested for further analysis. For quantification of amyloid in liver and spleen, Congo red birefringence was visualized microscopically under cross-polarized illumination and digitally recorded. The area of birefringent material was determined by selecting (using a spectral segmentation method) and quantifying the amyloid-associated pixels. The amyloid burden index (ABI), a measure of amyloid content, was expressed as the percentage area occupied by amyloid in each organ. Quantification of amyloid in the livers and spleens of 2A4 and TY11-treated mice revealed no significant difference between the two treatments. However, the TY11-treated mice that survived to day 42 for comparison with 2A4-treated mice were those that did not develop a morbid degree or distribution of AA amyloid to thereby result in morbidity. The hepatosplenic amyloid burden is also monitored during the course of the survival study to assess an increase in amyloid burden that correlates with morbidity.

In a third study, mAb 2A4 was compared to the isotype-matched mAb JH70, which has no reported reactivity in mice. In addition blood chemistry and other parameters were monitored throughout the treatment period. Male and female H2/huIL-6 mice born between Aug. 1, 2008 and Sep. 7, 2008 were used in this study. Twenty three female mice and 16 male mice were bled via the retro-orbital sinus. Whole blood was used for chemical characterization of blood urea nitrogen (BUN) and alanine aminotransferase (ALT) to measure renal and hepatic function by using the VetScan VS2 (Abaxis, Union City, Calif.). The serum concentration of 12 other proteins and analytes were simultaneously measured. A complete blood count (CBC) was performed using the VetScan HM5 platform. In addition, each mouse was administered a low dose (~50-60 µCi) of radioiodinated human serum amyloid P component ($^{125}$I-SAP) in 5 mg/mL bovine serum albumin to assess the amyloid burden of the mice prior to initiation of the disease process. The percent of $^{125}$I-SAP retained at 24 h post-injection (pi) was measured by placing each mouse into a dose calibrator. Retention of $^{125}$I-SAP greater than that observed in non-transgenic (control) mice was indicative of amyloid disease. Finally, serum was used to measure the concentration of serum amyloid protein A (sAA) using a commercial ELISA assay. A summary of these pre-treatment data, selected blood chemistry values, and the treatments given to each mouse are shown below in Tables 9 and 10.

TABLE 9

Summary Of Pre-Treatment Data And MAb Therapy For Each Animal

| Mouse # | sAA conc. (µg/mL) | Sex | DOB | $^{125}$I-SAP retention (%) | Therapy (Group No.) |
|---|---|---|---|---|---|
| 3488 | 360 | F | Aug. 1, 2008 | 9 | 2A4 (1) |
| 3489 | 996 | F | Aug. 1, 2008 | 29 | 2A4 (1) |

TABLE 9-continued

Summary Of Pre-Treatment Data And MAb Therapy For Each Animal

| Mouse # | sAA conc. (µg/mL) | Sex | DOB | $^{125}$I-SAP retention (%) | Therapy (Group No.) |
|---|---|---|---|---|---|
| 3490 | 472 | F | Aug. 1, 2008 | 10 | 2A4 (1) |
| 3492 | 2068 | M | Aug. 1, 2008 | 13 | 2A4 (1) |
| 3493 | 1740 | M | Aug. 1, 2008 | 11 | JH70 (1) |
| 3494 | 1272 | M | Aug. 1, 2008 | 10 | JH70 (1) |
| 3495 | 1436 | M | Aug. 1, 2008 | 13 | JH70 (1) |
| 3496 | 2080 | M | Aug. 1, 2008 | 9 | 2A4 (1) |
| 3498 | 268 | M | Aug. 1, 2008 | 9 | 2A4 (1) |
| 3500 | 700 | F | Aug. 11, 2008 | 11 | JH70 (1) |
| 3501 | ND | F | Aug. 11, 2008 | 9 | JH70 (1) |
| 3503 | 1040 | F | Aug. 11, 2008 | 11 | JH70 (1) |
| 3504 | 960 | F | Aug. 11, 2008 | 10 | JH70 (1) |
| 3513[1] | 4400 | M | Aug. 13, 2008 | 60 | 2A4 (1) |
| 3514[1] | 4400 | M | Aug. 13, 2008 | 40 | 2A4 (1) |
| 3515 | 2800 | M | Aug. 13, 2008 | 13 | 2A4 (1) |
| 3521 | 1480 | M | Aug. 18, 2008 | 11 | 2A4 (1) |
| 3524 | 1680 | M | Aug. 18, 2008 | 9 | 2A4 (1) |
| 3549 | 720 | F | Sep. 6, 2008 | 9 | 2A4 (2) |
| 3550 | 760 | F | Sep. 6, 2008 | 9 | 2A4 (2) |
| 3552[2] | 0 | F | Sep. 6, 2008 | 11 | 2A4 (2) |
| 3553 | 1160 | F | Sep. 6, 2008 | 12 | 2A4 (2) |
| 3558 | 1660 | M | Sep. 6, 2008 | 9 | JH70 (2) |
| 3559 | 3520 | M | Sep. 6, 2008 | 12 | JH70 (2) |
| 3562 | 1312 | F | Sep. 6, 2008 | 11 | JH70 (2) |
| 3563 | 1120 | M | Sep. 6, 2008 | 9 | JH70 (2) |
| 3564 | 2512 | M | Sep. 6, 2008 | 11 | 2A4 (2) |
| 3565 | 1960 | M | Sep. 6, 2008 | 10 | 2A4 (2) |
| 3567 | 1880 | F | Sep. 6, 2008 | 12 | 2A4 (2) |
| 3570 | 792 | F | Sep. 7, 2008 | 13 | 2A4 (2) |
| 3573 | 700 | F | Sep. 7, 2008 | 8 | 2A4 (2) |
| 3577[2] | 0 | F | Sep. 7, 2008 | 10 | 2A4 (2) |
| 3578[2] | 0 | F | Sep. 7, 2008 | 9 | 2A4 (2) |
| 3579 | 1120 | F | Sep. 7, 2008 | 10 | 2A4 (2) |
| 3580[2] | 0 | F | Sep. 7, 2008 | 8 | JH70 (2) |
| 3581 | 700 | F | Sep. 7, 2008 | 9 | JH70 (2) |
| 3582 | 1680 | F | Sep. 7, 2008 | 9 | JH70 (2) |
| 3583 | 804 | F | Sep. 7, 2008 | 9 | JH70 (2) |
| 3584 | 1040 | F | Sep. 7, 2008 | 14 | JH70 (2) |

[1] homozygous IL-6 animals with high sAA levels and amyloid disease early in life.
[2] wild type mice without circulating sAA and no amyloid disease. $^{125}$I-SAP retention in these animals is considered normal and reflecting no amyloid burden.

TABLE 10

Normal Values For Blood Chemistry Parameters In H2/huIL-6 Mice

| | BUN (mg/dL) | | GLU (mg/dL) | | ALT (U/L) | | ALB (g/dL) | | TP (g/dL) | | GLOB (g/dL) | |
|---|---|---|---|---|---|---|---|---|---|---|---|---|
| | F | M | F | M | F | M | F | M | F | M | F | M |
| Mean | 21.1 | 23.8 | 144.7 | 151.2 | 37.6 | 42.3 | 2.5 | 1.9 | 5.6 | 6.2 | 3.1 | 4.4 |
| SD | 4.0 | 2.7 | 14.0 | 17.6 | 16.3 | 24.3 | 0.3 | 0.4 | 0.2 | 0.6 | 0.4 | 0.6 |
| n | 18 | 13 | 18 | 13 | 18 | 13 | 18 | 13 | 18 | 13 | 18 | 13 |
| High | 28.0 | 30.0 | 184.0 | 179.0 | 79.0 | 105.0 | 3.0 | 2.6 | 6.0 | 7.4 | 3.7 | 5.8 |
| Low | 15.0 | 20.0 | 126.0 | 119.0 | 21.0 | 23.0 | 2.0 | 1.2 | 5.1 | 5.5 | 2.6 | 3.4 |
| Median | 20.0 | 24.0 | 143.0 | 154.0 | 32.5 | 32.0 | 2.4 | 1.9 | 5.6 | 6.0 | 3.2 | 4.3 |

BUN, blood urea nitrogen; GLU, glucose; ALT, alanine aminotransferase; ALB, albumin; TP, total serum protein; GLOB, immunoglobulin; F, female; M, male; SD, standard deviation; n is the number of mice used to determine the values.

At the start of the third study (week 0), all of the all the H2/huIL-6 mice received 100 μg iv of amyloid enhancing factor (1 mg/mL). One week thereafter, therapy began and each mouse was administered 100 μg of either mAb 2A4 or JH70 sc as outlined in Table 9. The mAb injections continued weekly for 7 weeks.

At 2 wk post-AEF, CBC, blood chemistry, and serum sAA measurements were made using blood collected via the retro-orbital sinus. At this time also, the mice in group 1 were administered ~60 μCi of $^{125}$I-SAP in BSA as before, to assess the accumulation of amyloid as evidenced by the retention of the radiolabeled SAP. Several of the animals showed an adverse effect of extreme distress, and therefore, evaluation of amyloid burden using $^{125}$I-SAP was discontinued. Results of selected blood chemistry parameters, acquired 2 wk post-AEF are shown in Table 11.

TABLE 11

| | BUN (mg/dL) | | GLU (mg/dL) | | ALT (U/L) | | ALB (g/dL) | | TP (g/dL) | | GLOB (g/dL) | |
|---|---|---|---|---|---|---|---|---|---|---|---|---|
| | F | M | F | M | F | M | F | M | F | M | F | M |
| Mean | 31.4 | 52.1 | 145.1 | 129.8 | 33.9 | 63.3 | 2.3 | 1.8 | 6.5 | 8.1 | 4.2 | 6.2 |
| SD | 24.3 | 39.1 | 16.6 | 25.6 | 6.9 | 30.6 | 0.3 | 0.5 | 1.0 | 1.7 | 1.1 | 1.5 |
| n | 15 | 13 | 15 | 13 | 15 | 13 | 15 | 13 | 15 | 13 | 15 | 12 |
| High | 100.0 | 159.0 | 177.0 | 178.0 | 46.0 | 134.0 | 2.7 | 3.0 | 8.6 | 11.7 | 7.0 | 9.6 |
| Low | 16.0 | 20.0 | 104.0 | 82.0 | 22.0 | 32.0 | 1.7 | 1.0 | 5.2 | 6.0 | 3.1 | 4.5 |
| Median | 22.0 | 31.0 | 150.0 | 120.0 | 32.0 | 54.0 | 2.3 | 1.7 | 6.5 | 7.5 | 4.0 | 6.0 |

BUN, blood urea nitrogen; GLU, glucose; ALT, alanine aminotransferase; ALB, albumin; TP, total serum protein; GLOB, immunoglobulin; F, female; M, male; SD, standard deviation; n is the number of mice used to determine the values.

At 8 weeks post-AEF, the mice were bled a final time and immediately thereafter were administered ~200 μCi of $^{125}$I-SAP using 5% normal mouse serum as carrier. In response to this treatment, a few animals showed some unusual behavior that abated within 30 min. Twenty four hours later, the mice were injected with x-ray CT contrast agent (~200 μL iv in the tail vein) and were then sacrificed by isoflurane overdose. Single photon emission (SPECT) and x-ray (CT) tomographic images of each animal were acquired. The organs were harvested and the amount of radioactivity in each sample was calculated and expressed as % injected dose per gram of tissue. Additionally, a portion of each tissue was fixed overnight in buffered formalin in preparation for sectioning and microscopic analysis.

TABLE 12

Percentage of animals surviving

| Days post injection | TY11-treated | 2A4-treated |
|---|---|---|
| 0 | 100.00 | 100.00 |
| 41 | | 100.00 |
| 42 | | 100.00 |
| 53 | 85.71 | 100.00 |
| 55 | 71.43 | 100.00 |
| 56 | 64.29 | 100.00 |
| 57 | 64.29 | 100.00 |

Approximately 65% of the mAb JH70-treated mice that were assessable survived to the end of the study. In contrast, none of the 2A4 mice that were assessable died during the 57 days. Analysis of the survival data using the standard methods demonstrated a significant difference in the survival curves (P=0.015 using Mantel-Cox test and P=0.016 using Grehan-Breslow-Wilcoxon test).

The final blood chemistry data were analyzed according to the therapy that each mouse received. Because of differences in the mean parameter values associated with male and female H2/huIL-6 mice (at the time of sacrifice, BUN levels in female mice were higher for both 2A4-treated and JH70-treated mice), only the female mice that survived are included in Table 13 below.

TABLE 13

| | BUN (mg/dL) | | GLU (mg/dL) | | ALT (U/L) | | ALB (g/dL) | | TP (g/dL) | | GLOB (g/dL) | |
|---|---|---|---|---|---|---|---|---|---|---|---|---|
| | 2A4 | JH70 | 2A4 | JH70 | 2A4 | JH70 | 2A4 | JH70 | 2A4 | JH70 | 2A4 | JH70 |
| Mean | 60.7 | 73.3 | 107.8 | 100.1 | 45.5 | 119.7 | 2.3 | 2.2 | 9.2 | 9.1 | 7.0 | 7.1 |
| SD | 27.2 | 25.7 | 27.0 | 13.3 | 6.2 | 123.1 | 0.5 | 0.6 | 1.5 | 1.5 | 2.0 | 2.1 |
| n | 6.0 | 7.0 | 6.0 | 7.0 | 6.0 | 7.0 | 6.0 | 7.0 | 6.0 | 7.0 | 6.0 | 7.0 |
| High | 95.0 | 120.0 | 160.0 | 123.0 | 52.0 | 381.0 | 2.9 | 3.0 | 11.7 | 11.9 | 10.1 | 10.6 |
| Low | 17.0 | 36.0 | 83.0 | 83.0 | 35.0 | 33.0 | 1.5 | 1.2 | 7.2 | 7.5 | 4.3 | 5.3 |
| Median | 66.5 | 70.0 | 99.5 | 98.0 | 46.5 | 65.0 | 2.2 | 2.1 | 9.1 | 8.9 | 7.1 | 6.2 |

BUN, blood urea nitrogen; GLU, glucose; ALT, alanine aminotransferase; ALB, albumin; TP, total serum protein; GLOB, immunoglobulin; F, female; M, male; SD, standard deviation; n is the number of mice used to determine the values.

During the 7 wk therapy study, 2 mice were found dead and 3 mice were sacrificed because they were deemed unlikely to survive overnight and had a poor body condition score (<2; associated with >15% weight loss). Mice that experienced an adverse reaction to $^{125}$I-SAP injection and 1 mouse that was sacrificed due to complications that arose from a retro-orbital bleed were not evaluated as part of the survival analysis. The survival of the mice in each mAb treatment group is shown in Table 12.

Mice treated with 2A4 showed decreased serum blood urea nitrogen (BUN) and alanine aminotransferase (ALT) levels when compared to mice treated with JH70. BUN and ALT are markers of renal and hepatic function, respectively, and their reduced levels indicate that organ function may have been better preserved by 2A4 treatment.

What is claimed is:

1. A method of detecting an amyloid deposit in a subject comprising:
   (a) administering to the subject an antibody or antigen-binding fragment, which antibody or antigen-binding fragment comprises a light chain variable region comprising three complementarity determining regions set forth as SEQ ID NOs: 177, 169, and 170, and a heavy chain variable region comprising three complementarity determining regions set forth as SEQ ID NOs: 171, 172, and 173, and which antibody or antigen-binding fragment is bound to a detectable label; and
   (b) detecting the detectable label in the subject.

2. The method of claim 1, wherein the amyloid deposit is characterized by the presence of amyloid A protein fibrils.

3. The method of claim 2, wherein the subject suffers from or is susceptible to amyloid A amyloidosis associated with rheumatoid arthritis, juvenile chronic arthritis, ankylosing spondylitis, psoriasis, psoriatic arthropathy, Reiter's syndrome, Adult Still's disease, Bechet's syndrome, Crohn's disease, leprosy, tuberculosis, bronchiectasis, decubitus ulcers, chronic pyelonephritis, osteomyelitis, Whipple's disease, Hodgkin's lymphoma, renal carcinoma, carcinomas of gut, lung and urogenital tract, basal cell carcinoma, hairy cell leukemia, Familial Mediterranean Fever, or Castleman's Disease.

4. The method of claim 1, wherein the amyloid deposit is characterized by the presence of amyloid light chain-type (AL) protein fibrils.

5. The method of claim 4, wherein the subject suffers from or is susceptible to amyloid AL amyloidosis associated with peripheral or autonomic neuropathy, carpal tunnel syndrome, macroglossia, restrictive cardiomyopathy, arthropathy of large joints, immune dyscrasia, myeloma, monoclonal gammopathy, occult dyscrasia, or a chronic inflammatory disease.

6. The method of claim 5, wherein the AL amyloidosis is associated with a dyscrasia of the B lymphocyte lineage.

7. The method of claim 6, wherein the dyscrasia is a malignancy.

8. The method of claim 7, wherein the malignancy is multiple myeloma.

9. The method of claim 1, wherein the subject is a human.

10. The method of claim 1, wherein the antibody or fragment is a chimeric antibody, a human antibody, a humanized antibody, a single chain antibody, a tetrameric antibody, a tetravalent antibody, a multispecific antibody, a domain-specific antibody, a domain-deleted antibody, a fusion protein, a Fab fragment, a Fab' fragment, a F(ab')$_2$ fragment, a Fv fragment, or a ScFv fragment.

11. The method of claim 10, wherein the antibody or fragment is a chimeric or humanized antibody or fragment thereof.

12. The method of claim 11, wherein the isotype of the chimeric or humanized antibody is human IgG1.

13. The method of claim 11, wherein the antibody is a chimeric or humanized version of murine monoclonal antibody 7D8 (ATCC Accession Number PTA-9468).

14. The method of claim 13, wherein the antibody comprises a light chain variable region set forth as any one of SEQ ID NOs: 158, 159, 160, 174, 175, and 176, and a heavy chain variable region set forth as any one of SEQ ID NOs: 161, 162, and 163.

15. The method of claim 1, wherein the antibody or antigen-binding fragment comprises a light chain variable region comprising an amino acid sequence set forth as residues 20-131 of SEQ ID NO: 153 and a heavy chain variable region comprising an amino acid sequence set forth as residues 20-138 of SEQ ID NO: 154.

16. The method of claim 1, wherein the antibody is murine monoclonal antibody 7D8 (ATCC Accession Number PTA-9468).

17. The method of claim 1, wherein the antibody or antigen-binding fragment binds to monomeric amyloid protein with an affinity of less than about $10^7$ M$^{-1}$.

18. The method of claim 1, wherein the detectable label is a radiolabel.

19. The method of claim 18, wherein the radiolabel is $^{125}$I.

20. The method of claim 1, wherein the detecting is performed by SPECT/CT imaging.

21. The method of claim 1, wherein the detecting is performed by NMR spectroscopy.

* * * * *

SEQUENCE LISTING

<160> NUMBER OF SEQ ID NOS: 177

<210> SEQ ID NO 1
<211> LENGTH: 122
<212> TYPE: PRT
<213> ORGANISM: Homo sapiens

<400> SEQUENCE: 1

```
Met Lys Leu Leu Thr Gly Leu Val Phe Cys Ser Leu Val Leu Gly Val
1               5                   10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
    50                  55                  60

Arg Gly Pro Gly Gly Ala Trp Ala Ala Glu Val Ile Ser Asp Ala Arg
65                  70                  75                  80

Glu Asn Ile Gln Arg Phe Phe Gly His Gly Ala Glu Asp Ser Leu Ala
                85                  90                  95

Asp Gln Ala Ala Asn Glu Trp Gly Arg Ser Gly Lys Asp Pro Asn His
            100                 105                 110

Phe Arg Pro Ala Gly Leu Pro Glu Lys Tyr
        115                 120
```

<210> SEQ ID NO 2
<211> LENGTH: 76
<212> TYPE: PRT
<213> ORGANISM: Homo sapiens
<220> FEATURE:
<221> NAME/KEY: MISC_FEATURE
<223> OTHER INFORMATION: Human amyloid protein A peptide

<400> SEQUENCE: 2

```
Arg Ser Phe Phe Ser Phe Leu Gly Glu Ala Phe Asp Gly Ala Arg Asp
1               5                   10                  15

Met Tyr Arg Ala Tyr Ser Asp Met Arg Glu Ala Asn Tyr Ile Gly Ser
            20                  25                  30

Asp Lys Tyr Phe His Ala Arg Gly Asn Tyr Asp Ala Ala Lys Arg Gly
        35                  40                  45

Pro Gly Gly Ala Tyr Ala Ala Glu Val Ile Ser Asp Ala Arg Glu Asn
    50                  55                  60

Ile Gln Arg Phe Phe Gly His Gly Ala Glu Asp Ser
65                  70                  75
```

<210> SEQ ID NO 3
<211> LENGTH: 5
<212> TYPE: PRT
<213> ORGANISM: Artificial Sequence
<220> FEATURE:
<223> OTHER INFORMATION: Derived from amyloidosis peptide

<400> SEQUENCE: 3

```
Gly His Glu Asp Thr
1               5
```

<210> SEQ ID NO 4
<211> LENGTH: 7
<212> TYPE: PRT
<213> ORGANISM: Artificial Sequence

```
<220> FEATURE:
<223> OTHER INFORMATION: Derived from amyloid A protein

<400> SEQUENCE: 4

Gly His Gly Ala Glu Asp Ser
1               5

<210> SEQ ID NO 5
<211> LENGTH: 7
<212> TYPE: PRT
<213> ORGANISM: Artificial Sequence
<220> FEATURE:
<223> OTHER INFORMATION: Derived from amyloid A protein

<400> SEQUENCE: 5

Gly His Asp Ala Glu Asp Ser
1               5

<210> SEQ ID NO 6
<211> LENGTH: 7
<212> TYPE: PRT
<213> ORGANISM: Artificial Sequence
<220> FEATURE:
<223> OTHER INFORMATION: Derived from amyloid protein

<400> SEQUENCE: 6

Gly His Gly Ala Glu Asp Ser
1               5

<210> SEQ ID NO 7
<211> LENGTH: 7
<212> TYPE: PRT
<213> ORGANISM: Artificial Sequence
<220> FEATURE:
<223> OTHER INFORMATION: Derived from amyloid A protein

<400> SEQUENCE: 7

Gly Asp His Ala Glu Asp Ser
1               5

<210> SEQ ID NO 8
<211> LENGTH: 7
<212> TYPE: PRT
<213> ORGANISM: Artificial Sequence
<220> FEATURE:
<223> OTHER INFORMATION: Derived from amyloid A protein

<400> SEQUENCE: 8

Ser Thr Val Ile Glu Asp Ser
1               5

<210> SEQ ID NO 9
<211> LENGTH: 7
<212> TYPE: PRT
<213> ORGANISM: Artificial Sequence
<220> FEATURE:
<223> OTHER INFORMATION: Derived from amyloid A protein

<400> SEQUENCE: 9

Gly Arg Gly His Glu Asp Thr
1               5

<210> SEQ ID NO 10
<211> LENGTH: 7
<212> TYPE: PRT
<213> ORGANISM: Artificial Sequence
<220> FEATURE:
<223> OTHER INFORMATION: Derived from amyloid A protein
```

-continued

```
<400> SEQUENCE: 10

Gly His Gly Ala Glu Asp Ser
1               5

<210> SEQ ID NO 11
<211> LENGTH: 7
<212> TYPE: PRT
<213> ORGANISM: Artificial Sequence
<220> FEATURE:
<223> OTHER INFORMATION: Derived from amyloid A protein

<400> SEQUENCE: 11

Asn His Gly Leu Glu Thr Leu
1               5

<210> SEQ ID NO 12
<211> LENGTH: 4
<212> TYPE: PRT
<213> ORGANISM: Artificial Sequence
<220> FEATURE:
<223> OTHER INFORMATION: Derived from amyloidosis peptide

<400> SEQUENCE: 12

His Glu Asp Thr
1

<210> SEQ ID NO 13
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 13

Ala Glu Asp Ser
1

<210> SEQ ID NO 14
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 14

Ala Glu Asp Thr
1

<210> SEQ ID NO 15
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 15

His Glu Asp Ala
1

<210> SEQ ID NO 16
<211> LENGTH: 4
<212> TYPE: PRT
<213> ORGANISM: Artificial Sequence
<220> FEATURE:
```

```
<223> OTHER INFORMATION: AL V lambda fragment from amyloid protein

<400> SEQUENCE: 16

Thr Glu Asp Glu
1

<210> SEQ ID NO 17
<211> LENGTH: 4
<212> TYPE: PRT
<213> ORGANISM: Artificial Sequence
<220> FEATURE:
<223> OTHER INFORMATION: AL V lambda fragment from amyloid protein

<400> SEQUENCE: 17

Phe Glu Asp Asp
1

<210> SEQ ID NO 18
<211> LENGTH: 4
<212> TYPE: PRT
<213> ORGANISM: Artificial Sequence
<220> FEATURE:
<223> OTHER INFORMATION: AL V lambda fragment from amyloid protein
<220> FEATURE:
<221> NAME/KEY: MISC_FEATURE
<223> OTHER INFORMATION: Consensus sequence derived from human
      amyloidogenic proteins

<400> SEQUENCE: 18

Ser Glu Asp Glu
1

<210> SEQ ID NO 19
<211> LENGTH: 4
<212> TYPE: PRT
<213> ORGANISM: Artificial Sequence
<220> FEATURE:
<223> OTHER INFORMATION: AL V lambda fragment from amyloid protein
<220> FEATURE:
<221> NAME/KEY: MISC_FEATURE
<223> OTHER INFORMATION: Consensus sequence derived from human
      amyloidogenic proteins

<400> SEQUENCE: 19

Ala Glu Asp Glu
1

<210> SEQ ID NO 20
<211> LENGTH: 4
<212> TYPE: PRT
<213> ORGANISM: Artificial Sequence
<220> FEATURE:
<223> OTHER INFORMATION: AL V lambda fragment from amyloid protein

<400> SEQUENCE: 20

Pro Glu Asp Glu
1

<210> SEQ ID NO 21
<211> LENGTH: 4
<212> TYPE: PRT
<213> ORGANISM: Artificial Sequence
<220> FEATURE:
<223> OTHER INFORMATION: AL V kappa fragment from amyloid protein
<220> FEATURE:
<221> NAME/KEY: MISC_FEATURE
<223> OTHER INFORMATION: Consensue sequence derived from human
      amyloidogenic proteins
<220> FEATURE:
<221> NAME/KEY: MISC_FEATURE
```

```
<223> OTHER INFORMATION: Consensus sequence derived from human
      amyloidogenic proteins

<400> SEQUENCE: 21

Pro Glu Asp Ile
1

<210> SEQ ID NO 22
<211> LENGTH: 4
<212> TYPE: PRT
<213> ORGANISM: Artificial Sequence
<220> FEATURE:
<223> OTHER INFORMATION: AL V kappa fragment from amyloid protein
<220> FEATURE:
<221> NAME/KEY: MISC_FEATURE
<223> OTHER INFORMATION: Consensus sequence derived from human
      amyloidogenic proteins

<400> SEQUENCE: 22

Pro Glu Asp Phe
1

<210> SEQ ID NO 23
<211> LENGTH: 4
<212> TYPE: PRT
<213> ORGANISM: Artificial Sequence
<220> FEATURE:
<223> OTHER INFORMATION: AL V kappa fragment from amyloid protein
<220> FEATURE:
<221> NAME/KEY: MISC_FEATURE
<223> OTHER INFORMATION: Consensus sequence derived from human
      amyloidogenic proteins

<400> SEQUENCE: 23

Ala Glu Asp Val
1

<210> SEQ ID NO 24
<211> LENGTH: 4
<212> TYPE: PRT
<213> ORGANISM: Artificial Sequence
<220> FEATURE:
<223> OTHER INFORMATION: AL V kappa fragment from amyloid protein
<220> FEATURE:
<221> NAME/KEY: MISC_FEATURE
<223> OTHER INFORMATION: Consensus sequence derived from human
      amyloidogenic proteins

<400> SEQUENCE: 24

Ser Glu Asp Phe
1

<210> SEQ ID NO 25
<211> LENGTH: 4
<212> TYPE: PRT
<213> ORGANISM: Artificial Sequence
<220> FEATURE:
<223> OTHER INFORMATION: AL V kappa fragment from amyloid protein

<400> SEQUENCE: 25

Ser Glu Asp Ala
1

<210> SEQ ID NO 26
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins
```

```
<400> SEQUENCE: 26

Pro Glu Asp Ser
1

<210> SEQ ID NO 27
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 27

Pro Glu Asp Leu
1

<210> SEQ ID NO 28
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 28

Thr Glu Asp Val
1

<210> SEQ ID NO 29
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 29

Ser Glu Asp Ile
1

<210> SEQ ID NO 30
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 30

Thr Glu Asp Thr
1

<210> SEQ ID NO 31
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 31

Leu Glu Asp Gly
1

<210> SEQ ID NO 32
<211> LENGTH: 4
<212> TYPE: PRT
```

```
<213> ORGANISM: Artificial Sequence
<220> FEATURE:
<223> OTHER INFORMATION: Consensus sequence derived from human
      amyloidogenic proteins

<400> SEQUENCE: 32

Ala Glu Asp Met
1

<210> SEQ ID NO 33
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 33

His Glu Asp Ser
1

<210> SEQ ID NO 34
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 34

Cys Glu Asp Asp
1

<210> SEQ ID NO 35
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 35

Gln Glu Asp Ser
1

<210> SEQ ID NO 36
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 36

Arg Glu Asp Ser
1

<210> SEQ ID NO 37
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 37

Thr Glu Asp Gly
1
```

```
<210> SEQ ID NO 38
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 38

Gln Glu Asp Arg
1

<210> SEQ ID NO 39
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 39

Thr Glu Asp Leu
1

<210> SEQ ID NO 40
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 40

Pro Glu Asp Asn
1

<210> SEQ ID NO 41
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 41

Glu Glu Asp Pro
1

<210> SEQ ID NO 42
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 42

Leu Glu Asp Leu
1

<210> SEQ ID NO 43
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 43
```

Lys Glu Asp Ala
1

<210> SEQ ID NO 44
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 44

Ser Glu Asp Cys
1

<210> SEQ ID NO 45
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 45

Glu Glu Asp Asp
1

<210> SEQ ID NO 46
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 46

Ser Glu Asp Lys
1

<210> SEQ ID NO 47
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 47

Asp Glu Asp Asp
1

<210> SEQ ID NO 48
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 48

Asp Glu Asp Gly
1

<210> SEQ ID NO 49
<211> LENGTH: 4
<212> TYPE: PRT
<213> ORGANISM: Artificial Sequence
<220> FEATURE:

```
<223> OTHER INFORMATION: Consensus sequence derived from human
      amyloidogenic proteins

<400> SEQUENCE: 49

Leu Glu Asp Glu
1

<210> SEQ ID NO 50
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 50

Gly Glu Asp Ala
1

<210> SEQ ID NO 51
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 51

Val Glu Asp Phe
1

<210> SEQ ID NO 52
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 52

Tyr Glu Asp Glu
1

<210> SEQ ID NO 53
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 53

Ile Glu Asp Leu
1

<210> SEQ ID NO 54
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 54

Trp Glu Asp Tyr
1

<210> SEQ ID NO 55
```

```
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 55

Asp Glu Asp Trp
1

<210> SEQ ID NO 56
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 56

Ser Glu Asp Leu
1

<210> SEQ ID NO 57
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 57

Tyr Glu Asp Gln
1

<210> SEQ ID NO 58
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 58

Leu Glu Asp Trp
1

<210> SEQ ID NO 59
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 59

Tyr Glu Asp Arg
1

<210> SEQ ID NO 60
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 60

Pro Glu Asp Lys
```

```
<210> SEQ ID NO 61
<211> LENGTH: 10
<212> TYPE: PRT
<213> ORGANISM: Artificial Sequence
<220> FEATURE:
<223> OTHER INFORMATION: Non-amyloid portion of serum amyloid A protein

<400> SEQUENCE: 61

Gly His Glu Asp Thr Met Ala Asp Gln Glu
1               5                   10

<210> SEQ ID NO 62
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 62

Ala Glu Asp Ala
1

<210> SEQ ID NO 63
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 63

Gln Glu Asp Leu
1

<210> SEQ ID NO 64
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 64

Val Glu Asp Leu
1

<210> SEQ ID NO 65
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins

<400> SEQUENCE: 65

Leu Glu Asp Ala
1

<210> SEQ ID NO 66
<211> LENGTH: 4
<212> TYPE: PRT
<213> ORGANISM: Artificial Sequence
<220> FEATURE:
<223> OTHER INFORMATION: Consensus sequence derived from human
      amyloidogenic proteins
```

```
<400> SEQUENCE: 66

Ser Glu Asp Gly
1

<210> SEQ ID NO 67
<211> LENGTH: 16
<212> TYPE: PRT
<213> ORGANISM: Artificial Sequence
<220> FEATURE:
<223> OTHER INFORMATION: Derived from Malaria CS
<220> FEATURE:
<221> NAME/KEY: MISC_FEATURE
<223> OTHER INFORMATION: T3 epitope

<400> SEQUENCE: 67

Glu Lys Lys Ile Ala Lys Met Glu Lys Ala Ser Ser Val Phe Asn Val
1               5                   10                  15

<210> SEQ ID NO 68
<211> LENGTH: 10
<212> TYPE: PRT
<213> ORGANISM: Artificial Sequence
<220> FEATURE:
<223> OTHER INFORMATION: Derived from Hepititis B surface antigen
      residues 19-28

<400> SEQUENCE: 68

Phe Phe Leu Leu Thr Arg Ile Leu Thr Ile
1               5                   10

<210> SEQ ID NO 69
<211> LENGTH: 19
<212> TYPE: PRT
<213> ORGANISM: Artificial Sequence
<220> FEATURE:
<223> OTHER INFORMATION: Derived from mycobacterium heat shock protein
      65 residues 153-171

<400> SEQUENCE: 69

Asp Gln Ser Ile Gly Asp Leu Ile Ala Glu Ala Met Asp Lys Val Gly
1               5                   10                  15

Asn Glu Gly

<210> SEQ ID NO 70
<211> LENGTH: 14
<212> TYPE: PRT
<213> ORGANISM: Mycobacterium bovis
<220> FEATURE:
<221> NAME/KEY: MISC_FEATURE
<223> OTHER INFORMATION: Derived from Bacille Calmette-Guerin vaccine

<400> SEQUENCE: 70

Gln Val His Phe Gln Pro Leu Pro Pro Ala Val Val Lys Leu
1               5                   10

<210> SEQ ID NO 71
<211> LENGTH: 15
<212> TYPE: PRT
<213> ORGANISM: Artificial Sequence
<220> FEATURE:
<223> OTHER INFORMATION: Derived from Tetanus toxoid residues 830-844

<400> SEQUENCE: 71

Gln Tyr Ile Lys Ala Asn Ser Lys Phe Ile Gly Ile Thr Glu Leu
1               5                   10                  15

<210> SEQ ID NO 72
```

```
<211> LENGTH: 21
<212> TYPE: PRT
<213> ORGANISM: Artificial Sequence
<220> FEATURE:
<223> OTHER INFORMATION: Derived from Tetanus toxoid residues 947-967

<400> SEQUENCE: 72

Phe Asn Asn Phe Thr Val Ser Phe Trp Leu Arg Val Pro Lys Val Ser
1               5                   10                  15

Ala Ser His Leu Glu
            20

<210> SEQ ID NO 73
<211> LENGTH: 16
<212> TYPE: PRT
<213> ORGANISM: Human immunodeficiency virus
<220> FEATURE:
<221> NAME/KEY: MISC_FEATURE
<223> OTHER INFORMATION: HIV gb120 T1

<400> SEQUENCE: 73

Lys Gln Ile Ile Asn Met Trp Gln Glu Val Gly Lys Ala Met Tyr Ala
1               5                   10                  15

<210> SEQ ID NO 74
<211> LENGTH: 13
<212> TYPE: PRT
<213> ORGANISM: Artificial Sequence
<220> FEATURE:
<223> OTHER INFORMATION: Pan DR epitope
<220> FEATURE:
<221> NAME/KEY: MISC_FEATURE
<222> LOCATION: (3)..(3)
<223> OTHER INFORMATION: Xaa can be any naturally occurring amino acid

<400> SEQUENCE: 74

Ala Lys Xaa Val Ala Ala Trp Thr Leu Lys Ala Ala Ala
1               5                   10

<210> SEQ ID NO 75
<211> LENGTH: 36
<212> TYPE: PRT
<213> ORGANISM: Artificial Sequence
<220> FEATURE:
<223> OTHER INFORMATION: Fusion protein derived from Tetanus toxoid
      residues 830-844 and 947-967

<400> SEQUENCE: 75

Gln Tyr Ile Lys Ala Asn Ser Lys Phe Ile Gly Ile Thr Glu Leu Phe
1               5                   10                  15

Asn Asn Phe Thr Val Ser Phe Trp Leu Arg Val Pro Lys Val Ser Ala
            20                  25                  30

Ser His Leu Glu
        35

<210> SEQ ID NO 76
<211> LENGTH: 17
<212> TYPE: PRT
<213> ORGANISM: Artificial Sequence
<220> FEATURE:
<223> OTHER INFORMATION: Derived from ovalbumin residues 323-389

<400> SEQUENCE: 76

Ile Ser Gln Ala Val His Ala Ala His Ala Glu Ile Asn Glu Ala Gly
1               5                   10                  15

Arg
```

<210> SEQ ID NO 77
<211> LENGTH: 13
<212> TYPE: PRT
<213> ORGANISM: Artificial
<220> FEATURE:
<223> OTHER INFORMATION: Derived from hemagglutinin influenza A virus

<400> SEQUENCE: 77

Pro Lys Tyr Val Lys Gln Asn Thr Leu Lys Leu Ala Thr
1               5

-continued

```
<400> SEQUENCE: 81

Gln Gly Trp Leu Thr Phe Leu Lys Ala Ala Gly Gln Gly Ala Lys
1               5                   10                  15

<210> SEQ ID NO 82
<211> LENGTH: 10
<212> TYPE: PRT
<213> ORGANISM: Artificial Sequence
<220> FEATURE:
<223> OTHER INFORMATION: Derived from mouse amyloid A protein

<400> SEQUENCE: 82

Glu Ser Trp Arg Ser Phe Phe Lys Glu Ala
1               5                   10

<210> SEQ ID NO 83
<211> LENGTH: 15
<212> TYPE: PRT
<213> ORGANISM: Artificial Sequence
<220> FEATURE:
<223> OTHER INFORMATION: Derived from mouse amyloid A protein

<400> SEQUENCE: 83

Gly Phe Phe Ser Phe Val His Glu Ala Phe Gln Gly Ala Gly Asp
1               5                   10                  15

<210> SEQ ID NO 84
<211> LENGTH: 8
<212> TYPE: PRT
<213> ORGANISM: Artificial Sequence
<220> FEATURE:
<223> OTHER INFORMATION: Derived from mouse amyloid A protein

<400> SEQUENCE: 84

Glu Ala Gly Gln Gly Ser Arg Asp
1               5

<210> SEQ ID NO 85
<211> LENGTH: 14
<212> TYPE: PRT
<213> ORGANISM: Artificial Sequence
<220> FEATURE:
<223> OTHER INFORMATION: Derived from mouse amyloid A protein

<400> SEQUENCE: 85

Trp Tyr Ser Phe Phe Arg Glu Ala Val Gln Gly Thr Trp Asp
1               5                   10

<210> SEQ ID NO 86
<211> LENGTH: 99
<212> TYPE: PRT
<213> ORGANISM: Homo Sapiens
<220> FEATURE:
<221> NAME/KEY: MISC_FEATURE
<223> OTHER INFORMATION: Lambda 2 fragments from human amyloid deposits

<400> SEQUENCE: 86

Gly Ser Val Val Thr Gln Pro Pro Ser Val Ser Gly Ala Pro Arg Gln
1               5                   10                  15

Thr Val Ala Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Val Leu
        35                  40                  45

Ile Tyr Tyr Asp Asp Leu Leu Pro Ala Gly Val Ser Asp Arg Phe Ser
    50                  55                  60
```

Gly Ser Lys Ser Gly Thr Ser Ala Ser Leu Ala Ile Arg Gly Leu Gln
65                  70                  75                  80

Ser Glu Asp Glu Gly Asp Tyr Tyr Cys Ala Ala Trp Asp Asp Ser Leu
                85                  90                  95

Ser Ala Leu

<210> SEQ ID NO 87
<211> LENGTH: 7
<212> TYPE: PRT
<213> ORGANISM: Artificial Sequence
<220> FEATURE:
<223> OTHER INFORMATION: Derived from serum amyloid A protein

<400> SEQUENCE: 87

Cys Gly Gly His Glu Asp Thr
1               5

<210> SEQ ID NO 88
<211> LENGTH: 7
<212> TYPE: PRT
<213> ORGANISM: Artificial Sequence
<220> FEATURE:
<223> OTHER INFORMATION: Derived from serum amyloid A protein

<400> SEQUENCE: 88

Cys Gly Gly Ala Glu Asp Ser
1               5

<210> SEQ ID NO 89
<211> LENGTH: 10
<212> TYPE: PRT
<213> ORGANISM: Artificial Sequence
<220> FEATURE:
<223> OTHER INFORMATION: Derived from serum amyloid A protein

<400> SEQUENCE: 89

Gly His Glu Asp Thr Ile Ala Asp Gln Glu
1               5                   10

<210> SEQ ID NO 90
<211> LENGTH: 7
<212> TYPE: PRT
<213> ORGANISM: Artificial Sequence
<220> FEATURE:
<223> OTHER INFORMATION: Derived from serum amyloid A protein

<400> SEQUENCE: 90

Cys Gly Gly Ala Glu Asp Thr
1               5

<210> SEQ ID NO 91
<211> LENGTH: 7
<212> TYPE: PRT
<213> ORGANISM: Artificial Sequence
<220> FEATURE:
<223> OTHER INFORMATION: Derived from serum amyloid A protein

<400> SEQUENCE: 91

Cys Gly Gly His Ala Asp Thr
1               5

<210> SEQ ID NO 92
<211> LENGTH: 7
<212> TYPE: PRT
<213> ORGANISM: Artificial Sequence
<220> FEATURE:
<223> OTHER INFORMATION: Derived from serum amyloid A protein

```
<400> SEQUENCE: 92

Cys Gly Gly His Glu Ala Thr
1               5

<210> SEQ ID NO 93
<211> LENGTH: 7
<212> TYPE: PRT
<213> ORGANISM: Artificial Sequence
<220> FEATURE:
<223> OTHER INFORMATION: Derived from serum amyloid A protein

<400> SEQUENCE: 93

Cys Gly Gly His Glu Asp Ala
1               5

<210> SEQ ID NO 94
<211> LENGTH: 8
<212> TYPE: PRT
<213> ORGANISM: Artificial Sequence
<220> FEATURE:
<223> OTHER INFORMATION: Derived from serum amyloid A protein

<400> SEQUENCE: 94

Cys Gly Gly His Glu Asp Thr Met
1               5

<210> SEQ ID NO 95
<211> LENGTH: 9
<212> TYPE: PRT
<213> ORGANISM: Artificial Sequence
<220> FEATURE:
<223> OTHER INFORMATION: Derived from serum amyloid A protein

<400> SEQUENCE: 95

Cys Gly Gly His Glu Asp Thr Met Ala
1               5

<210> SEQ ID NO 96
<211> LENGTH: 10
<212> TYPE: PRT
<213> ORGANISM: Artificial Sequence
<220> FEATURE:
<223> OTHER INFORMATION: Derived from serum amyloid A protein

<400> SEQUENCE: 96

Cys Gly Gly His Glu Asp Thr Met Ala Asp
1               5                   10

<210> SEQ ID NO 97
<211> LENGTH: 6
<212> TYPE: PRT
<213> ORGANISM: Artificial Sequence
<220> FEATURE:
<223> OTHER INFORMATION: Derived from serum amyloid A protein

<400> SEQUENCE: 97

Cys Gly Gly His Glu Asp
1               5

<210> SEQ ID NO 98
<211> LENGTH: 122
<212> TYPE: PRT
<213> ORGANISM: Homo sapiens
<220> FEATURE:
<221> NAME/KEY: MISC_FEATURE
<223> OTHER INFORMATION: HSAA1
```

-continued

```
<400> SEQUENCE: 98

Met Lys Leu Leu Thr Gly Leu Val Phe Cys Ser Leu Val Leu Gly Val
1               5                   10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
    50                  55                  60

Arg Gly Pro Gly Gly Val Trp Ala Ala Glu Ala Ile Ser Asp Ala Arg
65                  70                  75                  80

Glu Asn Ile Gln Arg Phe Phe Gly His Gly Ala Glu Asp Ser Leu Ala
                85                  90                  95

Asp Gln Ala Ala Asn Glu Trp Gly Arg Ser Gly Lys Asp Pro Asn His
            100                 105                 110

Phe Arg Pro Ala Gly Leu Pro Glu Lys Tyr
        115                 120

<210> SEQ ID NO 99
<211> LENGTH: 122
<212> TYPE: PRT
<213> ORGANISM: Homo sapiens
<220> FEATURE:
<221> NAME/KEY: MISC_FEATURE
<223> OTHER INFORMATION: HSAA2

<400> SEQUENCE: 99

Met Lys Leu Leu Thr Gly Leu Val Phe Cys Ser Leu Val Leu Ser Val
1               5                   10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
    50                  55                  60

Arg Gly Pro Gly Gly Ala Trp Ala Ala Glu Val Ile Ser Asn Ala Arg
65                  70                  75                  80

Glu Asn Ile Gln Arg Leu Thr Gly His Gly Ala Glu Asp Ser Leu Ala
                85                  90                  95

Asp Gln Ala Ala Asn Lys Trp Gly Arg Ser Gly Arg Asp Pro Asn His
            100                 105                 110

Phe Arg Pro Ala Gly Leu Pro Glu Lys Tyr
        115                 120

<210> SEQ ID NO 100
<211> LENGTH: 122
<212> TYPE: PRT
<213> ORGANISM: Homo sapiens
<220> FEATURE:
<221> NAME/KEY: MISC_FEATURE
<223> OTHER INFORMATION: HSAA3

<400> SEQUENCE: 100

Met Lys Leu Ser Thr Gly Ile Ile Phe Cys Ser Leu Val Leu Gly Val
1               5                   10                  15

Ser Ser Gln Gly Trp Leu Thr Phe Leu Lys Ala Ala Gly Gln Gly Ala
            20                  25                  30

Lys Asp Met Trp Arg Ala Tyr Ser Asp Met Lys Glu Ala Asn Tyr Lys
        35                  40                  45
```

Lys Ser Asp Lys Tyr Phe His Ala Arg Gly Asn Tyr Asp Ala Val Gln
    50                  55                  60

Arg Gly Pro Gly Gly Val Trp Ala Thr Glu Val Ile Ser Asp Ala Arg
65                  70                  75                  80

Glu Asn Val Gln Arg Leu Thr Gly Asp His Ala Glu Ser Leu Ala
                85                  90                  95

Gly Gln Ala Thr Asn Lys Trp Gly Gln Ser Gly Lys Ser Pro Asn His
                100                 105                 110

Phe Arg Pro Ala Gly Leu Pro Glu Lys Tyr
            115                 120

<210> SEQ ID NO 101
<211> LENGTH: 130
<212> TYPE: PRT
<213> ORGANISM: Homo sapiens
<220> FEATURE:
<221> NAME/KEY: MISC_FEATURE
<223> OTHER INFORMATION: HSAA4

<400> SEQUENCE: 101

Met Arg Leu Phe Thr Gly Ile Val Phe Cys Ser Leu Val Met Gly Val
1               5                   10                  15

Thr Ser Glu Ser Trp Arg Ser Phe Phe Lys Glu Ala Leu Gln Gly Val
                20                  25                  30

Gly Asp Met Gly Arg Ala Tyr Trp Asp Ile Met Ile Ser Asn His Gln
            35                  40                  45

Asn Ser Asn Arg Tyr Leu Tyr Ala Arg Gly Asn Tyr Asp Ala Ala Gln
    50                  55                  60

Arg Gly Pro Gly Gly Val Trp Ala Ala Lys Leu Ile Ser Arg Ser Arg
65                  70                  75                  80

Val Tyr Leu Gln Gly Leu Ile Asp Tyr Tyr Leu Phe Gly Asn Ser Ser
                85                  90                  95

Thr Val Leu Glu Asp Ser Lys Ser Asn Glu Lys Ala Glu Glu Trp Gly
            100                 105                 110

Arg Ser Gly Lys Asp Pro Asp Arg Phe Arg Pro Asp Gly Leu Pro Lys
        115                 120                 125

Lys Tyr
    130

<210> SEQ ID NO 102
<211> LENGTH: 76
<212> TYPE: PRT
<213> ORGANISM: Homo sapiens
<220> FEATURE:
<221> NAME/KEY: MISC_FEATURE
<223> OTHER INFORMATION: HAA1

<400> SEQUENCE: 102

Arg Ser Phe Phe Ser Phe Leu Gly Glu Ala Phe Asp Gly Ala Arg Asp
1               5                   10                  15

Met Trp Arg Ala Tyr Ser Asp Met Arg Glu Ala Asn Tyr Ile Gly Ser
                20                  25                  30

Asp Lys Tyr Phe His Ala Arg Gly Asn Tyr Asp Ala Ala Lys Arg Gly
            35                  40                  45

Pro Gly Gly Val Trp Ala Ala Glu Ala Ile Ser Asp Ala Arg Glu Asn
    50                  55                  60

Ile Gln Arg Phe Phe Gly His Gly Ala Glu Asp Ser
65                  70                  75

<210> SEQ ID NO 103
<211> LENGTH: 76
<212> TYPE: PRT
<213> ORGANISM: Homo sapiens
<220> FEATURE:
<221> NAME/KEY: MISC_FEATURE
<223> OTHER INFORMATION: HAA2

<400> SEQUENCE: 103

Arg Ser Phe Phe Ser Phe Leu Gly Glu Ala Phe Asp Gly Ala Arg Asp
1               5                   10                  15

Met Trp Arg Ala Tyr Ser Asp Met Arg Glu Ala Asn Tyr Ile Gly Ser
            20                  25                  30

Asp Lys Tyr Phe His Ala Arg Gly Asn Tyr Asp Ala Ala Lys Arg Gly
        35                  40                  45

Pro Gly Gly Ala Trp Ala Ala Glu Val Ile Ser Asn Ala Arg Glu Asn
    50                  55                  60

Ile Gln Arg Leu Thr Gly His Gly Ala Glu Asp Ser
65                  70                  75

<210> SEQ ID NO 104
<211> LENGTH: 76
<212> TYPE: PRT
<213> ORGANISM: Homo sapiens
<220> FEATURE:
<221> NAME/KEY: MISC_FEATURE
<223> OTHER INFORMATION: HAA3

<400> SEQUENCE: 104

Gln Gly Trp Leu Thr Phe Leu Lys Ala Ala Gly Gln Gly Ala Lys Asp
1               5                   10                  15

Met Trp Arg Ala Tyr Ser Asp Met Lys Glu Ala Asn Tyr Lys Lys Ser
            20                  25                  30

Asp Lys Tyr Phe His Ala Arg Gly Asn Tyr Asp Ala Val Gln Arg Gly
        35                  40                  45

Pro Gly Gly Val Trp Ala Thr Glu Val Ile Ser Asp Ala Arg Glu Asn
    50                  55                  60

Val Gln Arg Leu Thr Gly Asp His Ala Glu Asp Ser
65                  70                  75

<210> SEQ ID NO 105
<211> LENGTH: 84
<212> TYPE: PRT
<213> ORGANISM: Homo sapiens
<220> FEATURE:
<221> NAME/KEY: MISC_FEATURE
<223> OTHER INFORMATION: HAA4

<400> SEQUENCE: 105

Glu Ser Trp Arg Ser Phe Phe Lys Glu Ala Leu Gln Gly Val Gly Asp
1               5                   10                  15

Met Gly Arg Ala Tyr Trp Asp Ile Met Ile Ser Asn His Gln Asn Ser
            20                  25                  30

Asn Arg Tyr Leu Tyr Ala Arg Gly Asn Tyr Asp Ala Ala Gln Arg Gly
        35                  40                  45

Pro Gly Gly Val Trp Ala Ala Lys Leu Ile Ser Arg Ser Arg Val Tyr
    50                  55                  60

Leu Gln Gly Leu Ile Asp Tyr Tyr Leu Phe Gly Asn Ser Ser Thr Val
65                  70                  75                  80

Ile Glu Asp Ser

```
<210> SEQ ID NO 106
<211> LENGTH: 117
<212> TYPE: PRT
<213> ORGANISM: Mus musculus
<220> FEATURE:
<221> NAME/KEY: MISC_FEATURE
<223> OTHER INFORMATION: MSAA1

<400> SEQUENCE: 106

Met Lys Leu Leu Thr Ser Leu Val Phe Cys Ser Leu Leu Leu Gly Val
1               5                   10                  15

Cys His Gly Gly Phe Phe Ser Phe Val His Glu Ala Phe Gln Gly Ala
            20                  25                  30

Gly Asp Met Trp Arg Ala Tyr Thr Asp Met Lys Glu Ala Asn Trp Lys
        35                  40                  45

Asn Ser Asp Lys Tyr Phe His Ala Arg Gly Asn Tyr Asp Ala Ala Gln
    50                  55                  60

Arg Gly Pro Gly Gly Val Trp Ala Ala Glu Lys Ile Ser Asp Gly Arg
65                  70                  75                  80

Glu Ala Phe Gln Glu Phe Phe Gly Arg Ile Ala Asp Gln Gly Ala Asn
                85                  90                  95

Arg His Gly Arg Ser Gly Lys Asp Pro Asn Tyr Tyr Arg Pro Pro Gly
            100                 105                 110

Leu Pro Asp Lys Tyr
            115

<210> SEQ ID NO 107
<211> LENGTH: 122
<212> TYPE: PRT
<213> ORGANISM: Mus musculus
<220> FEATURE:
<221> NAME/KEY: MISC_FEATURE
<223> OTHER INFORMATION: MSAA2

<400> SEQUENCE: 107

Met Lys Leu Leu Thr Ser Leu Val Phe Cys Ser Leu Leu Leu Gly Val
1               5                   10                  15

Cys His Gly Gly Phe Phe Ser Phe Ile Gly Glu Ala Phe Gln Gly Ala
            20                  25                  30

Gly Asp Met Trp Arg Ala Tyr Thr Asp Met Lys Glu Ala Gly Trp Lys
        35                  40                  45

Asp Gly Asp Lys Tyr Phe His Ala Arg Gly Asn Tyr Asp Ala Ala Gln
    50                  55                  60

Arg Gly Pro Gly Gly Val Trp Ala Ala Glu Lys Ile Ser Asp Ala Arg
65                  70                  75                  80

Glu Ser Phe Gln Glu Phe Phe Gly Arg Gly His Glu Asp Thr Met Ala
                85                  90                  95

Asp Gln Glu Ala Asn Arg His Gly Arg Ser Gly Lys Asp Pro Asn Tyr
            100                 105                 110

Tyr Arg Pro Pro Gly Leu Pro Ala Lys Tyr
            115                 120

<210> SEQ ID NO 108
<211> LENGTH: 122
<212> TYPE: PRT
<213> ORGANISM: Mus musculus
<220> FEATURE:
<221> NAME/KEY: MISC_FEATURE
<223> OTHER INFORMATION: MSAA3

<400> SEQUENCE: 108
```

```
Met Lys Pro Ser Ile Ala Ile Leu Cys Ile Leu Ile Leu Gly Val
1               5                   10                  15

Asp Ser Gln Arg Trp Val Gln Phe Met Lys Glu Ala Gly Gln Gly Ser
            20                  25                  30

Arg Asp Met Trp Arg Ala Tyr Ser Asp Met Lys Lys Ala Asn Trp Lys
        35                  40                  45

Asn Ser Asp Lys Tyr Phe His Ala Arg Gly Asn Tyr Asp Ala Ala Arg
50                  55                  60

Arg Gly Pro Gly Gly Ala Trp Ala Ala Lys Val Ile Ser Asp Ala Arg
65                  70                  75                  80

Glu Ala Val Gln Lys Phe Thr Gly His Gly Ala Glu Asp Ser Arg Ala
                85                  90                  95

Asp Gln Phe Ala Asn Glu Trp Gly Arg Ser Gly Lys Asp Pro Asn His
            100                 105                 110

Phe Arg Pro Ala Gly Leu Pro Lys Arg Tyr
        115                 120
```

<210> SEQ ID NO 109
<211> LENGTH: 130
<212> TYPE: PRT
<213> ORGANISM: Mus musculus
<220> FEATURE:
<221> NAME/KEY: MISC_FEATURE
<223> OTHER INFORMATION: MSAA4

<400> SEQUENCE: 109

```
Met Arg Leu Ala Thr Val Ile Val Leu Cys Ser Leu Phe Leu Gly Val
1               5                   10                  15

Ser Gly Asp Gly Trp Tyr Ser Phe Phe Arg Glu Ala Val Gln Gly Thr
            20                  25                  30

Trp Asp Leu Trp Arg Ala Tyr Arg Asp Asn Leu Glu Ala Asn Tyr Gln
        35                  40                  45

Asn Ala Asp Gln Tyr Phe Tyr Ala Arg Gly Asn Tyr Glu Ala Gln Gln
50                  55                  60

Arg Gly Ser Gly Gly Ile Trp Ala Ala Lys Ile Ile Ser Thr Ser Arg
65                  70                  75                  80

Lys Tyr Phe Gln Gly Leu Leu Asn Arg Tyr Tyr Phe Gly Ile Arg Asn
                85                  90                  95

His Gly Leu Glu Thr Leu Gln Ala Thr Gln Lys Ala Glu Glu Trp Gly
            100                 105                 110

Arg Ser Gly Lys Asn Pro Asn His Phe Arg Pro Glu Gly Leu Pro Glu
        115                 120                 125

Lys Phe
    130
```

<210> SEQ ID NO 110
<211> LENGTH: 85
<212> TYPE: PRT
<213> ORGANISM: Mus musculus
<220> FEATURE:
<221> NAME/KEY: MISC_FEATURE
<223> OTHER INFORMATION: MAA1

<400> SEQUENCE: 110

```
Gly Phe Phe Ser Phe Val His Glu Ala Phe Gln Gly Ala Gly Asp Met
1               5                   10                  15

Trp Arg Ala Tyr Thr Asp Met Lys Glu Ala Asn Trp Lys Asn Ser His
            20                  25                  30
```

-continued

Glu Asp Thr Ile Ala Asp Gln Glu Ala Asp Lys Tyr Phe His Ala Arg
                35                  40                  45

Gly Asn Tyr Asp Ala Ala Gln Arg Gly Pro Gly Gly Val Trp Ala Ala
         50                  55                  60

Glu Lys Ile Ser Asp Gly Arg Glu Ala Phe Gln Glu Phe Phe Gly Arg
 65                  70                  75                  80

Gly His Glu Asp Thr
                85

<210> SEQ ID NO 111
<211> LENGTH: 75
<212> TYPE: PRT
<213> ORGANISM: Mus musculus
<220> FEATURE:
<221> NAME/KEY: MISC_FEATURE
<223> OTHER INFORMATION: MAA2

<400> SEQUENCE: 111

Gly Phe Phe Ser Phe Ile Gly Glu Ala Phe Gln Gly Ala Gly Asp Met
 1               5                  10                  15

Trp Arg Ala Tyr Thr Asp Met Lys Glu Ala Gly Trp Lys Asp Gly Asp
                20                  25                  30

Lys Tyr Phe His Ala Arg Gly Asn Tyr Asp Ala Ala Gln Arg Gly Pro
                35                  40                  45

Gly Gly Val Trp Ala Ala Glu Lys Ile Ser Asp Ala Arg Glu Ser Phe
         50                  55                  60

Gln Glu Phe Phe Gly Arg Gly His Glu Asp Thr
 65                  70                  75

<210> SEQ ID NO 112
<211> LENGTH: 68
<212> TYPE: PRT
<213> ORGANISM: Mus musculus
<220> FEATURE:
<221> NAME/KEY: MISC_FEATURE
<223> OTHER INFORMATION: MAA3

<400> SEQUENCE: 112

Glu Ala Gly Gln Gly Ser Arg Asp Met Trp Arg Ala Tyr Ser Asp Met
 1               5                  10                  15

Lys Lys Ala Asn Trp Lys Asn Ser Asp Lys Tyr Phe His Ala Arg Gly
                20                  25                  30

Asn Tyr Asp Ala Ala Arg Arg Gly Pro Gly Gly Ala Trp Ala Ala Lys
                35                  40                  45

Val Ile Ser Asp Ala Arg Glu Ala Val Gln Lys Phe Thr Gly His Gly
         50                  55                  60

Ala Glu Asp Ser
 65

<210> SEQ ID NO 113
<211> LENGTH: 82
<212> TYPE: PRT
<213> ORGANISM: Mus musculus
<220> FEATURE:
<221> NAME/KEY: MISC_FEATURE
<223> OTHER INFORMATION: MAA4

<400> SEQUENCE: 113

Trp Tyr Ser Phe Phe Arg Glu Ala Val Gln Gly Thr Trp Asp Leu Trp
 1               5                  10                  15

Arg Ala Tyr Arg Asp Asn Leu Glu Ala Asn Tyr Gln Asn Ala Asp Gln
                20                  25                  30

```
Tyr Phe Tyr Ala Arg Gly Asn Tyr Glu Ala Gln Gln Arg Gly Ser Gly
            35                  40                  45

Gly Ile Trp Ala Ala Lys Ile Ile Ser Thr Ser Arg Lys Tyr Phe Gln
         50                  55                  60

Gly Leu Leu Asn Arg Tyr Tyr Phe Gly Ile Arg Asn His Gly Leu Glu
65                  70                  75                  80

Thr Leu

<210> SEQ ID NO 114
<211> LENGTH: 122
<212> TYPE: PRT
<213> ORGANISM: Homo sapiens
<220> FEATURE:
<221> NAME/KEY: MISC_FEATURE
<223> OTHER INFORMATION: HSAA1 alpha

<400> SEQUENCE: 114

Met Lys Leu Leu Thr Gly Leu Val Phe Cys Ser Leu Val Leu Gly Val
1               5                   10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
    50                  55                  60

Arg Gly Pro Gly Gly Val Trp Ala Ala Glu Ala Ile Ser Asp Ala Arg
65                  70                  75                  80

Glu Asn Ile Gln Arg Phe Phe Gly His Gly Ala Glu Asp Ser Leu Ala
                85                  90                  95

Asp Gln Ala Ala Asn Glu Trp Gly Arg Ser Gly Lys Asp Pro Asn His
            100                 105                 110

Phe Arg Pro Ala Gly Leu Pro Glu Lys Tyr
        115                 120

<210> SEQ ID NO 115
<211> LENGTH: 122
<212> TYPE: PRT
<213> ORGANISM: Homo sapiens
<220> FEATURE:
<221> NAME/KEY: MISC_FEATURE
<223> OTHER INFORMATION: HSSA1 beta

<400> SEQUENCE: 115

Met Lys Leu Leu Thr Gly Leu Val Phe Cys Ser Leu Val Leu Gly Val
1               5                   10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
    50                  55                  60

Arg Gly Pro Gly Gly Ala Trp Ala Ala Glu Val Ile Ser Asp Ala Arg
65                  70                  75                  80

Glu Asn Ile Gln Arg Phe Phe Gly His Asp Ala Glu Asp Ser Leu Ala
                85                  90                  95

Asp Gln Ala Ala Asn Glu Trp Gly Arg Ser Gly Lys Asp Pro Asn His
            100                 105                 110

Phe Arg Pro Ala Gly Leu Pro Glu Lys Tyr
```

-continued

```
              115                 120

<210> SEQ ID NO 116
<211> LENGTH: 122
<212> TYPE: PRT
<213> ORGANISM: Homo sapiens
<220> FEATURE:
<221> NAME/KEY: MISC_FEATURE
<223> OTHER INFORMATION: HSSA1 gamma

<400> SEQUENCE: 116

Met Lys Leu Leu Thr Gly Leu Val Phe Cys Ser Leu Val Leu Gly Val
1               5                   10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
    50                  55                  60

Arg Gly Pro Gly Gly Val Trp Ala Ala Glu Ala Ile Ser Asp Ala Arg
65                  70                  75                  80

Glu Asn Ile Gln Arg Phe Phe Gly His Asp Ala Glu Ser Leu Ala
                85                  90                  95

Asp Gln Ala Ala Asn Lys Trp Gly Arg Ser Gly Arg Asp Pro Asn His
            100                 105                 110

Phe Arg Pro Ala Gly Leu Pro Glu Lys Tyr
        115                 120

<210> SEQ ID NO 117
<211> LENGTH: 122
<212> TYPE: PRT
<213> ORGANISM: Homo sapiens
<220> FEATURE:
<221> NAME/KEY: MISC_FEATURE
<223> OTHER INFORMATION: HSAA2 alpha

<400> SEQUENCE: 117

Met Lys Leu Leu Thr Gly Leu Val Phe Cys Ser Leu Val Leu Ser Val
1               5                   10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
    50                  55                  60

Arg Gly Pro Gly Gly Ala Trp Ala Ala Glu Val Ile Ser Asn Ala Arg
65                  70                  75                  80

Glu Asn Ile Gln Arg Leu Thr Gly His Gly Ala Glu Asp Ser Leu Ala
                85                  90                  95

Asp Gln Ala Ala Asn Lys Trp Gly Arg Ser Gly Arg Asp Pro Asn His
            100                 105                 110

Phe Arg Pro Ala Gly Leu Pro Glu Lys Tyr
        115                 120

<210> SEQ ID NO 118
<211> LENGTH: 122
<212> TYPE: PRT
<213> ORGANISM: Homo sapiens
<220> FEATURE:
<221> NAME/KEY: MISC_FEATURE
<223> OTHER INFORMATION: HSAA2 beta
```

-continued

<400> SEQUENCE: 118

Met Lys Leu Leu Thr Gly Leu Val Phe Cys Ser Leu Val Leu Ser Val
1               5                   10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
    50                  55                  60

Arg Gly Pro Gly Gly Ala Trp Ala Ala Glu Val Ile Ser Asn Ala Arg
65                  70                  75                  80

Glu Asn Ile Gln Arg Leu Thr Gly Arg Gly Ala Glu Asp Ser Leu Ala
                85                  90                  95

Asp Gln Ala Ala Asn Lys Trp Gly Arg Ser Gly Arg Asp Pro Asn His
            100                 105                 110

Phe Arg Pro Ala Gly Leu Pro Glu Lys Tyr
            115                 120

<210> SEQ ID NO 119
<211> LENGTH: 104
<212> TYPE: PRT
<213> ORGANISM: Homo sapiens
<220> FEATURE:
<221> NAME/KEY: MISC_FEATURE
<223> OTHER INFORMATION: HAA1 beta isoform

<400> SEQUENCE: 119

Arg Ser Phe Phe Ser Phe Leu Gly Glu Ala Phe Asp Gly Ala Arg Asp
1               5                   10                  15

Met Trp Arg Ala Tyr Ser Asp Met Arg Glu Ala Asn Tyr Ile Gly Ser
            20                  25                  30

Asp Lys Tyr Phe His Ala Arg Gly Asn Tyr Asp Ala Ala Lys Arg Gly
        35                  40                  45

Pro Gly Gly Val Trp Ala Ala Glu Ala Ile Ser Asp Ala Arg Glu Asn
    50                  55                  60

Ile Gln Arg Phe Phe Gly His Gly Ala Glu Asp Ser Leu Ala Asp Gln
65                  70                  75                  80

Ala Ala Asn Glu Trp Gly Arg Ser Gly Lys Asp Pro Asn His Phe Arg
                85                  90                  95

Pro Ala Gly Leu Pro Glu Lys Tyr
            100

<210> SEQ ID NO 120
<211> LENGTH: 102
<212> TYPE: PRT
<213> ORGANISM: Mus musculus
<220> FEATURE:
<221> NAME/KEY: MISC_FEATURE
<223> OTHER INFORMATION: Serum amyloid A protein

<400> SEQUENCE: 120

Gly Phe Phe Ser Phe Ile Gly Glu Ala Phe Gln Gly Ala Gly Asp Met
1               5                   10                  15

Trp Arg Ala Tyr Thr Asp Met Lys Glu Ala Gly Trp Lys Asp Gly Asp
            20                  25                  30

Lys Tyr Phe His Ala Arg Gly Asn Tyr Asp Ala Ala Gln Arg Gly Pro
        35                  40                  45

Gly Gly Val Trp Ala Ala Glu Lys Ile Ser Asp Ala Arg Glu Ser Gln

```
            50                  55                  60
Glu Phe Phe Gly Arg Gly His Glu Asp Thr Met Ala Asp Gln Glu Ala
 65                  70                  75                  80

Asn Arg His Gly Arg Ser Gly Lys Asp Pro Asn Tyr Tyr Arg Pro Pro
                 85                  90                  95

Gly Leu Pro Ala Lys Tyr
            100

<210> SEQ ID NO 121
<211> LENGTH: 84
<212> TYPE: PRT
<213> ORGANISM: Canis familiaris
<220> FEATURE:
<221> NAME/KEY: MISC_FEATURE
<223> OTHER INFORMATION: Serum amyloid A protein

<400> SEQUENCE: 121

Trp Tyr Ser Phe Val Gly Glu Ala Ala Gln Gly Ala Trp Asp Met Leu
  1               5                  10                  15

Arg Ala Tyr Ser Asp Met Arg Glu Ala Asn Tyr Lys Asn Ser Asp Lys
                 20                  25                  30

Tyr Phe His Ala Arg Gly Asn Tyr Asp Ala Ala Gln Arg Gly Pro Gly
             35                  40                  45

Gly Ala Trp Ala Ala Lys Val Ile Ser Asp Ala Arg Glu Asn Ser Gln
         50                  55                  60

Arg Asp Ser Gly His Gly Ala Glu Asp Ser Lys Ala Asp Gln Ala Ala
 65                  70                  75                  80

Asn Glu Trp Gly

<210> SEQ ID NO 122
<211> LENGTH: 8
<212> TYPE: PRT
<213> ORGANISM: Homo sapiens

<400> SEQUENCE: 122

Ile Thr Asp Leu Leu Arg Phe Gly
  1               5

<210> SEQ ID NO 123
<211> LENGTH: 95
<212> TYPE: PRT
<213> ORGANISM: Homo sapiens
<220> FEATURE:
<221> NAME/KEY: MISC_FEATURE
<223> OTHER INFORMATION: kpla
<220> FEATURE:
<221> NAME/KEY: MISC_FEATURE
<223> OTHER INFORMATION: Germline sequences of V kappa light chain

<400> SEQUENCE: 123

Asp Ile Gln Met Thr Gln Ser Pro Ser Thr Leu Ser Ala Ser Val Gly
  1               5                  10                  15

Asp Arg Val Thr Ile Thr Cys Arg Ala Ser Gln Ser Ile Ser Ser Trp
                 20                  25                  30

Leu Ala Trp Tyr Gln Gln Lys Pro Gly Lys Ala Pro Lys Leu Leu Ile
             35                  40                  45

Tyr Lys Ala Ser Ser Leu Glu Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser
```

```
              85                  90                  95
```

<210> SEQ ID NO 124
<211> LENGTH: 17
<212> TYPE: PRT
<213> ORGANISM: Homo sapiens
<220> FEATURE:
<221> NAME/KEY: MISC_FEATURE
<223> OTHER INFORMATION: kp1b
<220> FEATURE:
<221> NAME/KEY: MISC_FEATURE
<223> OTHER INFORMATION: Germline sequences of V kappa light chain

<400> SEQUENCE: 124

```
Ser Gln Asp Asn Tyr Asn Asp Asn Thr Asp Phe Glu Ile Asp Asn Leu
1               5                  10                  15

Pro
```

<210> SEQ ID NO 125
<211> LENGTH: 11
<212> TYPE: PRT
<213> ORGANISM: Homo sapiens
<220> FEATURE:
<221> NAME/KEY: MISC_FEATURE
<223> OTHER INFORMATION: kp1c
<220> FEATURE:
<221> NAME/KEY: MISC_FEATURE
<223> OTHER INFORMATION: Germline sequences of V kappa light chain

<400> SEQUENCE: 125

```
Ser Tyr Asn Ala Gln Asp Glu Ser Tyr Thr Pro
1               5                  10
```

<210> SEQ ID NO 126
<211> LENGTH: 13
<212> TYPE: PRT
<213> ORGANISM: Homo sapiens
<220> FEATURE:
<221> NAME/KEY: MISC_FEATURE
<223> OTHER INFORMATION: kp1d
<220> FEATURE:
<221> NAME/KEY: MISC_FEATURE
<223> OTHER INFORMATION: Germline sequences of V kappa light chain

<400> SEQUENCE: 126

```
Ser Gly Arg Asn Asp Gly Arg Ala Gln Glu Leu His Pro
1               5                  10
```

<210> SEQ ID NO 127
<211> LENGTH: 11
<212> TYPE: PRT
<213> ORGANISM: Homo sapiens
<220> FEATURE:
<221> NAME/KEY: MISC_FEATURE
<223> OTHER INFORMATION: kp1e
<220> FEATURE:
<221> NAME/KEY: MISC_FEATURE
<223> OTHER INFORMATION: Germline sequences of V kappa light chain

<400> SEQUENCE: 127

```
Ser Gly Asn Tyr Phe Ser Ala Gln Asp Glu Pro
1               5                  10
```

<210> SEQ ID NO 128
<211> LENGTH: 11
<212> TYPE: PRT
<213> ORGANISM: Homo sapiens
<220> FEATURE:
<221> NAME/KEY: MISC_FEATURE
<223> OTHER INFORMATION: kp1f

```
<220> FEATURE:
<221> NAME/KEY: MISC_FEATURE
<223> OTHER INFORMATION: Germline sequences of V kappa light chain

<400> SEQUENCE: 128

Ala Leu Ser Gly Ala Asp Asp Glu Phe Asn Pro
1               5                   10

<210> SEQ ID NO 129
<211> LENGTH: 10
<212> TYPE: PRT
<213> ORGANISM: Homo sapiens
<220> FEATURE:
<221> NAME/KEY: MISC_FEATURE
<223> OTHER INFORMATION: kp1g
<220> FEATURE:
<221> NAME/KEY: MISC_FEATURE
<223> OTHER INFORMATION: Germline sequences of V kappa light chain

<400> SEQUENCE: 129

Ser Val Gly Ala Gln Asp Glu Ala Phe Pro
1               5                   10

<210> SEQ ID NO 130
<211> LENGTH: 51
<212> TYPE: PRT
<213> ORGANISM: Homo sapiens
<220> FEATURE:
<221> NAME/KEY: MISC_FEATURE
<223> OTHER INFORMATION: kp2a
<220> FEATURE:
<221> NAME/KEY: MISC_FEATURE
<223> OTHER INFORMATION: Germline sequences of V kappa light chain

<400> SEQUENCE: 130

Val Thr Leu Ser Pro Val Thr Pro Glu Pro Ala Ser Ser Ser Leu Leu
1               5                   10                  15

Asp Ser Asp Asp Gly Asn Thr Tyr Asp Leu Gln Ser Gln Thr Leu Tyr
            20                  25                  30

Arg Ala Asp Asp Lys Arg Val Glu Ala Glu Val Gly Val Met Arg Ile
        35                  40                  45

Glu Phe Pro
    50

<210> SEQ ID NO 131
<211> LENGTH: 49
<212> TYPE: PRT
<213> ORGANISM: Homo sapiens
<220> FEATURE:
<221> NAME/KEY: MISC_FEATURE
<223> OTHER INFORMATION: kp2b
<220> FEATURE:
<221> NAME/KEY: MISC_FEATURE
<223> OTHER INFORMATION: Germline sequences of V kappa light chain

<400> SEQUENCE: 131

Val Leu Ser Pro Val Thr Pro Glu Pro Ala Ser Ser Ser Leu Leu His
1               5                   10                  15

Ser Asn Gly Tyr Asn Tyr Asp Leu Gln Ser Gln Leu Gly Asn Arg Ala
            20                  25                  30

Asp Asp Lys Arg Val Glu Ala Glu Val Gly Val Met Ala Leu Gln Thr
        35                  40                  45

Pro

<210> SEQ ID NO 132
<211> LENGTH: 50
```

```
<212> TYPE: PRT
<213> ORGANISM: Homo sapiens
<220> FEATURE:
<221> NAME/KEY: MISC_FEATURE
<223> OTHER INFORMATION: kp2c
<220> FEATURE:
<221> NAME/KEY: MISC_FEATURE
<223> OTHER INFORMATION: Germline sequences of V kappa light chain

<400> SEQUENCE: 132

Val Thr Leu Ser Val Thr Pro Gln Pro Ala Ser Ser Lys Ser Leu Leu
1               5                   10                  15

His Ser Asp Gly Lys Thr Tyr Tyr Leu Gln Pro Gln Glu Val Asn Arg
            20                  25                  30

Phe Asp Asp Lys Arg Val Glu Ala Glu Val Gly Val Met Ser Ile Gln
        35                  40                  45

Leu Pro
    50

<210> SEQ ID NO 133
<211> LENGTH: 26
<212> TYPE: PRT
<213> ORGANISM: Homo sapiens
<220> FEATURE:
<221> NAME/KEY: MISC_FEATURE
<223> OTHER INFORMATION: kp3a
<220> FEATURE:
<221> NAME/KEY: MISC_FEATURE
<223> OTHER INFORMATION: Germline sequences of V kappa light chain

<400> SEQUENCE: 133

Glu Val Ala Val Pro Glu Ala Leu Ser Val Asn Gln Arg Gly Thr Arg
1               5                   10                  15

Ala Thr Ile Ala Ser Glu Val Asn Trp Pro
            20                  25

<210> SEQ ID NO 134
<211> LENGTH: 29
<212> TYPE: PRT
<213> ORGANISM: Homo sapiens
<220> FEATURE:
<221> NAME/KEY: MISC_FEATURE
<223> OTHER INFORMATION: kp3b
<220> FEATURE:
<221> NAME/KEY: MISC_FEATURE
<223> OTHER INFORMATION: Germline sequences of V kappa light chain

<400> SEQUENCE: 134

Glu Val Leu Gly Leu Pro Glu Ala Leu Ser Val Ser Tyr Gln Arg Gly
1               5                   10                  15

Arg Ala Thr Ile Asp Asp Arg Glu Glu Val Gly Ser Pro
            20                  25

<210> SEQ ID NO 135
<211> LENGTH: 31
<212> TYPE: PRT
<213> ORGANISM: Homo sapiens
<220> FEATURE:
<221> NAME/KEY: MISC_FEATURE
<223> OTHER INFORMATION: kp3c
<220> FEATURE:
<221> NAME/KEY: MISC_FEATURE
<223> OTHER INFORMATION: Germline sequences of V kappa light chain

<400> SEQUENCE: 135

Glu Val Leu Ala Leu Pro Glu Ala Leu Ser Val Ser Tyr Gln Arg Asp
1               5                   10                  15
```

Asn Arg Ala Thr Ile Ala Asp Glu Glu Val Arg Ser Asn Trp Pro
            20                  25                  30

<210> SEQ ID NO 136
<211> LENGTH: 35
<212> TYPE: PRT
<213> ORGANISM: Homo sapiens
<220> FEATURE:
<221> NAME/KEY: MISC_FEATURE
<223> OTHER INFORMATION: kp4
<220> FEATURE:
<221> NAME/KEY: MISC_FEATURE
<223> OTHER INFORMATION: Germline sequences of V lambda light chain

<400> SEQUENCE: 136

Val Asp Ser Ala Val Leu Glu Ala Asn Lys Ser Val Leu Tyr Ser Ser
1               5                   10                  15

Asn Asn Lys Asn Tyr Gln Pro Trp Thr Arg Asp Asp Ala Glu Val Val
            20                  25                  30

Tyr Thr Pro
        35

<210> SEQ ID NO 137
<211> LENGTH: 49
<212> TYPE: PRT
<213> ORGANISM: Homo sapiens
<220> FEATURE:
<221> NAME/KEY: MISC_FEATURE
<223> OTHER INFORMATION: kp5
<220> FEATURE:
<221> NAME/KEY: MISC_FEATURE
<223> OTHER INFORMATION: V lambda light chain

<400> SEQUENCE: 137

Glu Thr Thr Leu Ala Phe Met Thr Pro Lys Asn Ser Lys Asp Asp Asp
1               5                   10                  15

Asp Met Asn Glu Ala Ile Phe Ile Gln Glu Thr Thr Val Pro Ile Pro
            20                  25                  30

Tyr Asp Asn Asn Ile Glu Ser Glu Ala Tyr Phe Leu His Asp Asn Phe
        35                  40                  45

Pro

<210> SEQ ID NO 138
<211> LENGTH: 97
<212> TYPE: PRT
<213> ORGANISM: Homo sapiens
<220> FEATURE:
<221> NAME/KEY: MISC_FEATURE
<223> OTHER INFORMATION: lm1a
<220> FEATURE:
<221> NAME/KEY: MISC_FEATURE
<223> OTHER INFORMATION: V lambda light chain

<400> SEQUENCE: 138

Gln Ser Val Leu Thr Gln Pro Pro Ser Val Ser Ala Ala Pro Gly Gln
1               5                   10                  15

Val Thr Ile Ser Cys Ser Gly Ser Ser Ser Asn Ile Gly Asn Asn Tyr
            20                  25                  30

Val Ser Trp Tyr Gln Gln Leu Pro Gly Thr Ala Pro Lys Leu Leu Ile
        35                  40                  45

Tyr Glu Asn Asn Lys Arg Pro Ser Gly Ile Pro Asp Arg Phe Ser Gly
    50                  55                  60

Ser Lys Ser Gly Thr Ser Ala Thr Leu Gly Ile Thr Gly Leu Gln Thr
65                  70                  75                  80

```
Gly Asp Glu Ala Asp Tyr Tyr Cys Gly Thr Trp Asp Ser Ser Leu Ser
                85                  90                  95

Ala

<210> SEQ ID NO 139
<211> LENGTH: 19
<212> TYPE: PRT
<213> ORGANISM: Homo sapiens
<220> FEATURE:
<221> NAME/KEY: MISC_FEATURE
<223> OTHER INFORMATION: lm1b
<220> FEATURE:
<221> NAME/KEY: MISC_FEATURE
<223> OTHER INFORMATION: V lambda light chain

<400> SEQUENCE: 139

Ala Gly Thr Arg Ser Tyr Arg Gln Val Ser Ala Ser Arg Ser Glu Ala
1               5                   10                  15

Ala Asp Gly

<210> SEQ ID NO 140
<211> LENGTH: 21
<212> TYPE: PRT
<213> ORGANISM: Homo sapiens
<220> FEATURE:
<221> NAME/KEY: MISC_FEATURE
<223> OTHER INFORMATION: lm1c
<220> FEATURE:
<221> NAME/KEY: MISC_FEATURE
<223> OTHER INFORMATION: V lambda light chain

<400> SEQUENCE: 140

Val Gly Arg Thr Ala Gly Tyr Asp His Gly Ser Asn Val Ser Ala Ala
1               5                   10                  15

Glu Gln Ser Tyr Gly
            20

<210> SEQ ID NO 141
<211> LENGTH: 27
<212> TYPE: PRT
<213> ORGANISM: Homo sapiens
<220> FEATURE:
<221> NAME/KEY: MISC_FEATURE
<223> OTHER INFORMATION: lm2a
<220> FEATURE:
<221> NAME/KEY: MISC_FEATURE
<223> OTHER INFORMATION: V lambda light chain

<400> SEQUENCE: 141

Ala Ala Gly Ser Ser Ile Thr Thr Asp Val Ser Tyr Leu His Lys Met
1               5                   10                  15

Gly Ser Val Ser Ala Ala Glu Gln Ser Tyr Gly
            20                  25

<210> SEQ ID NO 142
<211> LENGTH: 34
<212> TYPE: PRT
<213> ORGANISM: Homo sapiens
<220> FEATURE:
<221> NAME/KEY: MISC_FEATURE
<223> OTHER INFORMATION: lm2b
<220> FEATURE:
<221> NAME/KEY: MISC_FEATURE
<223> OTHER INFORMATION: V lambda light chain

<400> SEQUENCE: 142

Ala Arg Gly Ser Val Ile Thr Thr Asp Val Gly Tyr His Lys Met Asp
1               5                   10                  15
```

```
Val Ser Val Asn Thr Ser Thr Ser Ala Glu Cys Ser Tyr Ala Gly Tyr
            20                  25                  30

Thr Phe

<210> SEQ ID NO 143
<211> LENGTH: 41
<212> TYPE: PRT
<213> ORGANISM: Homo sapiens
<220> FEATURE:
<221> NAME/KEY: MISC_FEATURE
<223> OTHER INFORMATION: lm3a
<220> FEATURE:
<221> NAME/KEY: MISC_FEATURE
<223> OTHER INFORMATION: V lambda light chain

<400> SEQUENCE: 143

Ser Tyr Val Lys Thr Ala Arg Thr Gly Asn Ile Gly Ser Lys Ser
1               5                   10                  15

His Lys Gln Val Val Asp Asp Ser Asp Glu Asn Asn Thr Thr Ser
            20                  25                  30

Arg Val Glu Ala Gln Val Ser Asp His
        35                  40

<210> SEQ ID NO 144
<211> LENGTH: 38
<212> TYPE: PRT
<213> ORGANISM: Homo sapiens
<220> FEATURE:
<221> NAME/KEY: MISC_FEATURE
<223> OTHER INFORMATION: lm3b
<220> FEATURE:
<221> NAME/KEY: MISC_FEATURE
<223> OTHER INFORMATION: V lambda light chain

<400> SEQUENCE: 144

Ser Tyr Glu Val Ser Thr Ala Arg Thr Asp Ala Leu Pro Lys Gln Ala
1               5                   10                  15

Tyr Lys Gln Val Val Lys Asp Ser Glu Glu Ser Thr Val Thr Ser Val
            20                  25                  30

Ala Glu Gln Ser Ala Gly
        35

<210> SEQ ID NO 145
<211> LENGTH: 39
<212> TYPE: PRT
<213> ORGANISM: Homo sapiens
<220> FEATURE:
<221> NAME/KEY: MISC_FEATURE
<223> OTHER INFORMATION: lm3c
<220> FEATURE:
<221> NAME/KEY: MISC_FEATURE
<223> OTHER INFORMATION: V lambda light chain

<400> SEQUENCE: 145

Ser Tyr Glu Val Ser Thr Ala Ser Thr Asp Lys Leu Gly Asp Lys Ala
1               5                   10                  15

Cys Lys Gln Ser Val Val Gln Asp Ser Glu Asn Asn Thr Thr Ser Thr
            20                  25                  30

Ala Met Gln Ala Thr Ala His
        35

<210> SEQ ID NO 146
<211> LENGTH: 23
<212> TYPE: PRT
<213> ORGANISM: Homo sapiens
```

```
<220> FEATURE:
<221> NAME/KEY: MISC_FEATURE
<223> OTHER INFORMATION: lm4
<220> FEATURE:
<221> NAME/KEY: MISC_FEATURE
<223> OTHER INFORMATION: V lambda light chain

<400> SEQUENCE: 146

Ser Glu Asp Ala Val Leu Thr Arg Thr Gln Asp Leu Arg Ser Tyr Ala
1               5                   10                  15

Lys Gln Val Val Gly Lys Asn
            20

<210> SEQ ID NO 147
<211> LENGTH: 38
<212> TYPE: PRT
<213> ORGANISM: Homo sapiens
<220> FEATURE:
<221> NAME/KEY: MISC_FEATURE
<223> OTHER INFORMATION: lm6
<220> FEATURE:
<221> NAME/KEY: MISC_FEATURE
<223> OTHER INFORMATION: V lambda light chain

<400> SEQUENCE: 147

Asn Phe Met His Glu Ser Lys Thr Thr Arg Gly Ser Ala Ser Gln Arg
1               5                   10                  15

Ser Ser Thr Thr Val Asp Gln Val Ile Asp Ser Ser Asn Ser Thr Ser
            20                  25                  30

Lys Glu Gln Ser Tyr Asn
        35

<210> SEQ ID NO 148
<211> LENGTH: 57
<212> TYPE: PRT
<213> ORGANISM: Homo sapiens
<220> FEATURE:
<221> NAME/KEY: MISC_FEATURE
<223> OTHER INFORMATION: lm7
<220> FEATURE:
<221> NAME/KEY: MISC_FEATURE
<223> OTHER INFORMATION: V lambda light chain

<400> SEQUENCE: 148

Thr Val Glu Leu Thr Val Ser Gly Thr Leu Thr Ala Ser Thr Gly Ala
1               5                   10                  15

Val Thr Ser Gly Tyr Pro Asn Phe Lys Gln Arg Ala Ser Thr Ser Asn
            20                  25                  30

Lys His Trp Thr Ala Leu Leu Gly Lys Ala Thr Leu Ser Val Pro Glu
        35                  40                  45

Glu Leu Leu Tyr Tyr Gly Gly Ala Gln
    50                  55

<210> SEQ ID NO 149
<211> LENGTH: 50
<212> TYPE: PRT
<213> ORGANISM: Homo sapiens
<220> FEATURE:
<221> NAME/KEY: MISC_FEATURE
<223> OTHER INFORMATION: lm8
<220> FEATURE:
<221> NAME/KEY: MISC_FEATURE
<223> OTHER INFORMATION: V lambda light chain

<400> SEQUENCE: 149

Leu Ser Ala Ser Leu Ala Ser Lys Leu Thr Thr Leu Gly His Ser Ser
1               5                   10                  15
```

```
Tyr Ala Ile Ala His Gln Glu Lys Gly Arg Tyr Met Lys Leu Ser Asp
            20                  25                  30

Gly Gly Asp Ser Ala Glu Arg Tyr Thr Ser Ser Glu Gln Gly Thr
        35                  40                  45

Gly Ile
    50

<210> SEQ ID NO 150
<211> LENGTH: 98
<212> TYPE: PRT
<213> ORGANISM: Homo sapiens
<220> FEATURE:
<221> NAME/KEY: MISC_FEATURE
<223> OTHER INFORMATION: V lambda Wil

<400> SEQUENCE: 150

Asn Phe Leu Leu Thr Gln Pro His Ser Val Ser Glu Ser Pro Gly Lys
1               5                   10                  15

Thr Val Thr Ile Ser Cys Thr Arg Ser Ser Gly Ser Ile Ala Asn Asn
            20                  25                  30

Tyr Val His Trp Tyr Gln Gln Arg Pro Gly Ser Ser Pro Thr Thr Val
        35                  40                  45

Ile Phe Glu Asp Asp His Arg Pro Ser Gly Val Pro Asp Arg Phe Ser
50                  55                  60

Gly Ser Val Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp His
                85                  90                  95

Asn Asn

<210> SEQ ID NO 151
<211> LENGTH: 4
<212> TYPE: PRT
<213> ORGANISM: Artificial Sequence
<220> FEATURE:
<223> OTHER INFORMATION: AL V kappa fragment from amyloid protein
<220> FEATURE:
<221> NAME/KEY: MISC_FEATURE
<223> OTHER INFORMATION: Consensus sequence derived from human
      amyloidogenic proteins

<400> SEQUENCE: 151

Pro Glu Asp Val
1

<210> SEQ ID NO 152
<211> LENGTH: 131
<212> TYPE: PRT
<213> ORGANISM: Mus musculus
<220> FEATURE:
<221> NAME/KEY: MISC_FEATURE
<223> OTHER INFORMATION: Murine 2A4 and 8G9 v kappa light chain
<220> FEATURE:
<221> NAME/KEY: SIGNAL
<222> LOCATION: (1)..(19)
<223> OTHER INFORMATION: Leader sequence
<220> FEATURE:
<221> NAME/KEY: mat_peptide
<222> LOCATION: (20)..(131)
<220> FEATURE:
<221> NAME/KEY: MISC_FEATURE
<222> LOCATION: (43)..(58)
<223> OTHER INFORMATION: CDR 1
<220> FEATURE:
<221> NAME/KEY: MISC_FEATURE
<222> LOCATION: (74)..(80)
```

```
<223> OTHER INFORMATION: CDR 2
<220> FEATURE:
<221> NAME/KEY: MISC_FEATURE
<222> LOCATION: (113)..(121)
<223> OTHER INFORMATION: CDR 3

<400> SEQUENCE: 152

Met Lys Leu Pro Val Arg Leu Leu Val Leu Met Phe Trp Ile Pro Ala
                -15                 -10                 -5
Ser Ser Ser Asp Val Val Met Thr Gln Thr Pro Leu Ser Leu Pro Val
        -1  1               5                   10
Ser Leu Gly Asp Gln Ala Ser Ile Ser Cys Arg Ser Ser Gln Ser Leu
        15                  20                  25
Val His Ser Thr Gly Asn Thr Tyr Leu His Trp Tyr Leu Gln Lys Pro
30                  35                  40                  45
Gly Gln Ser Pro Lys Leu Leu Ile Tyr Lys Val Ser Asn Arg Phe Ser
                50                  55                  60
Gly Val Pro Asp Arg Phe Ser Gly Ser Gly Ser Gly Thr Tyr Phe Thr
                65                  70                  75
Leu Lys Ile Ser Arg Val Glu Ala Glu Asp Leu Gly Val Tyr Phe Cys
                80                  85                  90
Ser Gln Ser Thr His Val Pro Phe Thr Phe Gly Gly Gly Thr Lys Leu
                95                  100                 105
Glu Ile Lys
110

<210> SEQ ID NO 153
<211> LENGTH: 131
<212> TYPE: PRT
<213> ORGANISM: Mus musculus
<220> FEATURE:
<221> NAME/KEY: MISC_FEATURE
<223> OTHER INFORMATION: Murine 7D8 v kappa light chain
<220> FEATURE:
<221> NAME/KEY: SIGNAL
<222> LOCATION: (1)..(19)
<223> OTHER INFORMATION: Leader sequence
<220> FEATURE:
<221> NAME/KEY: mat_peptide
<222> LOCATION: (20)..(131)
<220> FEATURE:
<221> NAME/KEY: MISC_FEATURE
<222> LOCATION: (43)..(58)
<223> OTHER INFORMATION: CDR 1
<220> FEATURE:
<221> NAME/KEY: MISC_FEATURE
<222> LOCATION: (74)..(80)
<223> OTHER INFORMATION: CDR 2
<220> FEATURE:
<221> NAME/KEY: MISC_FEATURE
<222> LOCATION: (113)..(121)
<223> OTHER INFORMATION: CDR 3

<400> SEQUENCE: 153

Met Lys Leu Pro Val Arg Leu Leu Val Leu Met Phe Trp Ile Pro Ala
                -15                 -10                 -5
Ser Ser Ser Asp Val Val Met Thr Gln Thr Pro Leu Ser Leu Pro Val
        -1  1               5                   10
Ser Leu Gly Asp Gln Ala Ser Ile Ser Cys Arg Ser Ser Leu Ser Leu
        15                  20                  25
Val His Ser Thr Gly Asn Thr Tyr Leu His Trp Tyr Leu Gln Lys Pro
30                  35                  40                  45
Gly Gln Ser Pro Lys Leu Leu Ile Tyr Lys Val Ser Asn Arg Phe Ser
                50                  55                  60
```

```
Gly Val Pro Asp Arg Phe Ser Gly Ser Gly Ser Gly Thr Tyr Phe Thr
            65                  70                  75

Leu Lys Ile Ser Arg Val Glu Ala Glu Asp Leu Gly Val Tyr Phe Cys
        80                  85                  90

Ser Gln Ser Thr His Val Pro Phe Thr Phe Gly Gly Gly Thr Lys Leu
    95                 100                 105

Glu Ile Lys
110

<210> SEQ ID NO 154
<211> LENGTH: 138
<212> TYPE: PRT
<213> ORGANISM: Mus musculus
<220> FEATURE:
<221> NAME/KEY: MISC_FEATURE
<223> OTHER INFORMATION: Murine 2A4, 8G9 and 7D8 v heavy chain
<220> FEATURE:
<221> NAME/KEY: SIGNAL
<222> LOCATION: (1)..(19)
<223> OTHER INFORMATION: Leader sequence
<220> FEATURE:
<221> NAME/KEY: mat_peptide
<222> LOCATION: (20)..(138)
<220> FEATURE:
<221> NAME/KEY: MISC_FEATURE
<222> LOCATION: (45)..(54)
<223> OTHER INFORMATION: CDR 1
<220> FEATURE:
<221> NAME/KEY: MISC_FEATURE
<222> LOCATION: (69)..(87)
<223> OTHER INFORMATION: CDR 2
<220> FEATURE:
<221> NAME/KEY: MISC_FEATURE
<222> LOCATION: (120)..(127)
<223> OTHER INFORMATION: CDR 3

<400> SEQUENCE: 154

Met Val Leu Gly Leu Lys Trp Val Phe Phe Val Val Phe Tyr Gln Gly
                -15                 -10                 -5

Val His Cys Glu Val Gln Leu Val Glu Ser Gly Gly Arg Leu Val Gln
        -1   1               5                  10

Pro Lys Gly Ser Leu Lys Leu Ser Cys Ala Ala Ser Gly Phe Thr Phe
    15                  20                  25

Asn Thr Tyr Ala Met Tyr Trp Ile Arg Gln Ala Pro Gly Lys Gly Leu
30                  35                  40                  45

Glu Trp Val Ala Arg Ile Arg Ser Lys Ser Asn Asn Tyr Ala Ile Tyr
                50                  55                  60

Tyr Ala Asp Ser Val Lys Asp Arg Phe Thr Ile Phe Arg Asp Asp Ser
            65                  70                  75

Gln Ser Met Leu Tyr Leu Gln Met Asn Asn Leu Lys Thr Glu Asp Thr
        80                  85                  90

Ala Met Tyr Tyr Cys Val Arg Pro Tyr Ser Asp Ser Phe Ala Tyr Trp
    95                 100                 105

Gly Gln Gly Thr Leu Val Thr Val Ser Ala
110                 115

<210> SEQ ID NO 155
<211> LENGTH: 112
<212> TYPE: PRT
<213> ORGANISM: Artificial Sequence
<220> FEATURE:
<223> OTHER INFORMATION: Humanized 2A4 and 8G9 v kappa light chain
      version 1

<400> SEQUENCE: 155
```

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Thr Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Phe Thr Phe Gly Gly Gly Thr Lys Val Glu Ile Lys
                100                 105                 110

<210> SEQ ID NO 156
<211> LENGTH: 112
<212> TYPE: PRT
<213> ORGANISM: Artificial Sequence
<220> FEATURE:
<223> OTHER INFORMATION: Humanized 2A4 and 8G9 v kappa light chain
      version 2

<400> SEQUENCE: 156

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Thr Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Phe Thr Phe Gly Gly Gly Thr Lys Val Glu Ile Lys
                100                 105                 110

<210> SEQ ID NO 157
<211> LENGTH: 112
<212> TYPE: PRT
<213> ORGANISM: Artificial Sequence
<220> FEATURE:
<223> OTHER INFORMATION: Humanized 2A4 and 8G9 v kappa light chain
      version 3

<400> SEQUENCE: 157

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Thr Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser

```
                    85                  90                  95

Thr His Val Pro Phe Thr Phe Gly Gly Gly Thr Lys Val Glu Ile Lys
            100                 105                 110

<210> SEQ ID NO 158
<211> LENGTH: 112
<212> TYPE: PRT
<213> ORGANISM: Artificial Sequence
<220> FEATURE:
<223> OTHER INFORMATION: Humanized 7D8 v kappa light chain version 1

<400> SEQUENCE: 158

Asp Val Val Met Thr Gln Ser Pro Leu Ser Leu Pro Val Thr Pro Gly
1               5                   10                  15

Glu Pro Ala Ser Ile Ser Cys Arg Ser Ser Leu Ser Leu Val His Ser
            20                  25                  30

Thr Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Phe Thr Phe Gly Gln Gly Thr Lys Leu Glu Ile Lys
            100                 105                 110

<210> SEQ ID NO 159
<211> LENGTH: 112
<212> TYPE: PRT
<213> ORGANISM: Artificial Sequence
<220> FEATURE:
<223> OTHER INFORMATION: Humanized 7D8 v kappa light chain version 2

<400> SEQUENCE: 159

Asp Val Val Met Thr Gln Ser Pro Leu Ser Leu Pro Val Thr Pro Gly
1               5                   10                  15

Glu Pro Ala Ser Ile Ser Cys Arg Ser Ser Leu Ser Leu Val His Ser
            20                  25                  30

Thr Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Phe Thr Phe Gly Gln Gly Thr Lys Leu Glu Ile Lys
            100                 105                 110

<210> SEQ ID NO 160
<211> LENGTH: 112
<212> TYPE: PRT
<213> ORGANISM: Artificial Sequence
<220> FEATURE:
<223> OTHER INFORMATION: Humanized 7D8 v kappa light chain version 3

<400> SEQUENCE: 160

Asp Val Val Met Thr Gln Ser Pro Leu Ser Leu Pro Val Thr Pro Gly
1               5                   10                  15
```

Glu Pro Ala Ser Ile Ser Cys Arg Ser Ser Leu Ser Leu Val His Ser
            20                  25                  30

Thr Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Phe Thr Phe Gly Gln Gly Thr Lys Leu Glu Ile Lys
            100                 105                 110

<210> SEQ ID NO 161
<211> LENGTH: 119
<212> TYPE: PRT
<213> ORGANISM: Artificial Sequence
<220> FEATURE:
<223> OTHER INFORMATION: Humanized 2A4, 8G9 and 7D8 heavy chain
      version 1

<400> SEQUENCE: 161

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Tyr Trp Ile Arg Gln Ala Pro Gly Lys Gly Leu Glu Trp Val
        35                  40                  45

Ala Arg Ile Arg Ser Lys Ser Asn Asn Tyr Ala Ile Tyr Tyr Ala Asp
    50                  55                  60

Ser Val Lys Asp Arg Phe Thr Ile Phe Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg Pro Tyr Ser Asp Ser Phe Ala Tyr Trp Gly Gln Gly
            100                 105                 110

Thr Leu Val Thr Val Ser Ser
        115

<210> SEQ ID NO 162
<211> LENGTH: 119
<212> TYPE: PRT
<213> ORGANISM: Artificial Sequence
<220> FEATURE:
<223> OTHER INFORMATION: Humanized 2A4, 8G9 and 7D8 heavy chain version
      2

<400> SEQUENCE: 162

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Tyr Trp Ile Arg Gln Ala Pro Gly Lys Gly Leu Glu Trp Val
        35                  40                  45

Ala Arg Ile Arg Ser Lys Ser Asn Asn Tyr Ala Ile Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr

```
                     85                  90                  95

Tyr Cys Val Arg Pro Tyr Ser Asp Ser Phe Ala Tyr Trp Gly Gln Gly
                100                 105                 110

Thr Leu Val Thr Val Ser Ser
            115

<210> SEQ ID NO 163
<211> LENGTH: 119
<212> TYPE: PRT
<213> ORGANISM: Artificial Sequence
<220> FEATURE:
<223> OTHER INFORMATION: Humanized 2A4, 7D8 and 8g9 heavy chain version
      3

<400> SEQUENCE: 163

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Tyr Trp Ile Arg Gln Ala Pro Gly Lys Gly Leu Glu Trp Val
        35                  40                  45

Ala Arg Ile Arg Ser Lys Ser Asn Asn Tyr Ala Ile Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Pro Tyr Ser Asp Ser Phe Ala Tyr Trp Gly Gln Gly
                100                 105                 110

Thr Leu Val Thr Val Ser Ser
            115

<210> SEQ ID NO 164
<211> LENGTH: 119
<212> TYPE: PRT
<213> ORGANISM: Mus musculus

<400> SEQUENCE: 164

Glu Val Gln Leu Val Glu Ser Gly Gly Arg Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Tyr Trp Ile Arg Gln Ala Pro Gly Lys Gly Leu Glu Trp Val
        35                  40                  45

Ala Arg Ile Arg Ser Lys Ser Asn Asn Tyr Ala Ile Tyr Tyr Ala Asp
    50                  55                  60

Ser Val Lys Asp Arg Phe Thr Ile Phe Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Pro Tyr Ser Asp Ser Phe Ala Tyr Trp Gly Gln Gly
                100                 105                 110

Thr Leu Val Thr Val Ser Ala
            115

<210> SEQ ID NO 165
<211> LENGTH: 120
<212> TYPE: PRT
<213> ORGANISM: Homo sapiens
```

```
<220> FEATURE:
<221> NAME/KEY: MISC_FEATURE
<223> OTHER INFORMATION: Human heavy chain framework

<400> SEQUENCE: 165

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala Asn Ser Tyr Thr Thr Glu Tyr Ala Ala
50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Tyr Val Val Gly Ala Thr Leu Asp Tyr Trp Gly Gln
            100                 105                 110

Gly Thr Leu Val Thr Val Ser Ser
        115                 120

<210> SEQ ID NO 166
<211> LENGTH: 113
<212> TYPE: PRT
<213> ORGANISM: Homo sapiens
<220> FEATURE:
<221> NAME/KEY: MISC_FEATURE
<223> OTHER INFORMATION: Human v kappa light chain framework

<400> SEQUENCE: 166

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg

<210> SEQ ID NO 167
<211> LENGTH: 276
<212> TYPE: PRT
<213> ORGANISM: Homo sapiens
<220> FEATURE:
<221> NAME/KEY: MISC_FEATURE
<223> OTHER INFORMATION: Human v kappa light chain framework

<400> SEQUENCE: 167

Met Lys Tyr Leu Leu Pro Thr Ala Ala Ala Gly Leu Leu Leu Leu Ala
1               5                   10                  15

Ala Gln Pro Ala Met Ala Asp Val Val Met Thr Gln Ser Pro Leu Ser
            20                  25                  30
```

```
Leu Pro Val Thr Pro Gly Glu Pro Ala Ser Ile Ser Cys Arg Ser Ser
            35                  40                  45

Gln Ser Leu Leu His Ser Asn Gly Tyr Asn Tyr Leu Asp Trp Tyr Leu
 50                  55                  60

Gln Lys Pro Gly Gln Ser Pro Gln Leu Leu Ile Tyr Leu Gly Ser Asn
 65                  70                  75                  80

Arg Ala Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Met Gln Ala Leu Gln Thr Pro Tyr Thr Phe Gly Gln Gly
            115                 120                 125

Thr Lys Leu Glu Ile Lys Arg Thr Val Ala Ala Pro Ser Val Phe Ile
        130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys Ser Ala Arg Gln Ser Thr Pro Phe Val Cys Glu Tyr Gln Gly Gln
                245                 250                 255

Ser Ser Asp Leu Pro Gln Pro Pro Val Asn Ala Gly Gly Ser Gly
            260                 265                 270

Gly Gly Ser Gly
        275

<210> SEQ ID NO 168
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: 2A4 VL CDR1

<400> SEQUENCE: 168

Arg Ser Ser Gln Ser Leu Val His Ser Thr Gly Asn Thr Tyr Leu His
1               5                   10                  15

<210> SEQ ID NO 169
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: 2A4 VL CDR2

<400> SEQUENCE: 169

Lys Val Ser Asn Arg Phe Ser
1               5
```

```
<210> SEQ ID NO 170
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: 2A4 VL CDR3

<400> SEQUENCE: 170

Ser Gln Ser Thr His Val Pro Phe Thr
1               5

<210> SEQ ID NO 171
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: 2A4 VH CDR1

<400> SEQUENCE: 171

Gly Phe Thr Phe Asn Thr Tyr Ala Met Tyr
1               5                   10

<210> SEQ ID NO 172
<211> LENGTH: 19
<212> TYPE: PRT
<213> ORGANISM: Mus musculus
<220> FEATURE:
<221> NAME/KEY: MISC_FEATURE
<222> LOCATION: (1)..(19)
<223> OTHER INFORMATION: 2A4 VH CDR2

<400> SEQUENCE: 172

Arg Ile Arg Ser Lys Ser Asn Asn Tyr Ala Ile Tyr Tyr Ala Asp Ser
1               5                   10                  15

Val Lys Asp

<210> SEQ ID NO 173
<211> LENGTH: 8
<212> TYPE: PRT
<213> ORGANISM: Mus musculus
<220> FEATURE:
<221> NAME/KEY: MISC_FEATURE
<222> LOCATION: (1)..(8)
<223> OTHER INFORMATION: 2A4 VH CDR3

<400> SEQUENCE: 173

Pro Tyr Ser Asp Ser Phe Ala Tyr
1               5

<210> SEQ ID NO 174
<211> LENGTH: 112
<212> TYPE: PRT
<213> ORGANISM: Artificial Sequence
<220> FEATURE:
<223> OTHER INFORMATION: Humanized 7D8 v kappa light chain version 4

<400> SEQUENCE: 174

Asp Val Val Met Thr Gln Ser Pro Leu Ser Leu Pro Val Thr Pro Gly
1               5                   10                  15

Glu Pro Ala Ser Ile Ser Cys Arg Ser Ser Leu Ser Leu Val His Ser
                20                  25                  30

Thr Gly Asn Thr Tyr Leu His Trp Tyr Leu Gln Lys Pro Gly Gln Ser
        35                  40                  45
```

Pro Gln Leu Leu Ile Tyr Lys Val Ser Asn Arg Phe Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Phe Thr Phe Gly Gly Gly Thr Lys Leu Glu Ile Lys
            100                 105                 110

<210> SEQ ID NO 175
<211> LENGTH: 112
<212> TYPE: PRT
<213> ORGANISM: Artificial Sequence
<220> FEATURE:
<223> OTHER INFORMATION: Humanized 7D8 v kappa light chain version 5

<400> SEQUENCE: 175

Asp Val Val Met Thr Gln Ser Pro Leu Ser Leu Pro Val Thr Pro Gly
1               5                   10                  15

Glu Pro Ala Ser Ile Ser Cys Arg Ser Ser Leu Ser Leu Val His Ser
            20                  25                  30

Thr Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Phe Thr Phe Gly Gly Gly Thr Lys Leu Glu Ile Lys
            100                 105                 110

<210> SEQ ID NO 176
<211> LENGTH: 112
<212> TYPE: PRT
<213> ORGANISM: Artificial Sequence
<220> FEATURE:
<223> OTHER INFORMATION: Humanized 7D8 v kappa light chain version 6

<400> SEQUENCE: 176

Asp Val Val Met Thr Gln Ser Pro Leu Ser Leu Pro Val Thr Pro Gly
1               5                   10                  15

Glu Pro Ala Ser Ile Ser Cys Arg Ser Ser Leu Ser Leu Val His Ser
            20                  25                  30

Thr Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Phe Thr Phe Gly Gly Gly Thr Lys Leu Glu Ile Lys
            100                 105                 110

<210> SEQ ID NO 177
<211> LENGTH: 16
<212> TYPE: PRT
<213> ORGANISM: Mus musculus -continued

```
<400> SEQUENCE: 177

Arg Ser Ser Leu Ser Leu Val His Ser Thr Gly Asn Thr Tyr Leu His
1               5                   10                  15
```